(12) United States Patent
Chu et al.

(10) Patent No.: US 9,282,958 B2
(45) Date of Patent: Mar. 15, 2016

(54) DEVICES AND METHOD FOR TREATING PELVIC DYSFUNCTIONS

(75) Inventors: Michael S. H. Chu, Brookline, MA (US); Hamid Davoudi, Westwood, MA (US); Ty Fairneny, Hopkinton, MA (US); James Goddard, Pepperell, MA (US); Roger P. Goldberg, Evanston, IL (US); Jianmin Li, Lexington, MA (US); Steven A. Olivieri, Shrewsbury, MA (US); John Petricca, Ashland, MA (US); Jozef Slanda, Milford, MA (US); Ken Toso, Westborough, MA (US); Michael Weiser, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1365 days.

(21) Appl. No.: 12/341,701

(22) Filed: Dec. 22, 2008

(65) Prior Publication Data

US 2009/0171143 A1 Jul. 2, 2009

Related U.S. Application Data

(60) Provisional application No. 61/017,257, filed on Dec. 28, 2007, provisional application No. 61/103,065, filed on Oct. 6, 2008, provisional application No. 61/017,212, filed on Dec. 28, 2007.

(51) Int. Cl.
*A61F 2/00* (2006.01)
*A61F 2/02* (2006.01)
(Continued)

(52) U.S. Cl.
CPC ......... *A61B 17/0401* (2013.01); *A61B 17/0482* (2013.01); *A61B 17/06109* (2013.01);
(Continued)

(58) Field of Classification Search
USPC ......... 600/37, 29, 30; 128/897, 899; 606/151, 606/222–231
See application file for complete search history.

(56) References Cited

U.S. PATENT DOCUMENTS

| 669,034 A | 2/1901 | Manly |
| 3,123,077 A | 3/1964 | Alcamo |

(Continued)

FOREIGN PATENT DOCUMENTS

| EP | 0 412 664 A1 | 2/1991 |
| EP | 1 201 189 A2 | 5/2002 |

(Continued)

OTHER PUBLICATIONS

International Search Report and Written Opinion for PCT/US08/88178; mailed on Jul. 6, 2009; 15 pages.
(Continued)

*Primary Examiner* — Catherine B Kuhlman
*Assistant Examiner* — Shannon McBride

(57) ABSTRACT

In one embodiment, a method includes securing an implant that includes a pre-formed loop to a vaginal apex. An end of the suture is inserted through a selected portion of a pelvic tissue to dispose at least a portion of the implant within a pelvic region of the patient. The end of the suture is drawn through the loop while simultaneously advancing a uterus to approximate the vaginal apex to the selected portion of pelvic tissue. An apparatus includes an implant and a suture coupled to the implant having a pre-formed loop. configured to receive a portion of a delivery device therethrough. A trocar is coupled to an end of the suture that can be releasably coupled to an end of the delivery device. The trocar can be inserted through a pelvic tissue and drawn through the loop forming a knot to secure the implant to the pelvic tissue.

13 Claims, 93 Drawing Sheets

(51) Int. Cl.
*A61B 17/04* (2006.01)
*A61B 17/06* (2006.01)
*A61B 19/02* (2006.01)
*A61B 17/00* (2006.01)

(52) U.S. Cl.
CPC ........... *A61B19/0256* (2013.01); *A61F 2/0045* (2013.01); *A61B 2017/00805* (2013.01); *A61B 2017/0475* (2013.01); *A61B 2017/0496* (2013.01); *A61B 2017/06042* (2013.01); *A61B 2017/06176* (2013.01)

(56) References Cited

U.S. PATENT DOCUMENTS

| | | | |
|---|---|---|---|
| 3,580,256 A * | 5/1971 | Wilkinson et al. | 606/228 |
| 4,324,331 A | 4/1982 | Ignasiak | |
| 4,792,336 A | 12/1988 | Hlavacek et al. | |
| 4,919,667 A | 4/1990 | Richmond | |
| 4,998,912 A | 3/1991 | Scarbrough et al. | |
| 5,013,292 A | 5/1991 | Lemay | |
| 5,082,112 A | 1/1992 | Dunklee | |
| 5,149,329 A | 9/1992 | Richardson | |
| 5,217,466 A | 6/1993 | Hasson | |
| 5,217,486 A | 6/1993 | Rice et al. | |
| 5,217,494 A | 6/1993 | Coggins et al. | |
| 5,263,969 A | 11/1993 | Phillips | |
| 5,356,432 A | 10/1994 | Rutkow et al. | |
| 5,362,294 A | 11/1994 | Seitzinger | |
| 5,383,905 A | 1/1995 | Golds et al. | |
| 5,405,359 A | 4/1995 | Pierce | |
| 5,425,747 A | 6/1995 | Brotz | |
| 5,458,636 A | 10/1995 | Brancato | |
| 5,485,917 A | 1/1996 | Early | |
| 5,527,342 A * | 6/1996 | Pietrzak et al. | 606/232 |
| 5,534,008 A | 7/1996 | Acksel | |
| 5,562,689 A | 10/1996 | Green et al. | |
| 5,584,859 A | 12/1996 | Brotz | |
| 5,643,311 A | 7/1997 | Smith et al. | |
| 5,683,402 A | 11/1997 | Cosgrove et al. | |
| 5,702,397 A | 12/1997 | Goble et al. | |
| 5,741,277 A | 4/1998 | Gordon et al. | |
| 5,840,011 A | 11/1998 | Landgrebe et al. | |
| 5,899,909 A | 5/1999 | Claren et al. | |
| 5,931,855 A * | 8/1999 | Buncke | 606/228 |
| 5,948,001 A | 9/1999 | Larsen | |
| 5,976,127 A | 11/1999 | Lax | |
| 6,010,447 A | 1/2000 | Kardjian | |
| 6,012,580 A | 1/2000 | Peters et al. | |
| 6,039,686 A | 3/2000 | Kovac | |
| 6,042,534 A | 3/2000 | Gellman et al. | |
| 6,042,536 A | 3/2000 | Tihon et al. | |
| 6,042,592 A | 3/2000 | Schmitt | |
| 6,044,847 A | 4/2000 | Carter et al. | |
| 6,197,036 B1 | 3/2001 | Tripp et al. | |
| 6,200,330 B1 | 3/2001 | Benderev et al. | |
| 6,221,005 B1 | 4/2001 | Bruckner et al. | |
| 6,267,772 B1 | 7/2001 | Mulhauser et al. | |
| 6,273,852 B1 | 8/2001 | Lehe et al. | |
| 6,306,079 B1 | 10/2001 | Trabucco | |
| 6,322,492 B1 | 11/2001 | Kovac | |
| 6,328,686 B1 | 12/2001 | Kovac | |
| 6,375,662 B1 | 4/2002 | Schmitt | |
| 6,382,214 B1 | 5/2002 | Raz et al. | |
| 6,406,423 B1 | 6/2002 | Scetbon | |
| 6,478,727 B2 | 11/2002 | Scetbon | |
| 6,491,703 B1 | 12/2002 | Ulmsten | |
| 6,502,578 B2 | 1/2003 | Raz et al. | |
| 6,506,190 B1 | 1/2003 | Walshe | |
| 6,544,273 B1 | 4/2003 | Harari et al. | |
| 6,547,800 B2 | 4/2003 | Foerster et al. | |
| 6,565,580 B1 | 5/2003 | Beretta | |
| 6,575,998 B2 | 6/2003 | Beyar | |
| 6,582,443 B2 | 6/2003 | Cabak et al. | |
| 6,592,515 B2 | 7/2003 | Thierfelder et al. | |
| 6,592,610 B2 | 7/2003 | Beyar | |
| 6,595,911 B2 | 7/2003 | LoVuolo | |
| 6,596,001 B2 | 7/2003 | Stormby et al. | |
| 6,599,235 B2 | 7/2003 | Kovac | |
| 6,599,310 B2 | 7/2003 | Leung et al. | |
| 6,612,977 B2 | 9/2003 | Staskin et al. | |
| 6,638,209 B2 | 10/2003 | Landgrebe | |
| 6,638,210 B2 | 10/2003 | Berger | |
| 6,638,211 B2 | 10/2003 | Suslian et al. | |
| 6,641,524 B2 | 11/2003 | Kovac | |
| 6,641,525 B2 | 11/2003 | Rocheleau et al. | |
| 6,648,899 B2 | 11/2003 | Kalinski et al. | |
| 6,648,921 B2 | 11/2003 | Anderson et al. | |
| 6,652,450 B2 | 11/2003 | Neisz et al. | |
| 6,666,817 B2 | 12/2003 | Li | |
| 6,669,706 B2 | 12/2003 | Schmitt et al. | |
| 6,669,735 B1 | 12/2003 | Pelissier | |
| 6,673,010 B2 | 1/2004 | Skiba et al. | |
| 6,691,711 B2 | 2/2004 | Raz et al. | |
| 6,695,855 B1 | 2/2004 | Gaston | |
| 6,702,827 B1 | 3/2004 | Lund et al. | |
| 6,730,110 B1 | 5/2004 | Harari et al. | |
| 6,746,455 B2 | 6/2004 | Beyar et al. | |
| 6,752,814 B2 | 6/2004 | Gellman et al. | |
| 6,755,781 B2 | 6/2004 | Gellman | |
| 6,808,487 B2 | 10/2004 | Migliari | |
| 6,830,052 B2 | 12/2004 | Carter et al. | |
| 6,848,152 B2 | 2/2005 | Genova et al. | |
| 6,881,184 B2 | 4/2005 | Zappala | |
| 6,890,338 B1 | 5/2005 | Davis et al. | |
| 6,908,425 B2 | 6/2005 | Luscombe | |
| 6,911,003 B2 | 6/2005 | Anderson et al. | |
| 6,911,034 B2 | 6/2005 | Nobles et al. | |
| 6,932,759 B2 | 8/2005 | Kammerer et al. | |
| 6,936,052 B2 | 8/2005 | Gellman et al. | |
| 6,946,003 B1 | 9/2005 | Wolowacz et al. | |
| 6,953,428 B2 | 10/2005 | Gellman et al. | |
| 6,960,160 B2 | 11/2005 | Browning | |
| 6,971,986 B2 | 12/2005 | Staskin et al. | |
| 6,991,597 B2 | 1/2006 | Gellman et al. | |
| 7,011,688 B2 | 3/2006 | Gryska et al. | |
| 7,025,772 B2 | 4/2006 | Gellman et al. | |
| 7,048,682 B2 | 5/2006 | Neisz et al. | |
| 7,056,333 B2 | 6/2006 | Walshe | |
| 7,070,556 B2 | 7/2006 | Anderson et al. | |
| 7,070,558 B2 | 7/2006 | Gellman et al. | |
| 7,083,568 B2 | 8/2006 | Neisz et al. | |
| 7,083,637 B1 | 8/2006 | Tannhauser | |
| 7,090,686 B2 | 8/2006 | Nobles et al. | |
| 7,094,199 B2 | 8/2006 | Petros et al. | |
| 7,112,171 B2 | 9/2006 | Rocheleau et al. | |
| 7,112,210 B2 | 9/2006 | Ulmsten et al. | |
| 7,122,039 B2 | 10/2006 | Chu | |
| 7,131,943 B2 | 11/2006 | Kammerer | |
| 7,131,944 B2 | 11/2006 | Jacquetin | |
| 7,198,597 B2 | 4/2007 | Siegel et al. | |
| 7,204,801 B2 | 4/2007 | Grocela | |
| 7,204,802 B2 | 4/2007 | De Leval | |
| 7,223,229 B2 | 5/2007 | Inman et al. | |
| 7,226,407 B2 | 6/2007 | Kammerer et al. | |
| 7,226,408 B2 | 6/2007 | Harari et al. | |
| 7,229,453 B2 | 6/2007 | Anderson et al. | |
| 7,235,043 B2 | 6/2007 | Gellman et al. | |
| 7,244,259 B2 | 7/2007 | Smith et al. | |
| 7,244,260 B2 | 7/2007 | Koseki | |
| 7,267,645 B2 | 9/2007 | Anderson et al. | |
| 7,291,104 B2 | 11/2007 | Neisz et al. | |
| 7,351,197 B2 | 4/2008 | Montpetit et al. | |
| 7,361,138 B2 | 4/2008 | Wagner et al. | |
| 7,364,541 B2 | 4/2008 | Chu et al. | |
| 7,402,133 B2 | 7/2008 | Chu et al. | |
| 7,413,540 B2 | 8/2008 | Gellman et al. | |
| 8,460,169 B2 * | 6/2013 | Lund et al. | 600/30 |
| 8,721,666 B2 * | 5/2014 | Schroeder et al. | 606/151 |
| 2002/0010457 A1 | 1/2002 | Duchon et al. | |
| 2002/0028980 A1 * | 3/2002 | Thierfelder et al. | 600/37 |
| 2002/0091373 A1 | 7/2002 | Berger | |
| 2002/0128670 A1 | 9/2002 | Ulmsten et al. | |
| 2002/0151909 A1 | 10/2002 | Gellman et al. | |

(56) References Cited

U.S. PATENT DOCUMENTS

| | | |
|---|---|---|
| 2002/0156489 A1 | 10/2002 | Gellman et al. |
| 2003/0065402 A1* | 4/2003 | Anderson et al. .......... 623/23.66 |
| 2003/0125715 A1 | 7/2003 | Kuehn et al. |
| 2003/0149334 A1 | 8/2003 | Ulmsten et al. |
| 2003/0220538 A1 | 11/2003 | Jacquetin |
| 2003/0225424 A1 | 12/2003 | Benderev |
| 2004/0006353 A1 | 1/2004 | Bosley, Jr. et al. |
| 2004/0039453 A1 | 2/2004 | Anderson et al. |
| 2004/0060409 A1* | 4/2004 | Leung et al. ............... 83/522.14 |
| 2004/0073234 A1 | 4/2004 | Chu et al. |
| 2004/0106847 A1 | 6/2004 | Benderev |
| 2004/0181243 A1 | 9/2004 | Chu et al. |
| 2004/0225181 A1 | 11/2004 | Chu et al. |
| 2004/0230206 A1 | 11/2004 | Gellman et al. |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0075666 A1* | 4/2005 | Maas et al. ..................... 606/224 |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107805 A1 | 5/2005 | Bouffier et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0192600 A1 | 9/2005 | Nicolo et al. |
| 2005/0245787 A1 | 11/2005 | Cox et al. |
| 2005/0250978 A1 | 11/2005 | Kammerer |
| 2005/0256366 A1 | 11/2005 | Chu |
| 2005/0256530 A1 | 11/2005 | Petros |
| 2005/0261547 A1 | 11/2005 | Bouffier |
| 2005/0277807 A1 | 12/2005 | MacLean et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 | 4/2006 | Mamo et al. |
| 2006/0122457 A1* | 6/2006 | Kovac et al. ..................... 600/37 |
| 2006/0173237 A1 | 8/2006 | Jacquetin |
| 2006/0205995 A1 | 9/2006 | Browning |
| 2006/0211911 A1 | 9/2006 | Jao et al. |
| 2006/0229596 A1 | 10/2006 | Weiser et al. |
| 2006/0252980 A1* | 11/2006 | Arnal et al. ..................... 600/29 |
| 2006/0264698 A1 | 11/2006 | Kondonis et al. |
| 2007/0005110 A1* | 1/2007 | Collier et al. ................. 606/228 |
| 2007/0123915 A1 | 5/2007 | Kammerer et al. |
| 2007/0161849 A1* | 7/2007 | Goldberg ........................ 600/30 |
| 2007/0173887 A1* | 7/2007 | Sasaki ........................... 606/232 |
| 2007/0203508 A1 | 8/2007 | White et al. |
| 2007/0276358 A1 | 11/2007 | Barzell et al. |
| 2008/0082177 A1* | 4/2008 | Yang et al. ................. 623/23.75 |
| 2008/0091221 A1 | 4/2008 | Brubaker et al. |
| 2008/0177132 A1* | 7/2008 | Alinsod et al. .................. 600/37 |
| 2008/0196729 A1* | 8/2008 | Browning ..................... 128/834 |
| 2009/0221867 A1* | 9/2009 | Ogdahl et al. .................. 600/37 |
| 2009/0221868 A1* | 9/2009 | Evans ............................. 600/37 |
| 2010/0256442 A1* | 10/2010 | Ogdahl et al. .................. 600/30 |

FOREIGN PATENT DOCUMENTS

| | | |
|---|---|---|
| EP | 1 508 305 A2 | 2/2005 |
| EP | 1 520 554 A2 | 4/2005 |
| GB | 670349 | 4/1952 |
| WO | WO 98/35632 A1 | 8/1998 |
| WO | WO 02/078571 A2 | 10/2002 |
| WO | WO 03/092546 A2 | 11/2003 |
| WO | WO 2005/122721 A2 | 12/2005 |
| WO | WO 2005112842 A1 * | 12/2005 |
| WO | WO 2006/046950 A1 | 5/2006 |
| WO | WO 2007/016698 A2 | 2/2007 |
| WO | WO 2007/019374 A2 | 2/2007 |
| WO | WO 2007/059199 A2 | 5/2007 |

OTHER PUBLICATIONS

International Preliminary Report on Patentability for PCT Application No. PCT/US2008/088178, mailed on Jul. 8, 2010, 11 pages.
Communication Relating to the Results of the Partial International Search for PCT/US08/88178, mailed on Mar. 18, 2009; 2 pages.

* cited by examiner

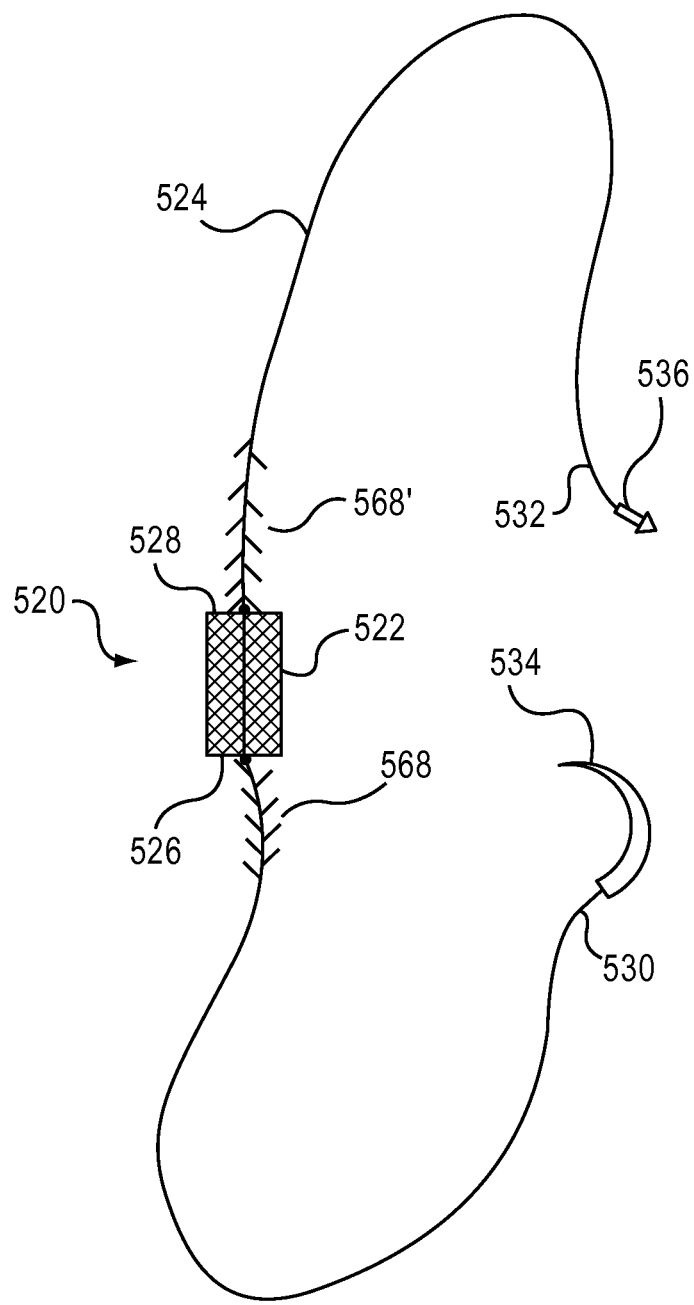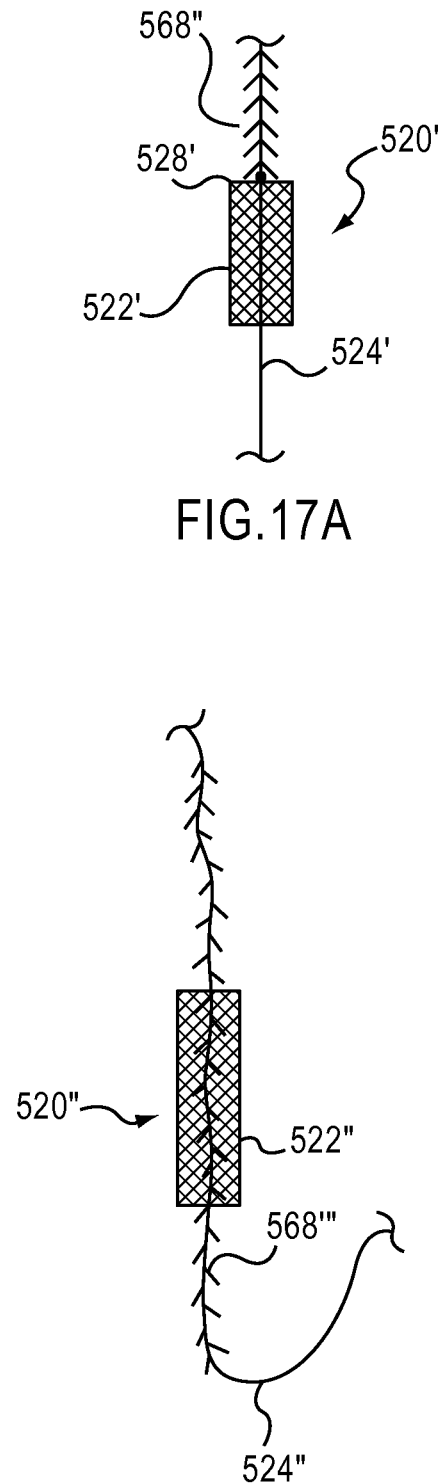
FIG.16
FIG.17A
FIG.17B

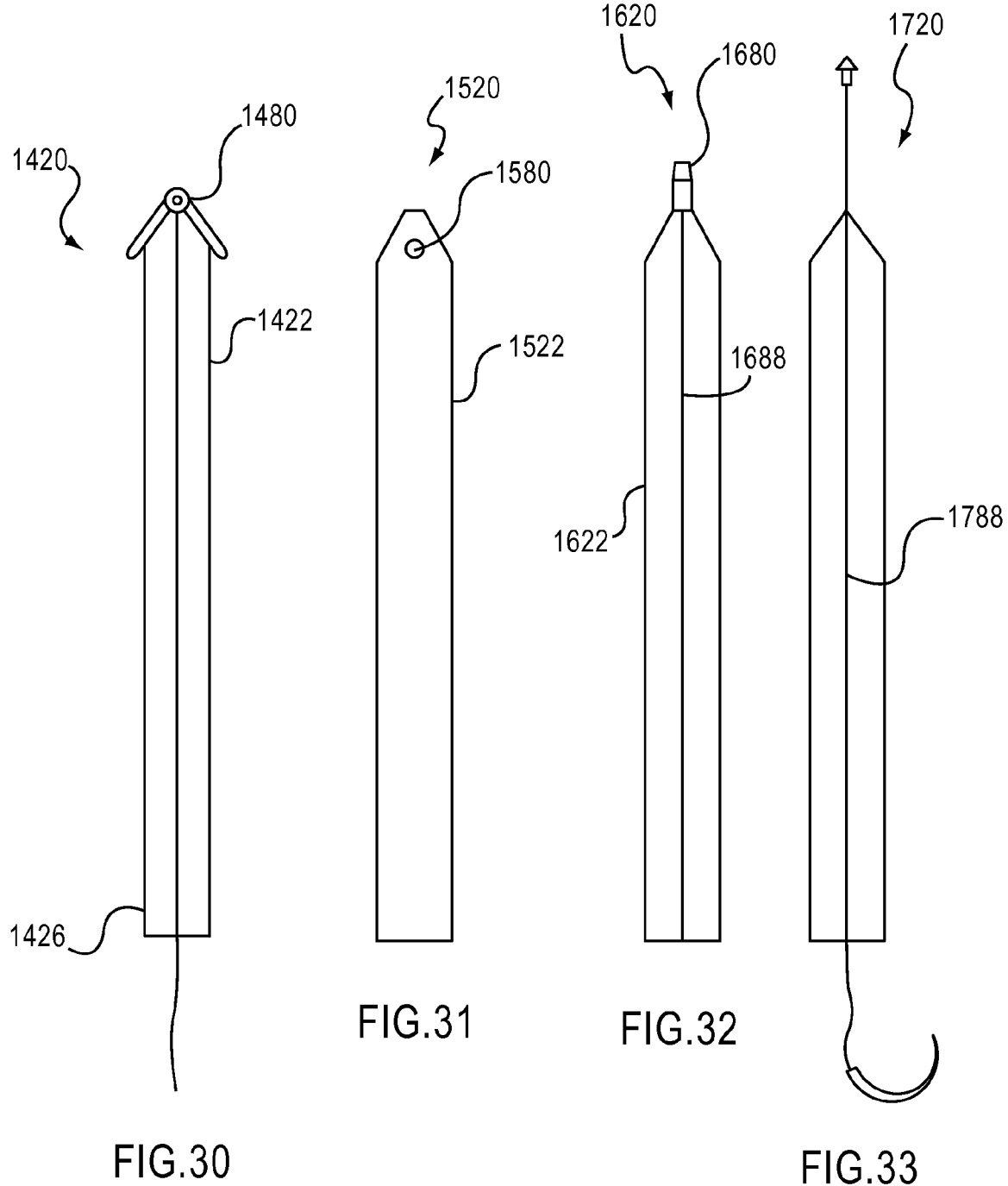

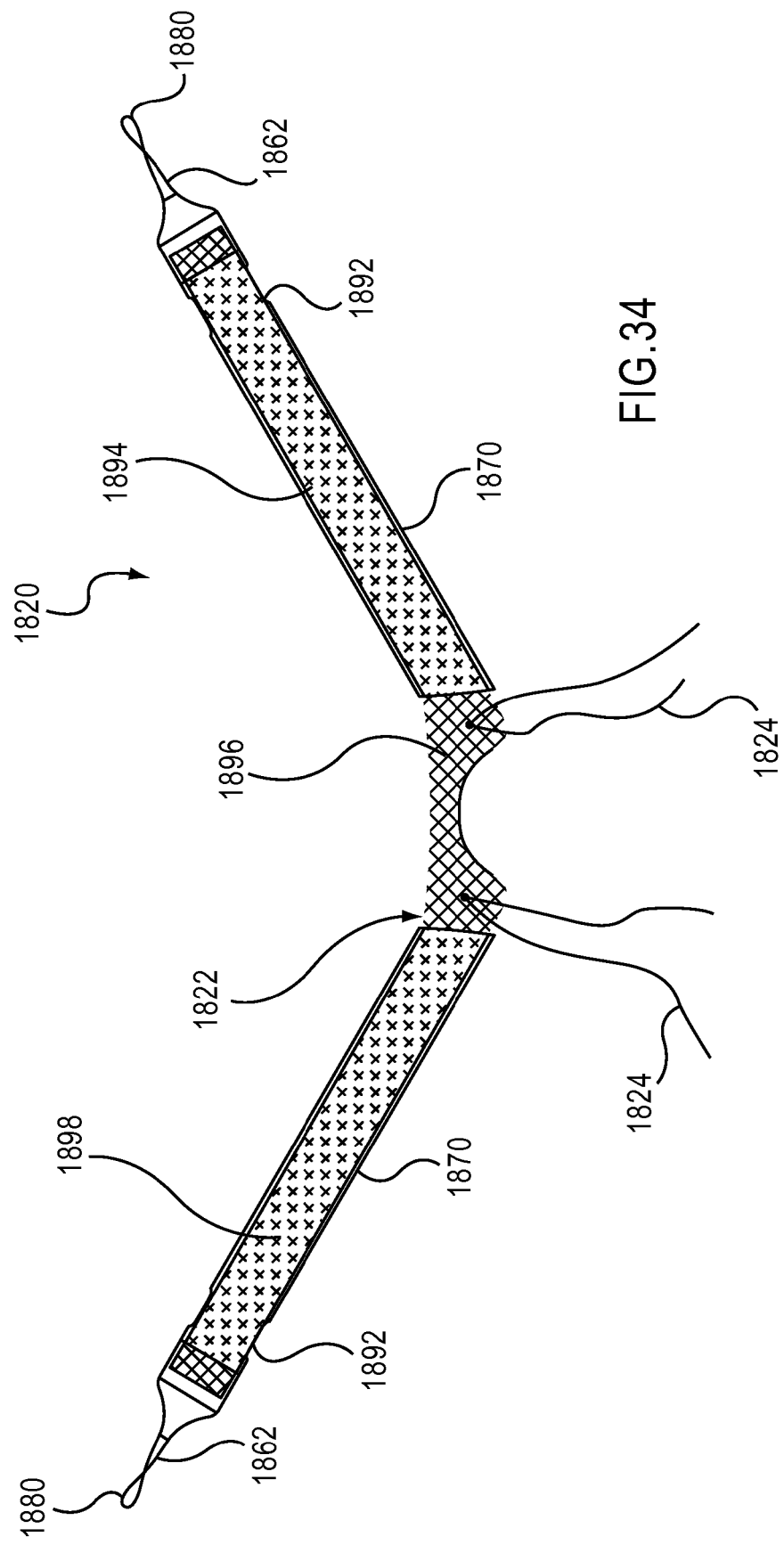

DEVICES AND METHOD FOR TREATING PELVIC DYSFUNCTIONS

CROSS-REFERENCE TO RELATED APPLICATIONS

This application claims priority to U.S. Provisional Patent Application Ser. No. 61/017,257, entitled "Apparatus and Method for Uterine Preservation," filed Dec. 28, 2007, the disclosure of which is hereby incorporated by reference in its entirety. This application also claims priority to U.S. Provisional Patent Application Ser. No. 61/103,065, entitled "Implant for Pelvic Floor Repair," filed Oct. 6, 2008, and U.S. Provisional Patent Application Ser. No. 61/017,212, entitled "Devices and Methods for Treating Pelvic Floor Dysfunctions," filed Dec. 28, 2007, each of the disclosures of which is hereby incorporated by reference in its entirety.

BACKGROUND

The invention relates generally to medical devices, and in particular to implants and methods for treating various pelvic dysfunctions including procedures to repair uterine prolapse, cystoceles, rectoceles, and vaginal vault prolapse.

A vaginal prolapse can be due to age or other factors and typically results in one of three types of prolapse: hysterocele, cystocele, and rectocele. A hysterocele occurs when the uterus descends into the vagina and is often treated with a hysterectomy followed by a vaginal vault suspension. A cystocele prolapse occurs when the bladder bulges or descends into the vagina and a rectocele occurs when the rectum bulges or descends into the vagina. It is often common for more than one of a hysterocele and cystocele, a hysterocele and a rectocele to occur at the same time. Treatment of vaginal vault prolapse, including a vaginal prolapse due to a hysterocele, can include a suturing procedure or the use of an implant for support or suspension.

Another procedure to treat a prolapse caused by a hysterocele is to perform a hysterectomy. Many patients, however, want to avoid a hysterectomy for a variety of reasons, including plans for future childbearing, concern about the invasiveness of the procedure, the difficulty of the recuperation, or fear of diminished sexual function. Some women are simply reluctant to "give up" this part of their body so closely associated with their reproductive health, childbearing, and femininity.

Uterine prolapse can be effectively treated without hysterectomy, with low morbidity and high rates of patient satisfaction. A properly performed uterine suspension procedure often results in a significantly better anatomic outcome than a hysterectomy. Yet, many hysterectomy procedures are performed for pelvic prolapse. Many patients remain unaware of uterine-sparing options because with the exception of a few dedicated sub-specialists, most surgeons receive no training in these techniques. In addition, known techniques can be difficult, and can require specialized training that many general practitioners have not undertaken.

Thus a need exists for an improved apparatus and method for providing minimally invasive procedures for repair of various pelvic dysfunctions, including uterine prolapses or hysteroceles, cystoceles, rectoceles and vaginal vault prolapse.

Some known implantation methods, suffer several disadvantages. Generally, the person performing the implantation removes the implant from any protective packaging before beginning the implantation process. Implants are often implanted free-hand (i.e., without guiding apparatuses), which can increase the risk of improper implantation. Implants are generally flexible and may be difficult for a single person to orient and manage during implantation. Additionally, implants often include sutures or straps that may become tangled during implantation. Finally, some implants can become damaged during the implantation procedure. Thus, a need also exists for improved implant dispensers and methods.

A pelvic floor repair graft can be used to repair uterine prolapse, cystoceles, rectoceles, vaginal vault prolapse, and/or utero-vaginal prolapse. A urinary incontinence sling may be used to treat urinary incontinence caused by hypermobility and/or intrinsic sphincter deficiency (ISD). Hypermobility occurs when the normal pelvic floor muscles can no longer provide the necessary support to the urethra and bladder neck. As a result, the bladder neck is free to drop when any downward pressure is applied and thus, involuntary leakage occurs. ISD may be caused by the weakening of the urethral sphincter muscles or closing mechanism. As a result of this weakening, the sphincter does not function normally regardless of the position of the bladder neck or urethra. A urinary incontinence sling can be fixed to body tissue to reconstitute the support for the urethra and/or bladder and treat hypermobility and/or ISD.

Known implant assemblies can include tissue anchors. Pelvic floor repair grafts and urinary incontinence slings, for example, can be held in place by tissue anchors and/or sutures. Tissue anchors are inserted into the tissue surrounding the area where the implant is disposed. Tissue anchors, however, can be inflexible and difficult to place. Sutures can be used to suture the implant to the tissue surrounding the area where the implant is disposed. The ends of the suture, however, must be tied or otherwise reconnected to the implant once the suture is positioned around and/or through the surrounding tissue. This can make it difficult to place the suture.

Thus, a need also exists for an implant that can be easily placed and retained within a body of a patient. Specifically, a need exists for improved pelvic floor repair grafts and urinary incontinence slings.

SUMMARY OF THE INVENTION

Apparatuses and methods for performing various medical procedures within a pelvic region of a patient are described herein. For example, medical procedures to treat uterine prolapse, vaginal vault prolapse, rectocele, and cystocele, are described herein. In one embodiment, a method includes securing an implant having a suture with a pre-formed loop coupled thereto to a vaginal apex. An end of the suture is inserted through a selected portion of a pelvic tissue such that at least a portion of the implant is disposed within a pelvic region of the patient. The end of the suture is drawn through the loop while simultaneously advancing a uterus to approximate the vaginal apex to the selected portion of pelvic tissue and support the uterus. In another embodiment, an apparatus includes an implant member and a suture coupled thereto. The suture has a pre-formed loop configured to receive a portion of a delivery device therethrough. A trocar needle is coupled to an end of the suture that can be releasably coupled to an end of the delivery device. The trocar can be inserted through a pelvic tissue and drawn through the loop such that a knot is formed to secure the implant to the pelvic tissue.

In one embodiment, an apparatus comprises a body having a first retention structure, a second retention structure, an aperture and an opening. The first retention structure is configured to maintain a suture loop in an open configuration. The second retention structure is configured to secure a free end portion of a suture. The aperture is configured to permit passage of a suturing device and the free end portion of the suture. The opening is configured to permit the free end portion of the suture to exit the body through the opening after the free end portion of the suture is passed through the body via the aperture.

In some embodiments, an apparatus includes a support member, a first strap, and a second strap. The support member is configured to support a uterus of a patient. The first strap extends from the support member and is configured to be secured to a first portion of a sacrospinous ligament. The second strap extends from the support member and is configured to be secured to a second portion of the sacrospinous ligament. The first strap and the second strap are configured to help retain the support member at least partially adjacent the uterus when the first strap is secured to the first portion of the sacrospinous ligament and the second strap is secured to the second portion of the sacrospinous ligament.

In some embodiments, an implant includes a support member and a suture. The support member is configured to support a portion of a body of a patient. In some embodiments, the support member is configured to support a pelvic floor of a patient. The suture of the implant has an elongate member and a barb coupled to the elongate member. The elongate member has an end portion coupled to the support member. The elongate member defines a center line. The barb extends from the elongate member at an angle acute to the center line defined by the elongate member when the elongate member is in a linear configuration. The suture of the implant is configured to be inserted into a tissue. The barb allows movement of the suture with respect to the tissue in a first direction and helps prevent movement of the suture with respect to the tissue in a second direction, different from the first direction, when the elongate member is disposed within the tissue of the patient.

BRIEF DESCRIPTION OF THE DRAWINGS

FIGS. 16-24 are each a front view of an implant assembly according to various embodiments of the invention.

FIGS. 28-33 are each a front view of an implant assembly according to other embodiments of the invention.

FIGS. 34 and 35 are each a front view of an implant assembly according to other embodiments of the invention.

DETAILED DESCRIPTION

Figure 1:
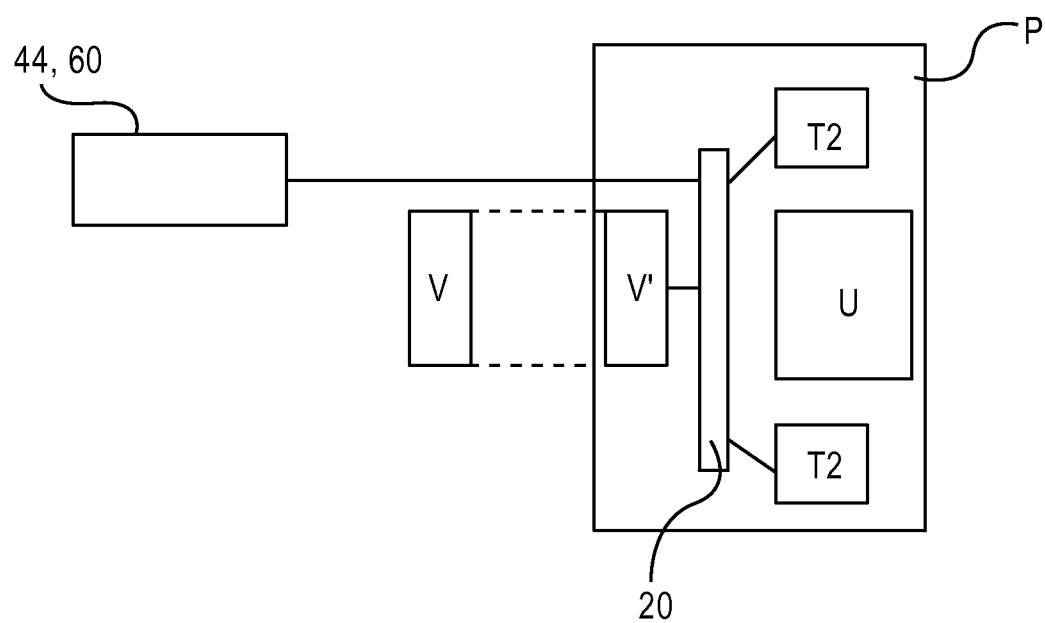
FIG. 1 is a schematic illustration of various components and medical devices that can be used in a method according to an embodiment of the invention.

An apparatus and method for performing various medical procedures within a pelvic region of a patient are described herein. For example, medical procedures to treat uterine prolapse, vaginal vault prolapse, rectocele, and cystocele, are described herein. Various implant assemblies are described herein that can be secured within a pelvic region (also referred to herein as "pelvis" or "pelvic space") and used to support a prolapsed uterus. One or more implant assemblies can be implanted into the patient's body depending on the particular treatment needed. Various delivery devices are also described for delivering and securing an implant assembly within the body of the patient.

In one embodiment, a method includes securing an implant having a suture with a pre-formed loop coupled thereto to a vagina apex. An end of the suture is inserted through a selected portion of a pelvic tissue such that at least a portion of the implant is disposed within a pelvic region of the patient. The end of the suture is drawn through the loop while simultaneously advancing a uterus to approximate the vaginal apex to the selected portion of pelvic tissue and to support the uterus. In another embodiment, an apparatus includes a pelvic implant and a suture coupled thereto. The suture has a pre-formed loop configured to receive a portion of a delivery device therethrough. A trocar needle is coupled to an end of the suture that can be releasably coupled to an end of the delivery device. The trocar needle can be inserted through a pelvic tissue and drawn through the loop such that a knot is formed to secure the implant to the pelvic tissue.

In some embodiments, a delivery system is provided for delivering an implant assembly into a pelvic region to repair a prolapsed uterus by repositioning and securing the uterus into its correct anatomical position. For example, one end or a portion of an implant assembly, can be secured to a portion of a vaginal apex of a patient, while another end or portion of the implant can be secured to a tissue within a pelvic region of the patient, such as a sacrospinous ligament. The implant can be tensioned to approximate the vaginal apex to the sacrospinous ligament. Eventual tissue in-growth can occur through the implant to further secure the uterus in position. For example, a portion of an implant can be formed with a mesh material configured to promote tissue in-growth.

In some embodiments, a portion of an implant member can be secured within a vaginal lumen of the patient. In some embodiments, an implant is secured to the undersurface of the epithelium of a vaginal wall without passing through the thickness of the vaginal wall. In other embodiments, a portion of an implant can be secured to a tendineus arch of levator muscle (also referred to herein as "arcus tendineus" and/or "white line"), to an iliococcygeus muscle, to a levator ani muscle, or to another levator muscle. Thus, the implant assemblies described herein can be secured within a pelvic region in a variety of different locations and can be used, for example, to support a uterus.

The various apparatuses described herein can be used, for example, as a uterine preservation-pelvic floor repair kit, but are not limited to such use. For example, the apparatuses and methods can be used when the uterus has already been removed from the patient. The apparatuses and methods can be used to approximate a uterus back to its original or normal anatomical position and repair other prolapses without having to remove the uterus. A kit (e.g. one or more implant assemblies) can be used in conjunction with an anterior, posterior, or total repair with or without apical repairs, as well as other pelvic floor repairs. In some embodiments, an implant assembly can be delivered and secured within a pelvic region using both a large needle passage(s) through an exterior incision(s), and a delivery device that is inserted through a vaginal incision. For example, an implant assembly can include two anterior arms that are placed and anchored through an obturator muscle using a needle delivery system, and two posterior arms that are anchored or secured to a sacrospinous ligament or iliococcygeus muscle and the vaginal apex by a delivery device such as a suturing device. An implant assembly can be used to approximate the vaginal apex to the sacrospinous ligament/iliococcygeus muscle to suspend the prolapsed uterus to a "correct" and "deep" anatomical position. In some embodiments, a kit can provide separate anterior and posterior implants.

In some embodiments, anterior straps of an implant assembly are not placed through an obturator (e.g., using a transobturator approach), but rather by retro-pubic, supra pubic, or pre-pubic approaches. In some embodiments, an implant can include mid-straps or arms (between anterior and posterior straps or arms) to suspend to the arcus tendineus to achieve a "higher" support of the vagina. Such straps can be placed using a suturing type delivery device, or a deep transobturator or transglutual needle approach. A deep transobturator needle typically has a larger diameter than a standard transobturator needle, and a transglutual needle can be configured to reach a sacrospinous ligament or arcus tendineus. A midline of an implant when placed within a pelvic region can support a cervix and is sometimes referred to as an apical repair. For example, an apical repair can refer to associating, a mid-line portion of an implant or a suture disposed at the mid-line, to the cervical area to suspend the cervix in a "higher" position. In use, a physician can also cut or trim an implant to modify or customize the implant for the particular use and/or patient. Although described primarily with reference to use to suspend a uterus, the implants and methods described herein can be used with an incontinence sling to support for example a urethra.

The implant assemblies and methods described herein can provide support directly after a medical procedure to properly position and securely suspend a vagina and/or other pelvic organs, in their original anatomical position. For example, in some procedures, the full length of a vagina can be regained and dislocation of the vagina can be prevented during the healing process. In some embodiments described herein, apical support is provided by approximating an area of a vaginal apex to a sacrospinous ligament by means of tying down sutures. Such apical support can be provided on one side of a pelvic region or both sides. Apical support is typically referred to support that is provided to a patient without a uterus. Typically, in an apical support procedure, support is superficially achieved with a single suture placed through the vaginal cuff and secured to the implant. Apical fixation then occurs after tissue in-growth around the suture. A support procedure performed on a patient with a uterus is typically referred to as uterine preservation. Uterine preservation can include the re-suspension of an otherwise healthy prolapsed uterus and eliminates the need for a hysterectomy.

In some embodiments, an apparatus includes a support member, a first strap, and a second strap. The support member is configured to support a uterus of a patient. The first strap extends from the support member and is configured to be secured to a first portion of a sacrospinous ligament. The second strap extends from the support member and is configured to be secured to a second portion of the sacrospinous ligament. The first strap and the second strap are configured to help retain the support member at least partially adjacent the uterus when the first strap is secured to the first portion of the sacrospinous ligament and the second strap is secured to the second portion of the sacrospinous ligament.

Implants can be delivered to a pelvic region of a patient using a variety of different delivery devices, only some examples of which are described herein. Various delivery aids are also described, some of which can be included as part of an implant (e.g., provided to a physician assembled) and some of which can be coupled to or associated with an implant just prior to implantation. Such delivery aids are typically removed after placing one or more straps of an implant at a desired tissue securement location, leaving the strap to engage the tissue and support the support portion of the implant. For example, a sleeve or dilator assembly can be used to lead an implant or a strap of an implant through a tissue in an intracorporeal location (i.e., within the patient's body), such as the sacrospinous ligament or arcus tendineus. In other embodiments, a sleeve or dilator assembly can be used to lead an implant or a strap of an implant through a tissue and to an extracorporeal location (outside the patient's body), such as through an obturator membrane or muscle and out through an exterior incision in the patient.

Some embodiments relate generally to implant delivery in relation to pelvic floor reconstruction, vaginal vault support, and uterine support including, for example, devices and methods for housing and protecting implants during sterilization, shipment and implantation. Devices and methods according to various embodiments may be capable of, for example, preventing entanglement of sutures, preventing damage to implants, and/or helping avoid user confusion during implantation.

In some embodiments, an implant dispenser is configured to aid in implantation, sterilization, shipment and delivery of an implant. In some embodiments, an implant dispenser manages and prevents entanglement of an implant and/or a suture coupled to the implant. In other embodiments, the implant dispenser includes markings to aid a user during implantation.

In one embodiment, an implant and a suture are attached to an implant dispenser and the implant dispenser is used to simplify a knot tying procedure during delivery of the implant. In such an embodiment, the suture is configured to secure the implant to the body of a patient. The implant dispenser may be a rigid or semi-rigid body and include an aperture, an opening and two retention structures. The opening in the body of the dispenser extends from a side edge of the implant dispenser into the aperture such that a suture extending through the implant dispenser via the aperture can be removed from the implant dispenser via the opening. A first retention structure is located about the aperture such that it secures a loop in the suture of the implant about the aperture in an open configuration or position. The loop in the suture can be formed, for example, by a knot in the suture. A second retention structure secures a free end portion of the suture of the implant to the implant dispenser.

In some embodiments, an implant includes a support member and a suture. The support member is configured to support a portion of a body of a patient. In some embodiments, the support member is configured to support a portion of a body of a patient located in or near a portion of a body of a patient located at or near the pelvic floor of the patient. The suture of the implant has an elongate member and a barb coupled to the elongate member. The elongate member has an end portion coupled to the support member. The elongate member defines a center line. The barb extends from the elongate member at an angle acute to the center line defined by the elongate member when the elongate member is in a linear configuration. The suture of the implant is configured to be inserted into a tissue. The barb allows movement of the suture with respect to the tissue in a first direction and helps prevent movement of the suture with respect to the tissue in a second direction, different from the first direction, when the elongate member is disposed within the tissue of the patient.

In some embodiments, an implant includes a support member, a first suture, and a second suture. The first suture includes an elongate member and a retention member. The elongate member of the first suture is coupled to the support member. The retention member of the first suture is coupled to the elongate member and helps retain the support member within a body of a patient. Similar to the first suture, the second suture includes an elongate member and a retention member. The elongate member of the second suture is coupled to the support member. The retention member of the second suture is coupled to the elongate member of the second suture and helps retain the support member within a body of a patient. The second suture is intertwined with the first suture.

In some embodiments, an implant includes a support member, a first suture, and a second suture. The support member has a first side portion and a second side portion. The first suture includes an elongate member and a plurality of retention members coupled to the elongate member. The elongate member of the first suture is coupled to the first side portion of the support member. The first suture is configured to be inserted into a tissue at a first location. The plurality of retention members allow movement of the first suture with respect to the tissue in a first direction and help prevent movement of the first suture with respect to the tissue in a second direction, different from the first direction, when the elongate member of the first suture is disposed within the tissue. Similar to the first suture, the second suture includes an elongate member and a plurality of retention members coupled to the elongate member. The elongate member of the second suture is coupled to the second side portion of the support member. The second suture is configured to be inserted into the tissue at a second location. The plurality of retention members allow movement of the second suture with respect to the tissue in a third direction and help prevent movement of the second suture with respect to the tissue in a fourth direction, different from the third direction, when the elongate member of the second suture is disposed within the tissue.

FIG. 1 is a schematic illustration of various components that can be used, for example, in a uterine suspension procedure to treat, for example, a uterine prolapse. An implant assembly 20 according to the invention can be a variety of different configurations and include a variety of different components. For example, an implant assembly 20 can include an implant member (also referred to herein as "implant"), one or more sutures coupled to the implant member, one or more needles coupled to the suture(s) or implant member, sleeves, dilators, connectors, strengthening members as well as other features described herein. In some embodiments, an implant assembly 20 includes only a suture or multiple sutures and is also referred to as a suture assembly. A suture assembly can be inserted into a pelvic region using the same or similar delivery devices as for an implant assembly. A suture assembly can also be used in conjunction with an implant assembly.

Some or all of the components of an implant assembly 20 can be configured to be implanted into a pelvic region P of a patient. Some components of an implant assembly 20 may be used during delivery of the implant assembly 20 into the pelvic region, and are subsequently removed from the remaining components of the implant assembly 20. For example, a needle may be cut off from a suture after inserting the implant assembly into a pelvic region of a patient. In some embodiments, the implant member can be formed, for example, with a mesh material to promote tissue in-growth through the implant member and further secure the implant assembly 20 in position within the pelvic region P.

An implant assembly 20 can be coupled to various different tissues within the pelvic region P, such as, for example, a sacrospinous ligament, a tendineus arch of levator muscle (also referred to herein as "arcus tendineus" and/or "white line"), or to an iliococcygeus muscle, or to other anatomical and/or tissue securement sites within the pelvic region of a patient. The implant assembly 20 can also be coupled to a vagina V of the patient, such as to the vaginal apex, to a wall of the vagina V, secured inside the vagina (e.g., within a vaginal lumen) or within the pelvic region. The implant assembly 20 can be used to support and reposition a uterus U of the patient. In some embodiments only one implant assembly is implanted on one side of the pelvic region P. In other embodiments, more than one implant assembly 20 is implanted, such as one implant assembly on contra lateral sides of the uterus of the patient. In yet other embodiments, a single implant assembly is implanted that spans both sides of the pelvic region.

There are various delivery devices that can be used to insert or deliver a portion or all of an implant assembly 20 into a pelvic region P. A delivery device 44 can be a suturing-type device that can be used to pass an end of a suture of an implant assembly 20 through a pelvic tissue T1 or T2. The delivery device 44 can be, for example, the Capio® Suture Capture Device manufactured by Boston Scientific Corporation. An example of such a suturing delivery device 44 is also described in U.S. Pat. No. 5,741,277 to Gordon et al., and U.S. Pat. No. 7,122,039 to Chu, the disclosures of which are hereby incorporated by reference in their entirety. The pelvic tissues T1 and T2 can be, for example, a sacrospinous ligament, a tendineus arch of levator muscle, an obturator muscle, an iliococcygeus muscle or any other anatomical structure or tissue within a pelvis. The delivery device 44 can also be used to pass a suture end through a wall of a vagina or to pass a suture through the epithelium of a vaginal wall without passing the suture through the vaginal wall.

Depending on the configuration of the implant assembly (or suture assembly) and/or the targeted location for securing the implant assembly 20 within a patient, other types of delivery device may be desirable. For example, a delivery device 60 can be inserted through an incision of a vagina, or through an exterior entry site (e.g., exterior incision through skin) on the patient. The delivery device 60 can be, for example, an Obtryx® Curve device, an Obtryx® Halo device, or a Lynx device all manufactured by Boston Scientific Corporation. An example of such a device is also described in U.S. Patent Pub. No. 2005/0075660 and U.S. Patent Pub. No. 2005/0177022, the disclosures of which are hereby incorporated by reference in their entirety. Such a delivery device 60 creates a path or passageway through for example, an obturator muscle (e.g., using a transobturator approach) or through, for example, an arcus tendineus (e.g., using a transglutual approach). For example, the delivery device 60 (also referred to herein as "delivery needle") can be passed through the exterior incision and into the vagina V where it can be coupled to an end of an implant assembly 20 (as described in more detail herein). Such a delivery device 60 can be used to draw the implant assembly 20 through a passageway formed by the delivery device 60 and through the exterior entry site.

To assist with delivery of an implant assembly 20, other devices can be used to hold a vagina V that has been inverted by a prolapse condition. For example, a holding device (not shown in FIG. 1) can be used to clamp on to the inverted vagina V. Such a device can be, for example, a tenaculum clamp. In some embodiments, a manipulator device (not shown in FIG. 1) can be coupled to a holding device and used to assist in the implant delivery and to reposition a uterus U of the patient. The holding device, the manipulator device or a combination of both, can be used to move the inverted vagina V inward (see V' in FIG. 1) and reposition the uterus U, while simultaneously securing the implant assembly 20 (e.g., knotting the suture ends) within the pelvic region P and/or to the vagina V of the patient.

Having described above various general examples, examples of specific embodiments are now described. These embodiments are only examples, and many other configurations of an implant and its various components are contemplated.

Figure 2:
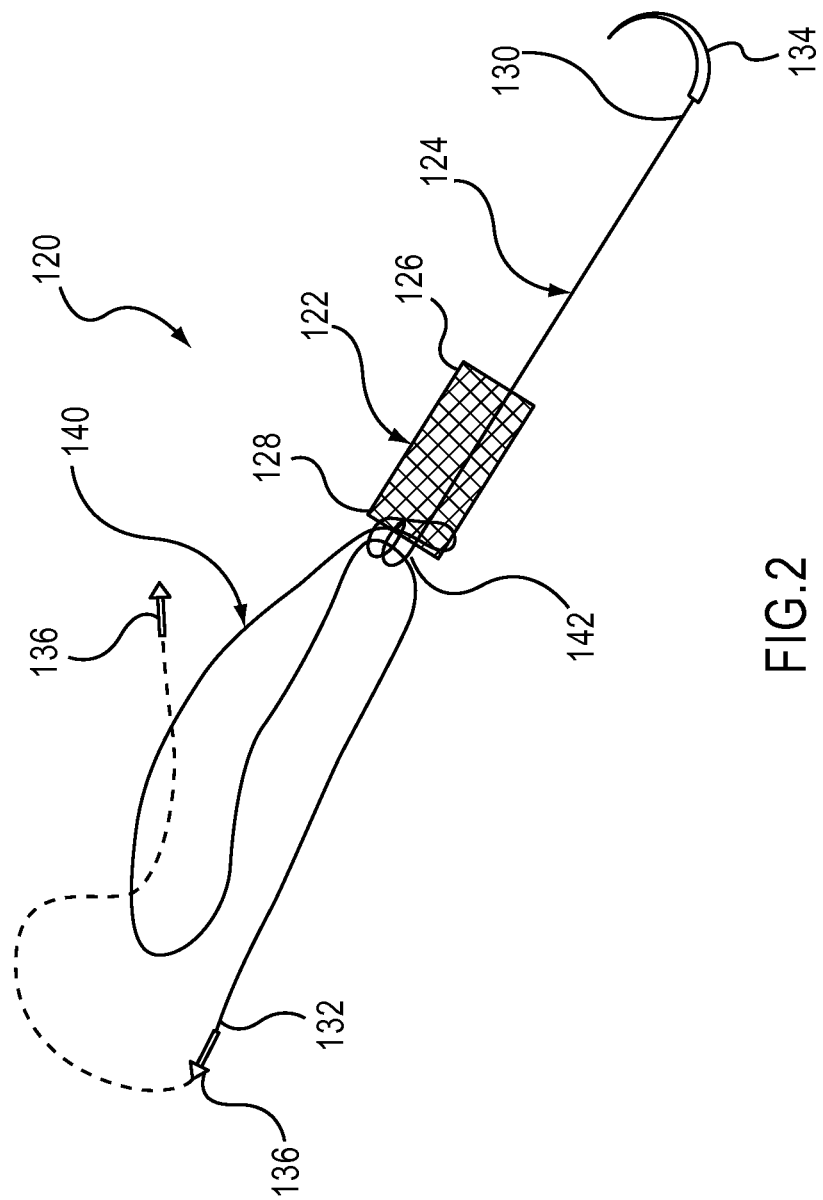
FIG. 2 is a side view of an embodiment of an implant assembly.

FIG. 2 illustrates an implant assembly according to an embodiment of the invention. An implant assembly 120 includes an implant member 122 (also referred to herein as "implant") having a mesh configuration to promote tissue in-growth through at least a portion of the implant member 122 when implanted within a pelvic region of a patient. The implant 122 can be a variety of different lengths and widths. For example, in some embodiments, the mesh portion of implant 122 can have a length of about 1.5 cm, and a width of about 1 cm. A suture 124 is coupled to and threaded through the implant 122 and extends from a first end 126 and a second end 128 of the implant 122. The suture 124 can be formed, for example, with a delayed bio-absorbable material to prevent long term irritation within a vagina, or other area of the pelvic region of a patient. A curved needle 134 is coupled to a first end 130 of the suture 124 and a trocar needle 136 is coupled to a second end 132 of the suture 124. In other embodiments a straight needle can be coupled to the first end 130 of suture 124 or the first end 130 of the suture 124 can be a free end (i.e., with no needle coupled thereto).

Figure 3:
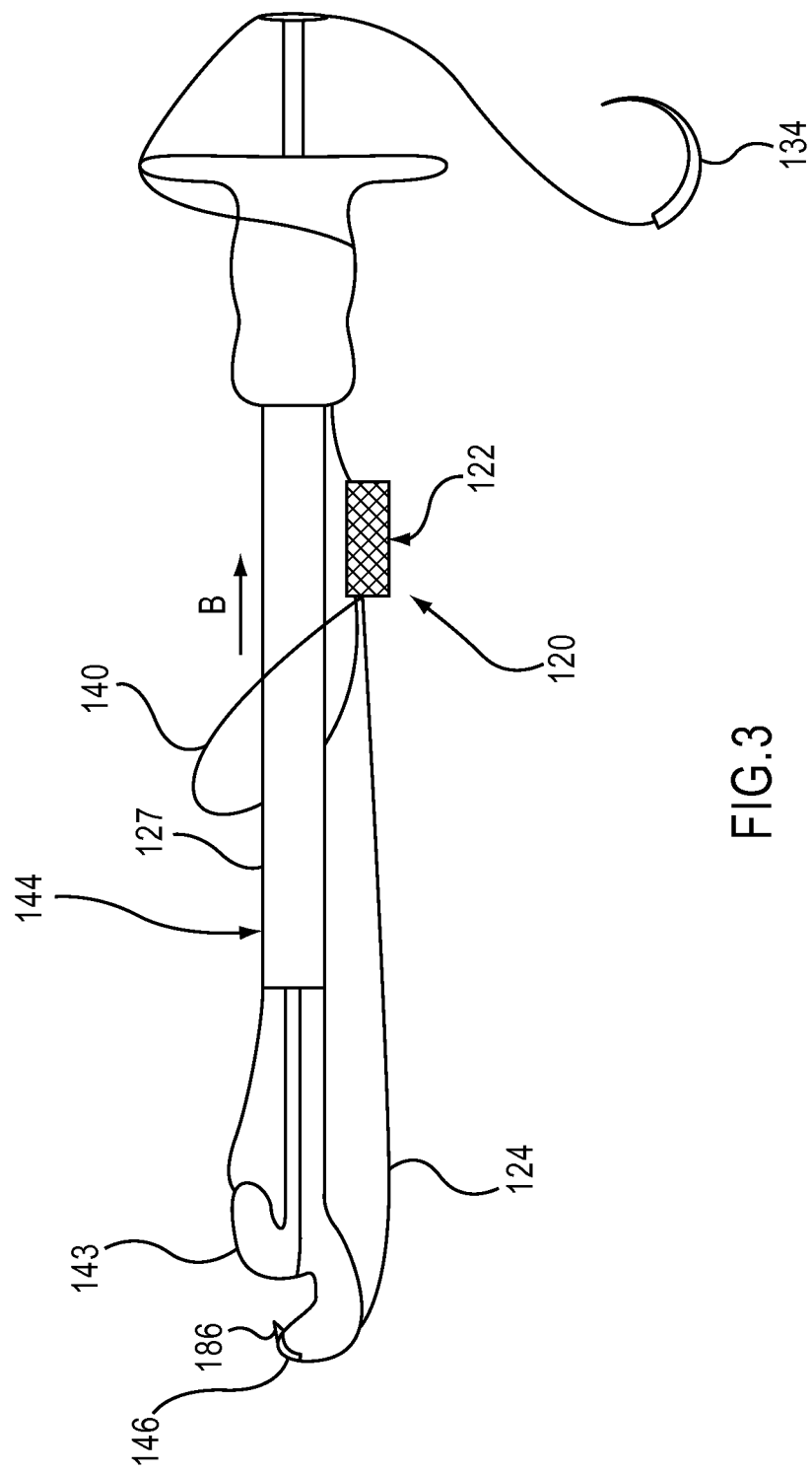
FIG. 3 is a side view of the implant assembly of FIG. 2 shown coupled to an embodiment of a delivery device.

In this embodiment, the suture 124 is coupled to the implant member 122 such that one or more loops 142 (two loops shown) are formed at its coupling location to the second end 128 of the implant 122, and a loop or noose 140 is formed, as shown in FIG. 2. The noose 140 can be used to assist in securing the suture (e.g., knotting) to a tissue. For example, the noose 140 can be placed over a shaft of a delivery device 144, as shown in FIG. 3. In other embodiments, the suture 124 can be secured to both ends of the implant 122. In still other embodiments, the suture 124 can be coupled to the implant 122 such that no loops are formed and the implant 122 is free to slide along the suture 124. In addition, the suture and implant member can be presented to a physician as separate components, such that the physician can couple and/or secure the implant member to the suture as desired.

The delivery device 144 can be a suturing device, such as the Capio® delivery device described previously. The delivery device 144 can be used to secure a portion of the implant assembly 120 to a tissue within a pelvic region of a patient, such as to a sacrospinous ligament, iliococcygeus muscle, arcus tendineus, or other anatomical structure or tissue. The loop 140 can be loosely positioned at various locations along the delivery device 144, such as near the catch 143, or near the shaft 127 of the delivery device 144. The trocar 136 is loaded onto to a throw or carrier 146 of the delivery device 144. Although the implant assembly 120 is shown with a loop 140, the loop 140 is not necessary for delivery of the implant assembly 120 using a delivery device 144.

Figure 4A:
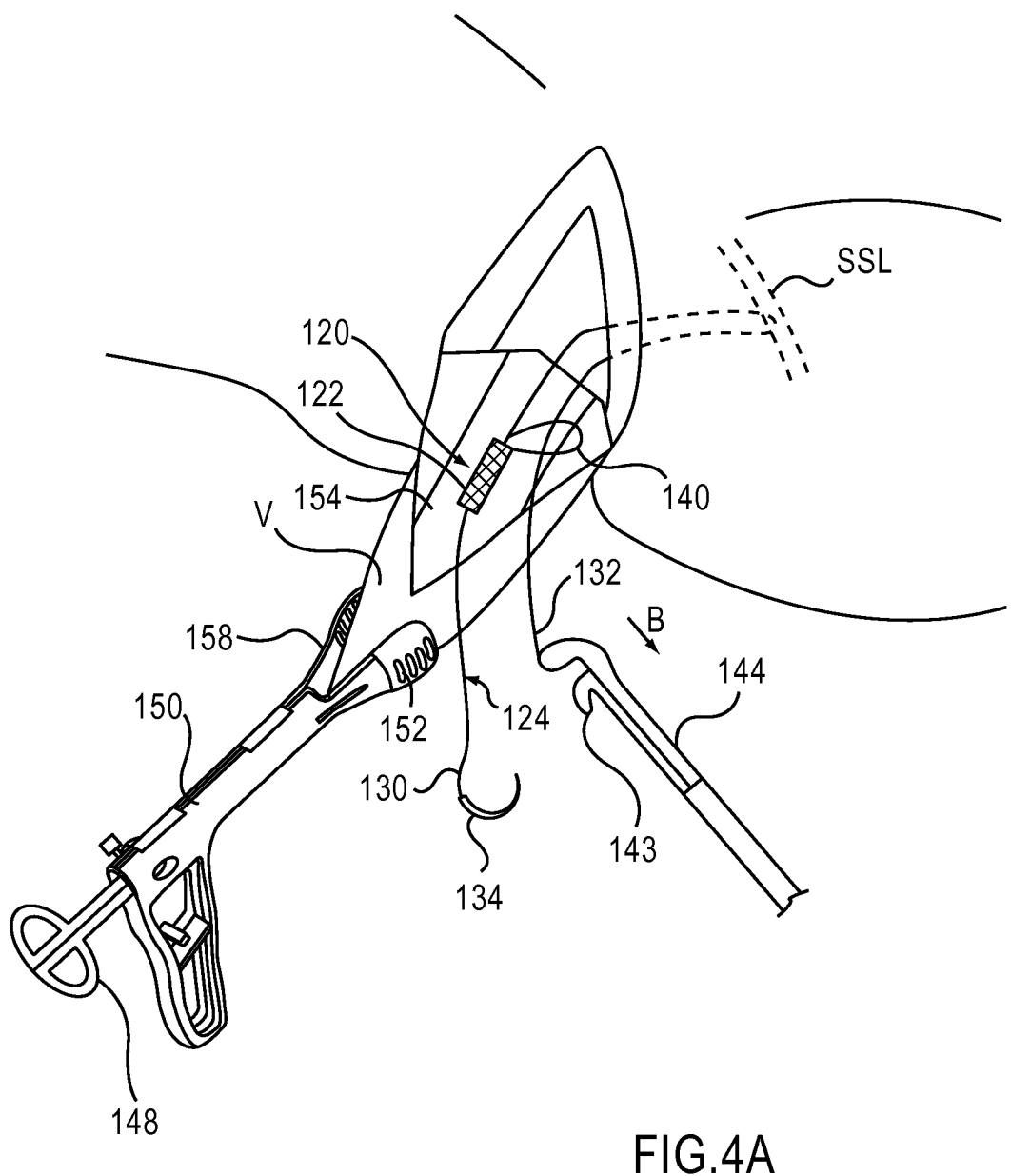
FIGS. 4A and 4B are each a perspective view of a manipulator device clamped to an inverted vagina of a patient and an embodiment of an implant assembly secured to a sacrospinous ligament of the patient.
Figure 4B:
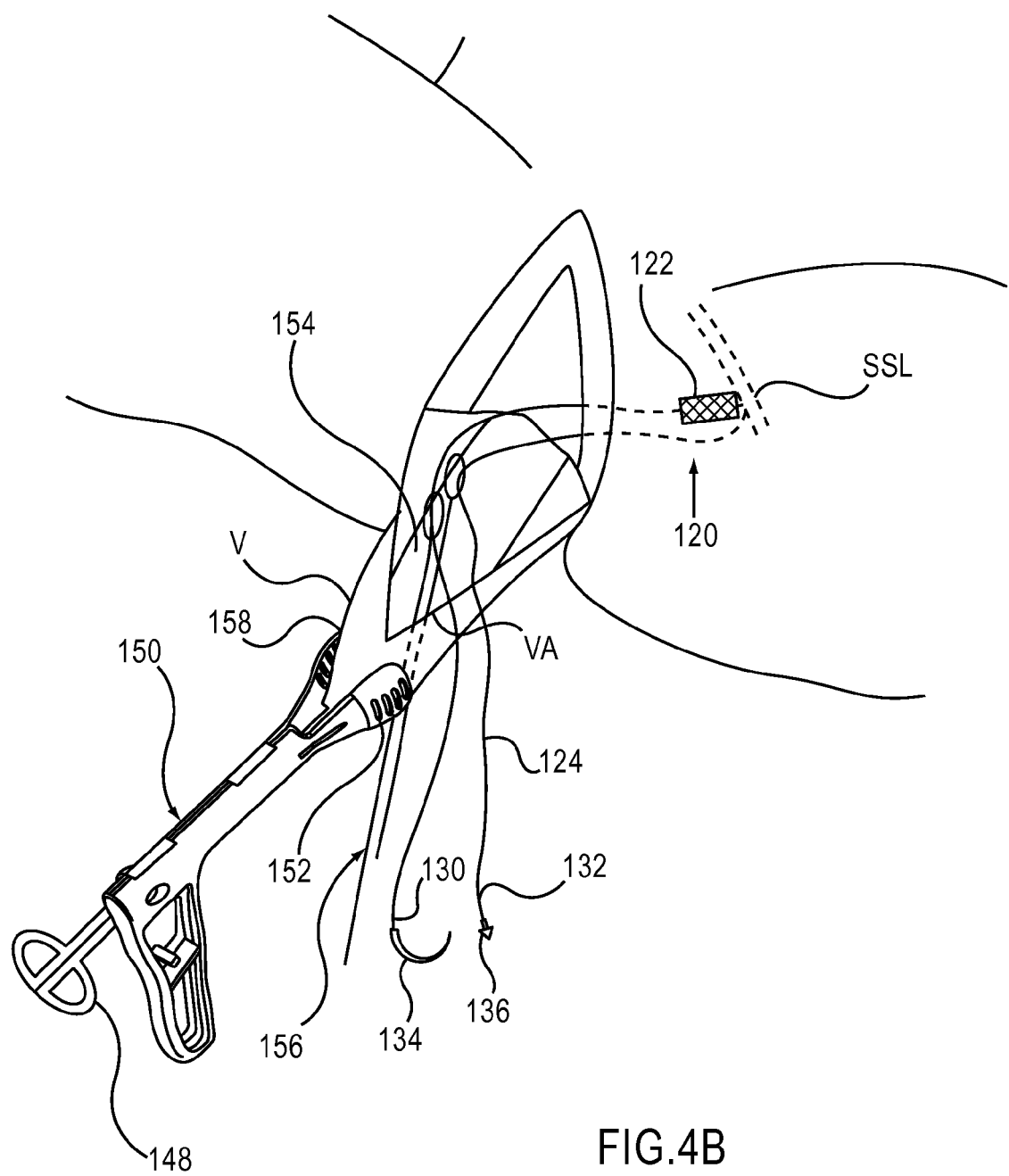
Figure 5:
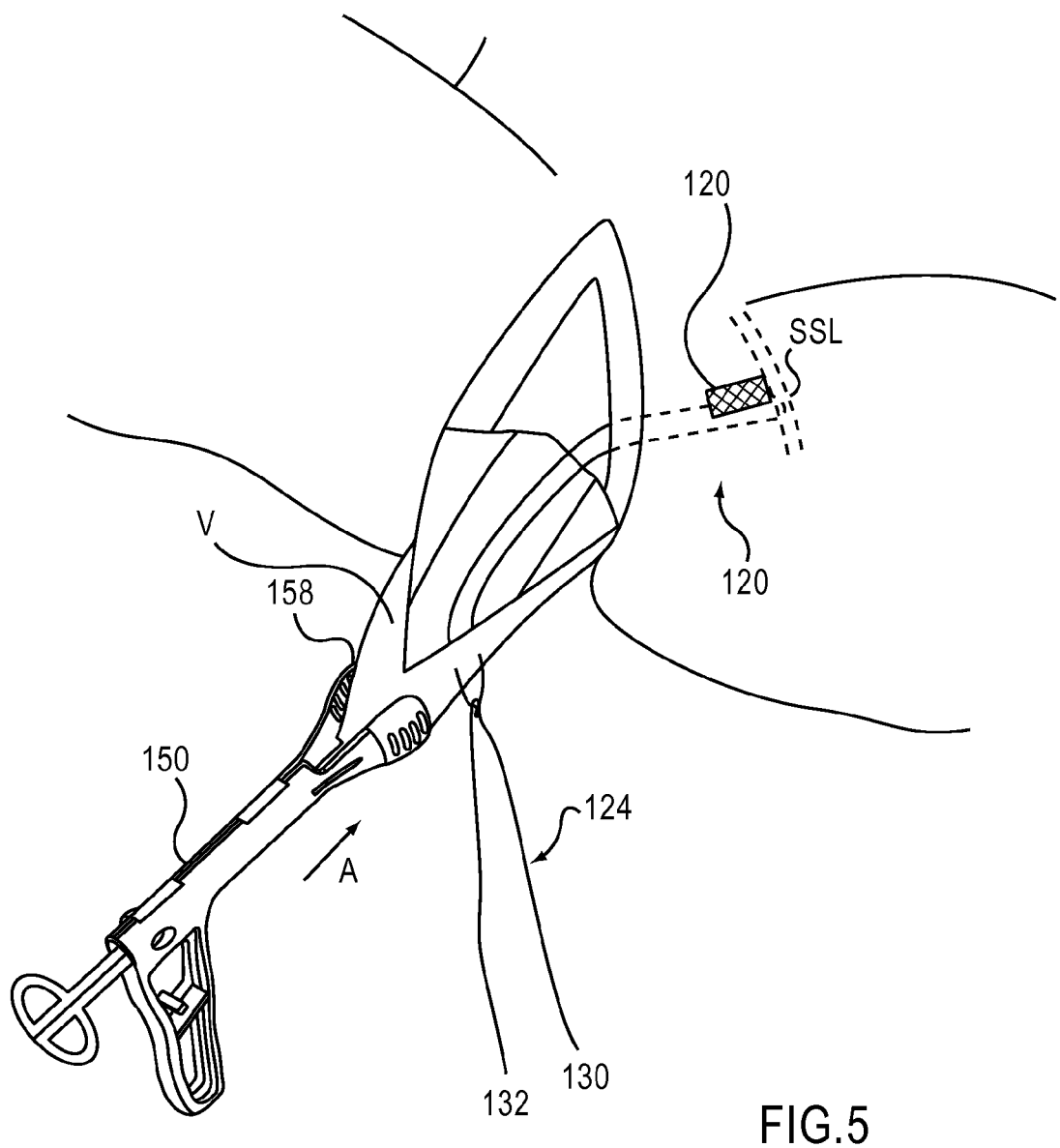
FIG. 5 is a perspective view of the manipulator device and implant assembly of FIGS. 4A and 4B shown with sutures extending through a wall of the vagina of the patient.

FIGS. 4A, 4B and 5 illustrate delivery or insertion of the implant assembly 120 into a pelvic region of a patient. In this embodiment, a holding device 148, such as a tenaculum clamp, is coupled to a manipulator device 150. The holding device 148 is clamped to an inverted vagina V near a cervix (not shown) of the patient. FIGS. 4A, 4B and 5 illustrate, for example, a grade 4 prolapse, however, the procedures described herein can be performed on other levels of prolapse, such as for example a grade 1, 2, or 3 prolapse. Also, although a holding device 148 and manipulator 150 are illustrated, it should be understood that various other medical devices can alternatively be used to clamp to the inverted vagina, and a manipulator device and/or holding device are not necessary. In this embodiment, the manipulator device 150 is coupled to the holding device 148 such that it can slide along a shaft (not shown) of the holding device 148 and be locked into position with a locking screw (not shown). The manipulator 150 defines multiple slots 152 at a leading end 158 of the manipulator device 150. The slots 152 can be used to help gage a depth of a vaginal formix to be formed, and can be used to gage the proper position and length of an anterior vaginal incision to be made. With the holding device 148 and manipulator device 150 clamped to the vagina V, an anterior vaginal incision 154 is made to the inverted vagina V. In FIGS. 4A, 4B and 5, the incision 154 (and inverted vagina V) are shown in a filleted or open formation.

With the implant assembly 120 loaded onto the delivery device 144 (as shown in FIG. 3), the implant assembly 120 can be inserted through the incision 154 and into a pelvic region of the patient. The trocar needle 136 on the second end 132 of suture 124 is drawn through the sacrospinous ligament SSL during a throw of the carrier 146 of the delivery device 144. The delivery device 144 is pulled through the loop 140 as shown in FIG. 4A (see also the dotted line path shown in FIG. 2). For example, using the delivery device 144, a plunger (not shown) of the delivery device 144 is pushed inward to pass the trocar needle 136 through the sacrospinous ligament. The trocar needle 136 is then caught in the catch 143 of the delivery device 144. The shaft 127 of the delivery device 144 is then removed from the body in the direction of arrow B as shown in FIGS. 3 and 4A. After the second end 132 of the suture 124 is pulled through the loop 140, the suture 124 (and trocar needle 136) can be removed from the delivery device 144. Continual pulling of the second end 132 of suture 124 will cause loop 140 to tighten and form a knot, which will draw the second end 128 of implant member 122 in contact against the SSL as shown in FIG. 4B. Another implant assembly can be delivered to the pelvic region on a contra lateral side in the same manner as described above.

After the implant assembly 120 has been pulled into contact with the SSL, a pair of suture passers 156 can optionally be used to pass the suture ends 130 and 132 through the wall of the vagina V. Another example of a suture passer that can be used is described in related U.S. Provisional Patent Application Ser. No. 60/970,620, the disclosure of which is hereby incorporated by reference in its entirety. As shown in FIG. 4B, a pair of free suture passers 156 are passed from a vaginal apex VA through a vaginal wall of the vagina V. The suture passers 156 can be used to pass the ends of suture 124 through a vaginal wall instead of using the needle 136 and the needle 134 on the ends of the suture 124. In such a case, the needles 134 and 136 can be cut off after inserting the implant assembly 120 into the pelvic region. Although not shown, the above described procedures can be performed on the contra lateral side of the vagina V.

Alternatively, if suture passers 156 are not used, the curved needle 134 can be used to pass the first end 130 through the vaginal wall and the trocar needle 136 can be reloaded on to the delivery device 144 to pass the end 132 through the vaginal wall. In some embodiments, an ink mark can optionally be placed on the vagina V by making a mark through a selected slot 152 of the manipulator 150. The mark can be used to identify a location for the needles 134 and 136 to pass through a wall of the vagina V. With the ends 130 and 132 of the suture 124 through the vaginal wall, the needles 134 and 136 can be cut off (if not done so already if suture passers were used), and the ends 130 and 132 can be crossed as shown in FIG. 5. The crossed portion of the suture 124 can then be placed near the leading edge 158 of the manipulator device 150. Although not shown, the suture on the contra lateral side can be processed concurrently or sequentially.

The manipulator 150 can then be advanced into the body of the patient in a direction A as shown in FIG. 5 such that the vagina forms a vaginal formix (not shown in FIG. 5). The manipulator 150 is maneuvered and maintained in the correct position to support the uterus. The suture ends 130 and 132 can be crossed again and pushed down with the user's finger or with a push rod (not shown) to form a knot to secure the first end 126 of the implant member 122 inside the vagina V (e.g., within the vaginal lumen). The uterus is then checked for support, the suture ends 130 and 132 are trimmed, and the vaginal incision is closed. In some embodiments, prior to advancing the manipulator, the ends 130 and 132 of the suture 124 can be placed through a slot(s) 152 on the manipulator 150 to help the user control the movement of the manipulator 150 with one hand, with the suture 124 held taught with the user's other hand. In alternative embodiments, the knot at the suture ends 130 and 132 can be replaced with crimps or ratchet anchors (not shown).

Figure 6:
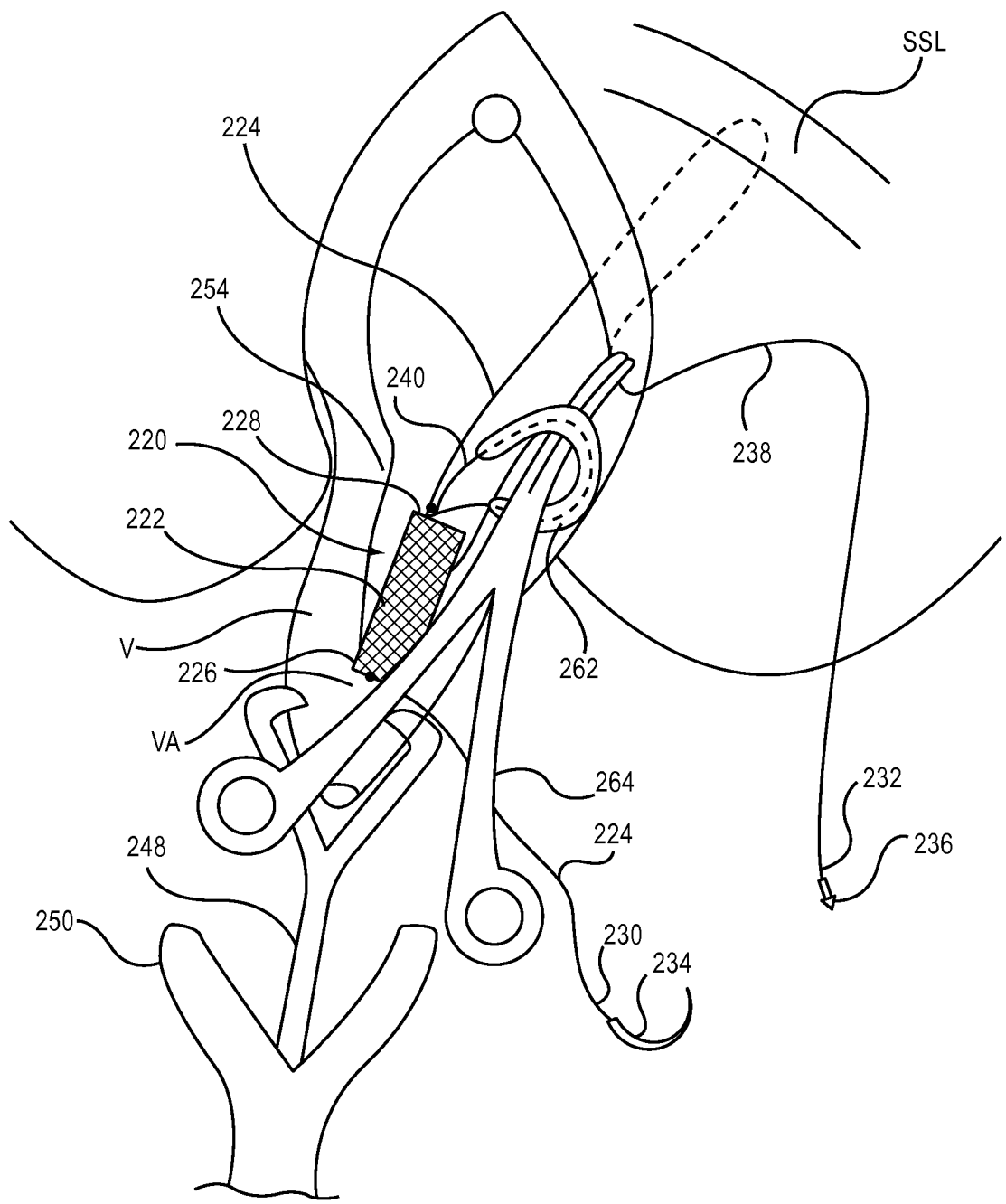
FIG. 6 is a perspective view of various devices used to treat an inverted vagina of a patient and an embodiment of an implant assembly secured to a vaginal apex (VA) of the patient.
Figure 7:
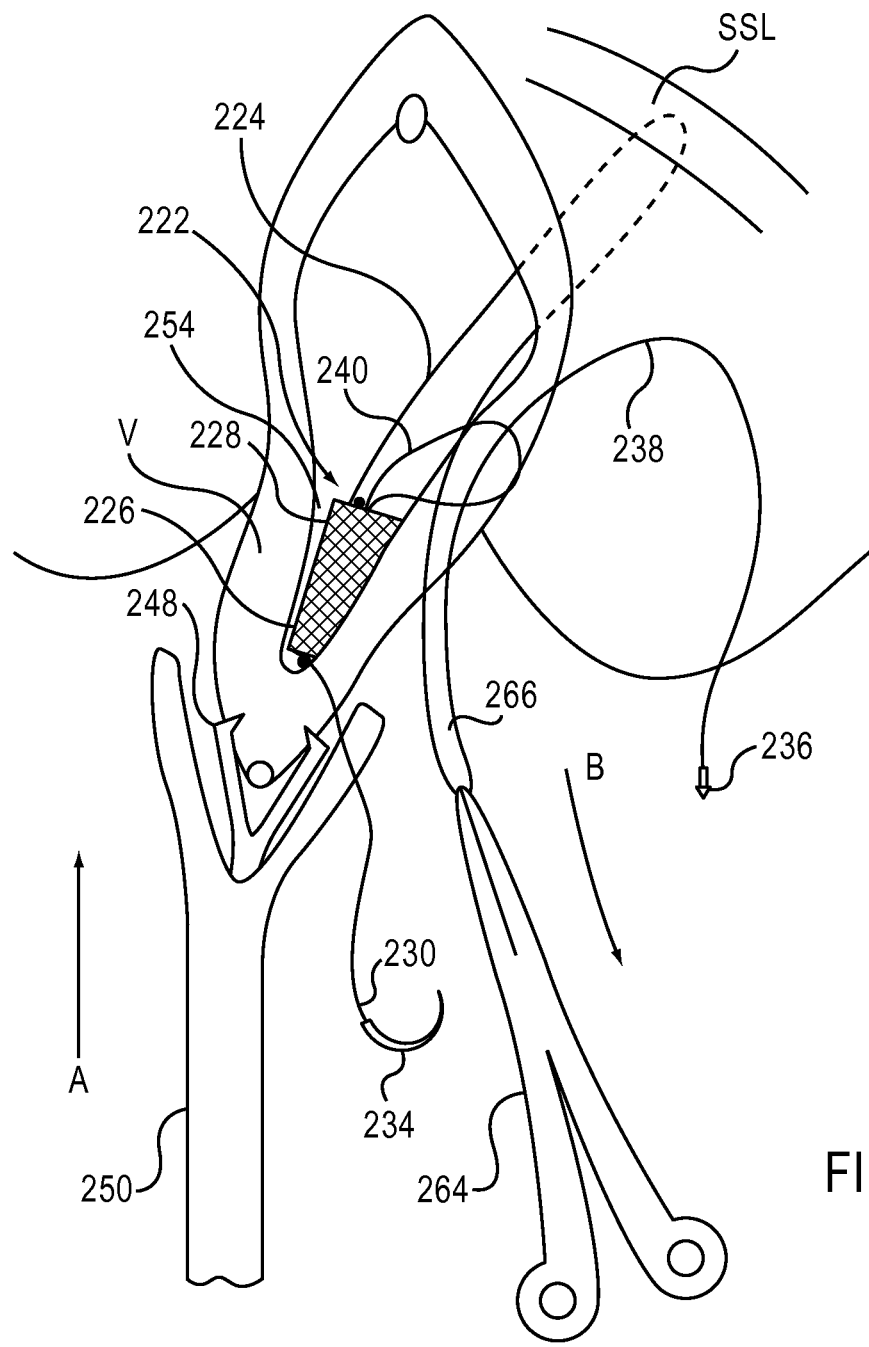
FIG. 7 is a perspective view of the devices and implant assembly of FIG. 6 shown with a portion of a suture coupled to a sacrospinous ligament and pulled through a loop of the suture.
Figure 8:
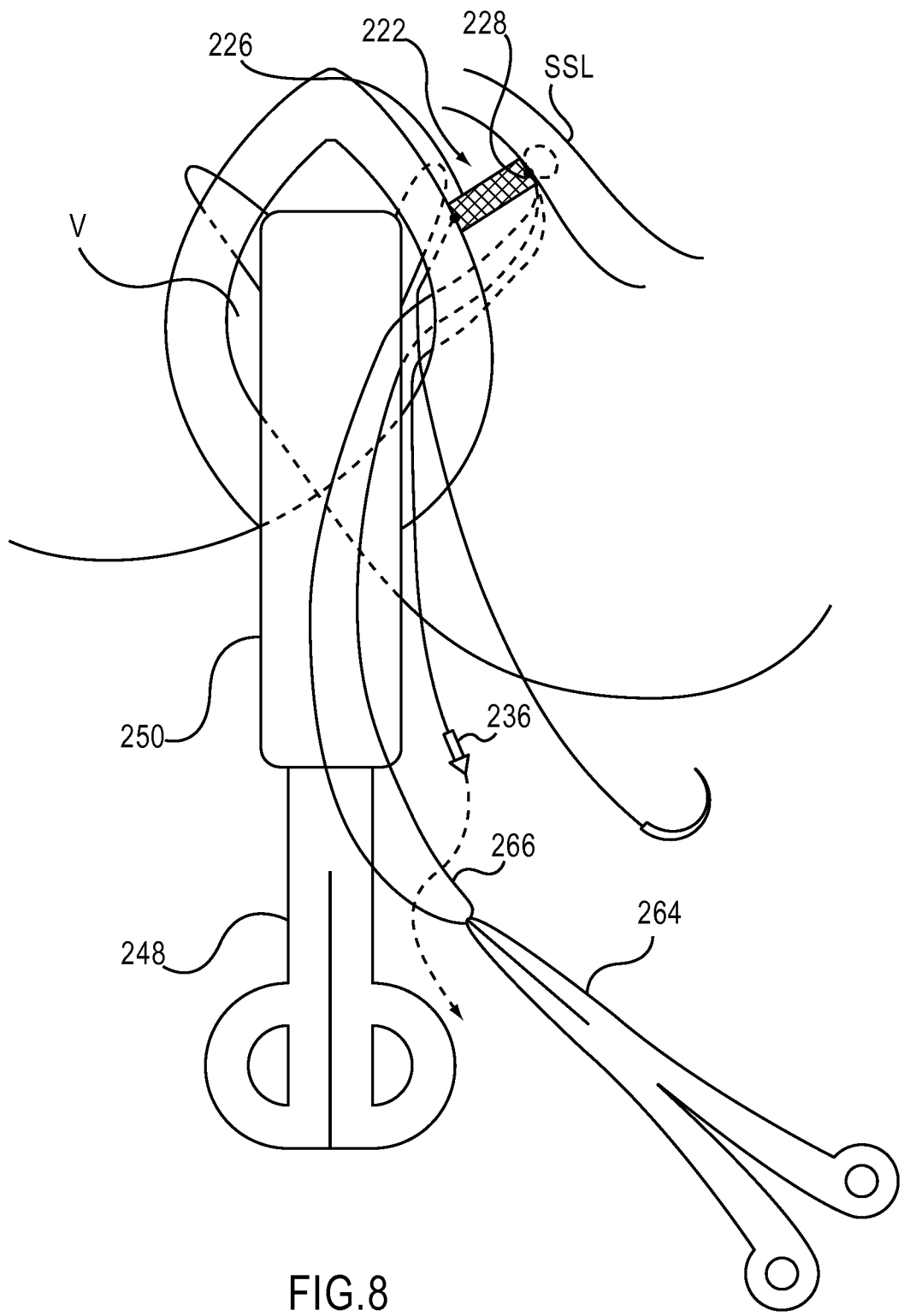
FIG. 8 is a front view of the devices and implant assembly of FIG. 6 illustrating the advancement of devices inward in the vagina and toward a uterus of the patient and the implant assembly secured to the sacrospinous ligament.

FIGS. 6-8 illustrate an implant assembly according to another embodiment of the invention. An implant assembly 220 is formed similar to the previous embodiment and includes an implant member 222, a suture 224 coupled to and weaved through at least a portion of the implant member 222, a curved needle 234 coupled to a first end 230 of the suture 224, and a trocar needle 236 coupled to a second end 232 of the suture 224. As with the previous embodiment, the implant member 222 is formed with a mesh material, and the suture 224 forms a loop or noose 240. In this embodiment, the implant assembly 220 also includes a retainer 262 releasably coupled to the loop 240. The retainer 262 helps maintain the loop 240 in an open position during implantation of the implant assembly 220. The retainer 262 can have, for example, a diameter of approximately 1.5 cm. The retainer 262 can also include a groove around its circumference in which the suture 224 can be placed. The loop 240 can be loosely placed over a shaft of a delivery device (not shown in FIGS. 6-8), such as delivery device 144 described above in FIG. 3, and the trocar needle 236 can be loaded into the carrier of the delivery device as previously described. In an alternative embodiment, a retainer can hold open the loop such that the loop is not placed over the shaft of the delivery device. As described below, the retainer can aid in tying the second knot.

As shown in FIGS. 6 and 7, a portion of a holding device 248 is shown coupled to an inverted vagina V and a portion of a manipulator device 250 is coupled to the holding device 248 in a similar manner as described in the previous embodiment. In FIG. 6 the holding device 248 is shown extended distally from the manipulator device 250. For example, the manipulator device 250 can be unlocked from the holding device 248 and slid down the shaft of the holding device 248 to provide more access t the vagina V, if desired. FIGS. 6-8 illustrate a procedure for delivering and implanting the implant assembly 220 by securing an end of the implant assembly 220 to the vagina V prior to securing the implant assembly 220 to a tissue within the pelvic region. As shown in FIG. 6, an anterior vaginal incision 254 is made in the inverted vagina V. The curved needle 234 is passed in to the vaginal apex VA, but not through a wall of the vagina V. A first end 226 of the implant member 222 is then tied securely to the wall of the vagina V with the suture 224. A delivery device, such as delivery device 144 can be used to pass the second end 232 of the suture 224 through the sacrospinous ligament SSL in the same manner as described in the previous embodiment. In this embodiment, rather than the delivery device 144 being pulled through the loop 240, the delivery device is removed from the patient's body, and a medical device, such as forceps 264 (or other device such as a clamp), is used to pull a suture portion 238 through the retainer 262 and loop 240. Once through the loop 240, the retainer 262 can be removed from the suture 224 as shown in FIG. 7.

As shown in FIG. 7, the suture portion 238 can be pulled in a direction of arrow B until the loop 240 is closed and a loop 266 is formed. The loop 266 can be used to further secure the implant as described in more detail below. Although not shown, the above procedures can also be performed on the contra lateral side. The needles 234 and 236 can optionally be cut-off or otherwise removed from the suture 224 at this point. As shown in FIG. 8, the manipulator device 250 is then advanced in a direction of arrow A (shown in FIG. 7), while the suture portion 238 continues to be pulled in the direction of arrow B (on both sides of the pelvic region if a second implant is being delivered on a contra lateral side). This will draw the second end 228 of the implant member 222 against and knotted to the SSL with the suture 224. The manipulator device 250 can be manipulated to reposition the vagina V and uterus (not shown) and support the uterus in a correct anatomical position. A final knot is achieved by inserting the second end 232 of the suture 224 into the loop 266 as shown by the dotted line path of the trocar 236 in FIG. 8. This will close the loop 266 to form the knot. As stated above, the above procedures can then be performed on the contra lateral side simultaneously or sequentially. Additional knot layers can optionally be formed by passing the second end 232 of suture 224 through the loop 266 multiple times. In addition, the first end 230 and the second end 232 of the suture 224 can again be knotted to form another suture bridge between the SSL and the vaginal formix. The uterus can then be checked for support, the sutures can be trimmed, and the vaginal incision closed.

Figure 9:
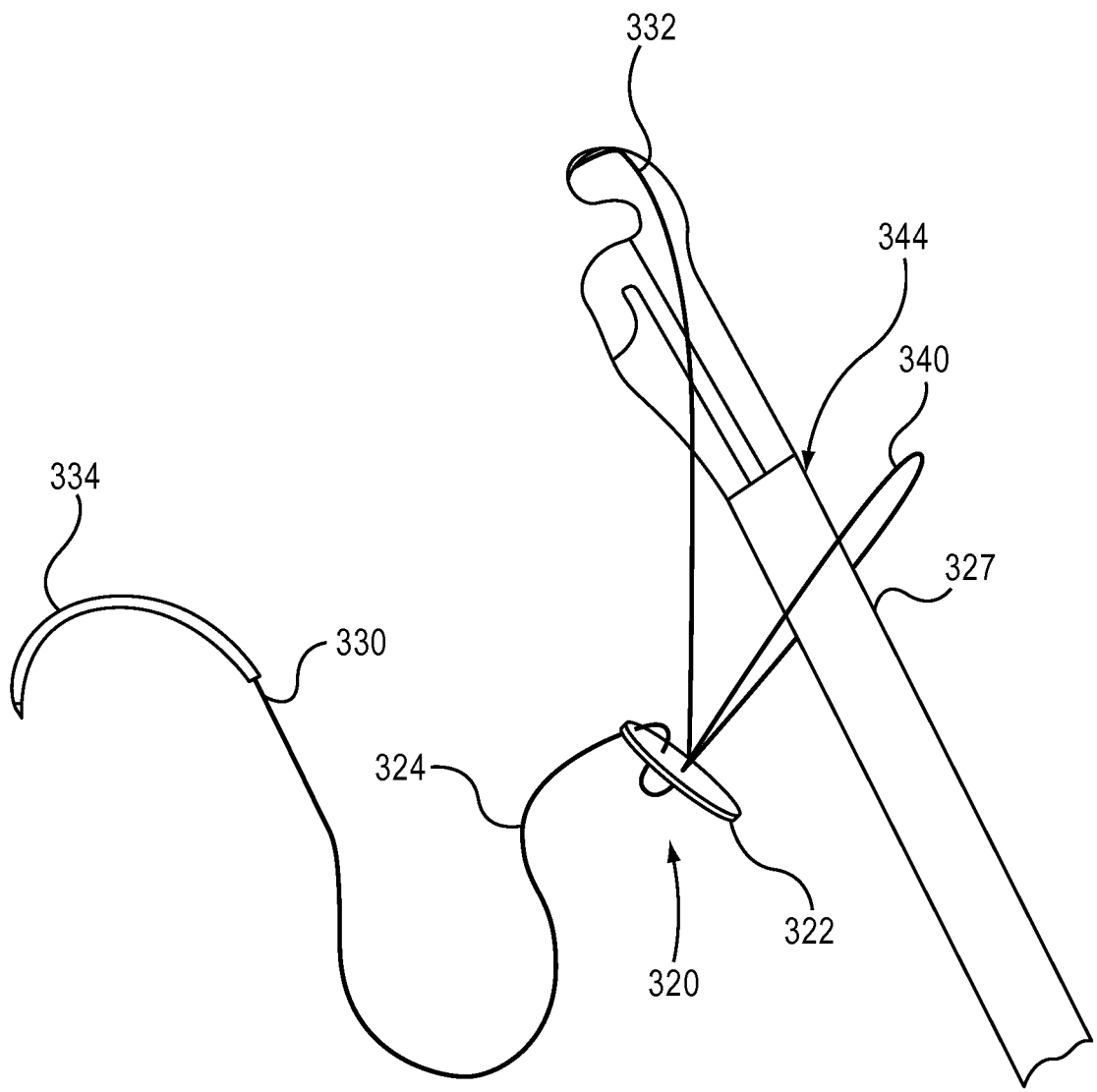
FIG. 9 is a side perspective view of another embodiment of an implant assembly shown coupled to a portion of a delivery device.

FIGS. 9-13 illustrate another embodiment of an implant assembly according to the invention. An implant assembly 320 is similar to the previous embodiments except in this embodiment the implant assembly 320 includes an implant member 322 having a circular or disc shaped configuration. The implant member 322 can have, for example a diameter of approximately 1.5 cm to 2 cm. Although shown circular, other shapes and configurations can alternatively be used. A suture 324 is threaded through an outer surface of the implant member 322 and secured to a center of the implant member 322 with a noose such that a loop 340 is formed as shown in FIG. 9. For example, the suture can be pulled through an opening defined by the implant (e.g., an opening in a mesh implant), or a needle coupled to an end of the suture can be passed through the implant. A curved needle 334 is coupled to a first end 330, and a trocar needle 336 (shown in FIG. 11) is coupled to a second end 332. In alternative embodiments, a straight needle can be coupled to the first end 332 instead of the curved needle 334, or the first end 332 of the suture 324 can have a free end (i.e., no needle). As described previously, and as shown in FIG. 9, the second end 332 (i.e., via the trocar needle) can be loaded on to, for example, a delivery device 344 with the loop 340 loosely placed over a shaft 327 of the device 344.

Figure 10:
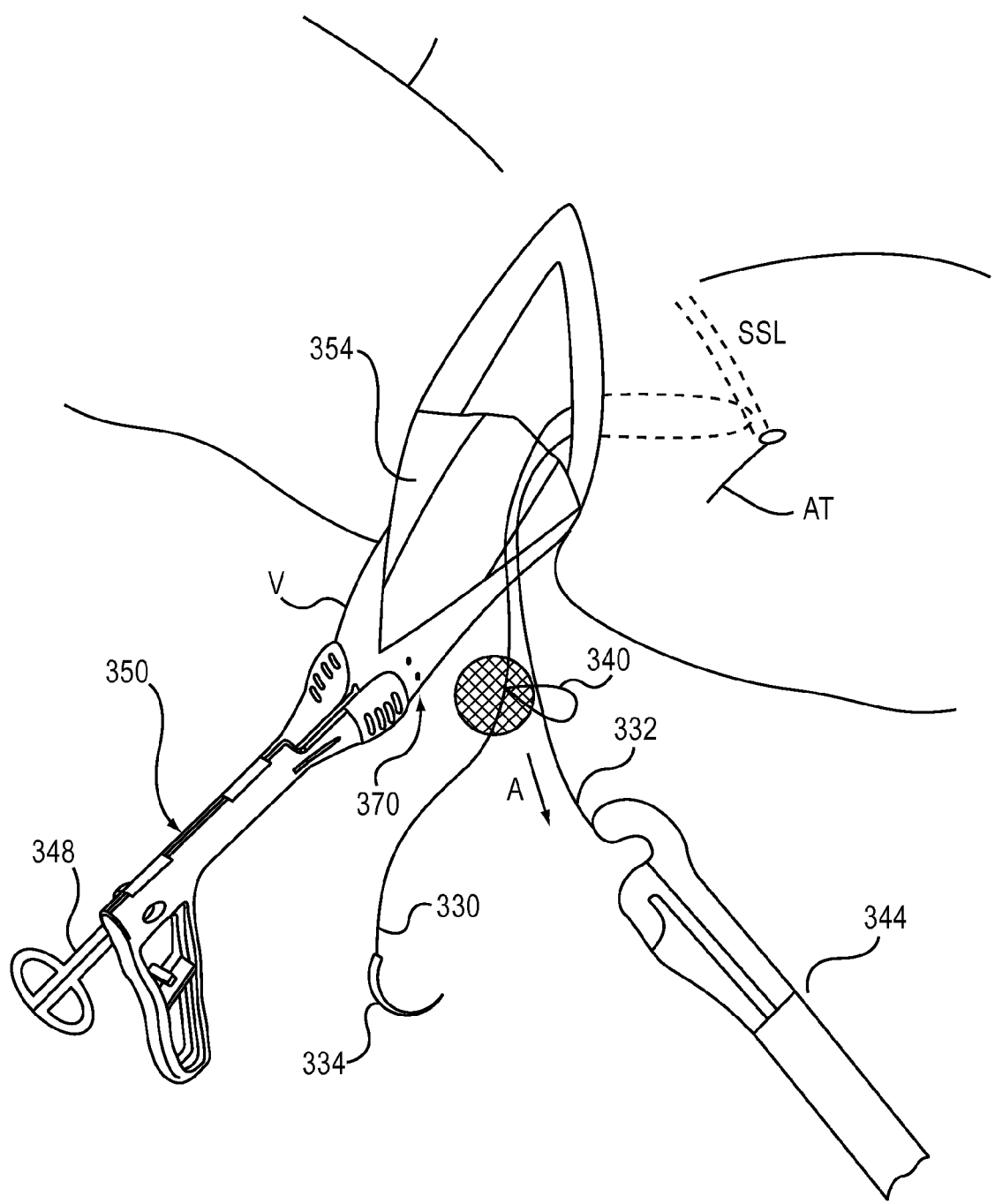
FIG. 10 is a perspective view illustrating a portion of the implant assembly of FIG. 9 being secured to a sacrospinous ligament.
Figure 11:
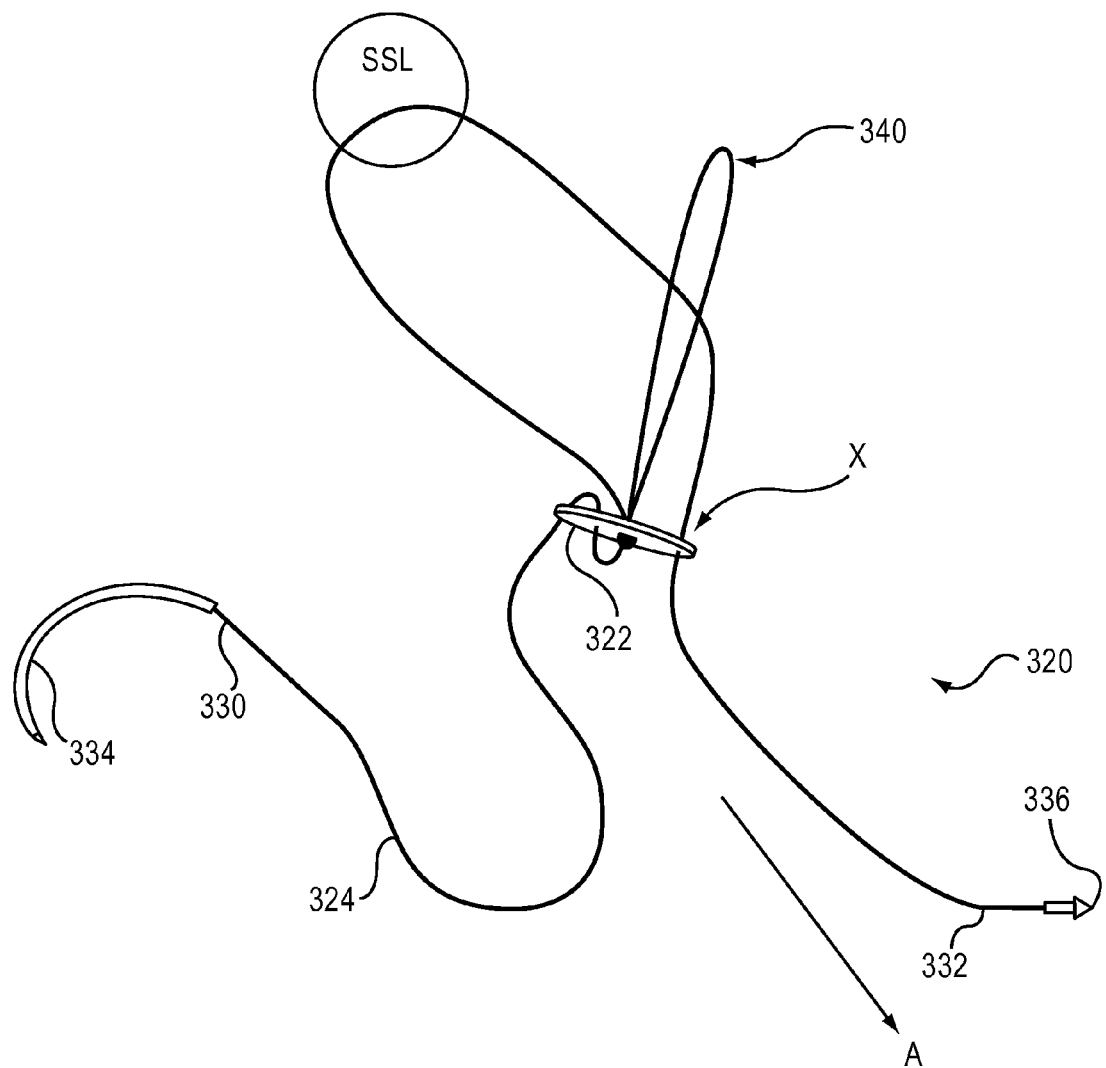
FIG. 11 is a side view of the implant assembly of FIG. 9 illustrating a portion of a suture drawn through a loop of the suture.

As shown in FIG. 10, a manipulator 350 and holding device 348 can be used to hold an inverted vagina V, as described above with reference to previous embodiments. Ink markings 370 can be made using slots in the manipulator device 350 as previously described with reference to FIG. 4B. The use of a manipulator device 350 and placing markings are optional and are shown here for illustration purposes only. After an anterior vaginal incision 354 (shown in FIG. 10) has been made, the second end 332 of the suture 324 can be passed through a sacrospinous ligament SSL in the same manner as described in previous embodiments using the delivery device 344. Retrieving the delivery device 344 from the body by moving the delivery device 344 in the direction of arrow A will place the return portion of the suture 324 through the loop 340, as shown in FIG. 10. The trocar needle 336 is removed from the delivery device 344 and can be threaded or pulled through the implant member 322 as shown at the location X in FIG. 11. Continual drawing of the second end 332 of suture 324 in the direction A (FIG. 11) tightens the loop 340 against the implant member 322 and pulleys the implant member 322 towards and against the SSL (as shown in FIG. 12) as the first end 330 of the suture 324 is held stationary.

Figure 12:
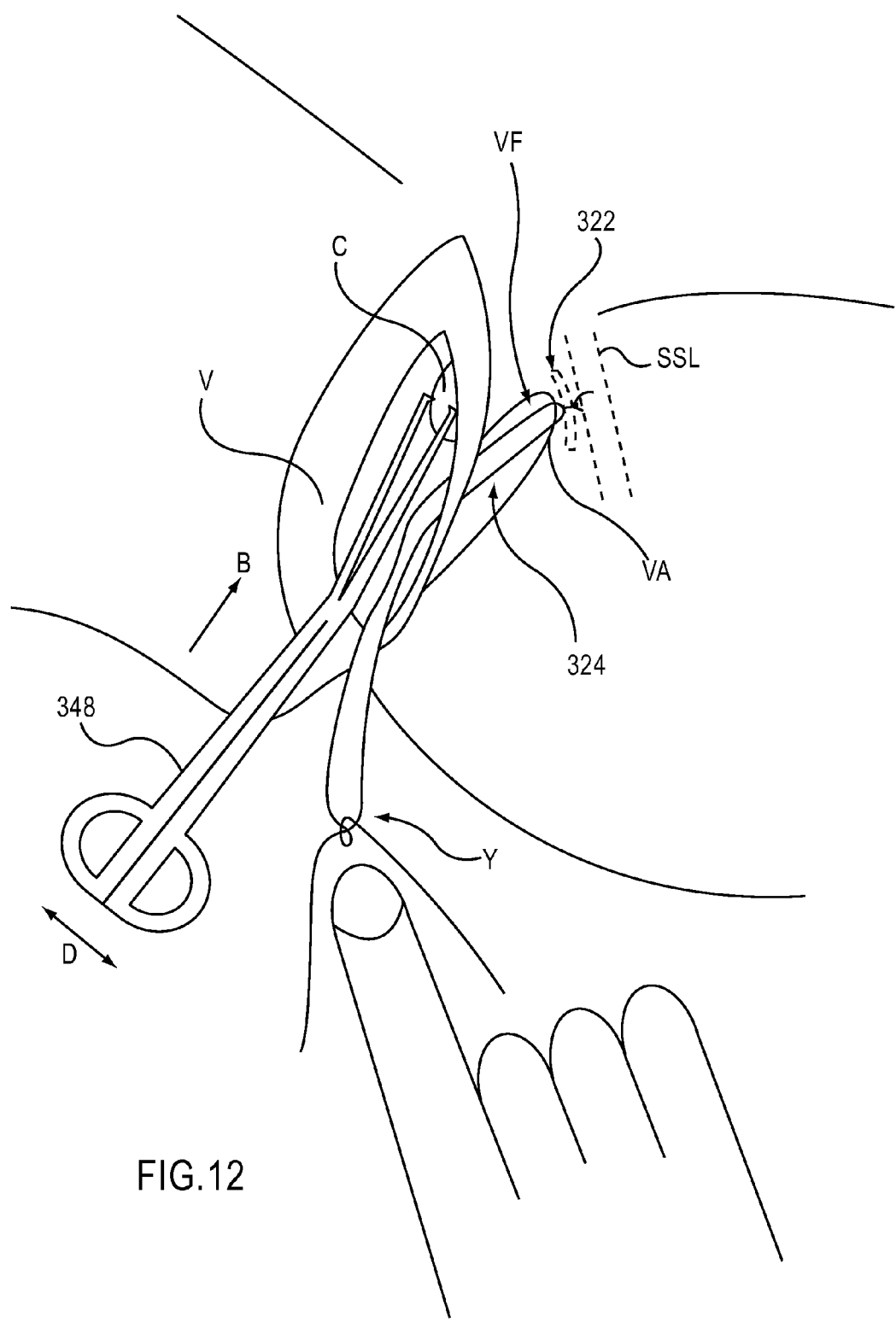
FIG. 12 is a perspective view illustrating the implant assembly of FIG. 9 shown secured to a sacrospinous ligament and vaginal apex of a patient.

As shown in FIG. 12, in this embodiment, the implant member 322 will be pulled to the sacrospinous ligament SSL such that an outer surface (rather than for example, an edge) of the implant member 322 is in contact with the sacrospinous ligament and an outer surface on an opposite side of the implant member 322 is in contact with a vaginal apex VA. Movement of the vagina V inward forms a vaginal formix VF. The suture ends 330 and 332 can be passed through a wall of the vagina V using the attached needles or using suture passers (not shown) as described above. The ink markings 370 can provide a guide to the desired location for passing the suture ends 330, 332. After the suture ends 330, 332 have been passed into the vagina, the manipulator device 350 can be removed as shown in FIG. 12. The holding device 348, still grasped to the cervix C, is inserted inward into the pelvic region in the direction of arrow B to revert the vagina and support the weight of the uterus (not shown) with the suture 324. The suture ends 330 and 332 are crossed over at Y (FIG. 12) to be tied, and a finger can be used to push in each layer of knot. The holding device 348 can be shifted from one side to the other, in the direction of arrow D (FIG. 12), for tying of the contra lateral side. One or multiple knots can be tied. If the suture 324 is formed of a bio-absorbable material, the suture 324 can be absorbed when tissue in-growth has occurred with the implant member 322. For example, soft permanent sutures may be left in place, while other stiffer permanent sutures and knots need to be removed, if the patient is sexually active.

Figure 13:
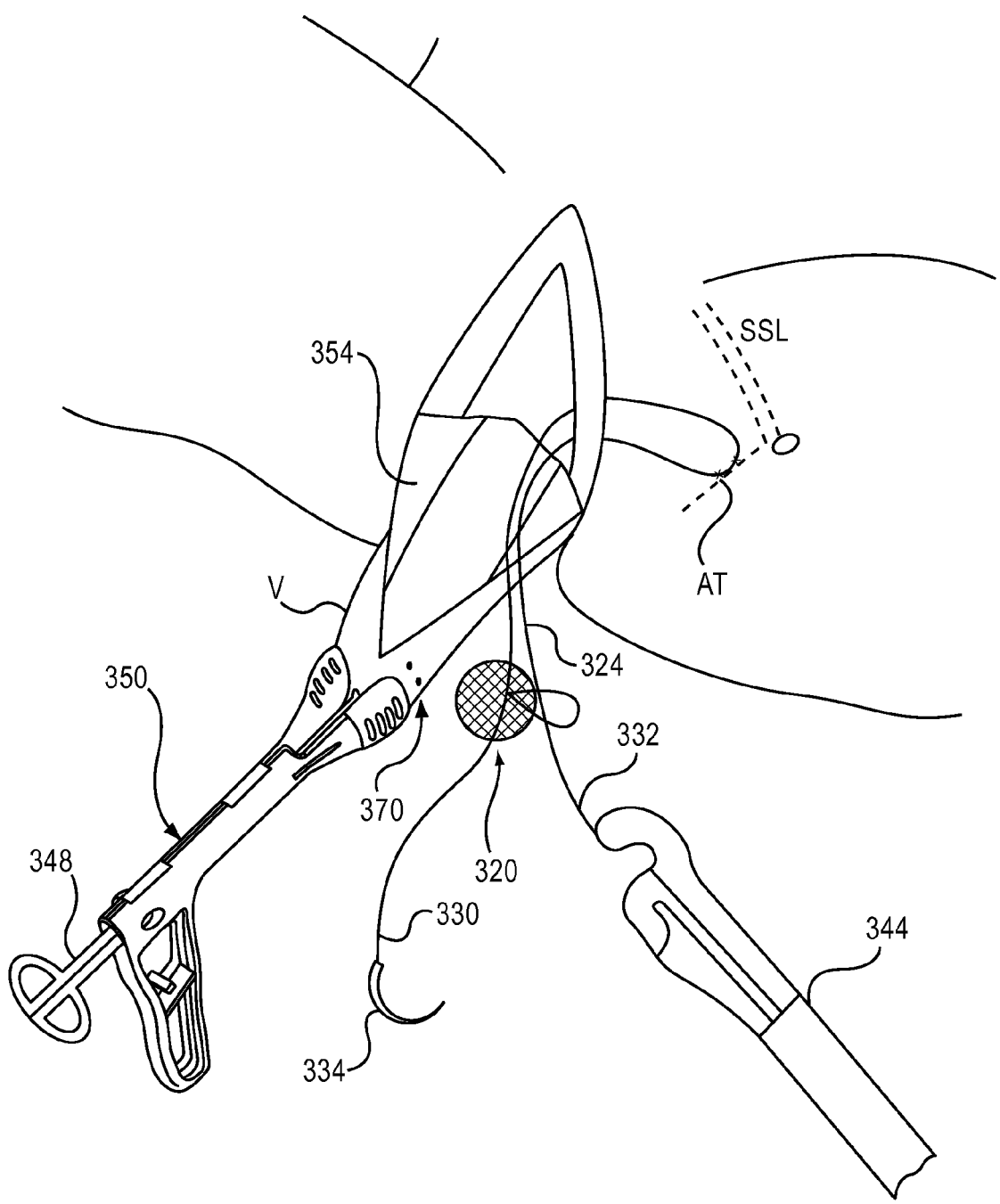
FIG. 13 is a perspective view illustrating the implant assembly of FIG. 9 shown being secured to an iliococcygeus muscle (I) of a patient.

The implant assembly 320 (and any of the implant assemblies described herein) can be implanted by securing to the sacrospinous ligament prior to securing to the vaginal apex as described above, or visa versa. The implant assemblies can also be secured to the vaginal apex within a vaginal lumen or within the pelvic region of the patient. The implant assemblies can also be secured to other anatomical tissue and/or locations. For example, FIG. 13 illustrates the implant assembly 320 secured in an area near an ischial spine. In this case, the suture 324 is secured to an arcus tendineus AT (i.e., white line), rather than to a sacrospinous ligament SSL. Alternatively, the implant assembly 320 can be secured to other tissue, such as the iliococcygeus muscle, or other surrounding muscles ligaments or tissue. The same steps described above for attachment of the implant assembly 320 to the SSL can be used to deliver and secure the implant assembly 320 to other areas within the pelvic region.

Figure 14A:
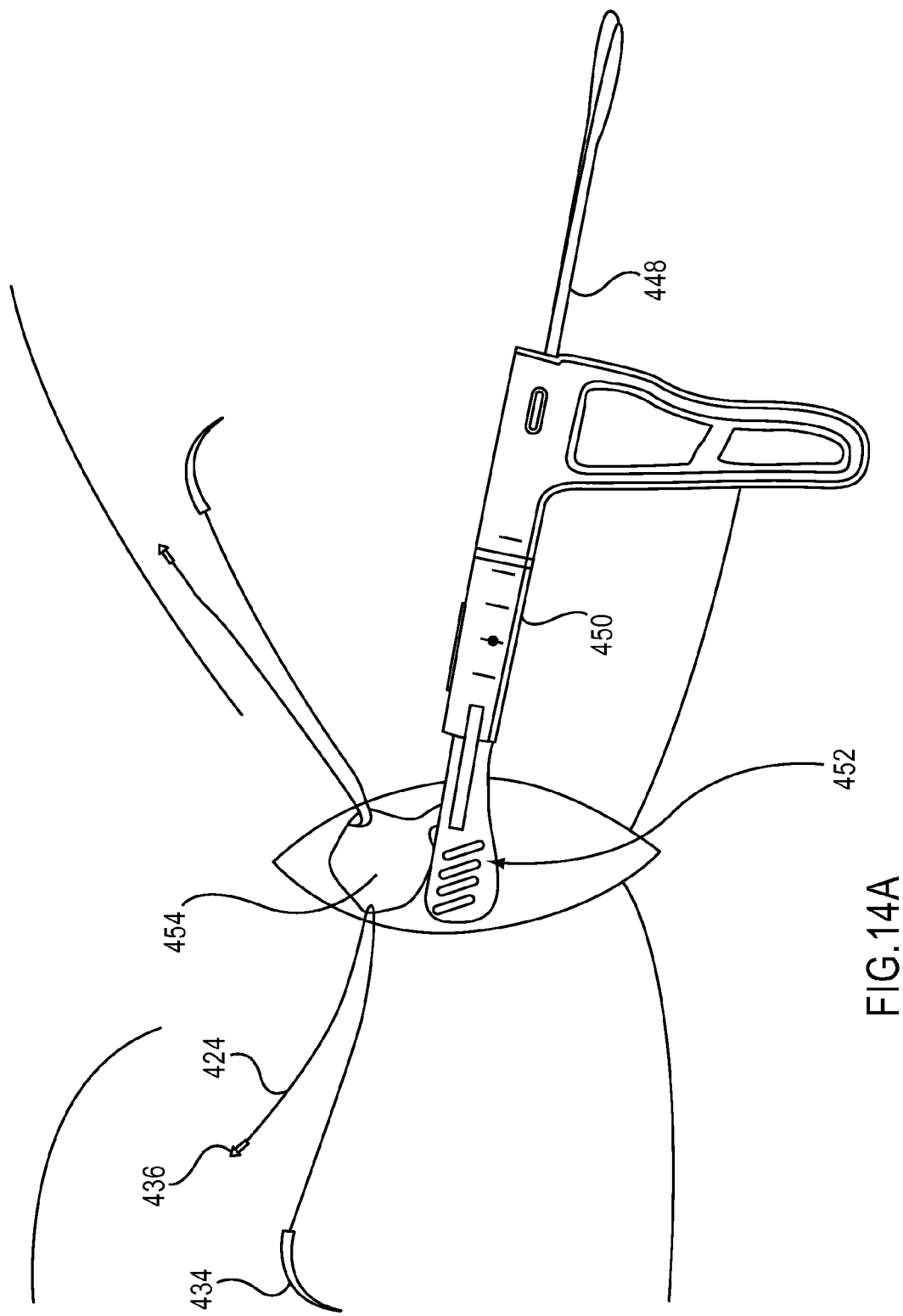
FIGS. 14A and 14B are each a side perspective view of a manipulator device clamped to a front view of a prolapsed vagina.
Figure 14B:
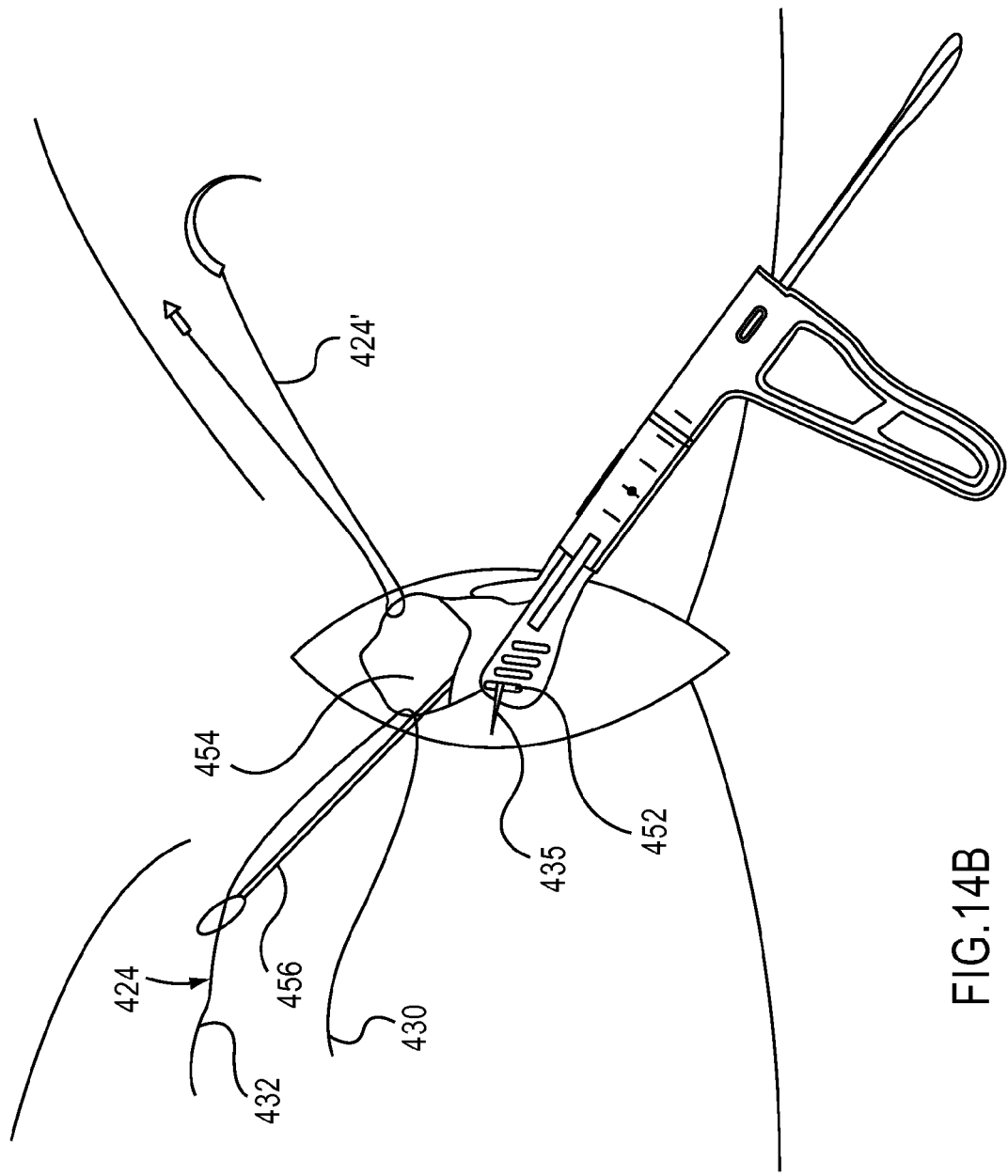

FIGS. 14A and 14B illustrate a medical procedure on a grade 2 uterine prolapse where the uterus is only slightly prolapsed from the vaginal opening and a suture passer and ink markings are used to pass a suture through a vaginal wall. As shown in FIG. 14A, a manipulator device 450 is coupled to a holding device 448 (e.g., tenaculum clamp). A push and pull technique can be used to push the holding device 448 and pull the manipulator device 450 in opposite directions to form a vaginal formix and to clearly identify a location for a suture to be passed. The manipulator device 450 can be locked to the tenaculum and then rotated to the side such that an alignment slot 452 on the manipulator device 450 is viewable by a user. Ink markings can then be placed on a vaginal wall through the selected slot 452 to identify a location for later needle passage, or suture passers can be placed directly through a selected slot 452 of the manipulator device 450. For example, as shown in FIG. 14B a sharp needle point 435 on a suture passer 456, can be placed through an anterior vaginal incision 454 and directed to perforate a vaginal wall and pass through the selected slot 452. Thus, after the suture 424 has been inserted into the pelvic region and secured to a tissue such as a sacrospinous ligament (as previously described) the needles (curved needle 434 and trocar needle 436) can be cut off from the suture 424 (as shown in FIG. 14B), and an end 432 of the suture 424 can be threaded through an eyelet of the suture passer 456. The end 432 of the suture 424 can then be pulled through the vaginal wall using the suture passer 456. This procedure can then be performed on the contra lateral side with a suture 424'. In some cases, two suture passers can be used, one for the end 432 of the suture 424 and the other for end 430 of the suture 424. In some cases, a first suture passer is passed through a top portion of a selected slot 452 and a second suture passer is placed through a bottom portion of the same slot. This will align the two ends of the suture 424 relatively close to each other for tying into a knot.

Figure 15:
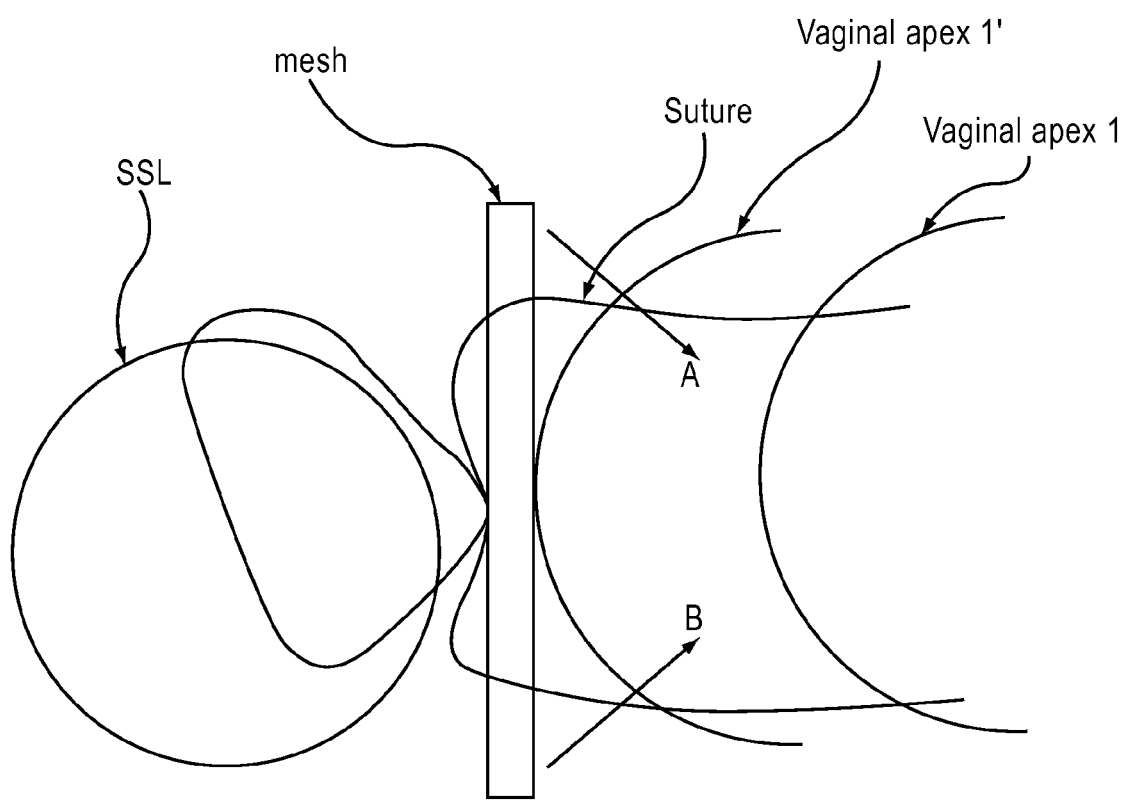
FIG. 15 is a schematic illustration showing variations in the length of a vaginal lumen and the interaction of an implant.

FIG. 15 is a schematic illustration showing the behavior of an implant when there is a "long vagina" (Vaginal apex 1') and a "short vagina" (Vaginal apex 1). With a long vagina, the implant will tend to remain somewhat upright as shown, with no gap between the SSL and the vaginal apex 1'. With a short vagina, the implant will tend to bend towards the vaginal apex 1, in the direction of arrow A and arrow B, to bridge the gap between the SSL and vaginal apex 1. In some cases, the gap can be, for example, 1 cm long.

FIGS. 16-24 illustrate implant assemblies according to various different embodiments of the invention. The implants illustrated can be delivered and secured to a pelvic region of a patient in any of the manners or procedures described above. FIGS. 16, 17A and 17B are implant assemblies that include at least one barbed portion. These embodiments illustrate an alternative to knotting or tying a suture for securing an implant and suture to a tissue (e.g., sacrospinous ligament, vaginal apex). FIG. 16 illustrates an implant assembly 520 that includes a mesh implant member 522 and a suture 524 coupled to and weaved through the implant 522. The suture 524 is knotted to a first end 526 and to a second end 528 of the implant 522. The implant assembly 520 also includes a curved needle 534 on a first end 530 of the suture 524, and a trocar needle 536 on a second end 532 of the suture 524. In this embodiment, a first barbed portion 568 is disposed on the suture 524 adjacent the first end 526 of the implant 522 with barbs angled in a first direction, and a second barbed portion 568' is disposed on the suture 524 adjacent the second end 528 of the implant 522 with barbs angled in a second direction. The barbed portions 568, 568' can be formed, for example, monolithically with the suture 524. A portion of the suture 524 can be frayed or cut to provide the barb portions 568, 568'.

The barbed portions 568, 568' can be used to secure or anchor the implant member 522 to a tissue (e.g., sacrospinous ligament, vaginal apex, etc.). The trocar needle 536 can be loaded onto a suturing delivery device, such as delivery devices 144 or 344 described previously to pass the suture 524 through a tissue, such as a sacrospinous ligament, within a pelvic region. The suture 524 can be pulled such that the barbs on the barbed portion 568' are pulled into the sacrospinous ligament and engage the tissue of the ligament for anchoring. Once the barbs on the barbed portions 568' are engaged in the tissue, the suture 524 is allowed to advance proximally in a direction away from the SSL, but not back out. The barbed portion 568 can be anchored to another tissue portion, such as a vaginal apex, in a similar manner.

FIG. 17A illustrates a portion of an implant assembly 520' including an implant member 522' and a suture 524'. In this embodiment, a barbed portion 568" is positioned only in one location; adjacent a second end 528' of the implant member 522'. Here, a first end of the suture 524' (the end having no barbs) can be knotted or tied to, for example, a vaginal apex of a patient, and the barbed end portion of the suture 524' can be secured to, for example, a sacrospinous ligament, using the barbed portion 568" as described above. Alternatively, a barbed portion can be positioned adjacent only a first end of an implant member. In such an embodiment, a second end (the end with no barbs) can be knotted or tied to a tissue within the pelvic region, to for example, a sacrospinous ligament as described previously, and the barbed portion can be used to anchor the implant member to a vaginal apex. In an embodiment including barbs, the suture can also be knotted or tied, if desired, for further securement of the implant to the tissue.

FIG. 17B illustrates a portion of an implant assembly 520" including an implant member 522" and a suture 524". In this embodiment, a barbed portion 568''' is positioned in a continuous configuration that extends through the mesh implant 522" and on a portion of the suture 524" adjacent to the ends of the implant 522". The barbed portion 568''' can be anchored to pelvic tissue and/or a vaginal apex as described above.

Figure 18:
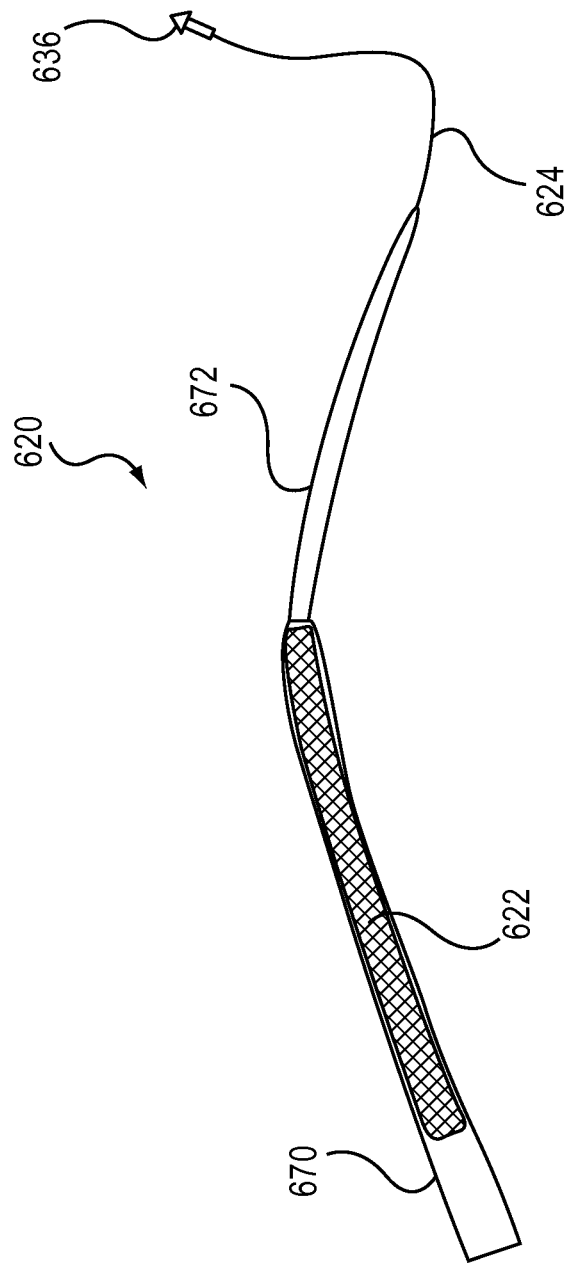

FIG. 18 illustrates an implant assembly including a dilator and a sleeve. An implant assembly 620 includes an implant member 622 coupled to a suture 624. The suture is coupled to one end of the implant member 622 and terminates at the other end with a trocar or needle 636. The suture 624 is tapered upwards by a dilator 672, which can be flexible and bendable. A sleeve 670 is folded and attached to an end of the dilator 672 and houses or encloses the implant member 622. The sleeve 670 provides for a smooth transition during insertion of the implant assembly 620 into a pelvic region, and can help prevent premature engagement of the implant member 622 with surrounding tissue during delivery. The trocar needle 636 can be associated with a delivery device, such as a delivery device 144 or 344, for delivery of the suture through a sacrospinous ligament as described above. The dilator 672 is also pulled through the sacrospinous ligament to enlarge the passageway for the implant member 622 to be pulled at least partially through the ligament. The implant member 622 can be positioned and tensioned to ensure the implant member 622 lays substantially flat within the pelvic region. The sleeve 670 can then be pulled (i.e., removed) from the implant member 622. The mesh configuration of the implant member 622 engages the surrounding tissue to secure the implant member 622 in position. In some embodiments, the implant member is formed with a mesh material and has one or more tanged portion, such as a tanged edge to engage the surrounding tissue. For example, the implant can have roughened or jagged edges or areas, such as can result from cutting a woven or knit mesh material. The tangs or tanged edges enhance anchoring of the implant within tissue, such as pelvic tissue, without the use of additional anchoring mechanisms or sutures. In some embodiments, an implant includes tangs on an edge along an entire length of the implant. In other embodiments, the implant includes tangs covering substantially all of an exterior surface of the implant. In some embodiments tangs are only on the end portions of the implant.

Figure 19:
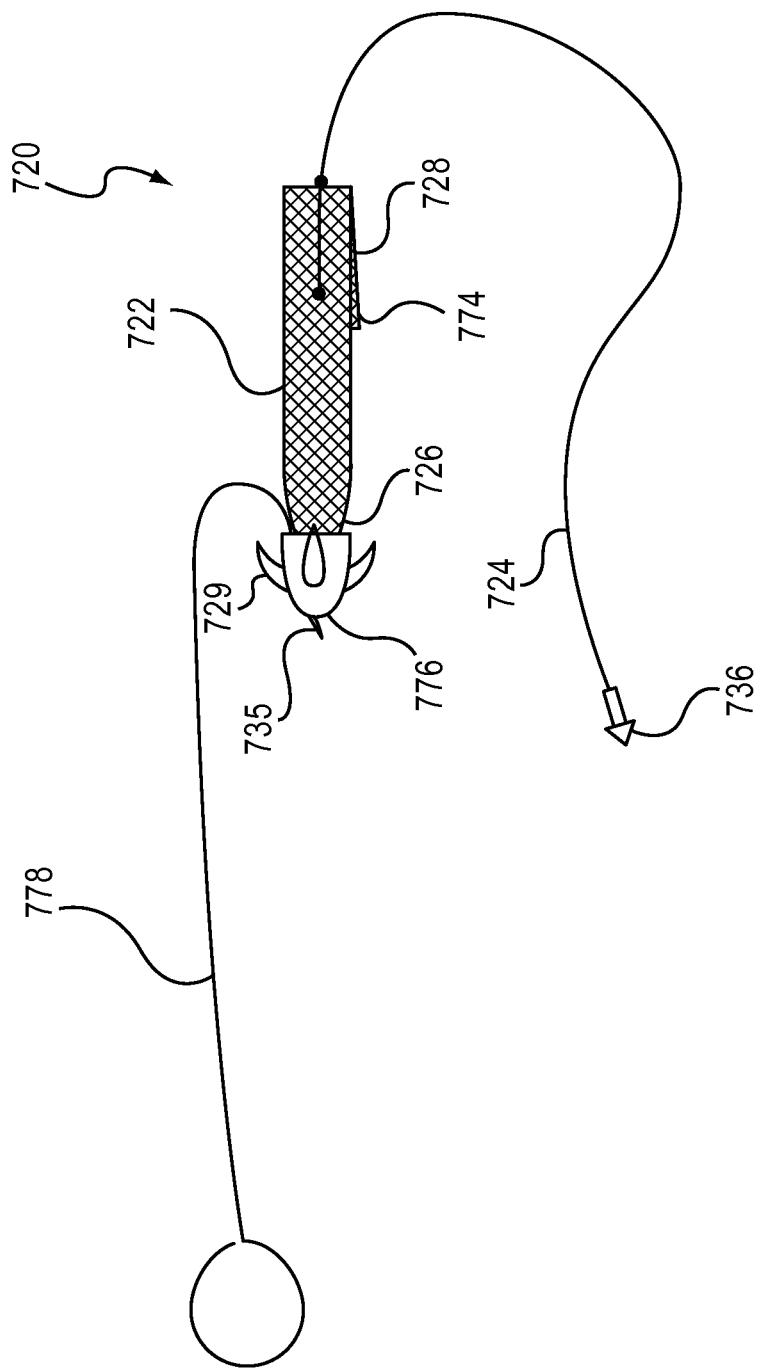

FIG. 19 illustrates an implant assembly 720 having an implant member 722 and a suture 724. In this embodiment, an anchor 776 is coupled to a first end 726 of the implant member 722 and the suture 724 is coupled adjacent a second end 728 of the implant member 722. A trocar 736 is coupled to an end of the suture 724 and can be loaded onto a delivery device, such as delivery device 144, for securing the implant member 722 to a tissue, such as, for example, a sacrospinous ligament. The anchor 776 can be a variety of different configurations having a portion, such as a barb 729, to engage tissue. The anchor 776 can be formed such that it is permanently secured to a tissue, or can be bio-absorbable. As shown in FIG. 19, a knot can be tied a distance from the second end 728 of the implant member 722 to create a flap 774. The flap 774 has no suture threaded through it and acts as an adjustment mechanism to overlap a sacrospinous ligament or vaginal apex if needed. For example, when the implant assembly 720 is secured to the sacrospinous ligament, the flap can be positioned to contact the sacrospinous ligament such that tissue in-growth will occur through the flap 774. The flap 774 then forms a bridge on the sacrospinous ligament and further secures the implant assembly 720 within the pelvic region. The flap 774 can be trimmed to length, if desired, before placement and securement to a tissue.

The anchor 776 can be secured to a vaginal apex using a U-shaped delivery device 778. A tip 735 of the device 778 can extend from the anchor 776, which provides for insertion through a tissue. The device 778 provides a reverse direction placement such that the barbs 729 of the anchor 776 can be secured, for example, into a vaginal apex corner.

Figure 20:
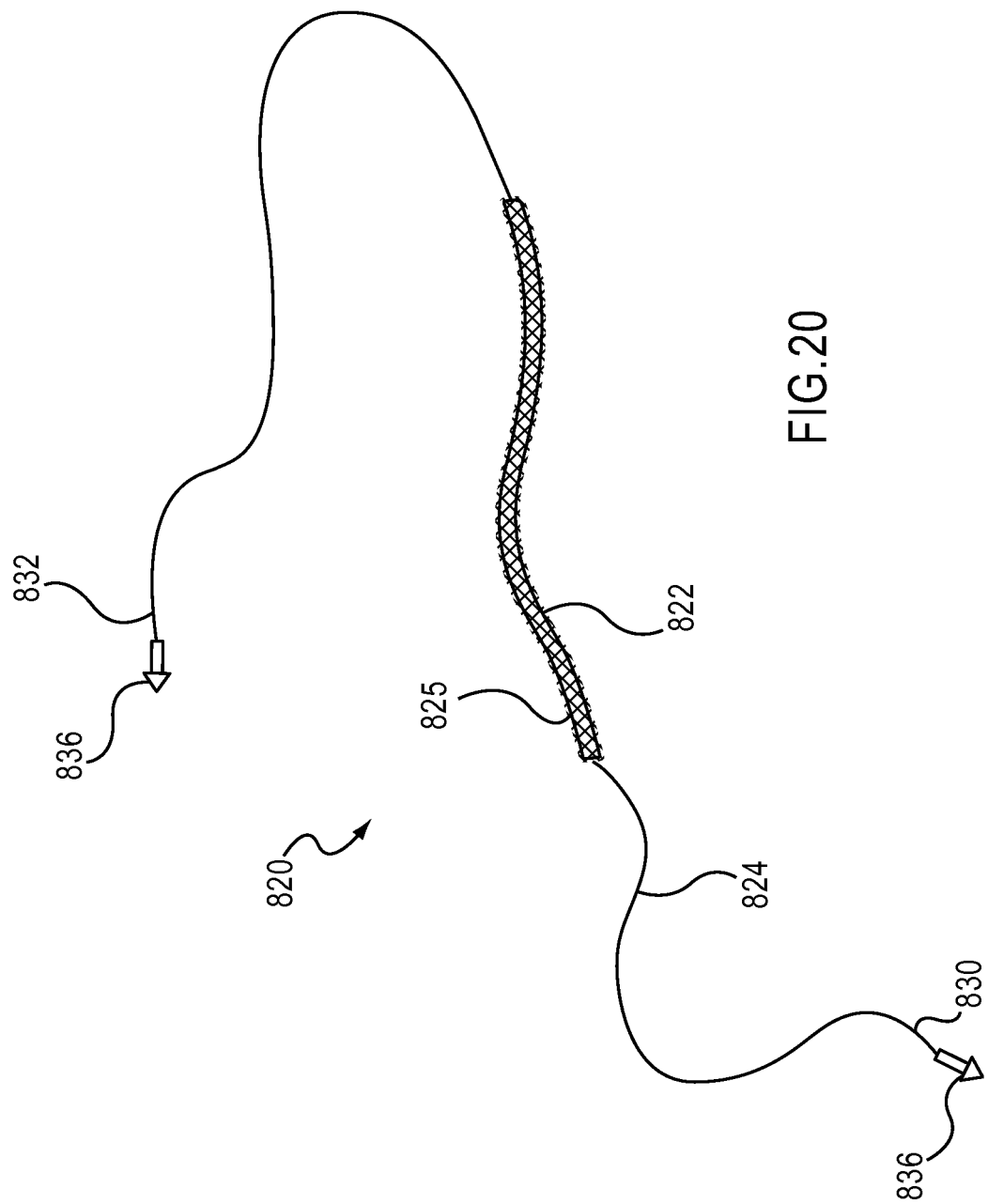

FIG. 20 illustrates an implant assembly 820 having an implant member 822 and a suture 824. In this embodiment, the implant member 822 is mesh and has a thin rope-like configuration. The implant member 822 is adjustable in that it can be pulled into a tissue (e.g., sacrospinous ligament) a desired distance. Trocar needles 836 are positioned on both a first and second end 830 and 832, respectively, of the suture 824 to use for placement with a delivery device, such as delivery device 144. The mesh implant 822 includes tangs 825 along at least a portion of an outer surface of the implant 822 that are used to anchor the implant member 822 in the tissue. A knot can also be thrown for further security using the suture 824 extending from the first and second ends 830 and 832, respectively, of the implant 822. For example, at the vaginal apex, the implant member 822 can be knotted or tied to the vaginal apex with the suture 824 as described in previous embodiments.

Figure 21:
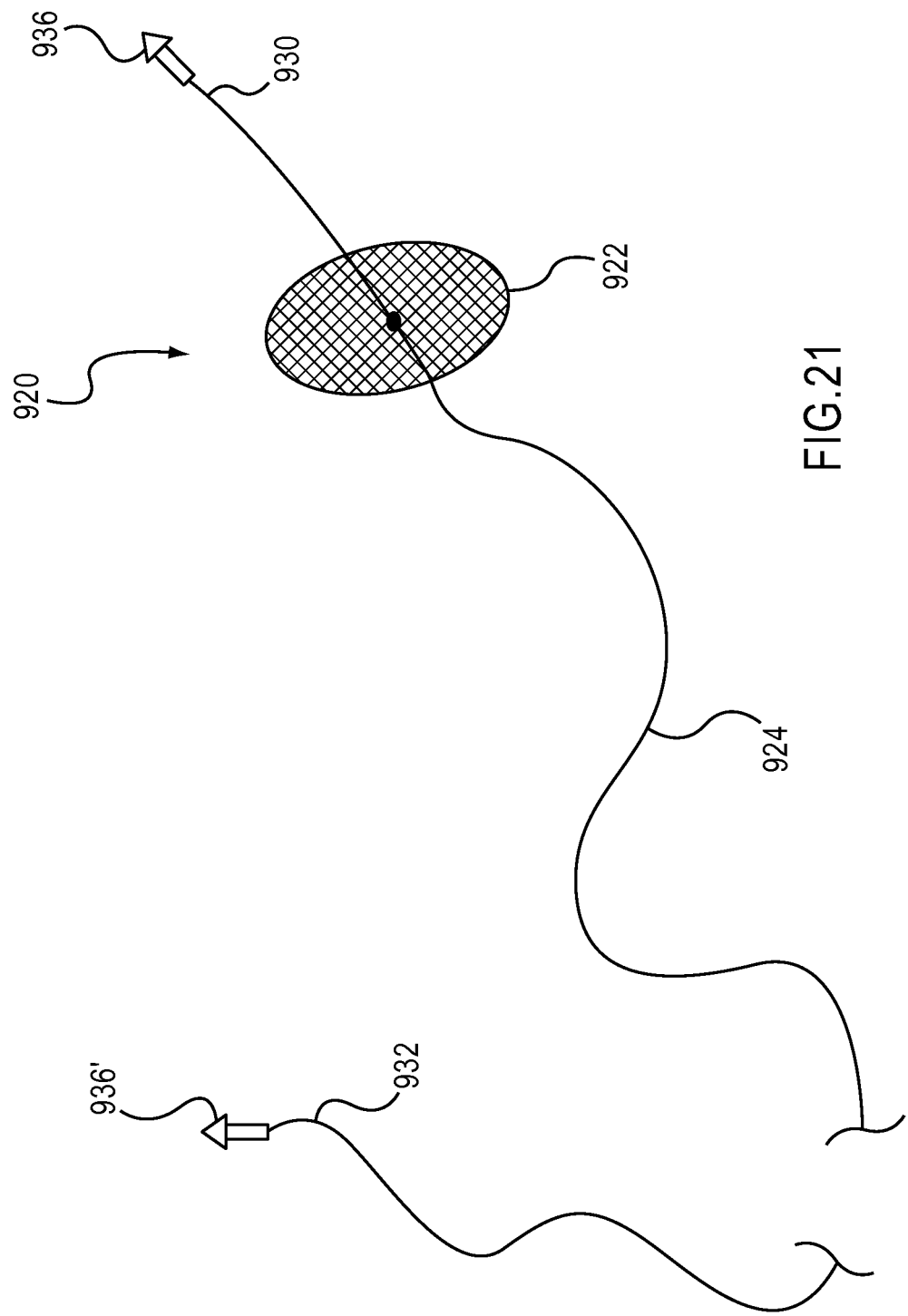

FIG. 21 illustrates an implant 920 having an implant member 922 and a suture 924. The implant 922 and suture 924 can be supplied to the user pre-assembled, or as separate components. Accordingly, the user can assemble the implant 922 to the suture 924 in different orientations. For example, the implant can be oriented widthwise or lengthwise relative to a longitudinal length of the suture. The suture 924 can also be passed through a center of the implant 922 to position the implant 922 in an upright position, or the suture can be passed through one end to create a flap. In other cases, only the suture 924 is used (i.e., no implant 922). Although shown circular, the implant 922 can also be any of a variety of different shapes and sizes. In FIG. 21, the implant 922 is shown in a widthwise orientation for use, for example, with a longer vagina or shorter gap between the vagina and a sacrospinous ligament. In the illustrated embodiment, the suture 924 is not knotted to the implant 922, which allows the implant 922 to slide along the length of suture 924; however, in some embodiments, the suture 924 is knotted to the implant 922.

In one use, the implant 922 is oriented close to a trocar 936 at a first end 930, as shown in FIG. 21. The trocar 936 at end 930 is associated with a delivery device, such as delivery device 144, to be placed into a tissue such as a sacrospinous ligament (SSL). A knot can be tied using the suture ends at the SSL, with the implant 922 positioned out of the way near the trocar 936. The trocar 936 can then be re-loaded onto the delivery device to be passed into a vaginal apex corner and unloaded from the catch of the delivery device external to the patient's body. The trocar 936' at the end 932 is then loaded onto the delivery device to be passed into the vaginal apex corner and unloaded from the catch external to the body. The procedure is repeated on the contra lateral side. A manipulator device (as described previously) can be used to assist in tensioning and securing the pairs of sutures on both sides of the vagina.

Figures 22, 23, 24:
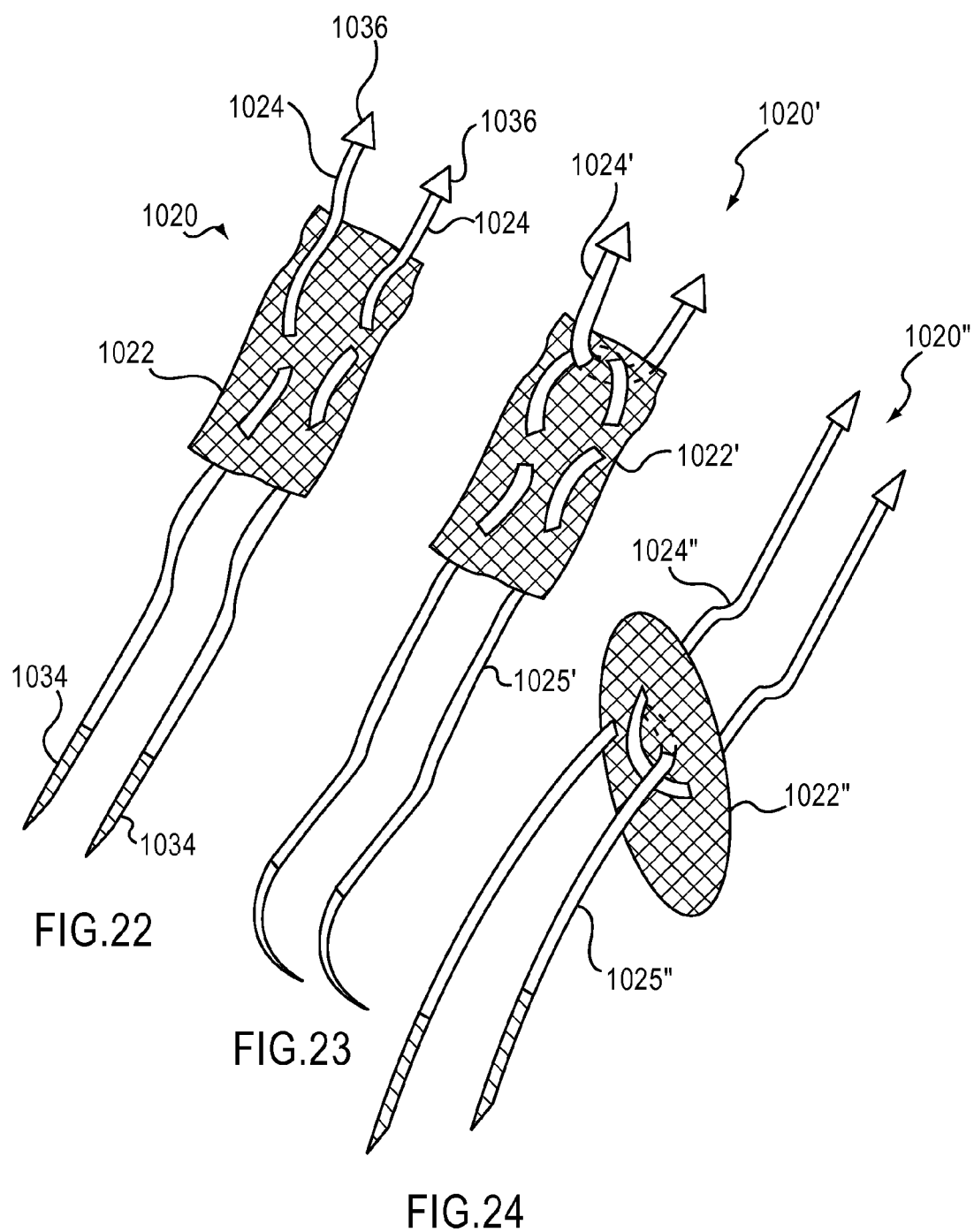

FIGS. 22-24 illustrate several different embodiments of an implant assembly, each having two sutures coupled to an implant member. The two sutures can be passed through a tissue using a delivery device, such as a delivery device 144, and can be knotted onto each other. The sutures can be absorbable, non-absorbable or one of each. A trocar needle can be positioned on an end of each of the sutures for delivery into a tissue (e.g., sacrospinous ligament) using the delivery device, and a curved, straight, or trocar needle can be positioned on the opposite end to pass the suture through, for example, a vaginal apex. In some embodiments, the suture ends are free of needles, for example, for use with a suture passer.

FIG. 22 is a top view of an implant assembly 1020 having an implant member 1022 and two sutures 1024 threaded therethrough. The sutures 1024 are not tied to the implant 1022, allowing the implant 1022 to slide along the length of the sutures 1024. A trocar needle 1036 is positioned on one end of each of the sutures 1024 and a straight needle 1034 is positioned at an opposite end of each suture 1024.

FIG. 23 is a top view of an implant 1020' that includes an implant 1022', a suture 1024' and a suture 1025'. In this embodiment, the sutures 1024' and 1025' are tied or looped onto each other securing the location of the implant 1022' to the sutures. Also, in this embodiment, the suture 1024' is non-absorbable for a permanent attachment to a tissue (e.g., the sacrospinous ligament), while the suture 1025' is absorbable for temporary attachment to, for example, the vaginal apex. The suture 1024' is sometimes referred to as the tie down suture and the suture 1025' is sometimes referred to as the tensioning suture. In alternative embodiments, suture 1024' is absorbable and suture 1025' is non-absorbable. Thus, sutures 1024' and 1025' can each be either absorbable or non-absorbable depending on the particular need. FIG. 24 illustrates a disc shaped implant assembly 1020" having a suture 1024" and a suture 1025" coupled to an implant member 1022". As in the previous embodiments, the sutures 1024" and 1025" can be absorbable, non-absorbable or a combination thereof.

Figure 25:
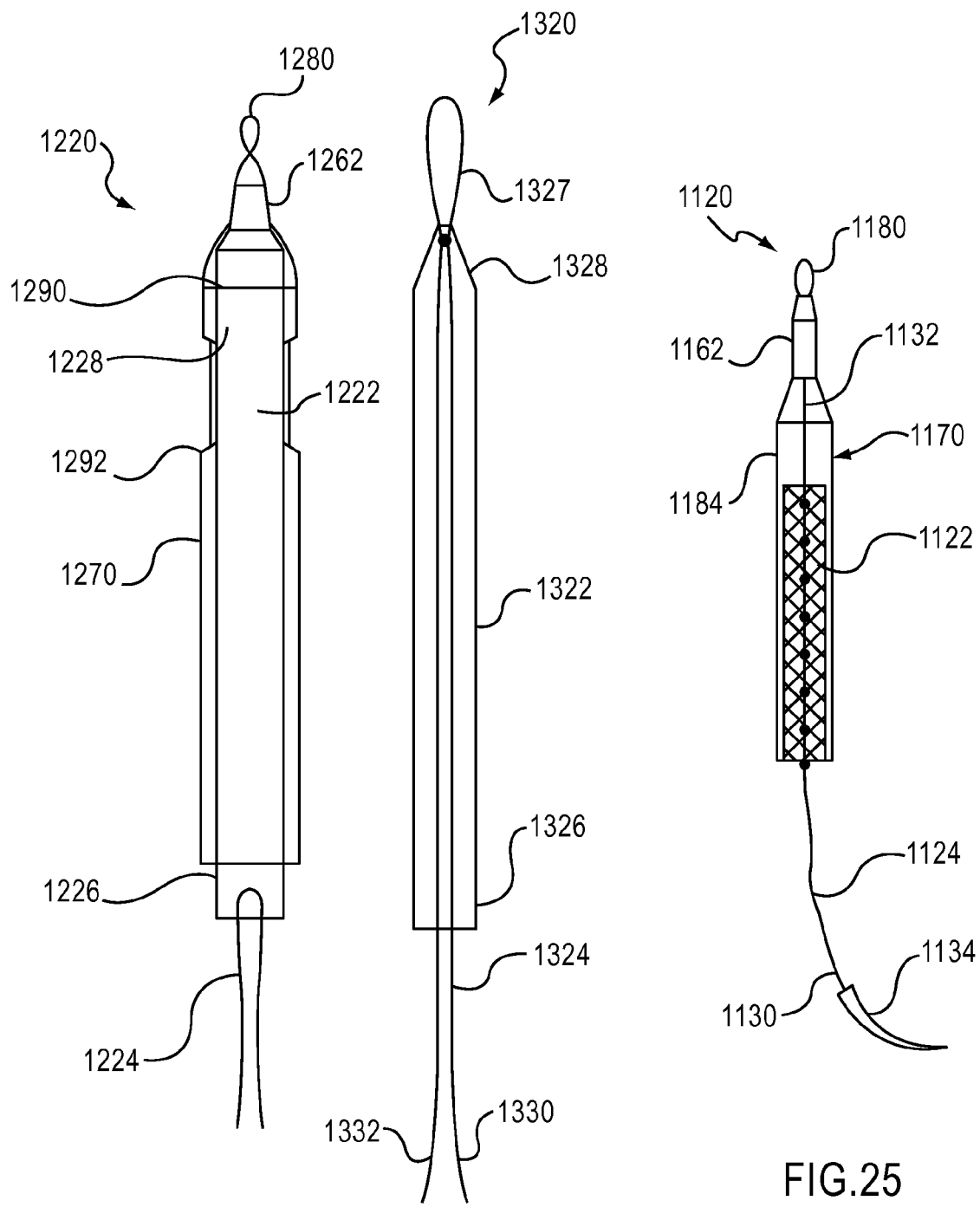
FIG. 25 is a front view of an implant assembly according to another embodiment of the invention.
Figure 26:
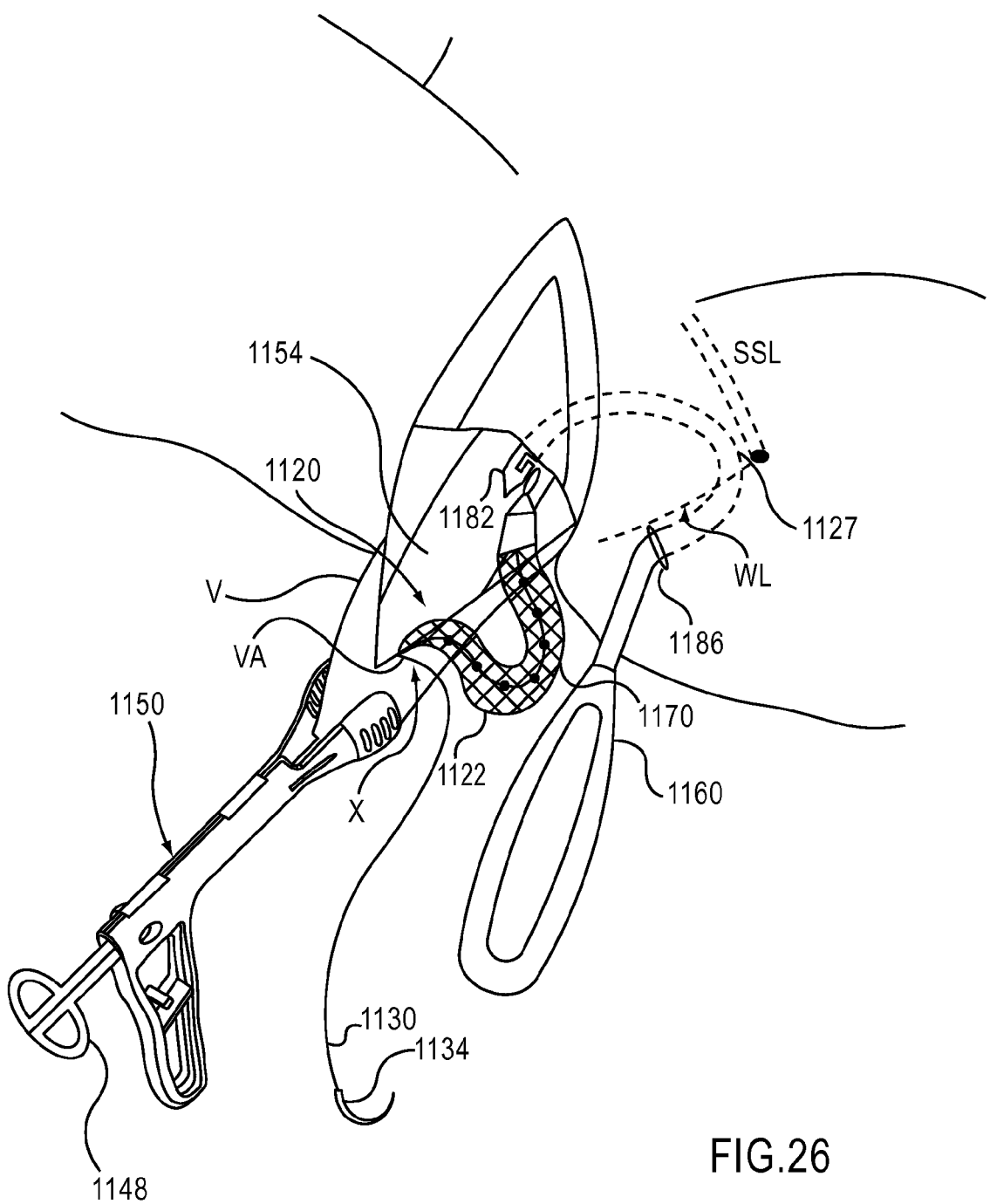
FIG. 26 is a perspective view of the implant assembly of FIG. 25 being delivered into a pelvic region of a patient.
Figure 27:
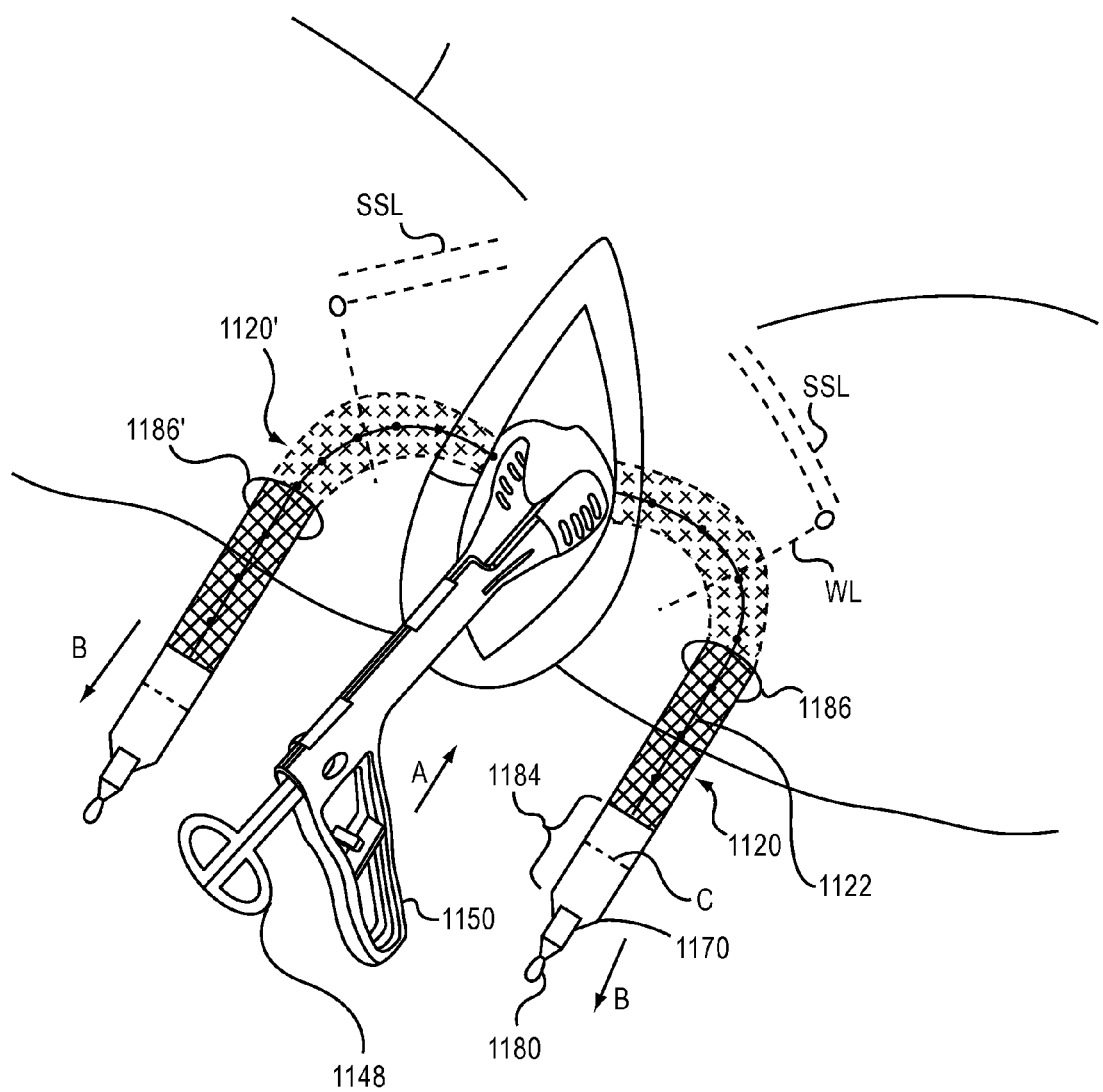
FIG. 27 is a perspective view illustrating two of the implant assembly of FIG. 26 each secured on opposite sides of uterus within a pelvic region of a patient.

FIGS. 25-27 illustrate an implant assembly and delivery method according to another embodiment of the invention. In this embodiment, an implant assembly 1120 includes an implant member 1122, a suture 1124 coupled to the implant 1122, and a sleeve 1170 substantially covering the implant 1122, and partially covering the suture 1124. The implant 1122 is formed with a mesh material and can have, for example, a length of about 5-10 cm and a width of about 1 cm. The suture 1124 is woven through the implant 1122 and is knotted intermittently to the implant 1122.

The sleeve 1170 can be for example, translucent, such that the implant 1120 can be viewed through the sleeve 1170. The sleeve 1170 includes a cut area 1184 that can be used in the removal of the sleeve as described in more detail below. The sleeve 1170 is used to protect the implant 1122 from premature engagement of tissue during delivery into a pelvic space. An end of the sleeve 1170 is coupled to a dilator 1162, and a connector 1180 is coupled to an opposite end of the dilator 1162. A curved needle 1134 is positioned on a first end 1130 of the suture 1124 and a second end 1132 of the suture 1124 is coupled to the dilator 1162. In some embodiments, the second end 1132 of the suture 1124 is coupled to the sleeve 1170 or both the sleeve 1170 and dilator 1162. Thus, the second end 1132 can exit the sleeve 1170 in the cut area 1184 or remain within the sleeve 1170.

To deliver the implant assembly 1120 into a pelvic region of a patient, a delivery device 1160 (also referred to herein as "delivery needle") (FIGS. 26 and 27) can be used. Although the delivery device 1160 is shown having a curved shaft 1127, in alternative embodiments, the shaft 1127 can be substantially straight, angled or curved at a different radius than shown in FIG. 26. Thus, delivery device 1160 is merely an example of the type of delivery device that can be used to deliver an implant assembly described herein. The connector 1180 of the implant 1020 can be releasably coupled to a notch 1182 (FIG. 26) at an end of the delivery needle 1160. A separate delivery needle 1160 is used for delivering an implant assembly to a the right and left sides of the patient, due to a difference in the direction of orientation of the shaft 1127 of the delivery needle 1160 for the respective sides.

A procedure to deliver an implant assembly 1120 is illustrated with reference to FIGS. 26 and 27. A cervix (not shown) of the patient can be grasped using a holding device 1148 (e.g., tenaculum clamp) as shown in FIG. 26. A manipulator device 1150 is coupled to the holding device 1148 such that it can slide along a shaft of the holding device 1148 to a desired position. An anterior incision 1154 is made in the inverted vagina V. The curved needle 1134 of the implant assembly 1120 is passed into the vaginal apex VA, but not through the vaginal wall, and tied securely to the vaginal wall at point X (FIG. 26). The above procedure can be repeated on the contra lateral side (not shown).

An exterior incision 1186 (also referred to as "entry site") is made on the patient, lateral to where the left inner edge of the pubic ramis bone ends (not shown) at the bottom of the left obturator foramen. Inserting the delivery needle 1160 at this location (i.e., exterior incision 1186) is sometimes referred to as a transobturator approach. In some procedures, a transglutual approach is used as described in more detail below with reference to a later embodiment. The delivery needle 1160 is inserted through the entry site 1186 and travels through tissue and through the left iliococcygeus muscle (not shown) and tendineus arch of levator ani muscle (i.e., white line) WL.

The delivery needle 1160 is further advanced through tissue within the pelvic region and exits within the vaginal incision 1154, shown in FIG. 26. The same procedure can be performed on the contra lateral side of the pelvic region using a second delivery needle (not shown) to deliver a second implant assembly 1120' (shown in FIG. 27).

The implant assemblies 1120, 1120' are connected to their respective delivery needle and drawn through the paths formed by the delivery needles, as shown in FIG. 27. For example, the notch 1182 of the delivery needle 1160 is connected to the loop connector 1180 of the implant assembly 1120. The delivery needle 1160 is then pulled back through the passageway formed by the delivery needle 1160 and out through the exterior incision 1186. The same process is done on the contra lateral side. FIG. 27 illustrates the implant assembly 1120 and implant assembly 1120' after being pulled from the vaginal incision 1154 and through the respective exterior incisions 1186 and 1186'. As shown in FIG. 27, the manipulator device 1150 is moved in the direction of arrow A as the implant assemblies 1120, 1120' are pulled and adjusted in the direction of arrows B.

When the manipulator device 1150 supports the uterus in the correct anatomical position, and the implant assemblies 1120, 1120' are correctly tensioned, the suture portion within the cut area 1184 is cut as indicated by the dashed line at C in FIG. 27 (without cutting all the way through the sleeve 1180) to release the implant 1122 from the sleeve 1170. The sleeve 1180 can then be pulled in the direction of arrow B to remove it from the implant 1122. The mesh implant 1122 is allowed to engage the surrounding tissue to secure itself to the tissue. For example, tangs or tanged edges on the implant 1120 can engage the surrounding tissue. The above procedure is done concurrently or repeated on the contra lateral side. The uterus can then be checked for support, the implant 1122 can be trimmed and the vaginal incision 1154 can be closed.

FIGS. 28-31 each illustrate an embodiment of an implant assembly that can be delivered to a pelvic region using a delivery needle 1160, or similar type of device as described above. Although not illustrated, each of the embodiments of an implant assembly in FIGS. 28-31 can include an implant member that is formed with a mesh material, and/or includes tangs or tanged edges. FIG. 28 is an implant assembly 1220 that includes an implant member 1222, a sleeve 1270 coupled to a second end 1228 of the implant 1222, a dilator 1262 coupled to the sleeve 1270 and a connector 1280 coupled to the dilator 1262. In this embodiment, the sleeve 1270 defines a window 1292 and a heat seal 1290 that is used to couple the implant 1222 to the sleeve 1270. The connector 1280 can be used to associate the implant assembly 1220 to a notch in a delivery needle, such as notch 1182 in FIG. 26. A suture 1224 is coupled to a first end 1226 of the implant 1222 to secure the implant 1122 to a vaginal apex. To remove the sleeve 1270 from the implant 1122 after delivering the implant 1222 to a pelvic region, the implant 1122 and one of two walls of the sleeve 1270 are cut at the location of the window 1292. This allows the sleeve 1270 to be pulled off the implant 1122 after delivery as described previously.

FIG. 29 illustrates an implant assembly 1320 having an implant member 1322 and a suture 1324. In this embodiment, the suture 1324 has a first end 1330 and a second end 1332 that both extend from a first end 1326 of the implant 1322. The suture 1324 extends through the implant 1322, and forms a loop 1327 that extends from a second end 1328 of the implant 1322. The suture 1324 is knotted to the implant 1322 at the second end 1328. The loop 1327 can be used to associate the implant assembly 1320 to an end of a delivery needle (e.g., delivery needle 1160).

FIG. 30 illustrates an implant assembly 1420 having a low-profile connector 1480 coupled to an implant member 1422. The connector 1480 can be used to associate the implant assembly 1420 to a delivery device. A suture 1424 extends from a first end 1426 of the implant 1422 and can be used to secure the implant 1422 to, for example, a vaginal apex. The suture 1424 can be woven through the implant 1422 as shown in FIG. 29. Alternatively, the suture 1424 can be tied to the first end 1426 or otherwise coupled thereto. FIG. 31 illustrates an implant assembly 1520 having an implant member 1522 that defines an opening 1580 that can be used as a connector to associate the implant assembly 1520 to a delivery needle. Although a suture is not shown in FIG. 31, the implant assembly 1520 can alternatively include a suture coupled to the implant 1522.

FIG. 32 illustrates an implant assembly 1620 having an axial connector 1680 for associating the implant assembly 1620 to a delivery needle. Such a connector can, for example define an internal passageway in which an end of a delivery needle can attach and form a friction fit. Alternatively, the connector 1680 can be configured to be inserted into an opening of a mating connector on an end of a delivery needle for a friction fit. Implant assembly 1620 also includes a back bone member 1688 that extends along a length of the implant 1622. The back bone member 1688 can be an insert molded component or a suture coupled to the implant 1622. For example, the backbone member 1688 can be a suture woven through the implant 1622. The backbone member 1688 can alternatively be a heat seal formed along a portion of the implant 1622. The back bone member 1688 adds strength to the implant assembly 1620 and helps prevent elongation of the implant 1622 when under tension. FIG. 33 illustrates an implant assembly 1720 having a back bone member 1788 that can be delivered using a delivery device, such as, a delivery device 144.

Figure 35:
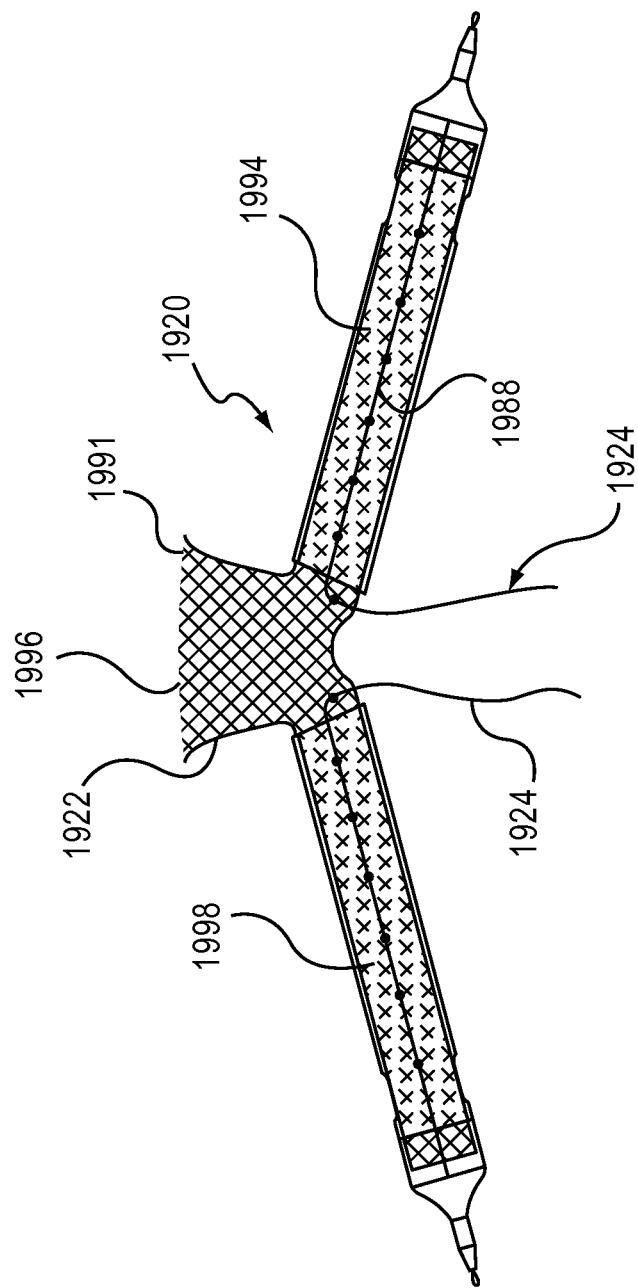

FIGS. 34 and 35 each illustrate a different implant assembly that can span from a left side to a right side of a pelvic region to support a uterus. The implant assemblies are similar to the previous embodiments and are delivered in a similar manner using a delivery device, such as delivery needle 1160. As shown in FIG. 34, an implant assembly 1820 includes an implant member 1822 having a first end portion 1894, a middle portion 1896 and a second end portion 1898. A pair of sutures 1824 are coupled to the middle portion 1896 and are used to secure the middle portion 1896 to a vaginal apex. For example, the sutures 1824 can be tied to the vaginal apex. Alternatively, the middle portion 1896 can be secured to the vaginal apex using, for example, staples, pins, fasteners, glue, anchors, or separate sutures not preassembled to the implant 1822. The implant assembly 1820 also includes a pair of sleeves 1870 disposed over each of the first end portion 1894 and the second end portion 1898. The sleeves 1870 define a window 1892 for removing the sleeve 1870 from the implant 1822 as described with reference to FIG. 28. A dilator 1862 and connector 1880 are coupled to the implant 1822 or sleeve 1870, and used as previously described to associate the implant assembly 1820 to a delivery needle. The delivery of the implant assembly 1820 to a pelvic region is described below with reference to FIGS. 36A and 36B.

FIG. 35 illustrates an implant assembly 1920 that is similar to the implant assembly 1820. The implant assembly 1920 includes an implant member 1922 with a first end portion 1994, a middle portion 1996, and a second end portion 1998. In this embodiment, a suture 1924 extends through (e.g., woven through) each of the first and second end portions 1994, 1998 of the implant 1922 and is knotted intermittently thereto. The portion of the sutures 1924 woven through the implant 1922 is the back bone member 1988. The backbone member 1988 provides strength and support to the implant 1922. As stated previously, an insert molded back bone member, or a heat seal, can alternatively be used. Also in this embodiment, the implant 1922 includes a flap 1991 associated with the middle portion 1996. The flap 1991 can be used, for example, to repair a cystocele.

Figure 36A:
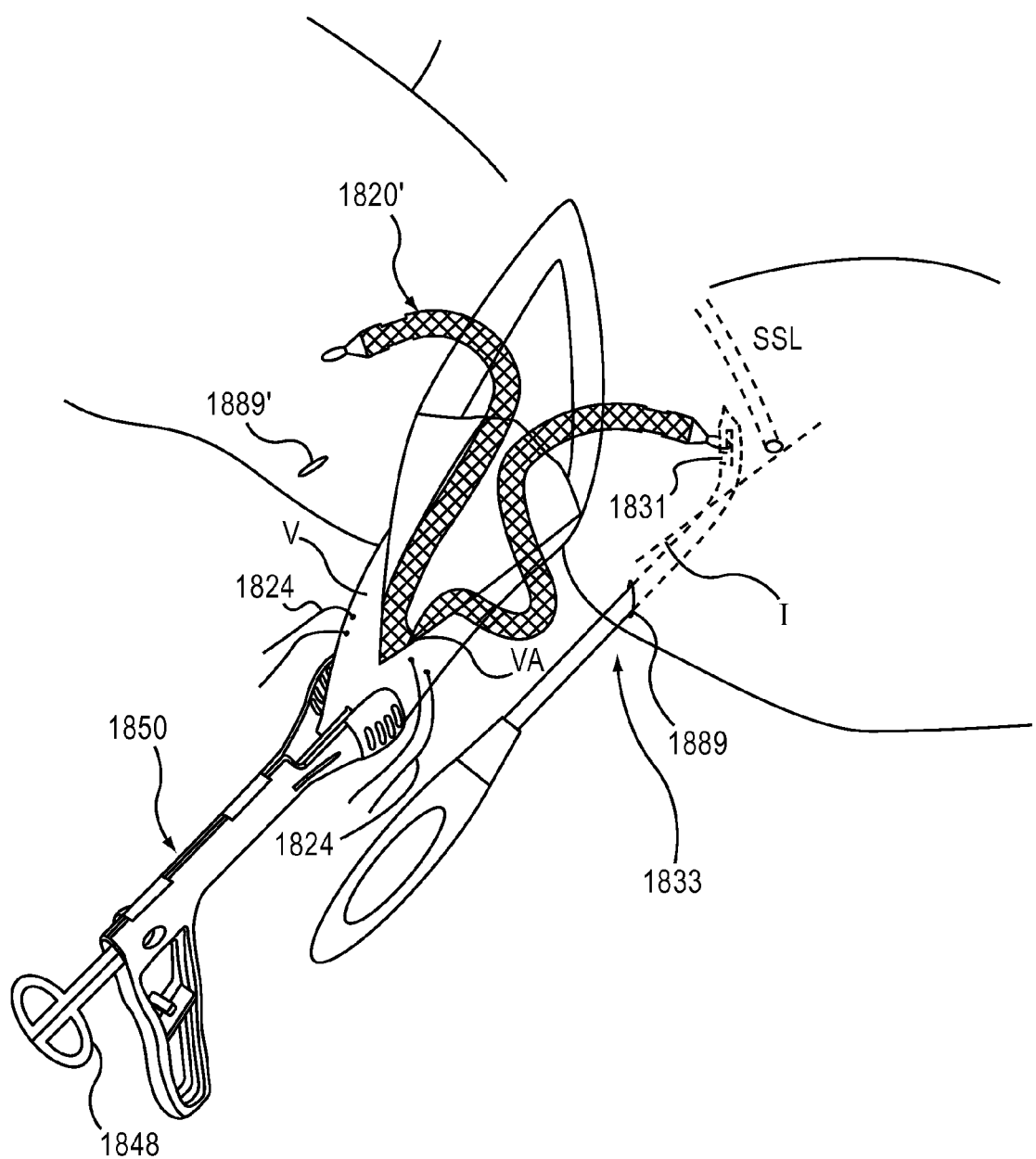
FIGS. 36A and 36B are each a perspective view showing the implant assembly of FIG. 34 being coupled within a pelvic region of a patient.
Figure 36B:
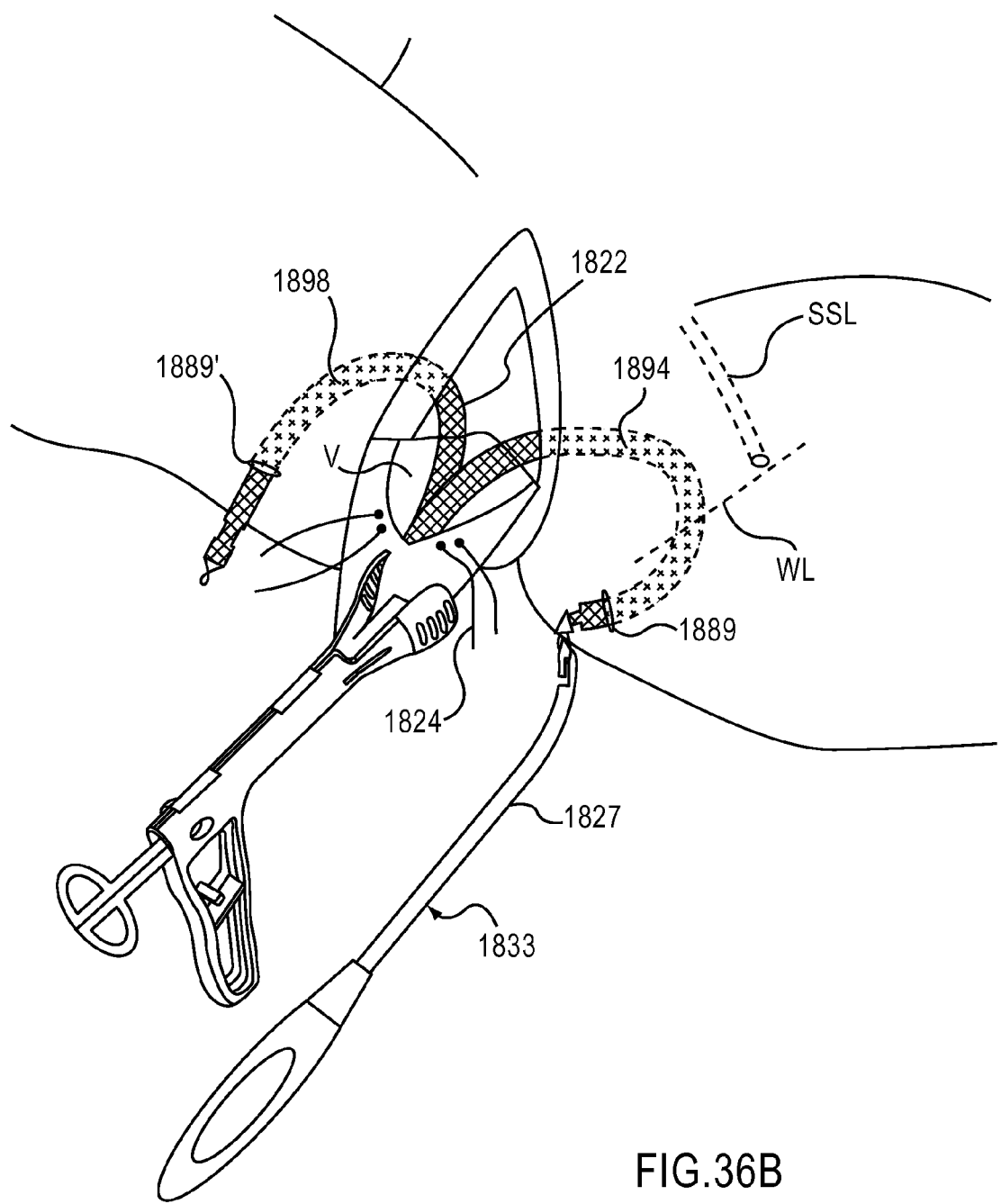

As stated above, to deliver either implant assembly 1820 or 1920, a delivery needle, such as delivery needle 1160, can be used. FIGS. 36A and 36B illustrate the delivery of only the implant assembly 1820, but it should be understood that the implant assembly 1920 can be delivered to a pelvic region in a similar manner. As shown in FIG. 36A, the implant assembly 1820 can be delivered to a pelvic region of a patient using a delivery needle 1833. The delivery needle 1833 has a straighter shaft 1827 than the delivery needle 1160 and can be used, for example, to deliver the implant assembly 1820 using a transglutual approach, rather than a transobturator approach. It is to be understood, however, that a transobturator approach (e.g., using a delivery needle 1160), or other types of approaches not specifically described, can alternatively be used. In a transglutual approach, the delivery device 1833 is inserted through an exterior incision 1889 located closer to the rectum than in the transobturator approach and is passed lateral to the vagina and the ischiopubic ramus. The transglutual approach can be used, for example to pass an implant through a white line. In some embodiments, a transglutual approach is used to pass an implant through a sacrospinous ligament.

In such a procedure, after the inverted vagina V has been clamped with a holding device 1848 (shown coupled to a manipulator device 1850) and an anterior vaginal incision has been made, the middle portion 1896 of the implant 1822 is secured to a vaginal apex VA using the sutures 1824. The sutures 1824 can be tied to the vaginal apex VA at a single location or at multiple locations. As described previously, suture passers, or needles coupled to the sutures can be used to pass the sutures through the vaginal wall. Alternatively, the sutures can be sutured to the undersurface of the epithelium without passing through the full thickness of the vaginal wall. FIG. 36A illustrates the sutures 1824 after being passed through a portion of the vaginal wall.

As stated above, the delivery needle 1833 is inserted through an exterior incision 1889. In addition, a second delivery device (not shown) can be inserted on the contra lateral side through an exterior incision 1889'. The connector 1888 on the first portion 1894 of the implant assembly 1822 is associated with a notch 1831 on an end of the delivery needle 1833. The same process is performed on the contra lateral side to connect the second portion 1898 of the implant assembly 1820 to the second delivery device. The delivery needle 1833 is then backed out through the path in which it entered, dragging and inserting the first portion 1894 of the implant assembly 1822 into the passageway created by the needle 1833 as shown in FIG. 36B. The second delivery needle (not shown) is also pulled back through the path in which it entered, dragging and inserting the second portion 1898 of the implant assembly 1820 into the passageway on the contra lateral side as shown in FIG. 36B. The implant assembly 1820 is tensioned on both sides, pulling the uterus (by the vaginal apex) into a correct anatomical position. The tensioning also adjusts the correct implant material length between the vaginal apex and the internal entry site for a long or short vagina. Any excess implant material is pulled through the external entry site 1889 (or 1889'). After the uterus is in the correct position, the sleeve 1870 of the implant assembly 1822 can be removed as described previously by cutting through a portion of the sleeves 1870 and the sutures 1824. Tanged portions of the implant 1822 engage the surrounding tissue in the passageway to anchor the implant 1822 in place until tissue in-growth occurs to reinforce the anchoring. The excess implant material extending outside of the entry site 1889 (and 1889') is trimmed.

Figure 37:
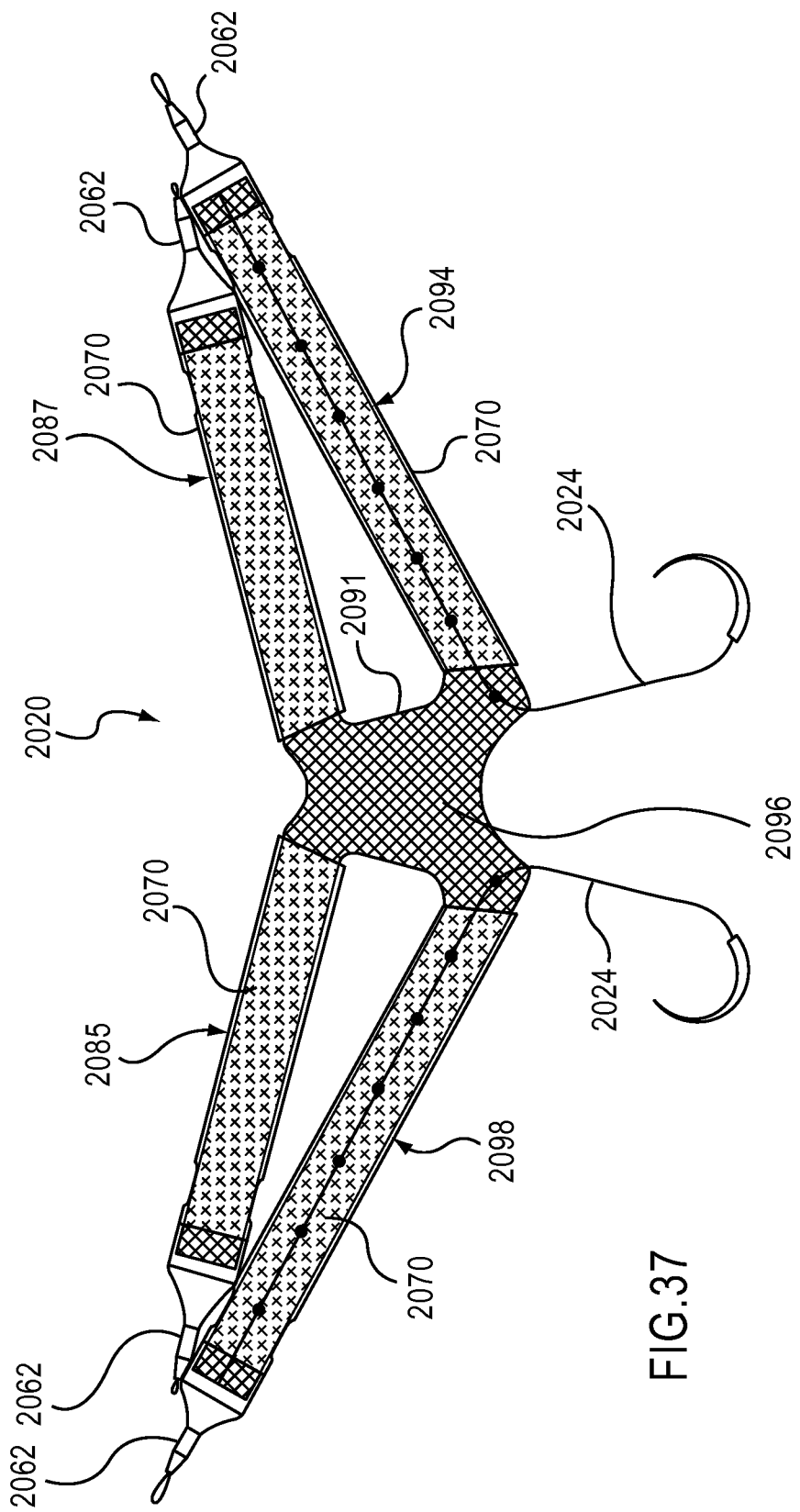
FIG. 37 is a front view of an embodiment of an implant assembly.
Figure 38:
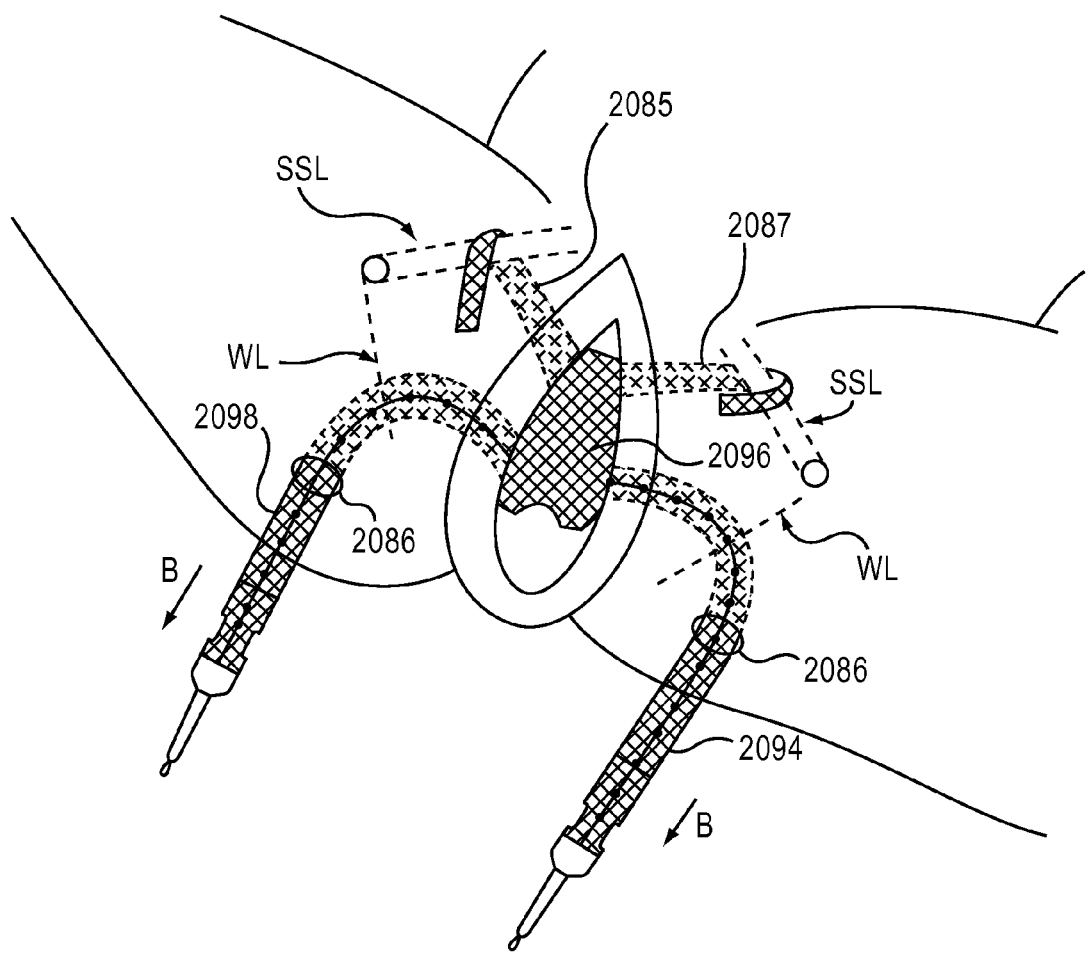
FIG. 38 is a perspective view of the implant assembly of FIG. 37 partially secured within a schematic representation of a pelvic region of a patient.

FIGS. 37 and 38 illustrate yet another embodiment of an implant assembly. In this embodiment, an implant assembly 2020 is similar to implant assemblies 1820 and 1920, except implant assembly 2020 includes four arms or portions. The implant assembly 2020 includes a first portion 2094, a second portion 2098, a middle portion 2096, a third portion 2087 and a fourth portion 2085. The first portion 2094 and the second portion 2098 are configured substantially the same as the first and second portions 1994 and 1998, respectively, of the embodiment of FIG. 35 having a suture woven through the implant 2022. The third portion 2087 and the fourth portion 2085 are configured substantially the same as the first and second portions of the embodiment of FIG. 34. A flap 2091 is associated with the middle portion 2096 and can be used, for example, for a cystocele repair. Sutures 2024 are coupled to the middle portion 2096 for anchoring the middle portion to a vaginal apex. As with the previous embodiments, alternative anchoring means can be used. A sleeve 2070 is disposed over the implant 2022 at each of the four portions (2094, 2098, 2087 and 2085) and a dilator 2062 is coupled to the sleeve 2062 as described in the previous embodiments.

To deliver the implant assembly 2022 to a pelvic region of a patient, delivery needles as previously described can be used. For example, a delivery needle 1160 or 1833 can be used depending on the particular approach (e.g., transobturator, transglutual, superpubic). As shown in FIG. 38, a delivery needle (not shown) such as the delivery needle 1833 can be inserted through an exterior entry site 2086 for a transglutual approach. Similarly, a second delivery needle (not shown) can be inserted through an entry site 2086 on the contra lateral side. The first portion 2094 of the implant assembly 2020 is associated to the first delivery needle, the second portion 2098 of the implant assembly 2020 is associated to the second delivery needle and each is drawn through the path created by the respective delivery needle. Another delivery device(s) can be used to deliver the third portion 2087 and the fourth portion 2085 of the implant 2022 to the pelvic region. For example, the third portion 2087 and the fourth portion can be delivered using a transobturator approach using a delivery device such as delivery needle 1833. Alternatively, the third portion 2087 and the fourth portion 2085 can be cut to remove the sleeve 2070 and dilator 2062. This allows the third portion 2087 and fourth portion 2085 to be secured using a suturing delivery device such as the delivery device 144. Alternatively. the third and fourth portions 2087 and 2985 can each be delivered using a super pubic approach using a delivery needle such as the delivery needle 1833. A super pubic approach, can include, for example, inserting the delivery device through a vaginal incision and toward an abdomen to secure the implant, for example, to abdominal fascia.

After delivery the four portions to the desired securement sites within the pelvic region, the implant assembly 2020 can be tensioned on all sides, pulling the uterus (by the vaginal apex) into a correct anatomical position. The tensioning also adjusts the correct implant material length between the vaginal apex and the implant internal entry sites for long or short vagina. Excess implant material exits the external incisions 2086. After the uterus is in the correct position, the sleeves on the implant assembly 2020 can be removed as described above for other embodiments. This allows the tangs of the implant to engage the surrounding tissue in the passageways and anchor the implant until tissue in-growth can occur to reinforce the anchoring. Each portion of the implant 2020 can be trimmed to length at its respective exterior entry site 2086.

Figure 39:
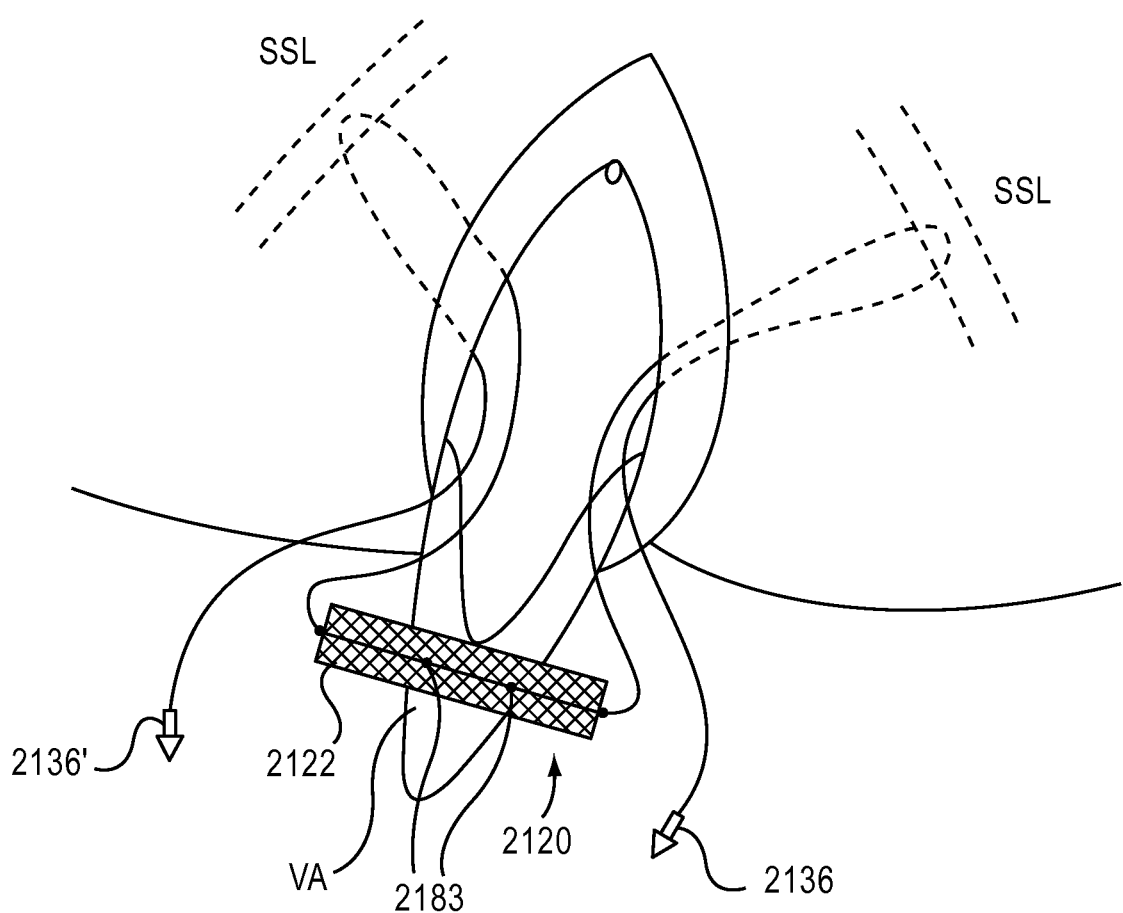
FIG. 39 is a perspective view of an embodiment of an implant assembly shown coupled to a vaginal apex of a patient.

FIG. 39 illustrates another embodiment of an implant assembly that spans from one sacrospinous ligament to another sacrospinous ligament to approximate a uterus into its correct anatomical position. In this embodiment, an implant assembly 2120 includes an implant member 2122 that is coupled at a mid-line to the epithelium of a vaginal wall (without passing through the vaginal wall) as indicated at 2183. Here, the implant 2122 is sutured to the epithelium at two locations, however, only one, or more than two can alternatively be used. The implant 2122 is also associated to the sacrospinous ligaments SSL on opposite sides of the patient's pelvic region. The implant assembly 2120 can be delivered and secured within the pelvic region using a suturing type delivery device such as delivery device 144 and 344 described above for previous embodiments. For example, a first trocar needle 2136 can be coupled to a first suture end 2132 and a second trocar needle 2136' can be coupled to a second suture end 2132'. The trocar needles 2136, 2136' can each be associated to a different suturing delivery device as described above. Alternatively, the same delivery device can be used to sequentially deliver each side of the implant 2122.

Figure 40:
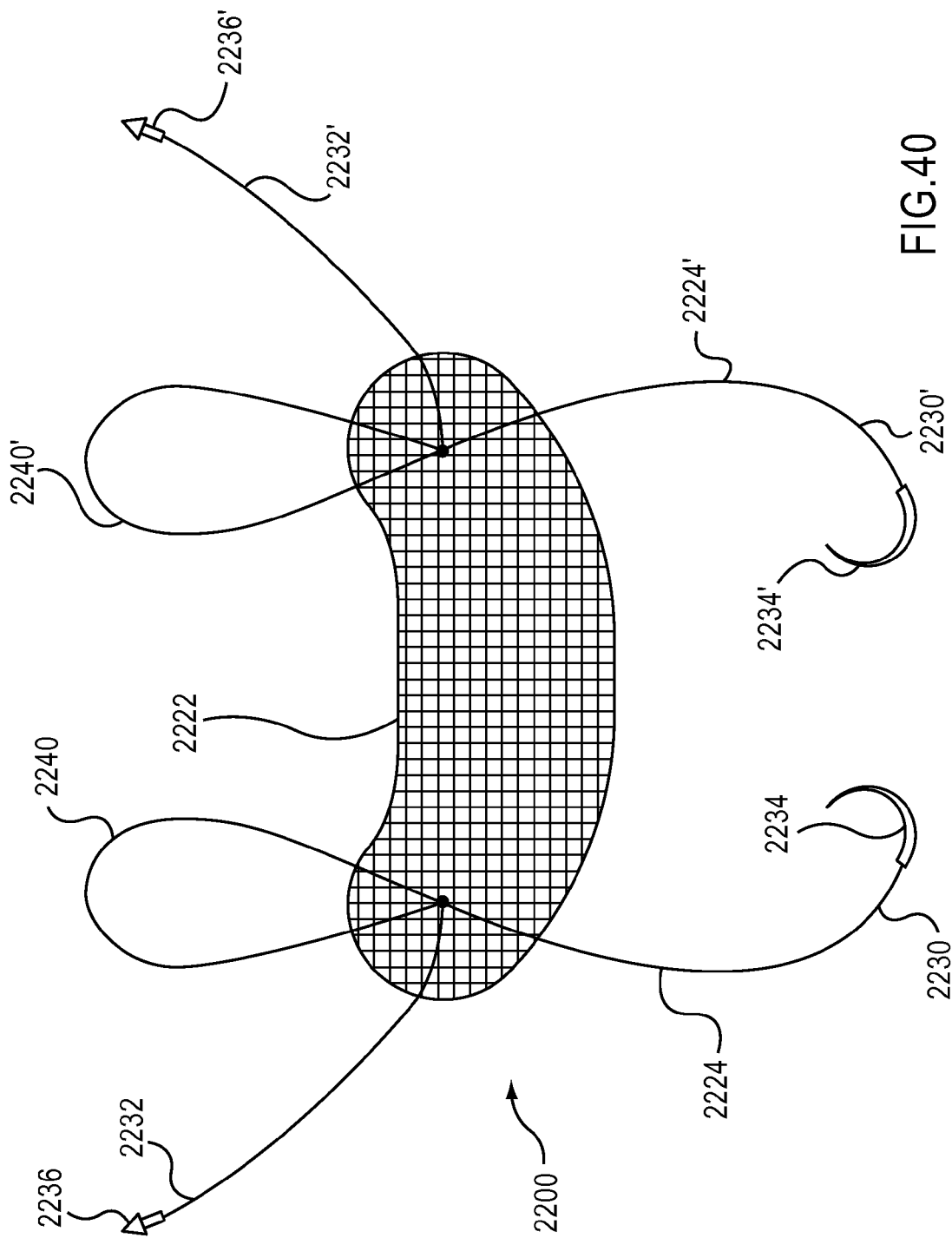
FIG. 40 is a front view of an embodiment of an implant assembly.
Figure 41:
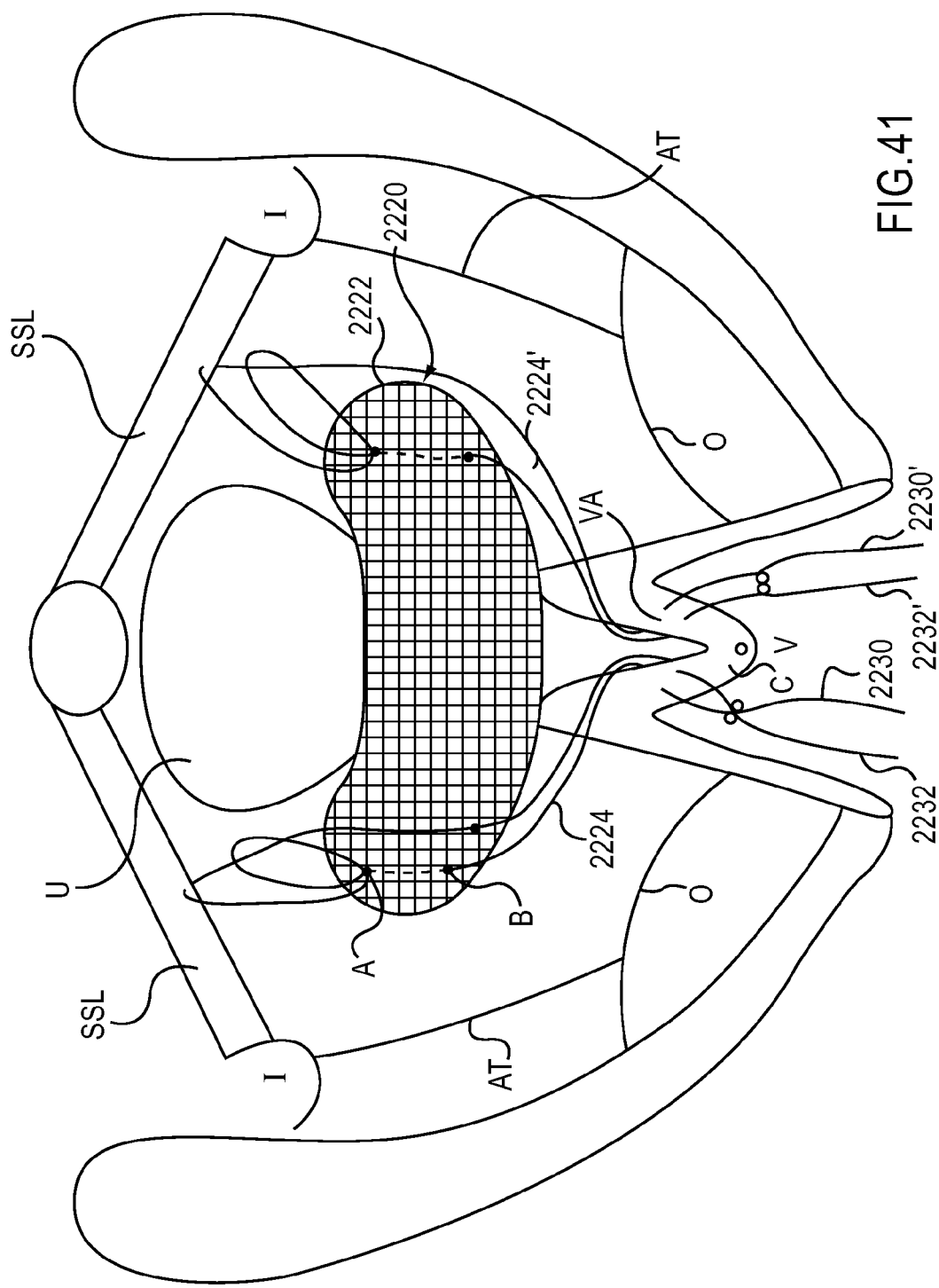
FIG. 41 is a front view of the implant assembly of FIG. 40 shown partially secured within a pelvic region of a patient.

FIGS. 40 and 41 illustrate another embodiment of a single implant assembly that can be secured to opposite sides of a pelvic region. This embodiment illustrates an implant assembly similar to implant assembly 2120 that can be delivered using a suturing type delivery device (e.g., delivery device 144 and 344). An implant assembly 2220 includes an implant member 2222, a first suture 2224 and a second suture 2224'. As shown in FIG. 40, a curved needle 2234, 2234' is coupled to an end 2230, 2230' and a trocar needle 2236, 2236' is coupled to a second end 2232, 2232' for association to a carrier of a delivery device. The sutures 2224, 2224' each form a loop 2240, 2240' as described previously to assist in delivery and securing of the implant 2222 within a pelvic region. As described above, in some embodiments, suture passers can be used instead of the curved needles for passing the suture through a vaginal apex.

FIG. 41 is a front view of a pelvic region that includes a representation of a uterus U, sacrospinous ligaments SSL, a vagina V, a vaginal apex VA, the arcus tendineus AT, obturators O, ischial spines I, and a cervix C for reference. FIG. 41 illustrates the securement sites for the implant assembly 2220 for repair of a grade 2 prolapse. In this embodiment, the sutures 2224, 2224' are shown placed through the sacrospinous ligament SSL on opposites sides of the uterus U and the implant 2222 partially drawn to the sacrospinous ligament SSL. In an actual procedure, however, when the loop or noose 2240, 2240' is closed or tightened, the implant 2222 would be in contact with the sacrospinous ligament. As described previously, as the sutures 2224, 2224' are tightened and knotted to the vaginal apex VA, a device, such as a holding device 148 and/or a manipulator device 150 previously described, can be used to move or approximate the vaginal apex VA to the sacrospinous ligament SSL. In this embodiment, the ends 2232, 2230 of the sutures 2224, 2224' are passed through the wall of the vaginal apex VA for securement thereto. A first knot can be tied in the vagina (e.g., vaginal lumen) after the sutures have been tensioned. A physician can use a finger to push the knot down into the vagina V, as well as to assist in repositioning the vagina deep in the pelvic region.

Figure 42:
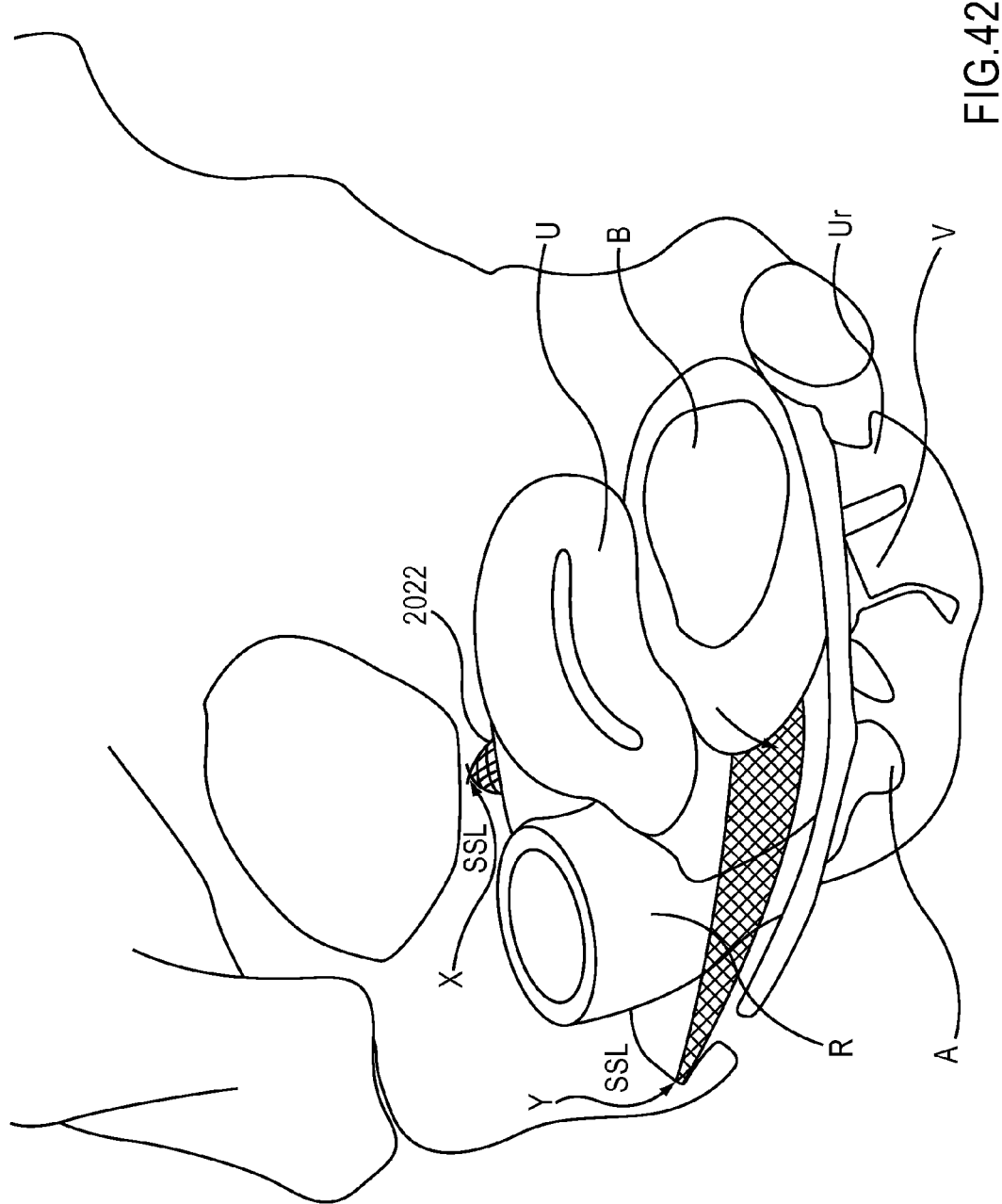
FIG. 42 is a partial cross-sectional side view of a pelvic region and an embodiment of an implant assembly secured to a sacrospinous ligament and vagina.

After the implant assembly has been secured, the implant supports or slings the uterus as shown in the partial cross-sectional side view of a pelvic space in FIG. 42. Most or some of the weight of the suspension can be supported by the sutures rather than the implant. Specifically, the suture that spans between the SSL and the vaginal apex. FIG. 42 illustrates the implant assembly 2220 secured to the sacrospinous ligament SSL on opposite sides of a uterus U at locations X and Y. A bladder B, urethra UR, rectum R, anus A, and vagina V are also illustrated for reference. A mid-point of the implant can be stretchable to accommodate different patients. The stretch allowable, can be, for example, in the range of 1 cm for every 4 cm of implant material. The stretch of the implant can also be controlled by folding or according the implant at a selected location on the implant The span of such a fold or according can be, for example, 1 cm on each side. For example, the suture 2224 in this span enters a top side of the implant 2222 at point A shown in FIG. 41, runs the length of 1 cm on the bottom side of the implant 2222 and is threaded back to the top side at point B. When the vaginal apex VA is approximated to the SSL, the threading of the suture 2224 will accordion or fold there between, as the two suture ends are tensioned and tied in the vagina.

Figure 43:
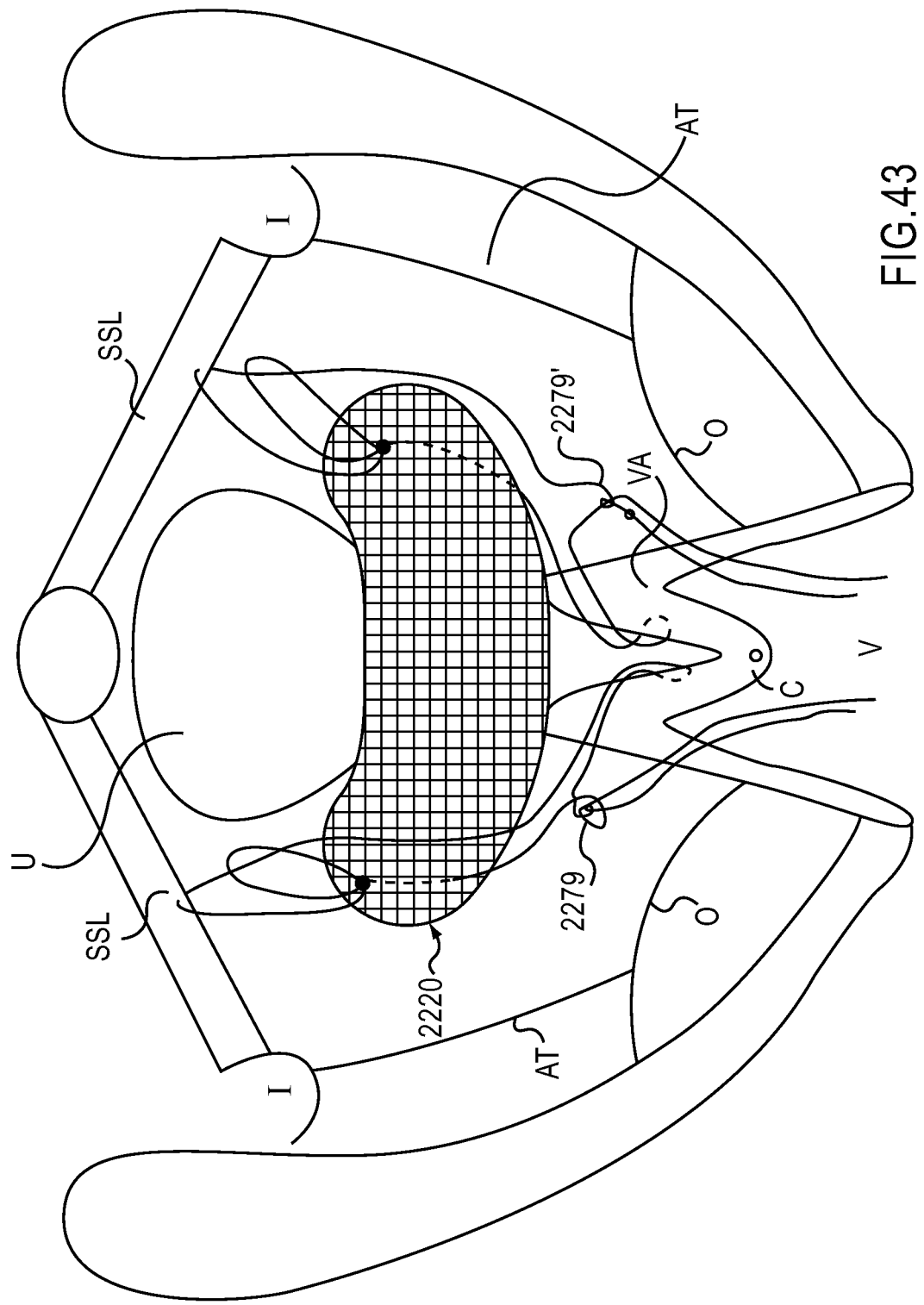
FIG. 43 is a front view of the implant assembly of FIG. 40 shown partially secured within a pelvic region of a patient.

FIG. 43 illustrates the implant assembly 2220 with the sutures 2224, 2224' secured at a different location than in FIG. 41. Here, the sutures 2224, 2224' are not passed through the wall of the vaginal apex VA. Instead, the curved needles 2234, 2234' (not shown in FIG. 43) are used to stitch the sutures 2224, 2224' in and out of the vaginal epithelium, but not all the way through the epithelium. The two suture ends can be tensioned and tied between the vaginal apex VA and the SSL as indicated at 2279, 2279'.

Figure 44:
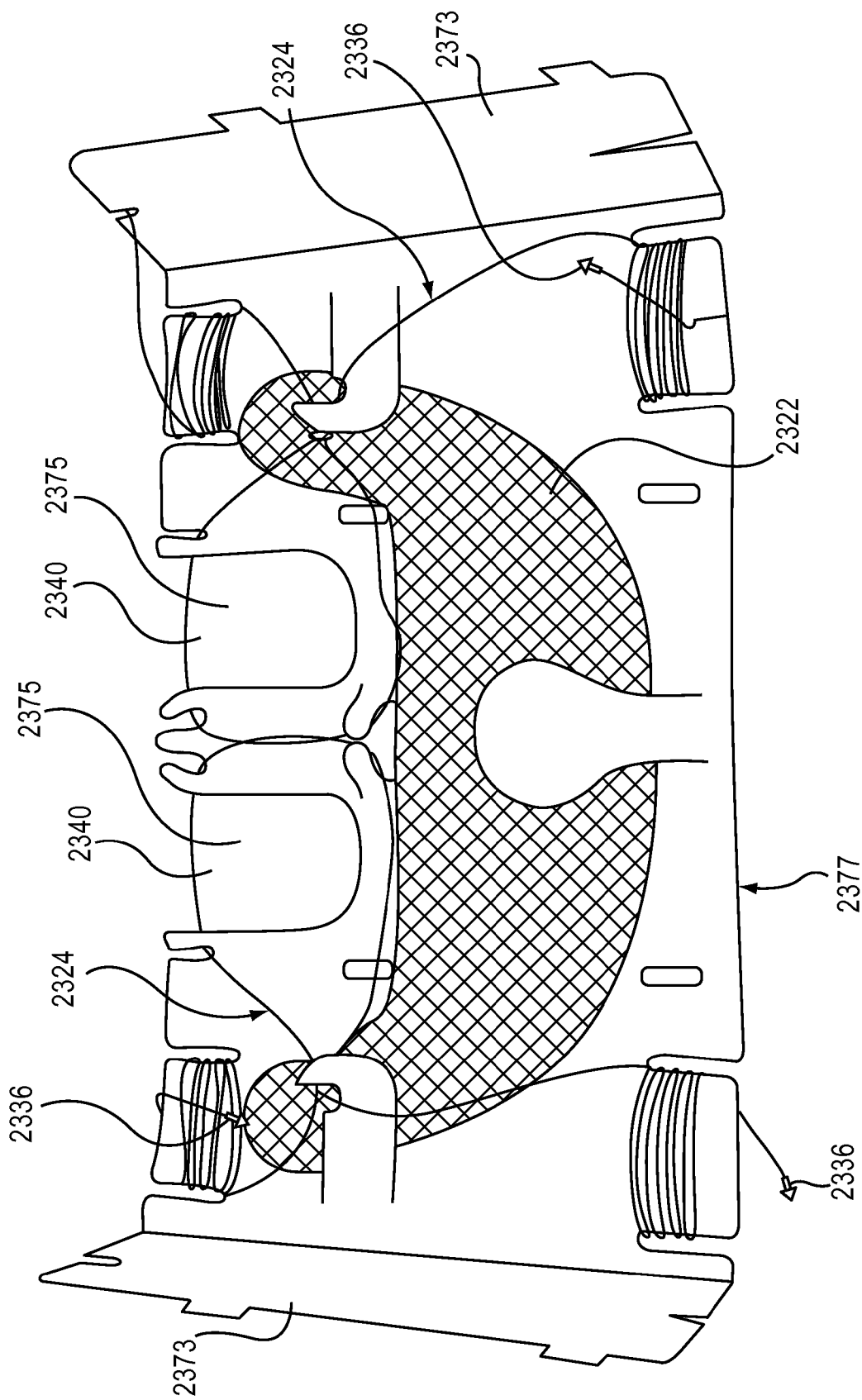
FIG. 44 is a front perspective view of an embodiment of a procedure assistance card shown in an open or first configuration.
Figure 45:
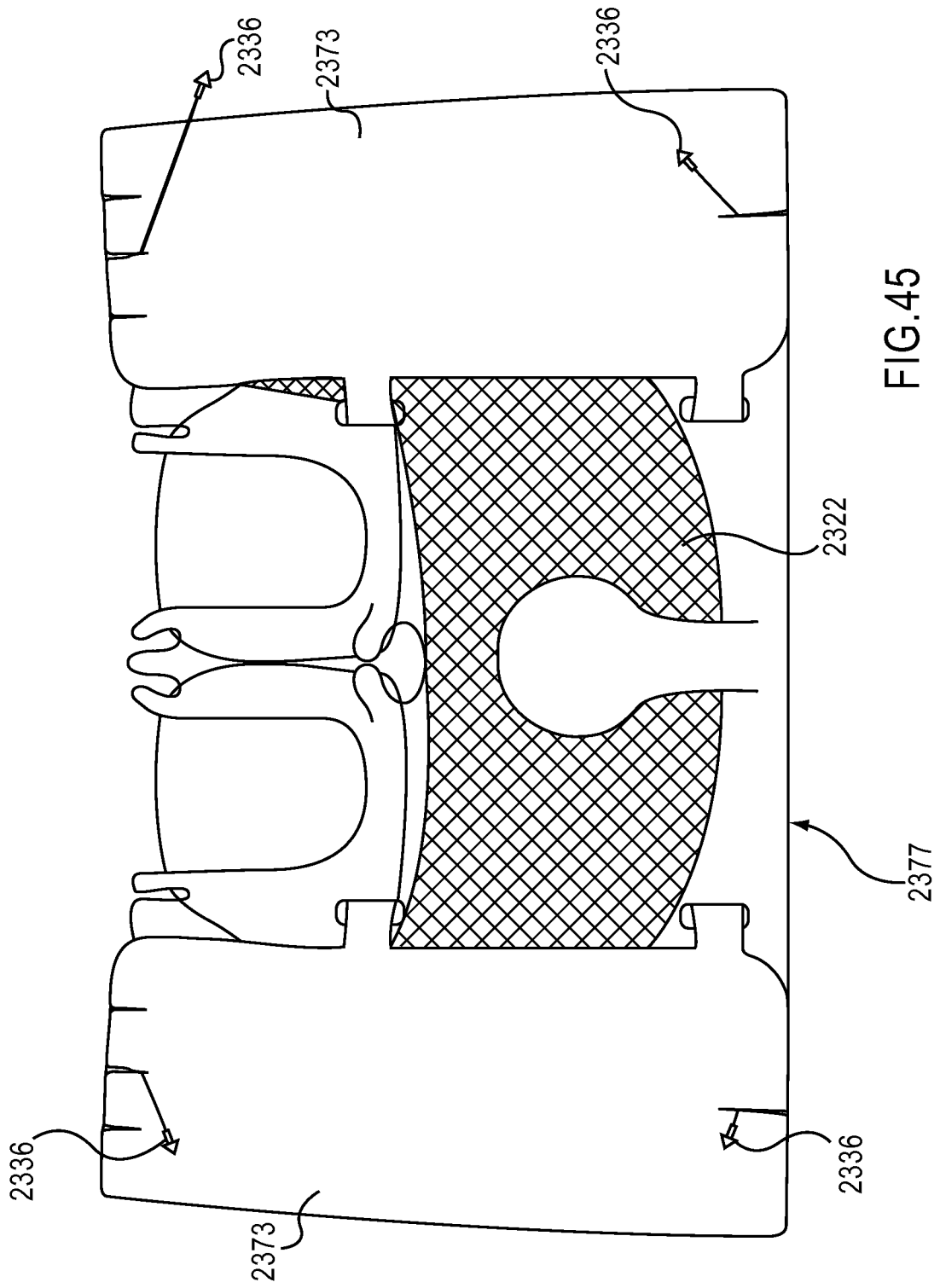
FIG. 45 is a plan view of the card of FIG. 44 shown in a closed or second configuration.

FIGS. 44 and 45 illustrate a procedure assistance member (also referred to herein as a "card" or a "dispenser" or an "implant dispenser") that can be used to assist in organizing an implant assembly during a medical procedure as described herein. The card can be used to package an implant assembly and to help a physician during a medical procedure to deliver and secure the implant assembly. An implant assembly 2300 is shown coupled to a card 2377. FIG. 44 shows the card 2377 in an open configuration and FIG. 45 illustrates the card 2377 in a folded or closed configuration. The implant assembly 2300 includes an implant member 2322, and two sutures 2324. The sutures 2324 form a loop 2340 that can be passed over a shaft of a delivery device, such as the delivery device 144. Although each of the sutures are described as being identical, it should be understood that the two sutures can have different configurations. Thus, the implant assembly 2300 is merely an example of an implant assembly that can be coupled to a card 2377. The implant assembly 2320 is coupled to the card to help organize the ends of the sutures 2324 and the implant member 2322. In this embodiment, the ends of the sutures 2324 each have a trocar needle 2336 coupled thereto for association to a delivery device, such as delivery device 144.

The implant assembly 2320 is coupled to the card 2377 using tabs and slots to maintain the implant 2322 in place and maintain the loops 2340 in an open position for insertion of a portion of a delivery device therethrough. The sutures 2324 are wound on to upper and lower tabs as illustrated in FIG. 44, and the loops 2340 are held in an open position by multiple tabs that are positioned about an opening 2375 defined by the card 2377. End portions 2373 of the card 2377 are then folded over on top of a portion of the implant 2322 and covering the wound portions of the sutures 2324 as shown in FIG. 45. The trocar needles 2336 are passed through upper and lower slots where they are held in place.

In use, a shaft of a delivery device (e.g., delivery device 144) is passed through the loop 2340. The trocar needle 2336 is then removed from the slot and a portion of the suture 2324 is unwound as the trocar needle 2336 is associated to a carrier of the delivery device. The loop 2340 still attached to the card 2377, can be left dangling on the shaft of the delivery device during use to place the suture through, for example, the SSL, uterosacral ligament, or the iliococcygeus muscle. The card 2377 can alternatively be clipped to the drapes by the physician if preferred. After placing the sutures 2324 through the SSL, the trocar needle 2336 is captured in the catch of the delivery device. As the delivery device is removed from the patient's body, the suture is pulled through the loop 2340. The trocar needle 2336 and suture 2324 can be, for example, clipped to the drape on the respective side/location or held by an assistant, to maintain suture organization. The associating of the implant to the SSL on the contra lateral side can then be performed.

Figure 46:
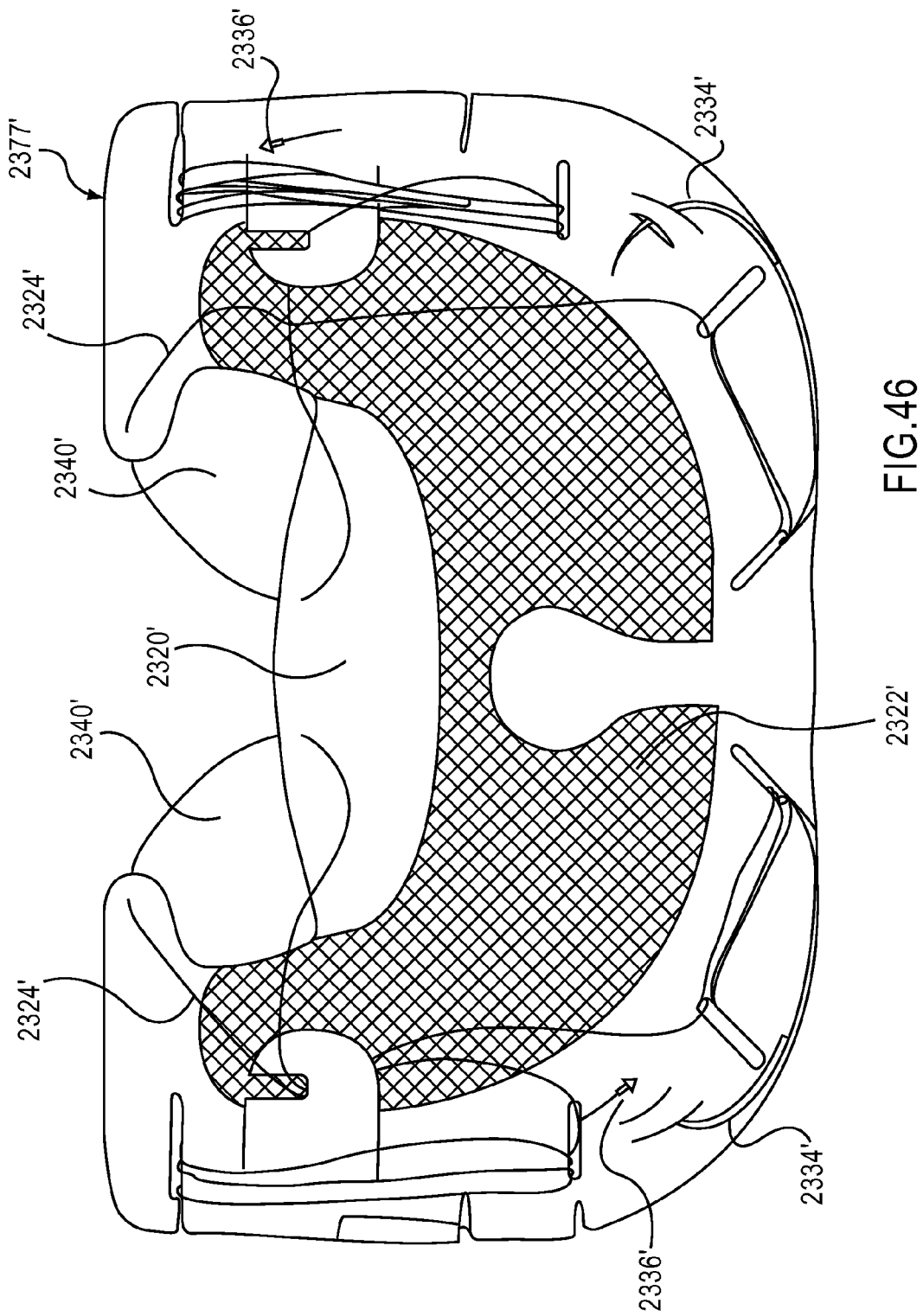
FIG. 46 is a plan view of another embodiment of a procedure assistance card.

The card 2377 can be used with other configurations of an implant assembly, such as for example, an implant assembly 2220 having curved needles and trocar needles. In addition, other card configurations can be used depending on the particular implant assembly and/or suture arrangement. FIG. 46 illustrates a card 2377' having a different configuration of tabs and slots than the card 2377. Here, the card 2377' is used to organize an implant assembly 2320' having an implant 2322', sutures 2324' forming a loop 2340', trocar needles 2336' and curved needles 2334'. The card 2377' can be used in a similar manner as described for card 2377.

Figure 47:
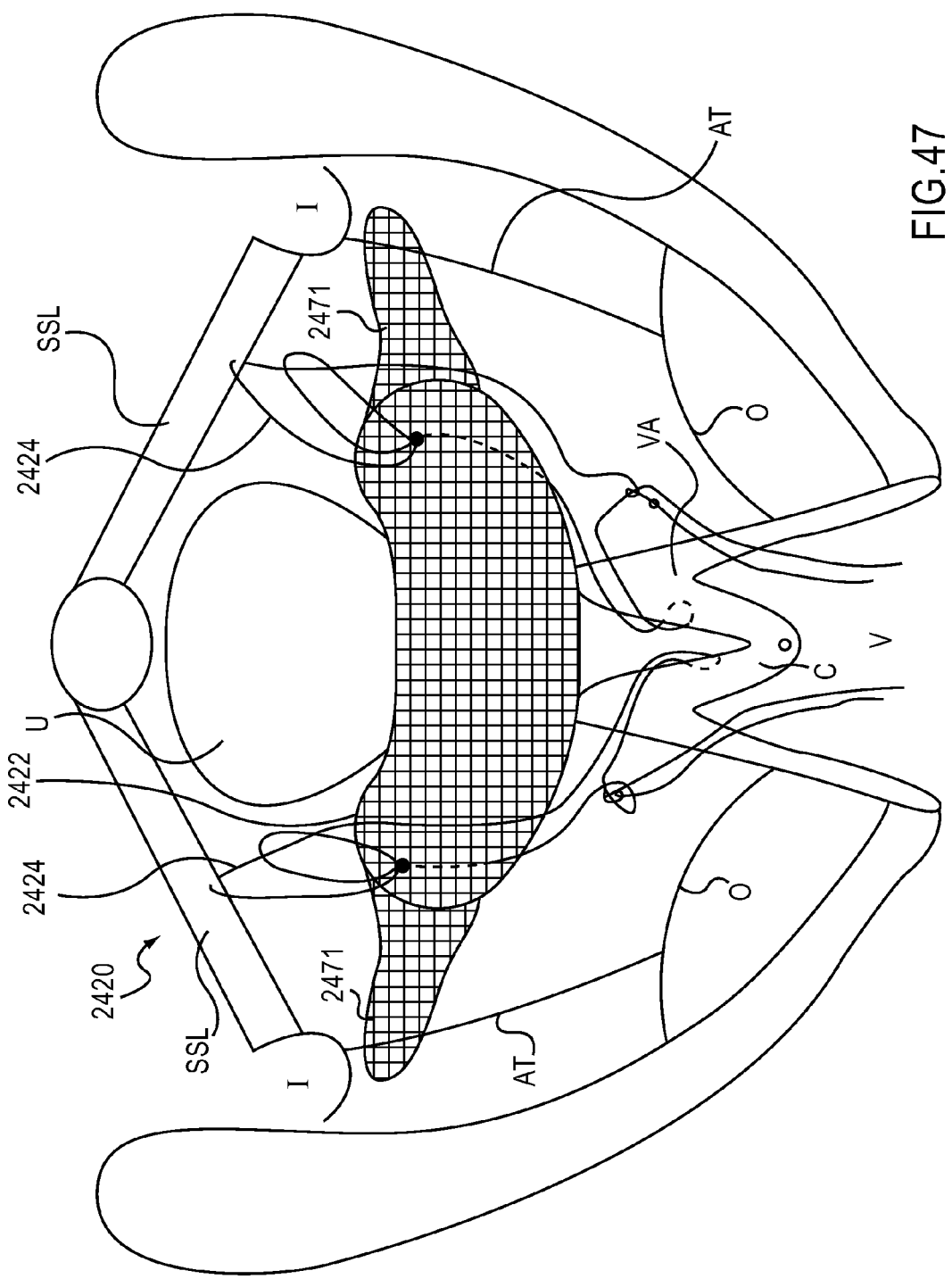
FIGS. 47-54 are each front views of embodiments of an implant assembly shown partially secured within a pelvic region of a patient.

FIGS. 47-53 illustrate embodiments of an implant assembly that span between, for example, left and right sacrospinous ligaments, and having various configurations that include one or more straps or arms. FIG. 47 illustrates an implant assembly 2420 that includes an implant member 2422, and two sutures 2424. In this embodiment, the implant 2422 includes straps 2471 that extend from end portions of the implant 2422. The sutures 2424 can be delivered and secured to the sacrospinous ligaments SSL on opposite sides of a uterus U as previously described. The straps 2471 can be placed through an arcus tendineus AT using, for example, a delivery needle (e.g., delivery needle 1160 shown in FIG. 26) using a deep transobturator approach. A separate delivery needle (e.g., a right hand and a left hand) is used for each side as the orientation of the curved portion of the needle is different for each side. In some embodiments, the implant assembly 2420 can includes two sleeves each of which covers a strap 2471 in a similar manner as described, for example, with respect to FIGS. 34 and 35. Alternatively, the straps 2471 can be delivered through the arcus tendineus AT using a delivery device, such as delivery device 144. The straps 2471 can help support the vagina V, for example, to a level of the white line (i.e., the AT), or the ischio spine I.

Figure 48:
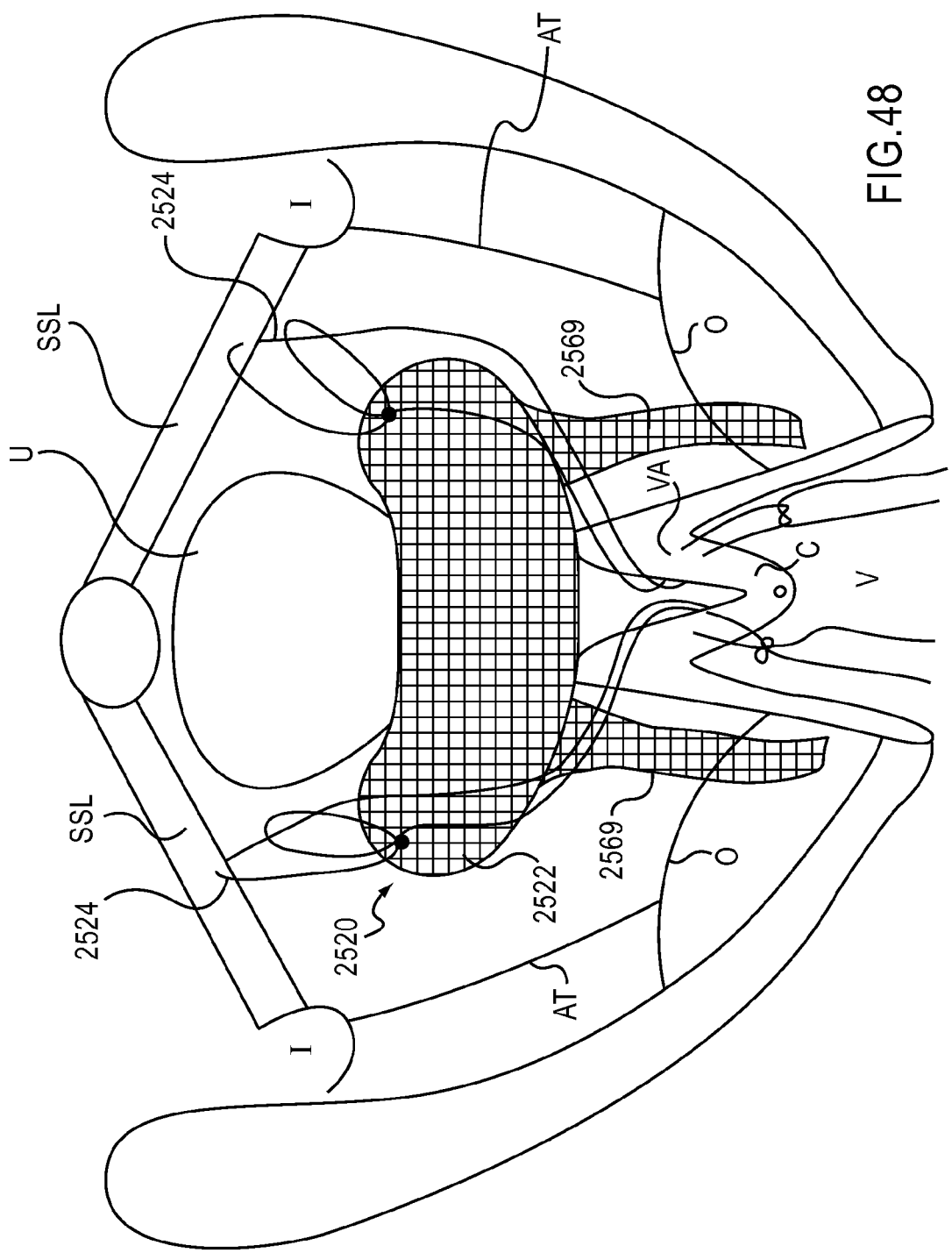
Figure 49:
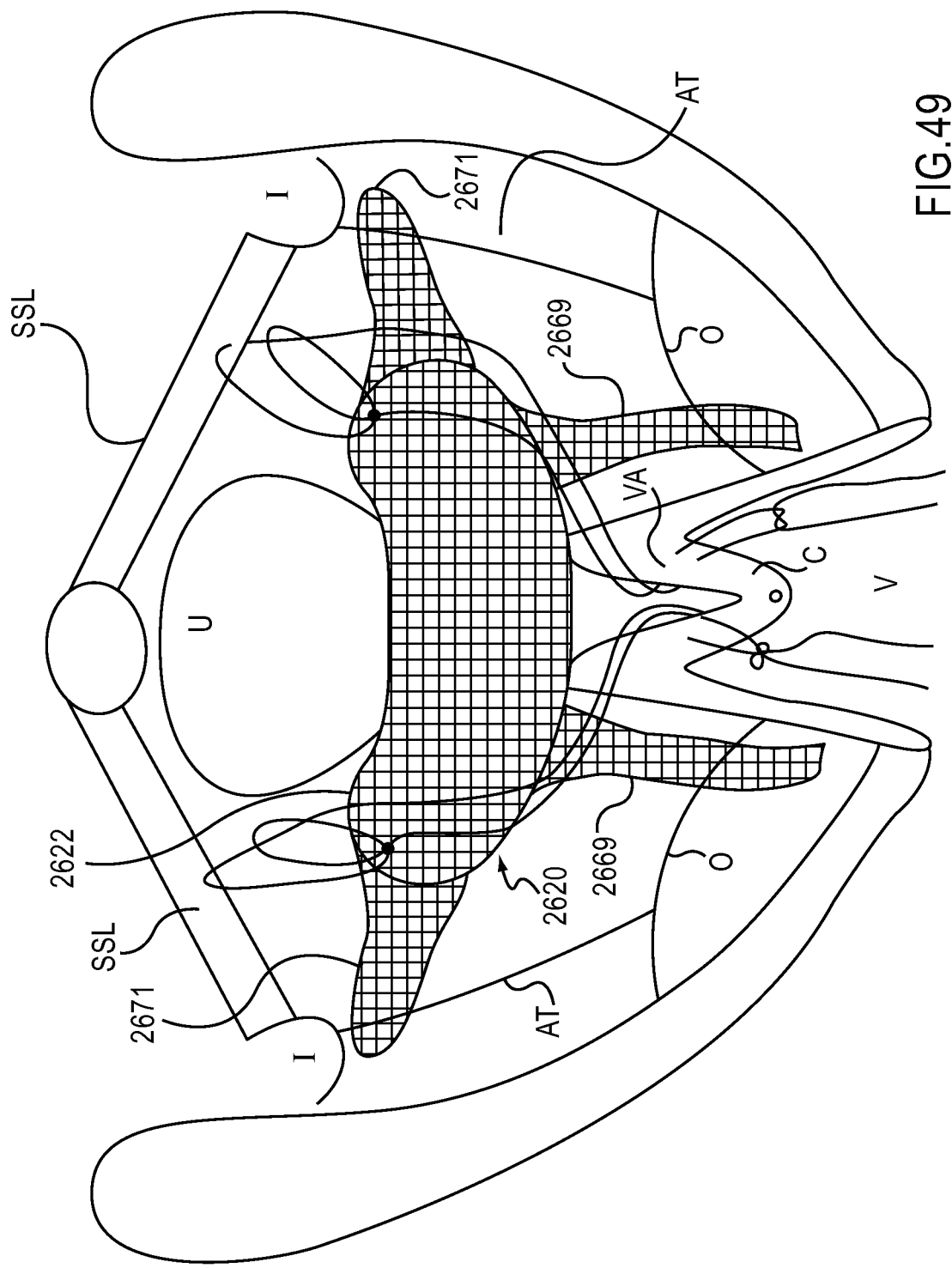

FIG. 48 illustrates a similar embodiment of an implant assembly. An implant assembly 2520 includes an implant member 2522 and two sutures 2524 coupled to the implant 2522. In this embodiment, the implant 2522 includes anterior straps 2569 that extend downward from an edge of the implant 2522. The straps 2569 can be placed through an upper obturator muscle O to help support, for example, a cystocele. The straps 2569 can be placed with a delivery device such as the delivery device 1160. FIG. 49 illustrates an implant assembly 2620 that includes straps 2671 similar to straps 2471 (FIG. 47) that can be secured to, for example, an arcus tendineus AT, and anterior straps 2669 similar to straps 2569 (FIG. 48) that can be secured to, for example, an obturator muscle O.

Figure 50:
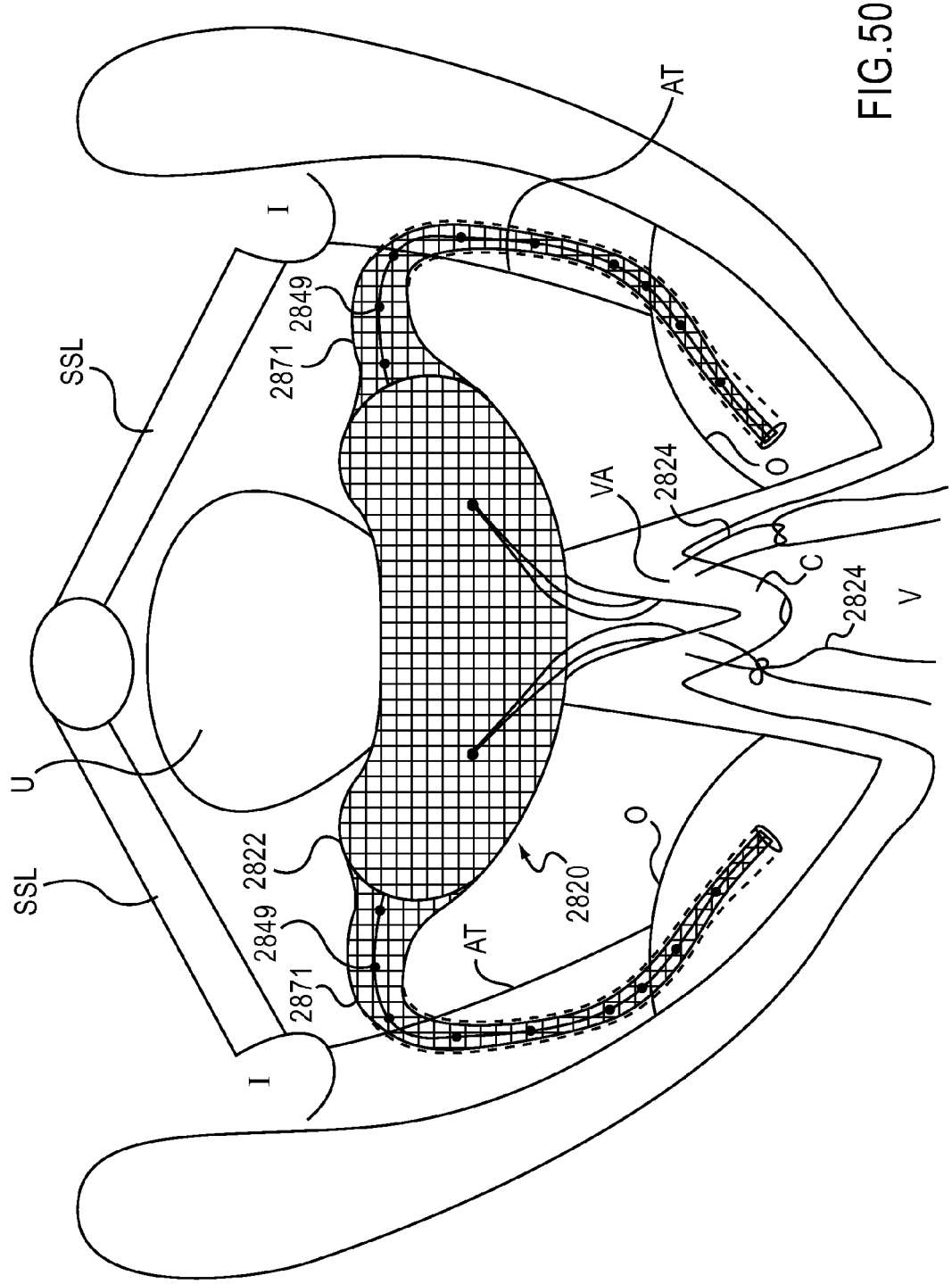
Figure 51:
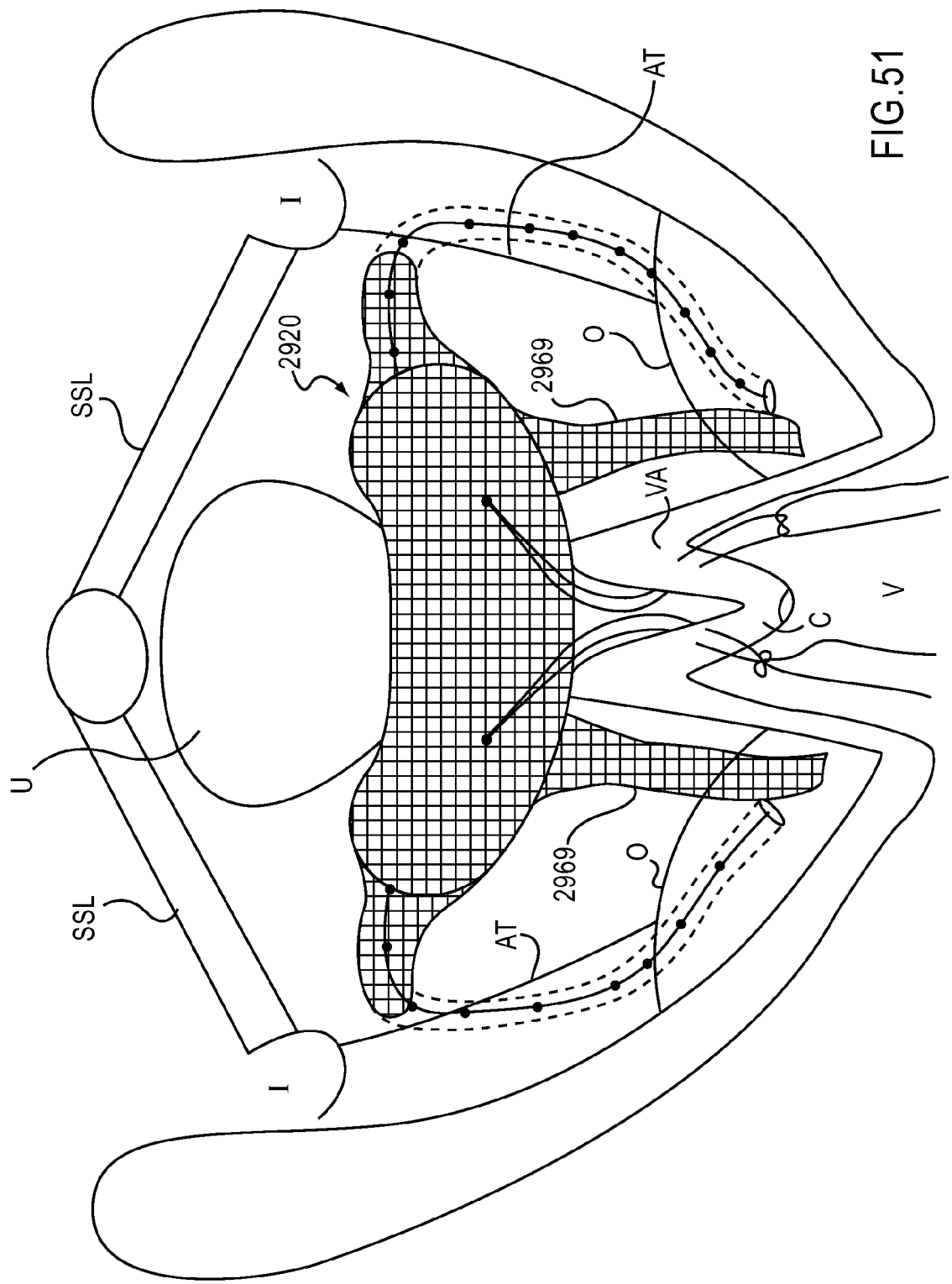

FIG. 50 illustrates an implant assembly 2820 having straps 2871 extending from ends of an implant member 2822. Here, sutures 2824 are used to secure the implant 2822 to the vaginal apex VA using, for example, a delivery device such as delivery device 144, or suture passers to pass the ends of the sutures 2824 through the wall of the vaginal apex VA. A procedure as described above with reference to, for example, FIG. 26, can be used to pull the straps 2871 through the arcus tendineus AT using a deep transobturator delivery needle.

As shown in FIG. 50, in this embodiment, the sutures 2824 are secured to the implant 2822 by an interval of knots 2849 extending through the length of the straps 2871. The knots 2849 can also be placed at other locations along the implant 2822. The knots 2849 can help the sutures 2824 support the weight of the uterus when the straps 2871 are trimmed to skin level. The straps 2871 and the sutures 2824 in the vaginal apex VA are initially placed, and then final tensioning and knotting in the vagina can occur. The straps 2871 can alternatively be placed using a suturing delivery device or a transglutual delivery needle. In another embodiment shown in FIG. 51, an implant assembly 2920 can include all of the features of implant assembly 2820, but with anterior straps 2969, similar to straps 2669 (FIG. 49), that can be placed through the upper obturator muscle O to help support a cystocele. The anterior straps 2969 can be placed using, for example a delivery needle, such as delivery needle 1160.

Figure 52:
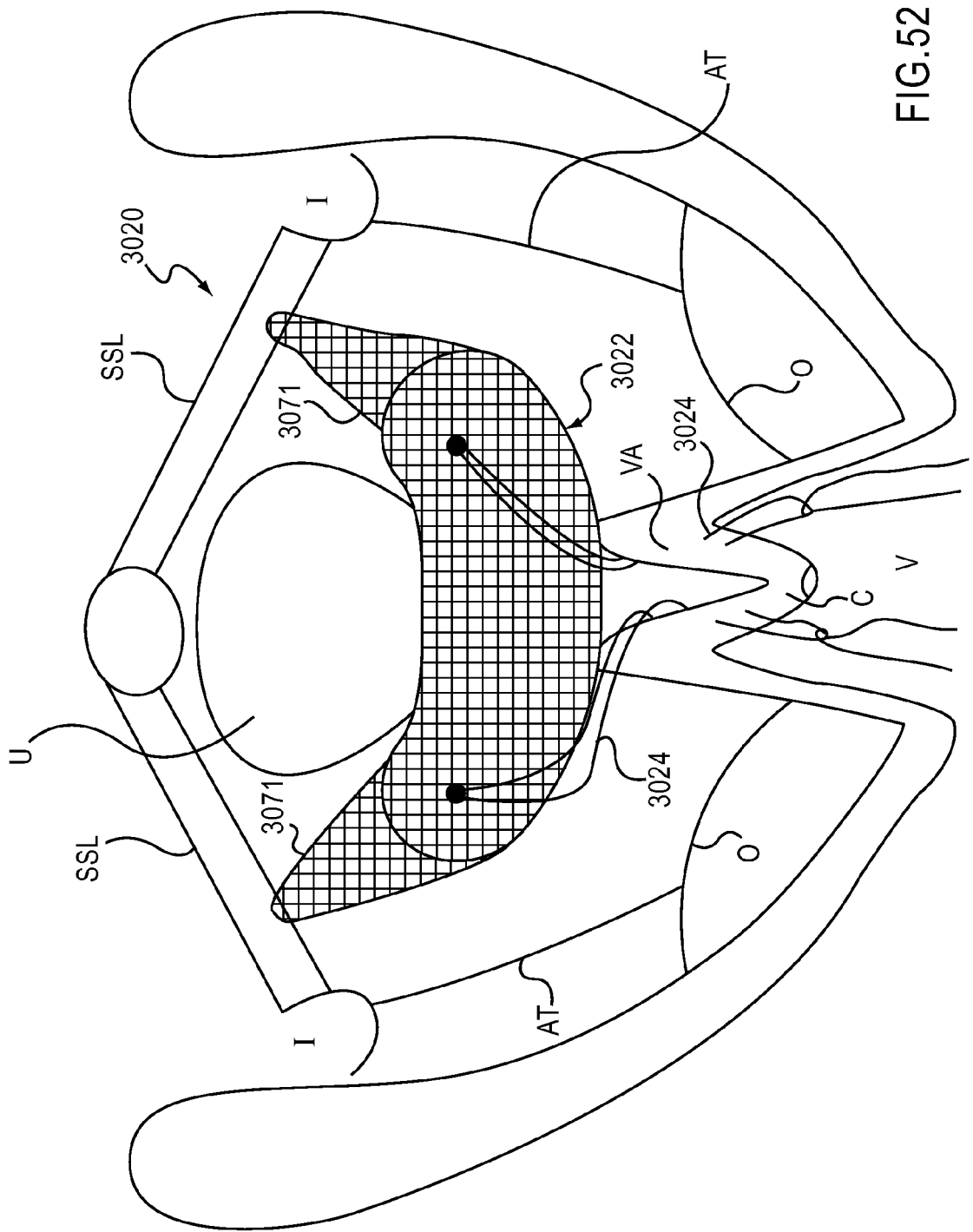

FIG. 52 illustrates an implant assembly 3020 having an implant member 3022, sutures 3024 and straps 3071. In this embodiment, the straps 3071 are secured directly to the sacrospinous ligament SSL without sutures. For example, the implant assembly 3020 can include sleeves that cover the straps 3071, and connectors to associate the implant strap 3071 to a delivery needle (see e.g., FIG. 37). A delivery needle such as delivery needle 1160 can then be passed into a vaginal incision and through the SSL. A notch on the delivery device can then be associated to the connector on the strap 3071 so that the delivery needle can pull the strap 3071 through the SSL. The sleeve and connector can then be cut from the implant assembly as previously described. The sutures 3024 are used to secure the implant 3022 to the vaginal apex VA. In alternative embodiments, the straps 3071 can be secured to the SSL using a suturing type delivery device. In such an embodiment, a suture and trocar needle can be coupled to the strap 3071 and used to associate the strap 3071 to the delivery device. After pulling the suture and portion of the strap 3071 through the SSL, the suture and trocar can be cut off.

Figure 53:
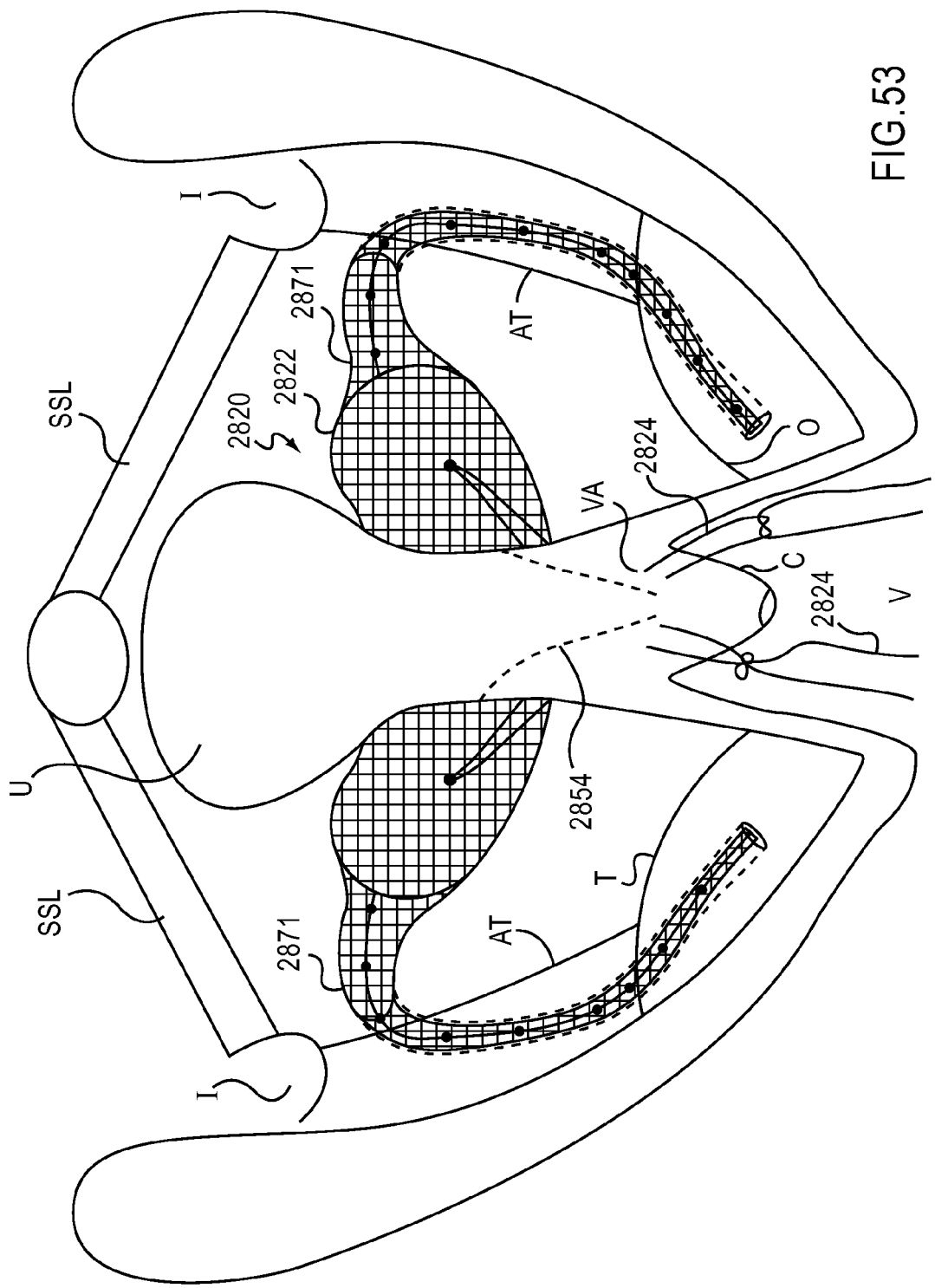

In some procedures it may be desirable to place the implant assembly posteriorly. FIG. 53 illustrates the implant assembly 2820 used for uterine preservation and posterior repair. For the posterior placement of implant assembly 2820, a posterior incision 2854 is made on an inverted vagina V. The supporting sutures 2824 are tied or knotted to the straps 2871 of the implant member 2822. The implant 2822 is placed through the incision 2854 and behind the uterus U. The straps 2871 can be pulled through the arcus tendineus AT using, for example, a deep transobturator delivery needle as described previously. The sutures 2824 are tied to the vaginal apex VA.

Figure 54:
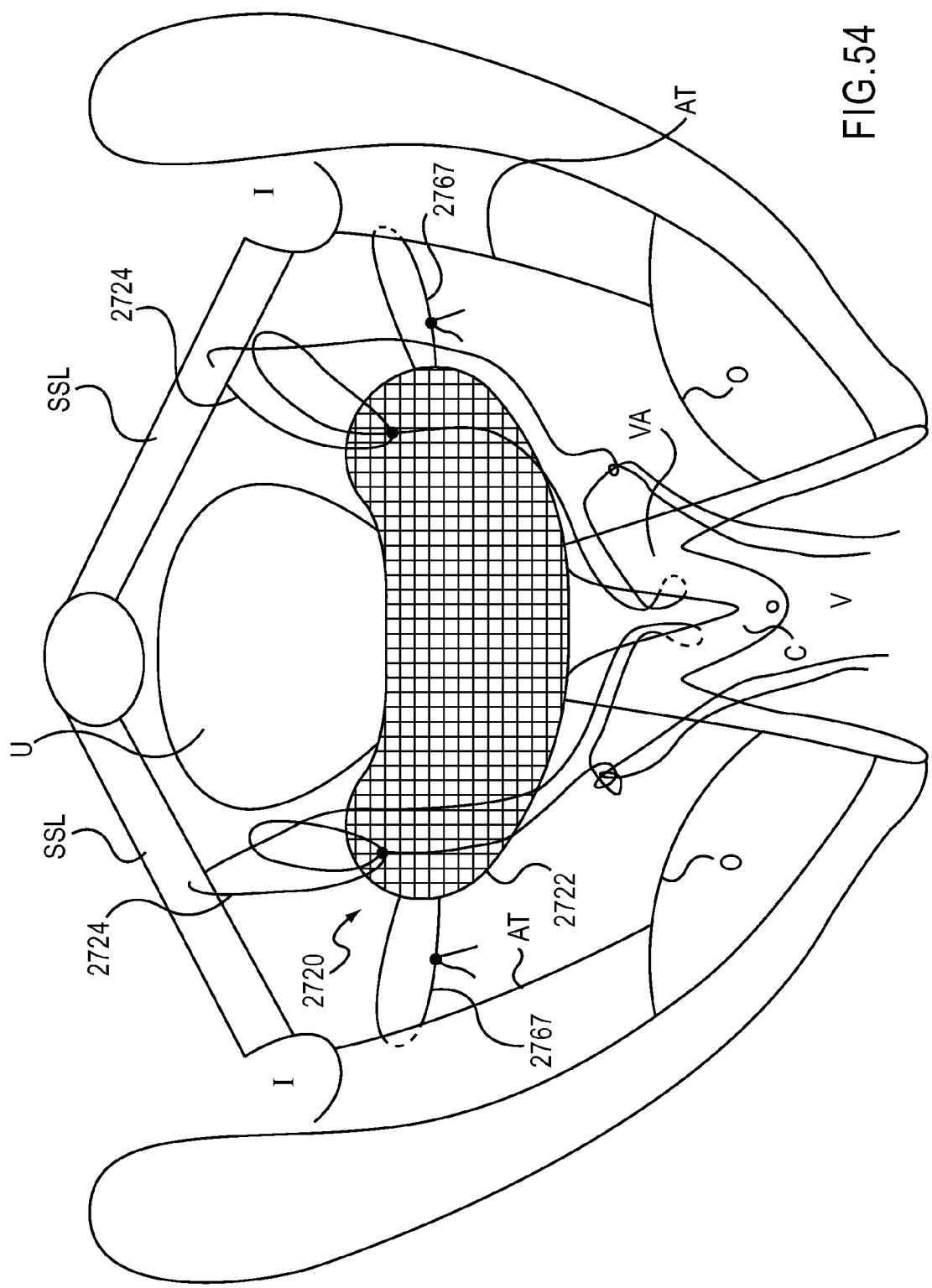

FIG. 54 illustrates another embodiment of an implant assembly 2720 that includes an implant member 2722 and sutures 2724. The sutures 2724 can be used to secure the implant 2722 to the sacrospinous ligament SSL on each side of the uterus U, and to the vaginal apex VA. In this embodiment, the implant 2722 is also secured to the arcus tendineus AT using sutures 2767. A delivery device, such as delivery device 144, or other suturing device, can be used to deliver and secure the sutures 2724, as well as the sutures 2767.

Figure 55:
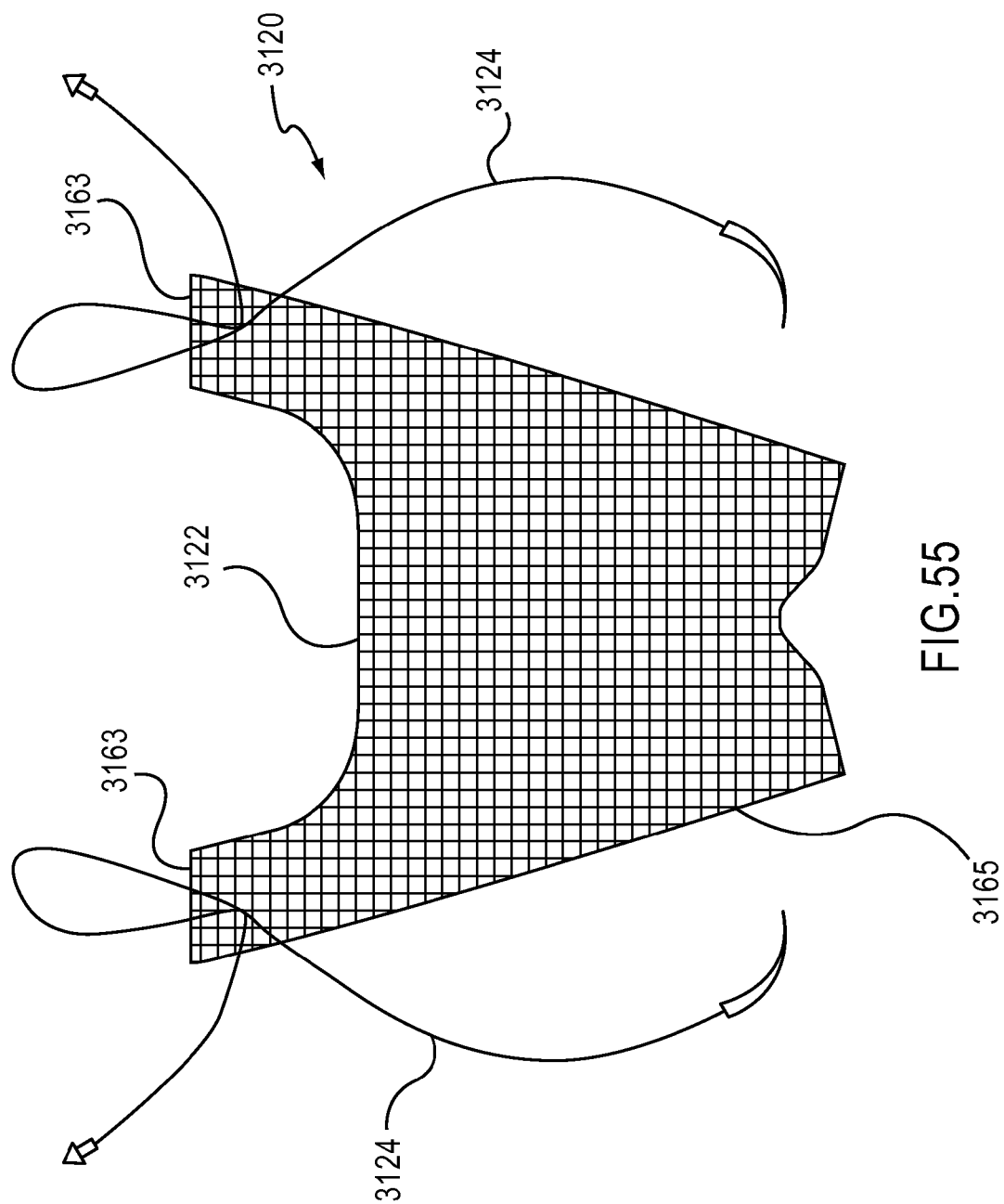
FIGS. 55-58 are each front views of embodiments of an implant assembly.

FIGS. 55-58 each illustrate a different configuration of an implant assembly including a support portion that can have various configurations. FIG. 55 illustrates an implant assembly 3120 having an implant member 3122 and sutures 3124. The implant 3122 includes a support portion 3165 and tabs 3163. The tabs 3163 are similar to straps described in previous embodiments, but have a shorter length that helps prevent over tensioning/slinging of a uterus. The implant assembly 3120 can be delivered, for example, using a suturing delivery device, such as delivery device 144. The sutures 3124 can each be coupled, for example, to a sacrospinous ligament, and the support portion 3165 can be secured to, for example, a vaginal apex, using a suture or other fastener.

Figure 56:
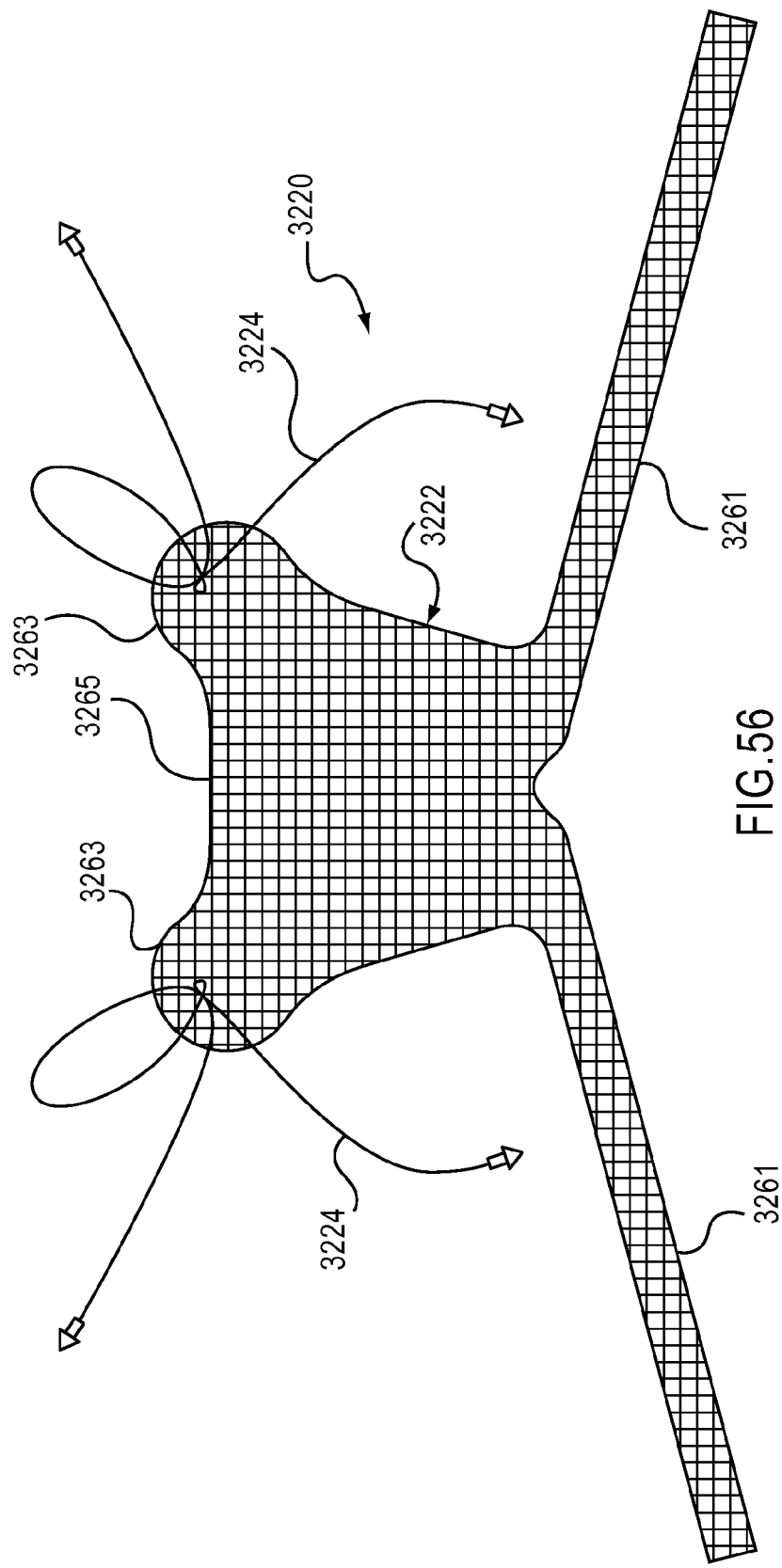
Figure 57:
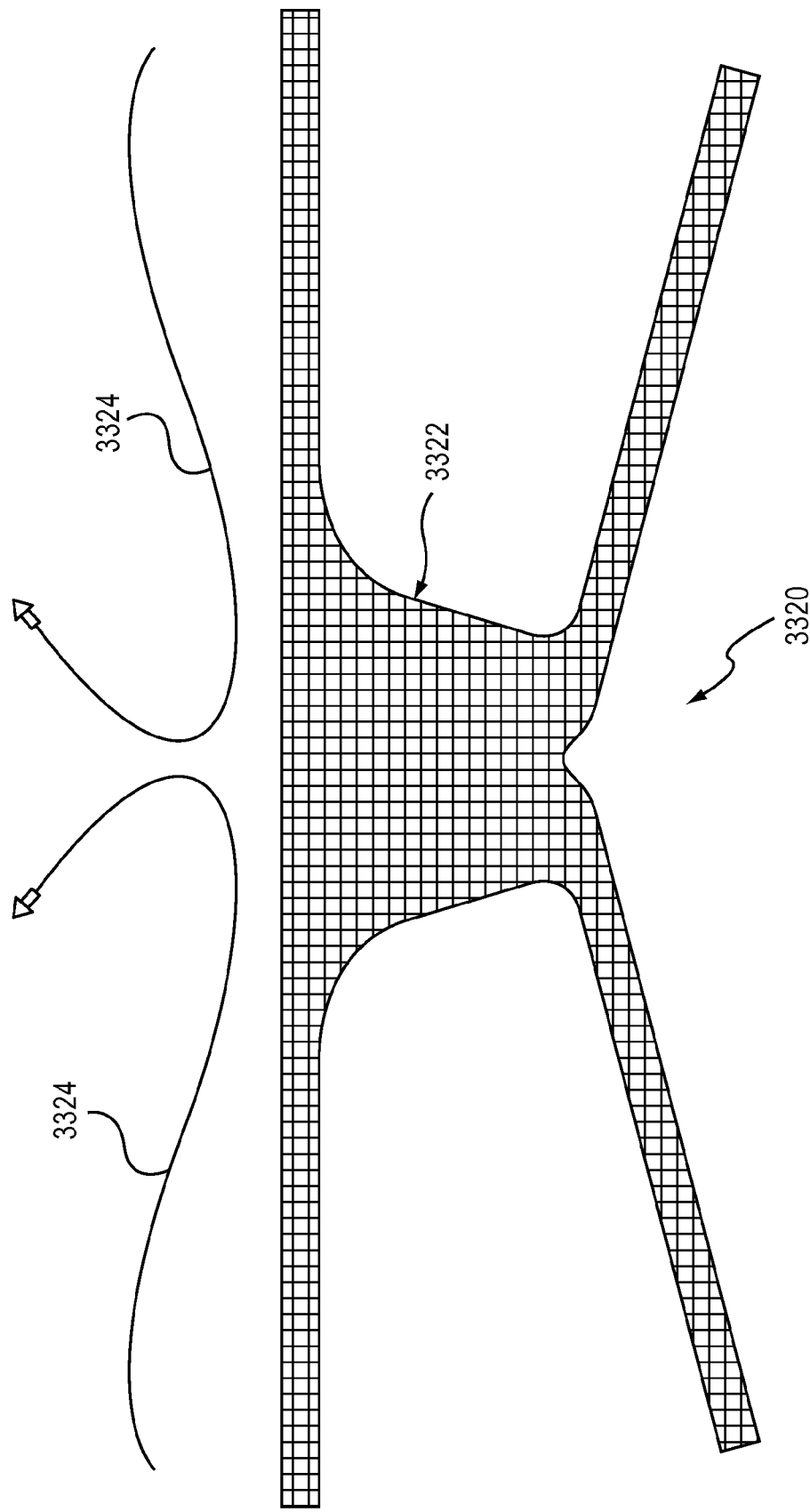

FIG. 56 illustrates an implant assembly 3220 having an implant member 3222 and sutures 3224. In this embodiment, the implant 3222 includes a support portion 3265, circular tabs 3263, and straps 3261. The straps 3261 can be delivered, for example, using a transobturator delivery needle, and a suturing device, such as a delivery device 144, or suture passer can be used to pass the sutures 3224 through a wall of a vaginal apex. The straps 3261 can be passed through, for example, an obturator muscle or an arcus tendineus. FIG. 57 illustrates an implant assembly 3320 having an implant member 3322 and two sutures 3324. In this embodiment, the implant 3322 and sutures 3324 are provided separately. A user can attach the sutures 3324 to the implant 3322 as needed for a particular procedure. The user can alternatively use attachment means, other than sutures for securing the implant within the pelvic region. For example, various configurations for an anchor can be used, such as T-fasteners. Such a fastener can be secured to, for example, a sacrospinous ligament, and tied to the implant. Other fasteners such as, for example, staples, barbs, or twists ties, can be used to associate the implant to the desired anatomic structure within the pelvic region.

Figure 58:
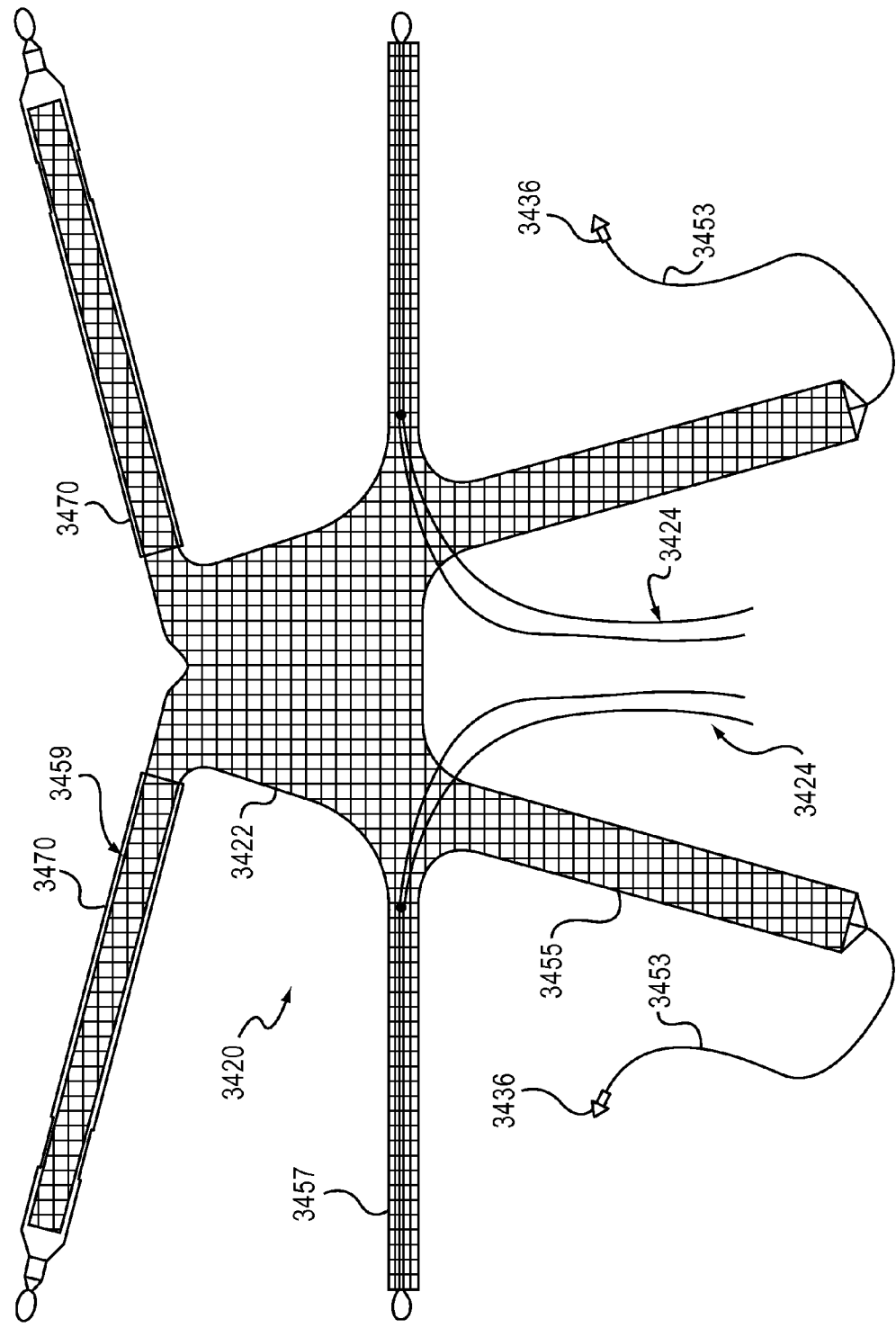

FIG. 58 illustrates a six strap implant assembly 3420 having an implant member 3422 that includes anterior straps 3459, mid-line straps 3457, and posterior straps 3455. Sutures 3424 are coupled to the implant 3422 to secure the implant 3422 to a vaginal apex. The anterior straps 3459 are partially covered by a sleeve 3470, and can be placed, for example, through an obturator using a delivery needle such as delivery needle 1160. The mid-line straps 3457 are not sleeved and can be placed through, for example, an arcus tendineus using a deep transobturator needle. The posterior straps 3455 can be pulled through, for example, the sacrospinous ligament and are anchored within the ligament. These are merely example locations, as the various straps can alternatively be secured to other anatomical structures (e.g., a levator muscle) within a pelvic region. In one example of securing the implant member 3422 within a pelvic region, a suturing device, such as a delivery device 144, can be used to secure the posterior straps 3455 to a sacrospinous ligament. For example, trocar needles 3436 disposed on the ends of sutures 3453 that are coupled to the posterior straps 3455, can be associated to the delivery device. The sutures 3453 (and trocar needles 3436) can be removed after delivery of the implant assembly 3420. In another example, the sutures 3424 can be secured to the vaginal apex VA using, for example, suture passers, or a suturing delivery device.

Figure 59:
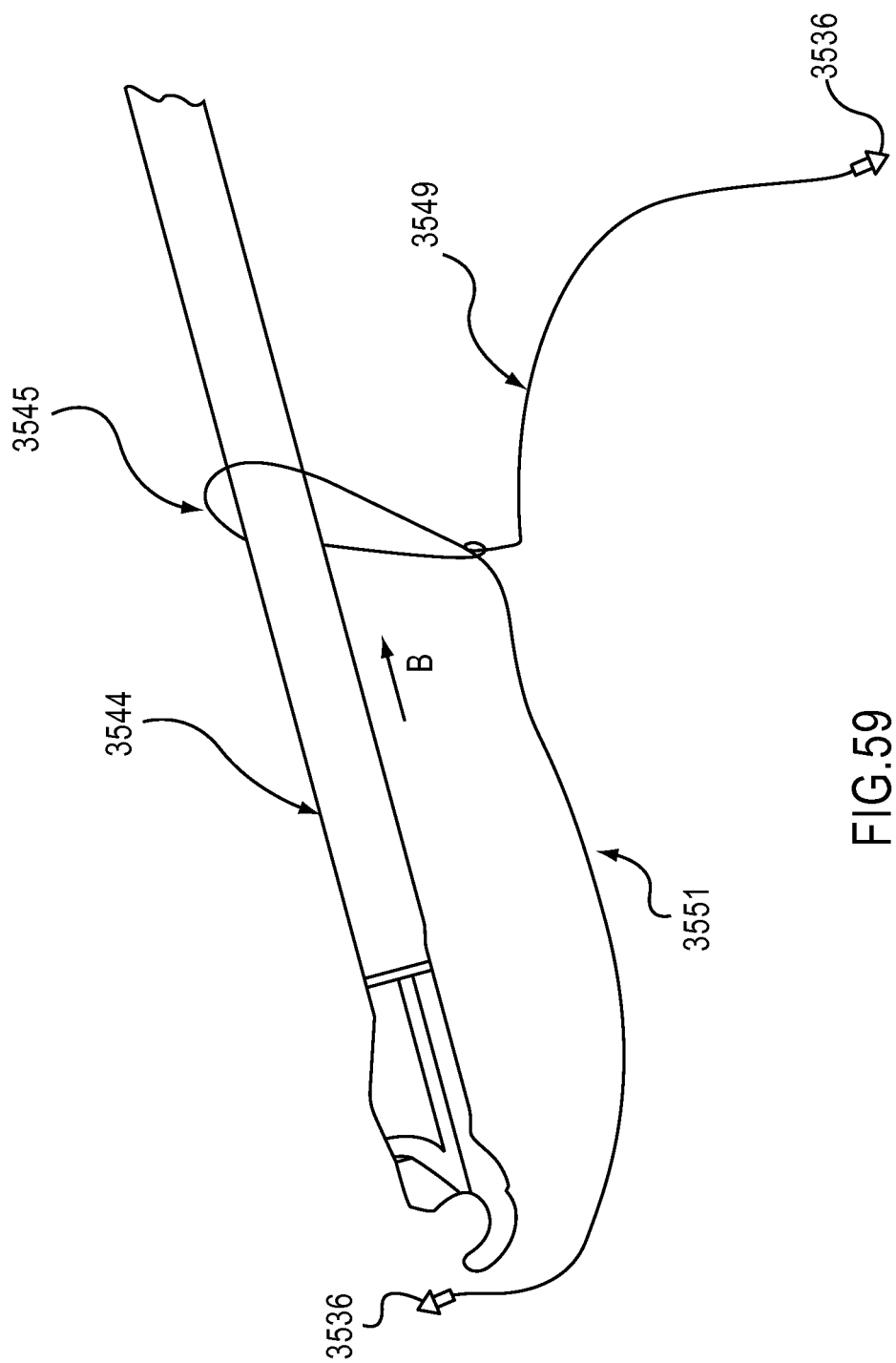
FIG. 59 is a side view of a delivery device and an embodiment of a suture assembly.

FIGS. 59-63 illustrate various embodiments of an implant assembly in the form of a suture assembly used to treat a vaginal prolapse and suspend a vagina in a patient with or without a uterus. FIG. 59 shows a suture assembly 3551 that includes a suture 3549, and trocar needles 3536 disposed at each end of the suture 3549 that are coupled to a suturing delivery device 3544. A noose or loop 3545 is formed with the suture 3549 and is shown loosely received on a shaft of the delivery device 3544, as described above in previous embodiments. In some embodiments, a suture assembly may not include a noose, but can be still be deployed using a delivery device, such as delivery device 144. In this embodiment, one or more sutures assemblies 3551 can be used to approximate a vagina to a sacrospinous ligament. The sutures 3549 can be used to support and/or re-suspend a vaginal prolapse, or can be used in conjunction with an implant member or implant assembly to secure the anatomy in place such that tissue in growth can occur.

Figure 60:
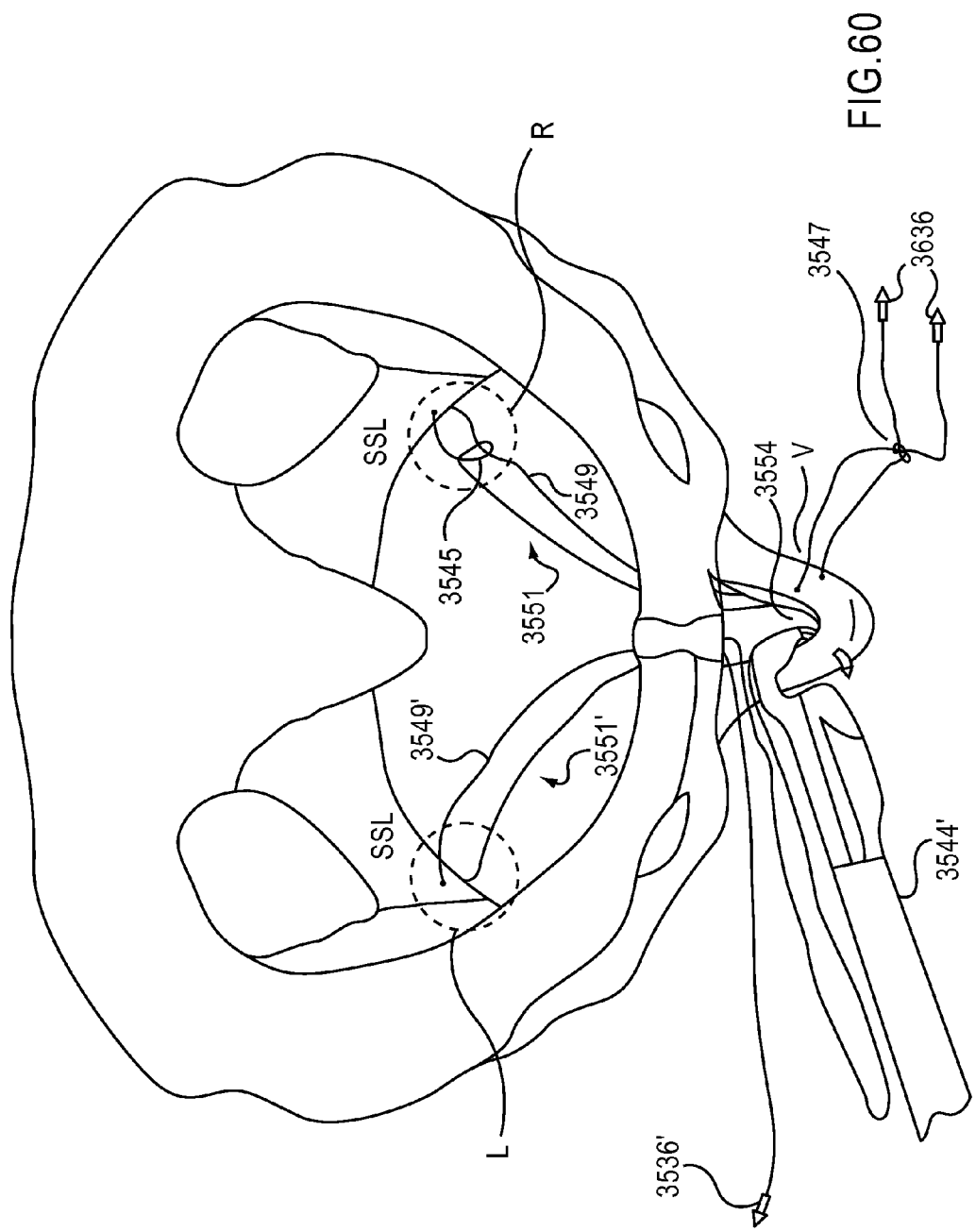
FIG. 60 is a top view of a pelvic region illustrating placement of embodiments of suture assemblies within the pelvic region.
Figure 61:
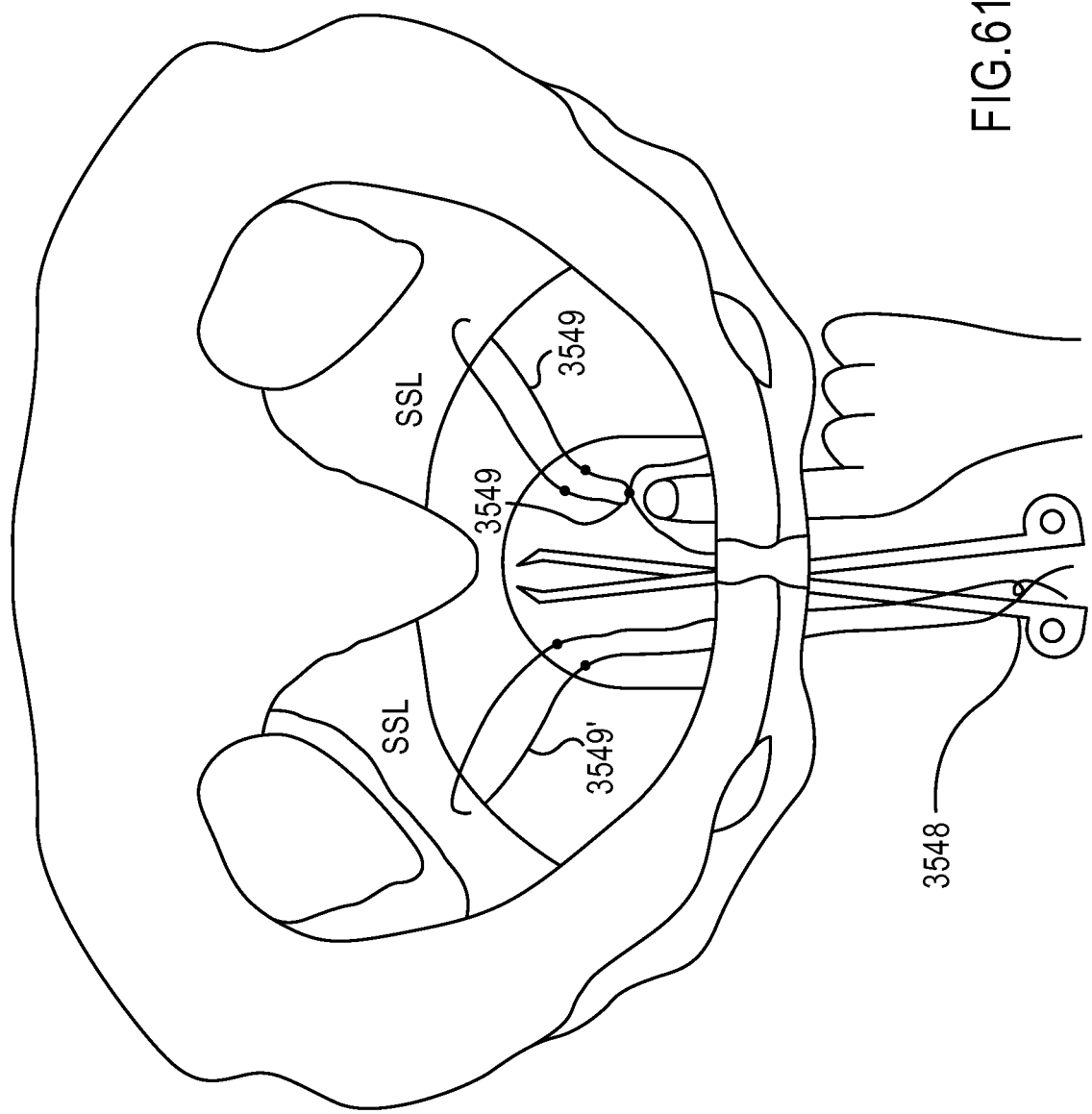
FIG. 61 is a top view of a pelvic region illustrating securement of the suture assemblies of FIG. 60.

FIGS. 60 and 61 are each top views of a pelvic region illustrating suture assemblies being secured to a sacrospinous ligament SSL on each side of a pelvic region in a patient with no uterus. The suture assembly 3551' is similar to the suture assembly 3551 shown in FIG. 59 except the suture assembly 3551' does not include a noose or loop (e.g., loop 3545). The suture assembly 3551' includes trocar needles 3536' on both ends of a suture 3549', however, only one trocar needle is shown in FIG. 60 as the other is loaded into a delivery device 3544'.

As shown in FIG. 60, the suture 3549' of suture assembly 3551' is shown passed through a SSL on a left side L of the pelvic region, and the suture 3549' of suture assembly 3551 is passed through a SSL on a right side R of the pelvic region. Each suture 3549, 3549' can be passed through the respective SSL using a suturing device, such as delivery device 3544 and delivery device 3544'. The same delivery device can be used for both the right and left sides. Alternatively, a different delivery device can be used for each side. As described previously, after the suture is passed through the SSL, the delivery device can be removed. For example, the delivery device 3544 can be pulled through the noose 3540 in the direction of arrow B as shown in FIG. 59. This will cause the noose 3540 of the suture assembly 3551 to tighten and pulley towards the SSL on the right side R and form a knot. The suture assembly 3551' on the left side of the pelvic region can be tightened and pulled toward the SSL in a similar manner by pulling the delivery device 3544' out of the pelvic region and out of the vagina V. The delivery devices 3544 and 3544' can be used to pass the ends of the sutures 3549 and 3549' though a wall of the vagina V. For example, FIG. 60 illustrates the delivery device 3544' passing a trocar needle of the suture assembly 3551' through an anterior vaginal incision 3554 and through a wall of a vagina V. After the sutures have been passed through the vaginal wall, the ends of the sutures 3549 and 3549' can be crossed, for example, as illustrated at point 3547 in FIG. 60.

To secure the suture assembly 3551, the suture 3549 is tensioned and a knot is formed (not shown) at or near the SSL on the right side R. As shown in FIG. 60, the suture 3549' of the suture assembly 3551' is not knotted at the SSL on the left side L. Although the two different types of implant assembly are illustrated in FIG. 60, it is to be understood, that the same type of implant assembly can be used on both sides. Simultaneously with tensioning the sutures 3549, 3549', the vagina V can be moved or reverted inward into the pelvic space. A manipulator device and/or holding device (or other medical device) as described above can be used to assist with manipulating the position of the vagina. FIG. 61 illustrates a holding device 3548 supporting the vagina V deep in the pelvic space to gain the full length of the vagina as a forefinger of the physician is used to push the crossed suture 3549 inward to form a knot to the vagina V. Additional knots can be formed in the same manner. A knot is formed on the contra lateral side in the same manner to suspend the vagina V symmetrically and deep within the pelvic space.

Figure 62:
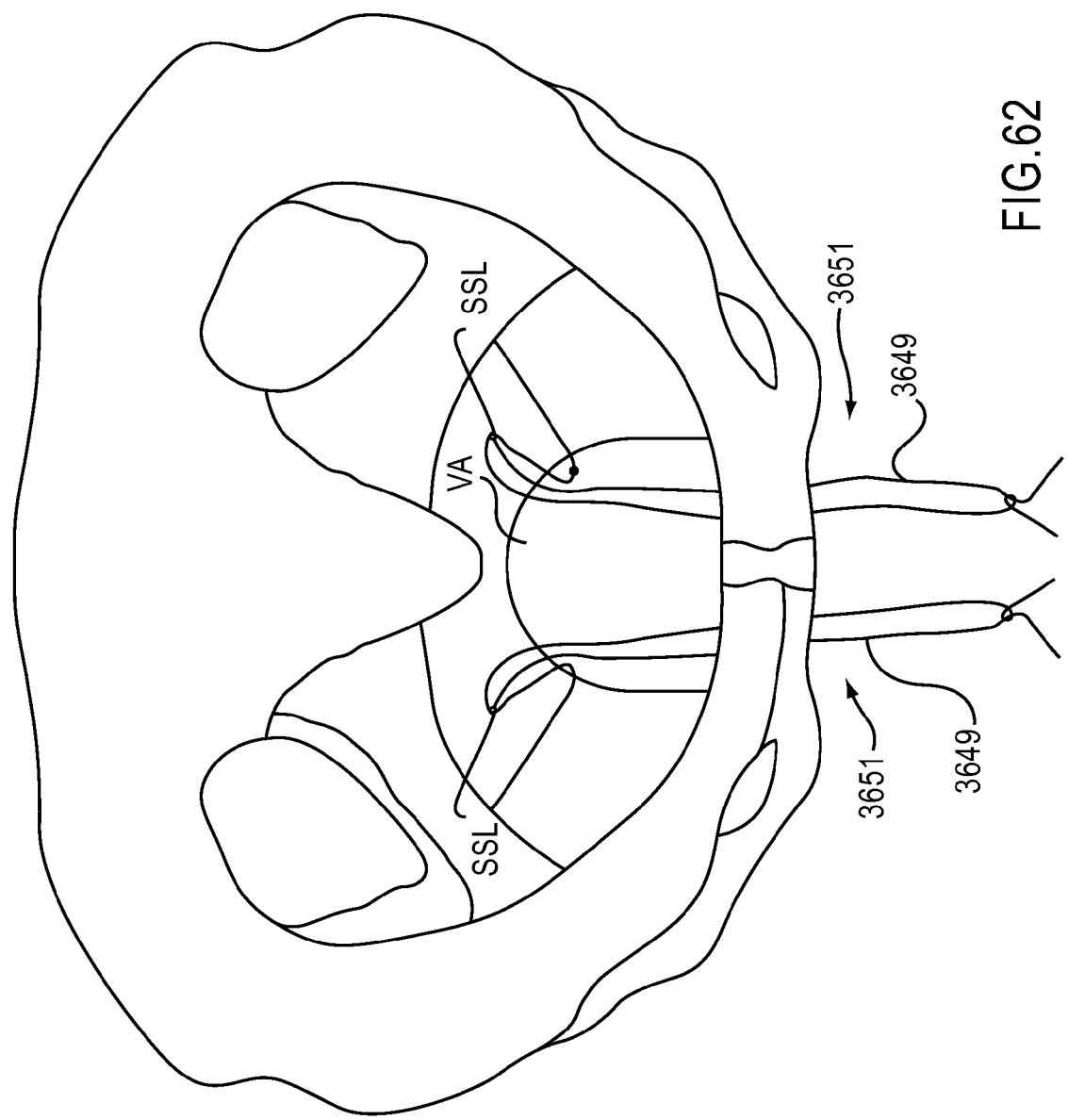
FIG. 62 is a top view of a pelvic region illustrating securement of a pair of suture assemblies within the pelvic region.
Figure 63:
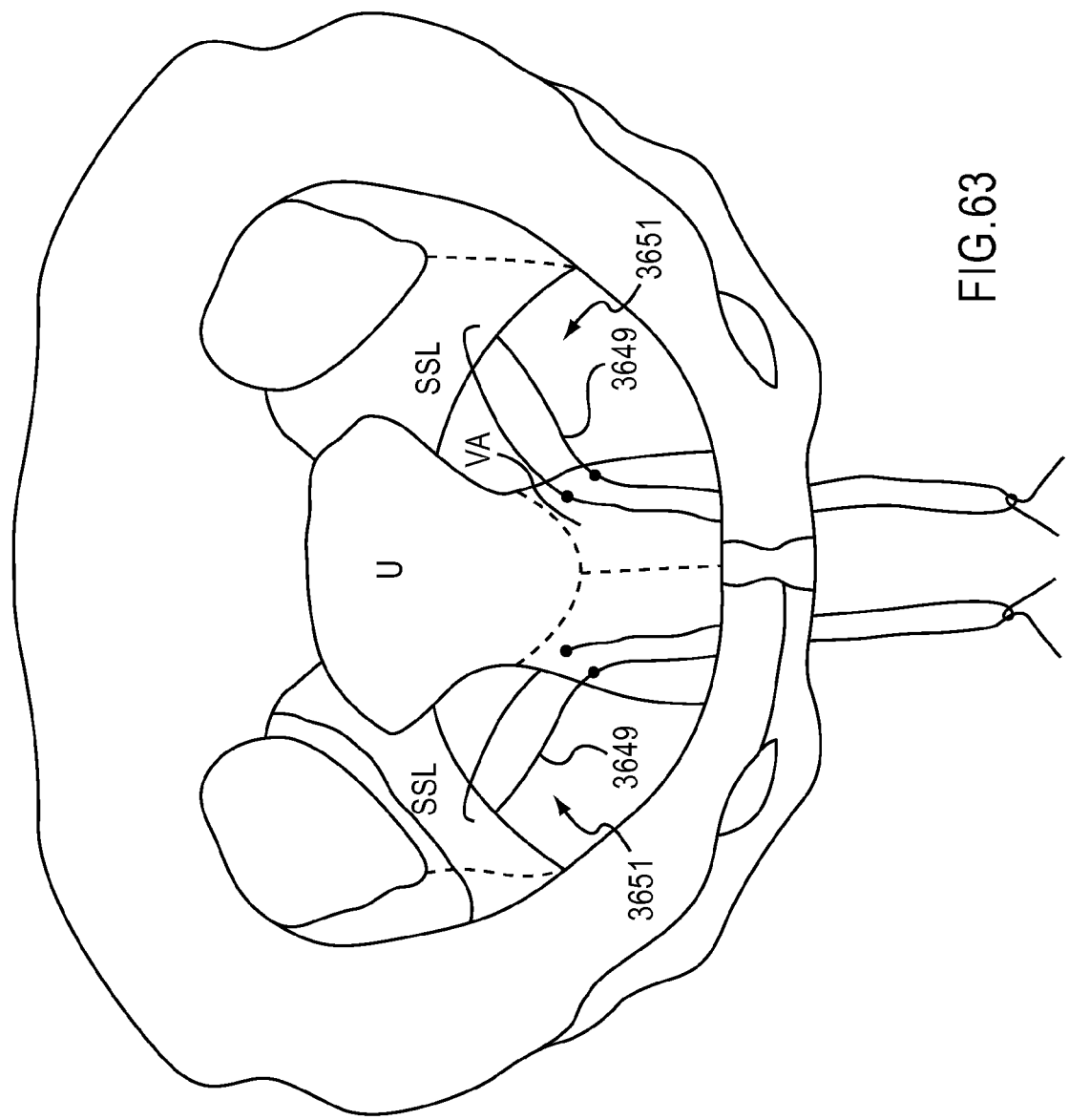
FIG. 63 is a top view of a pelvic region illustrating securement of a pair of suture assemblies within the pelvic region.

FIG. 62 illustrates another embodiment of a suture assembly where the suture assembly is secured with knots tied between a vaginal apex VA and a sacrospinous ligament SSL, rather that in the vaginal canal. A pair of suture assemblies 3651 each including a suture 3649 are shown passed through the sacrospinous ligament SSL on each side of a pelvic space. The sutures 3649 can be passed through a wall of the vagina and back through the vaginal wall, or can be passed through an undersurface of a portion of vaginal epithelium without passing through the vaginal wall. FIG. 62 illustrates the sutures 3649 passed through the wall of the vagina and knotted between the vaginal apex VA and the SSL in a pelvic region with no uterus. FIG. 63 illustrates the suture assemblies 3651 secured within a pelvic region when a uterus U is present.

Figure 64:
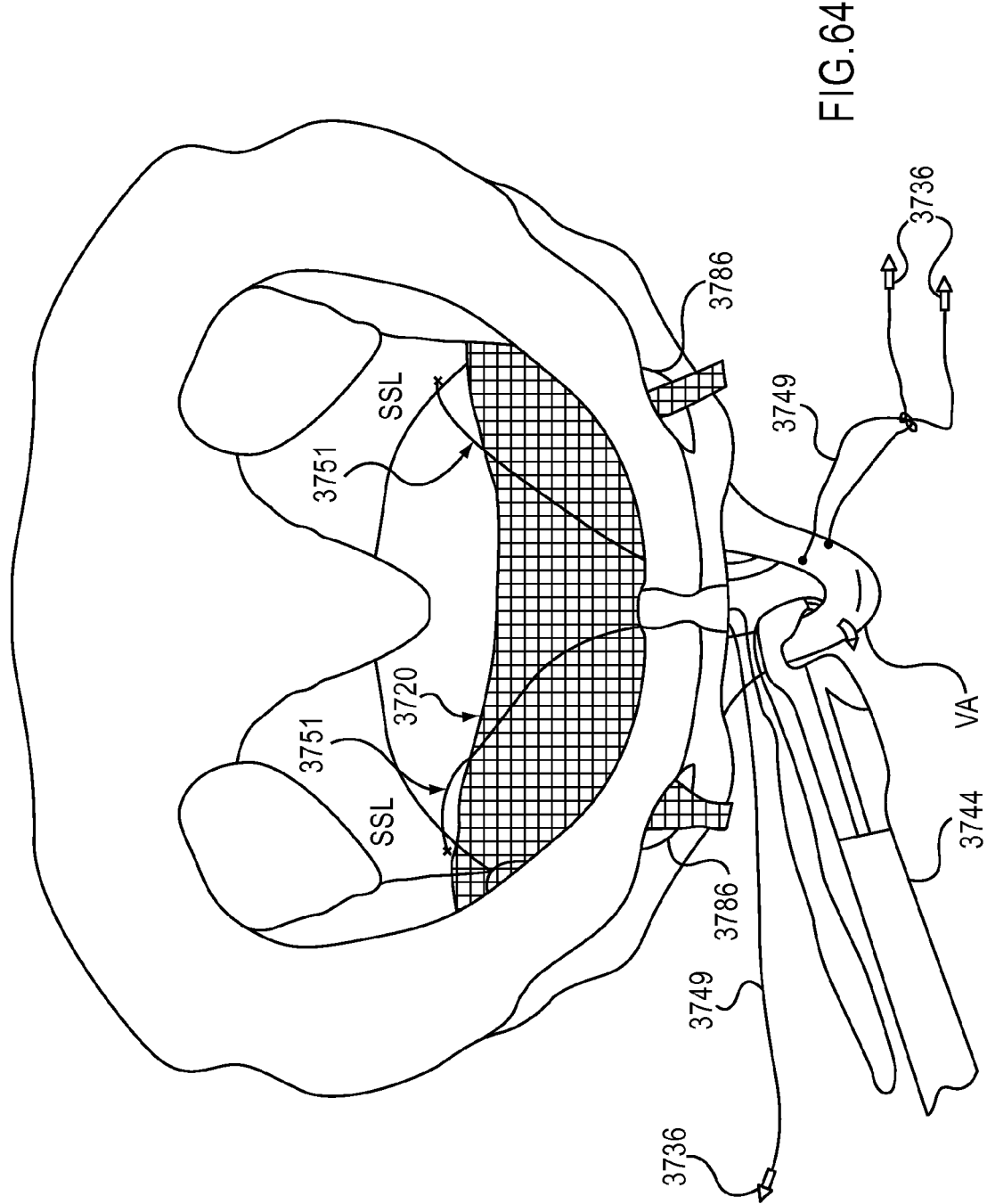
FIG. 64 is a top view of a pelvic region illustrating the placement of suture assemblies and an embodiment of an implant assembly within the pelvic region.

FIG. 64 illustrates yet another embodiment of the invention illustrating the use of a suture assembly in conjunction with an implant assembly. A pair of suture assemblies 3751 are shown being secured to a sacrospinous ligament SSL on each side of a pelvic space. Each of the suture assemblies 3751 include a suture 3749 and trocar needles 3736 disposed on ends of the suture 3749. The suture assemblies 3751 can be inserted and deployed within the pelvic space using, for example, a delivery device 3744. The delivery device 3744 can also be used to pass the sutures 3749 through a vaginal wall as shown in FIG. 64. An implant assembly 3720 (similar to implant assembly 2820 and 1920) includes an implant member 3722 and is shown inserted into the pelvic region. A portion of the implant member 3722 is pulled through, for example, an obturator muscle, using a delivery needle, such as delivery needle 1160 (see FIG. 26) and through an exterior incision 3786 on each side of the pelvic region. The implant member 3722 can also be secured to the vaginal apex VA using sutures or other anchoring means.

Figure 65:
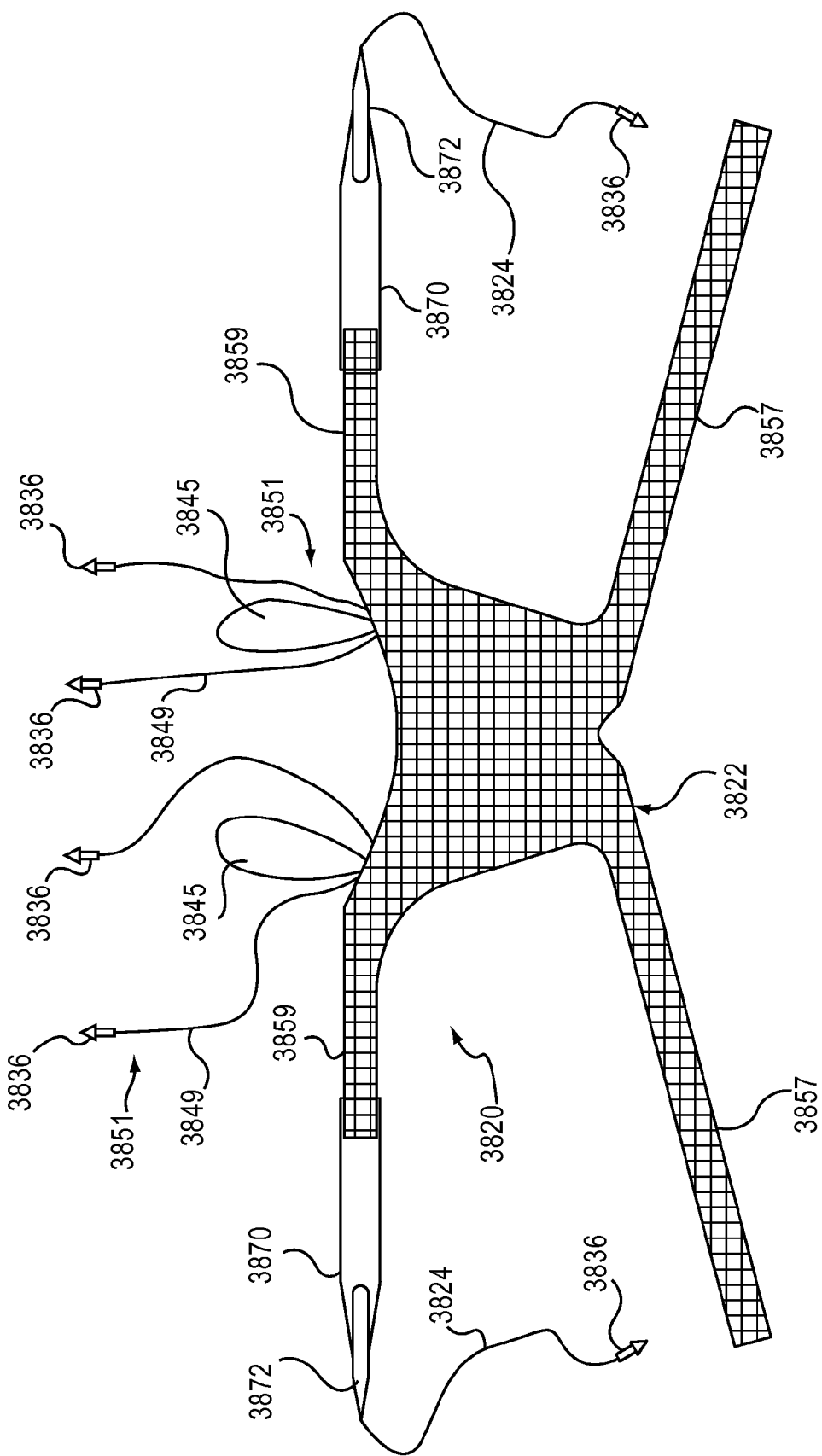
FIG. 65 is a front view of an implant assembly incorporating an embodiment of a suture assembly.

FIG. 65 illustrates an embodiment of an implant assembly with a suture assembly coupled directly to the implant assembly. An implant assembly 3820 includes an implant member 3822 having anterior straps 3859 and mid-line straps 3857. Sleeves 3870 are disposed over a portion of the anterior straps 3859, and dilators 3872 are coupled to the sleeves 3870. The sleeves 3870 and dilators 3872 are used to assist in the deployment of the implant assembly 3820 into a pelvic region of a patient as described previously with reference to other embodiments. Sutures 3824 are coupled to the dilators 3872, and trocar needles 3836 are coupled to an end of the sutures 3824. The trocar needles 3836 can be loaded onto a delivery device, such as delivery device 3744 previously described, and used to pass the sutures 3824 through, for example, an arcus tendineus. The mid-line straps 3857 can be passed through, for example, an obturator using a delivery needle as previously described.

A pair of suture assemblies 3851 each including a suture 3849 and a trocar needle 3936 on each end of the suture 3849, are tied to the implant member 3822 such that a noose 3845 is formed. The noose 3845 and trocar needle 3836 of each of the suture assemblies 3851 can be loaded onto a delivery device 3744 as previously described for deployment and securement of the suture 3849 to, for example, a sacrospinous ligament. The securement of a suture assembly 3851 on each side of the pelvic region can provide substantially equal tension to pull the implant assembly 3920 into place within the pelvic space. The straps (3859, 3857) can be placed before or after the suture assemblies 3851 are fully tensioned. The ends of sutures 3849 (and trocars 3836) can be passed through a wall of the vagina (e.g., through a vaginal apex) and secured similarly as previously described.

Figure 66:
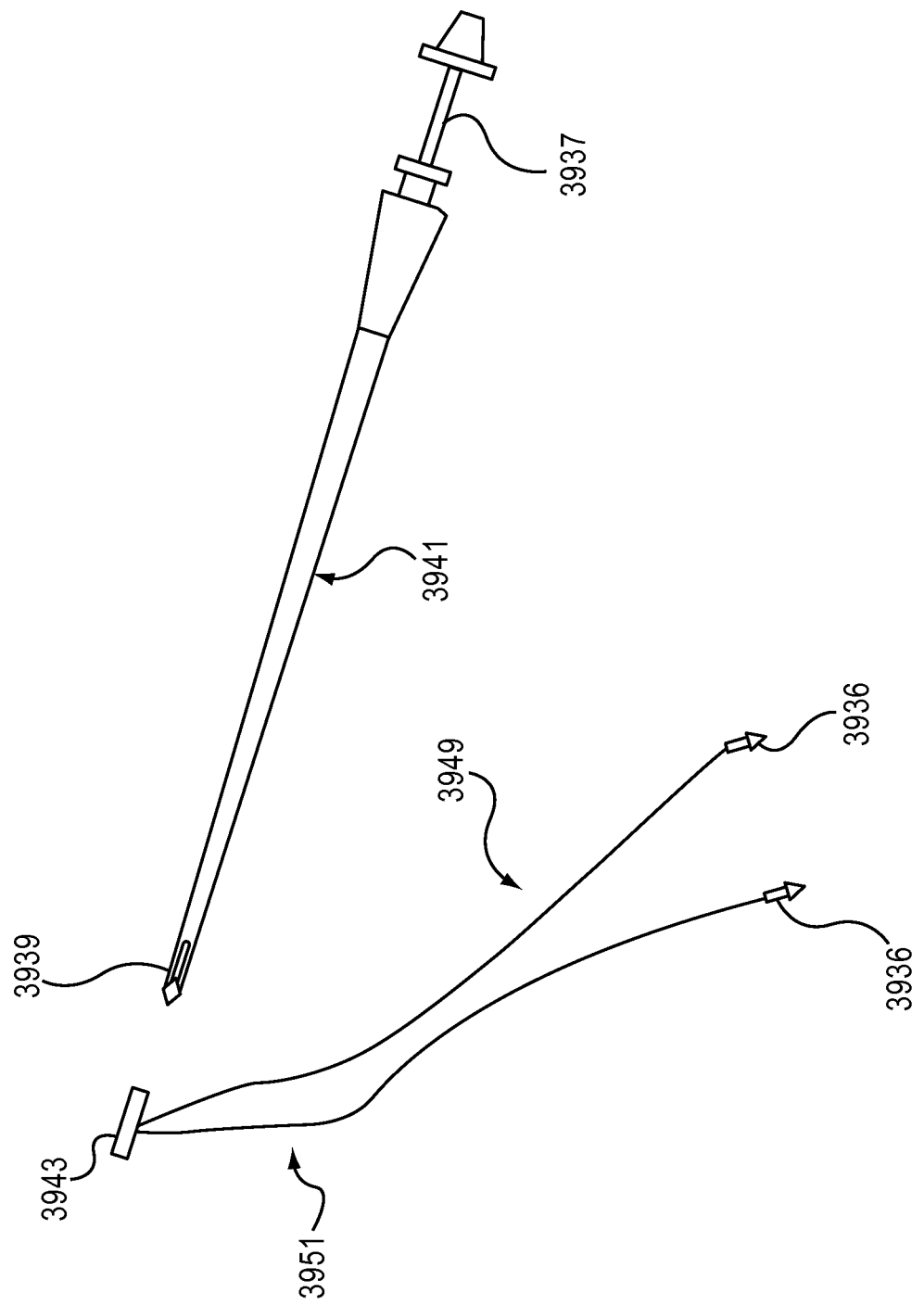
FIG. 66 is a side view of an embodiment of a delivery device and an embodiment of a suture assembly.
Figure 67:
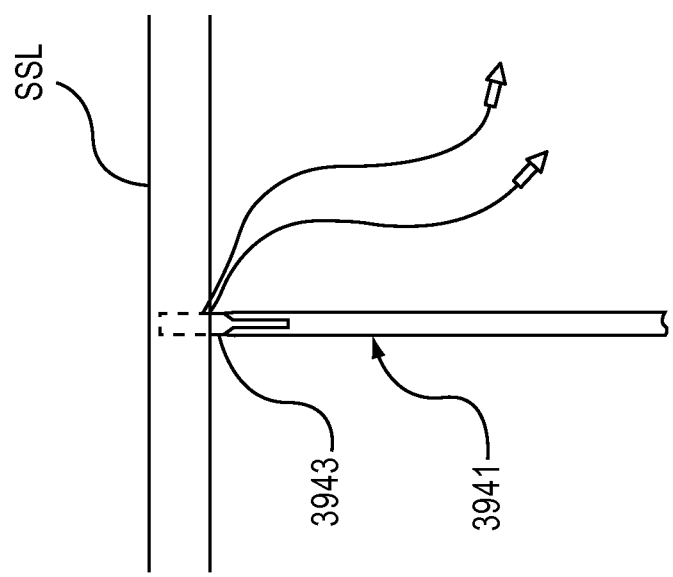
FIG. 67 is a front view of a portion of the delivery device of FIG. 66 with the suture assembly of FIG. 66 shown being inserted through a sacrospinous ligament.
Figure 68:
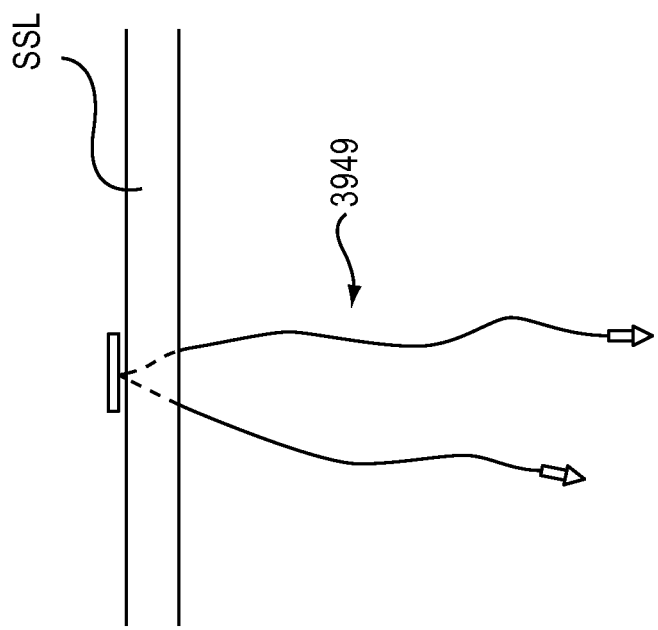
FIG. 68 is a front view of the suture assembly of FIG. 66 shown anchored to the sacrospinous ligament.

FIG. 66 illustrates another embodiment of a suture assembly and another embodiment of a delivery device. In this embodiment, a suture assembly 3951 includes a suture 3949, trocar needles 3936 and an anchor 3943. The anchor 3943 is shown as a T-type anchor, but it is to be understood that other embodiments of an anchor can alternatively be used. A delivery device 3941 includes a slot 3939 in which the anchor 3943 can be loaded to deliver the suture 3949 through, for example, a sacrospinous ligament. The delivery device 3941 also includes a pusher 3937 that is used to eject the anchor 3943 from the slot 3939 and push the anchor 3943 through a tissue portion such as a sacrospinous ligament SSL, as shown in FIG. 67. Once ejected and through the SSL, the anchor 3943 can form a "T" to anchor to the SSL as shown in FIG. 68. The ends of the suture 3949, using the trocars 3936, can be passed through a vaginal wall with a suturing type device, such as delivery device 144, or cut off and placed through the vaginal wall using, for example free needles, or suture passers. The sutures 3936 can be secured, for example, to a vaginal apex, with knots as previously described.

In another embodiment, the "T" anchor can have a curved shape such that it can be configured to be loaded onto a delivery device, such as delivery device 144. In such an embodiment, the delivery device can be configured to carry the anchor within a slot in the catch of the delivery device and used to deliver the anchor through the sacrospinous ligament. In such a configuration, the anchor would not be passed back through the SSL or retrieved by the catch of the delivery device as described above for previous embodiment, rather, the anchor would be released from the catch of the delivery device.

Figure 69:
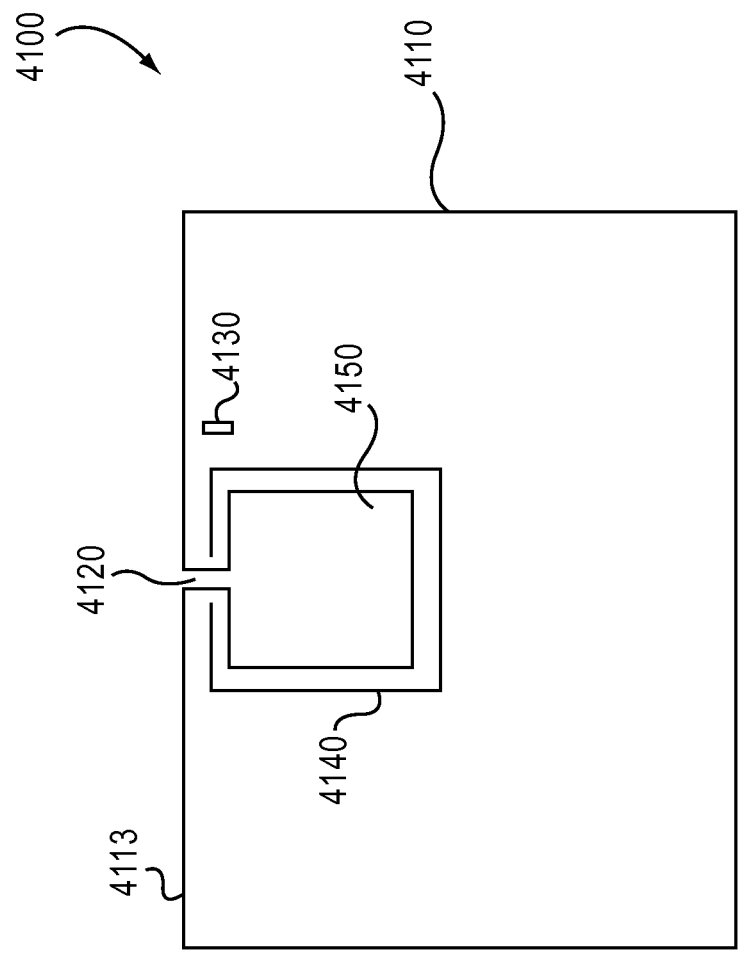
FIG. 69 is a schematic illustration of an implant dispenser, according to one embodiment.

FIG. 69 shows a system block diagram of an implant dispenser, according to one embodiment. As shown in FIG. 69, implant dispenser 4100 includes body 4110, opening 4120, a retention structure 4130, a retention structure 4140 and an aperture 4150. Retention structure 4140 is disposed about aperture 4150 such that a suture can be secured by retention structure 4140 about aperture 4150. Opening 4120 is located in body 4110 such that aperture 4150 is in communication with the exterior of body 4110, across edge 4113. Retention structure 4130 is disposed on body 4110 and configured such that a free end portion of a suture can be secured to retention structure 4130.

In some embodiments, as illustrated in FIG. 69, retention structure 4140 is configured to hold a suture loop in an open configuration about aperture 4150 such that no part of the suture loop traverses aperture 4150. In other embodiments, a retention structure is disposed such that a portion of a suture loop secured to the retention structure traverses a portion of the aperture. In such embodiments, the retention structure can be configured such that a suturing instrument can be passed through the aperture and a loop in a suture held in an open configuration by the retention structure.

In some embodiments, a retention structure can be a single, contiguous rib. In other embodiments, a retention structure can be a plurality of ribs or protrusions disposed about an aperture.

In some embodiments, the implant dispenser can have multiple apertures and/or openings, and/or additional retention structures. Such apertures and retention structures can be configured similar to aperture 4150, opening 420, retention structure 4130 and retention structure 4140 to accommodate additional sutures or free end portions of sutures. In other embodiments, the implant dispenser can include additional retention structures that can, for example, arrange, secure and/or manage additional sutures or portions of sutures.

Figure 70:
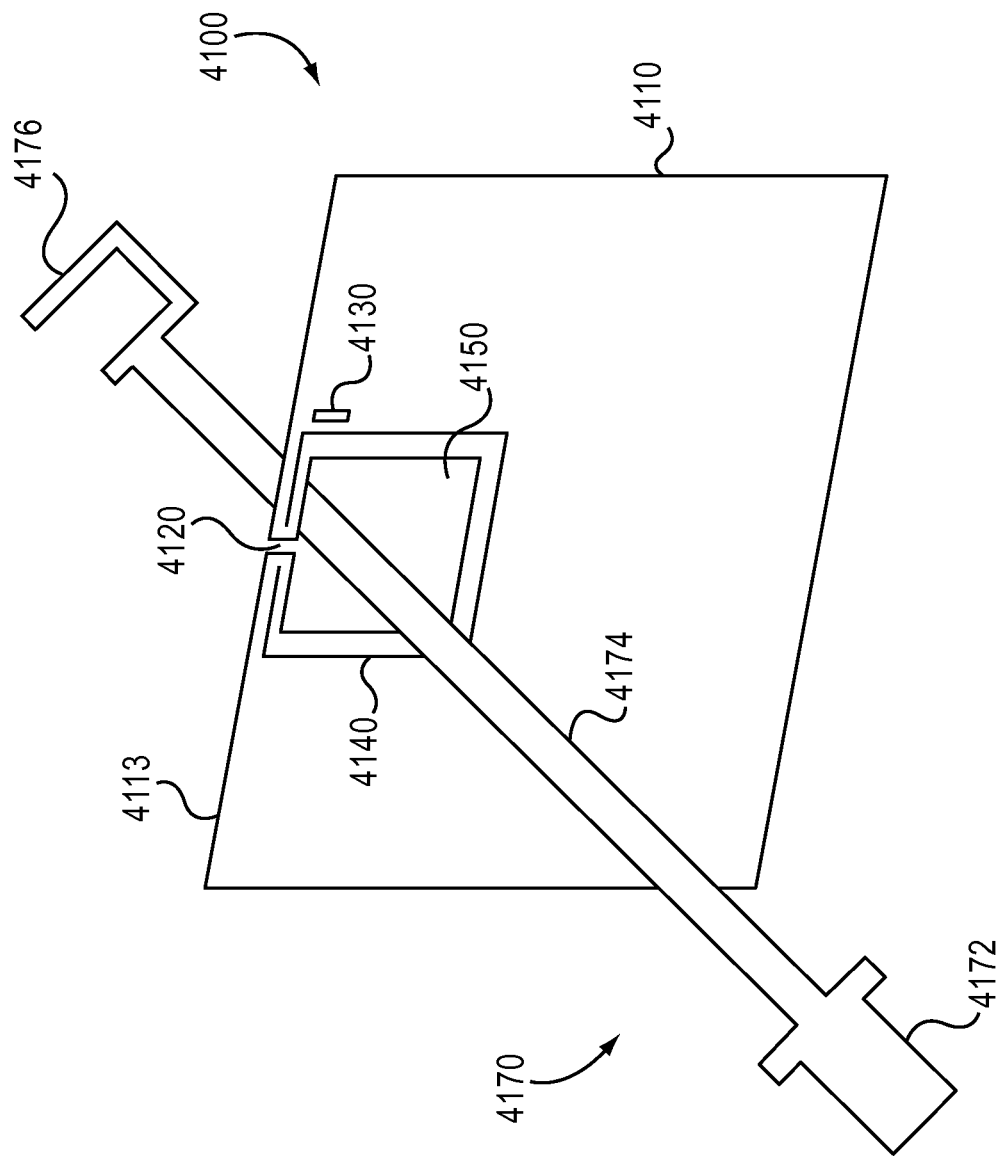
FIG. 70 is a schematic illustration of the implant dispenser of FIG. 69 and a suturing device.

FIG. 70 is a schematic illustration of the implant dispenser of FIG. 69 and a suturing device. As illustrated in FIG. 70, suturing device 4170 includes handle portion 4172, elongated portion 4174, and suturing portion 4176. Suturing device 4170 is configured to be passed through aperture 4150 of implant dispenser 4100 and is illustrated passed through aperture 4150 in FIG. 70.

In one embodiment, a doctor, or other person, delivering an implant into the body of a patient passes a portion of suturing device 4170 through implant dispenser 4100 via aperture 4150, removes a free end portion of a first suture from retention structure 4130 and attaches the free end portion of the first suture to suturing portion 4176 of suturing device 4170. The doctor then passes the free end portion of the first suture through a portion of the body of the patient using suturing device 4170. The doctor retracts suturing device 4170, drawing the attached free end portion of the first suture through aperture 4150 of implant dispenser 4100.

A knot is formed in the first suture as the free end portion of the suture is drawn through a loop in the first suture that is secured in an open configuration by retention structure 4140 about aperture 4150 of implant dispenser 4100. The doctor removes the loop in the first suture from retention structure 4140 and removes the free end portion of the first suture from implant dispenser 4100 via opening 4120. The doctor removes the free end portion of the suture from suturing portion 4176 of suturing device 4170 and the implant from implant dispenser 4100. The doctor then completes the implantation of the implant using the knot formed in the first suture. In some embodiments, the doctor passes a second suture through a portion of the body of the patient and uses the second suture to help secure a portion of the implant to the body of the patient.

In other embodiments, the steps described above can be performed in a different order. For example, the doctor can pass the second portion of the suture through a portion of the body of the patient before removing the implant from the implant dispenser. In some embodiments, this process can be repeated for tying two or more knots in sutures.

Figure 71:
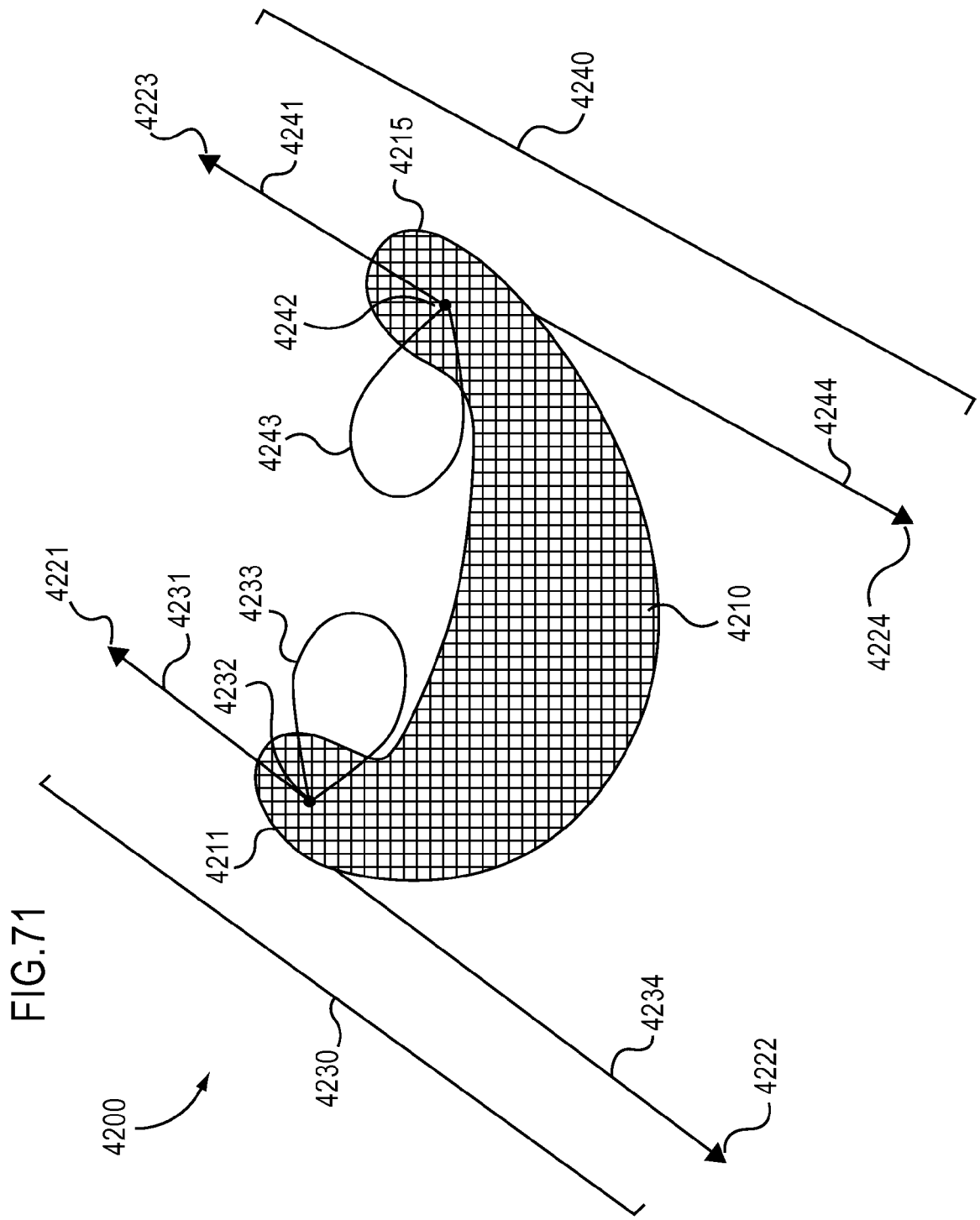
FIG. 71 is a perspective view of an implant for use with an implant dispenser, according to another embodiment.

FIG. 71 shows an embodiment of an implant 4200 for use with an implant dispenser. Implant 4200 includes implant body 4210 having tabs 4211 and 4215. Implant 4200 also includes suture 4230 and suture 4240 coupled to tabs 4211 and 4215. Suture 4230 has a first end portion 4231, a second end portion 4234, a knot 4232 and a loop 4233. Similarly, suture 4240 has a first end portion 4241, a second end portion 4244, a knot 4242 and a loop 4243. Suture darts 4221 and 4222 are attached to first end portion 4231 and second end portion 234 of suture 230, respectively. Suture darts 4223 and 4224 are attached to first end portion 4241 and second end portion 4244 of suture 4240, respectively. A suture dart can be, for example, a dart, a straight needle, a curved needle, and/or any other tissue introducer attached to a suture and/or implant. In some embodiments, no introducer is attached to a suture or can be removed (e.g., cut from a suture or implant) and a free needle can be used.

In other embodiments, implants can include more or fewer sutures and/or loops in sutures. In some embodiments, implants include sutures with a first end portion and a loop, but no second end portion. In some embodiments, implants include sutures without loops. In some embodiments, sutures, loops in sutures, and/or end portions of sutures can be of various colors or include marking, for example, to help a person using the implant and implant dispenser orient the implant and/or implant dispenser. In some embodiments, a knot in a suture can both form a loop in the suture and help secure the suture to an implant. In some embodiments, a knot in a suture can be a slip knot configured to allow a person implanting the implant to reduce the size of a loop in the suture.

In some embodiments, implants can include additional features such as various types of arms extending from a body portion of an implant for attaching the implant to the body of a patient. In some embodiments, implants can include one or more sleeves such as, for example, sleeves configured to protect arms or other portions of the implant and/or to aid in delivery or implantation of the implant.

Figure 72:
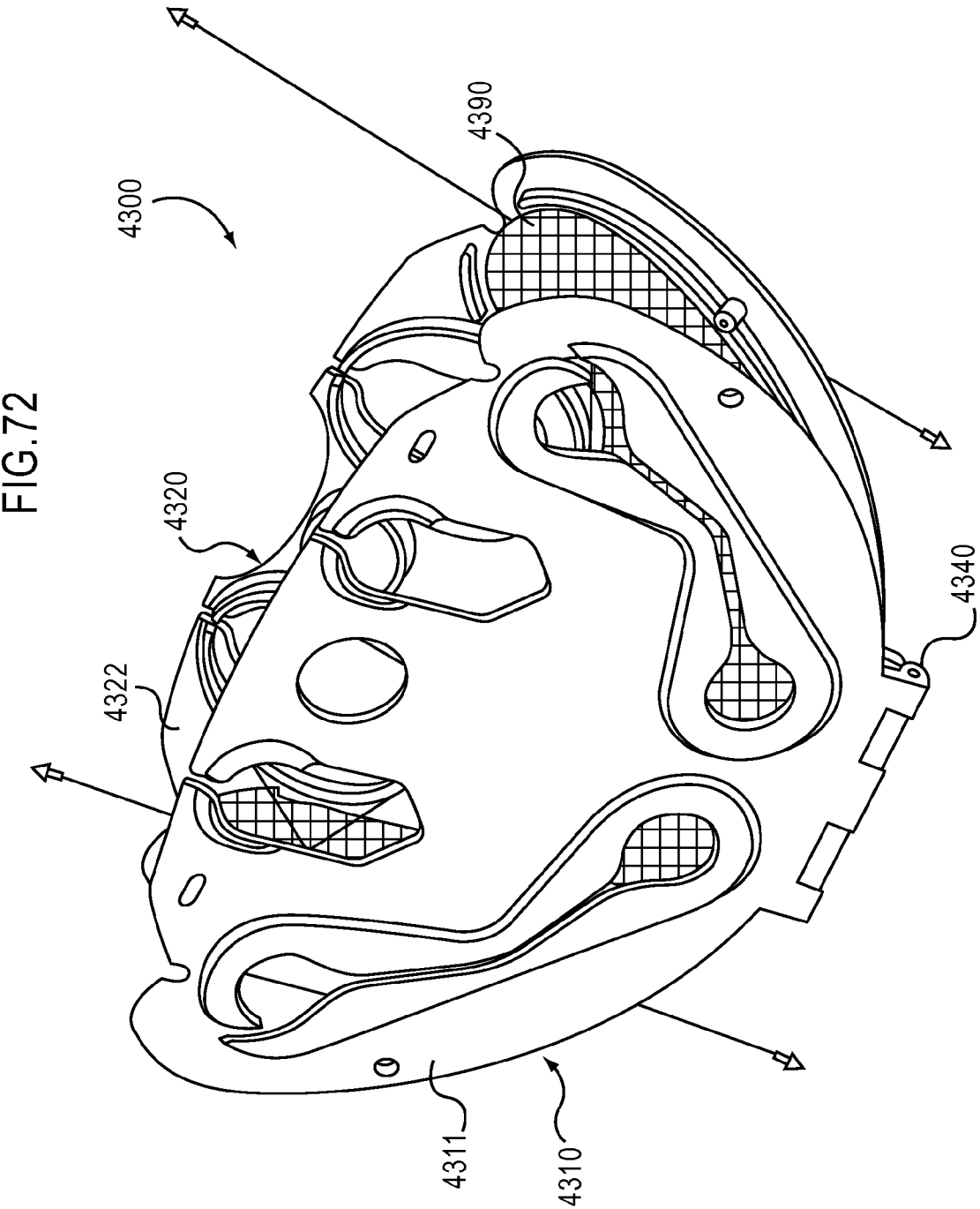
FIG. 72 is a perspective view of an implant dispenser, according to another embodiment.
Figure 73:
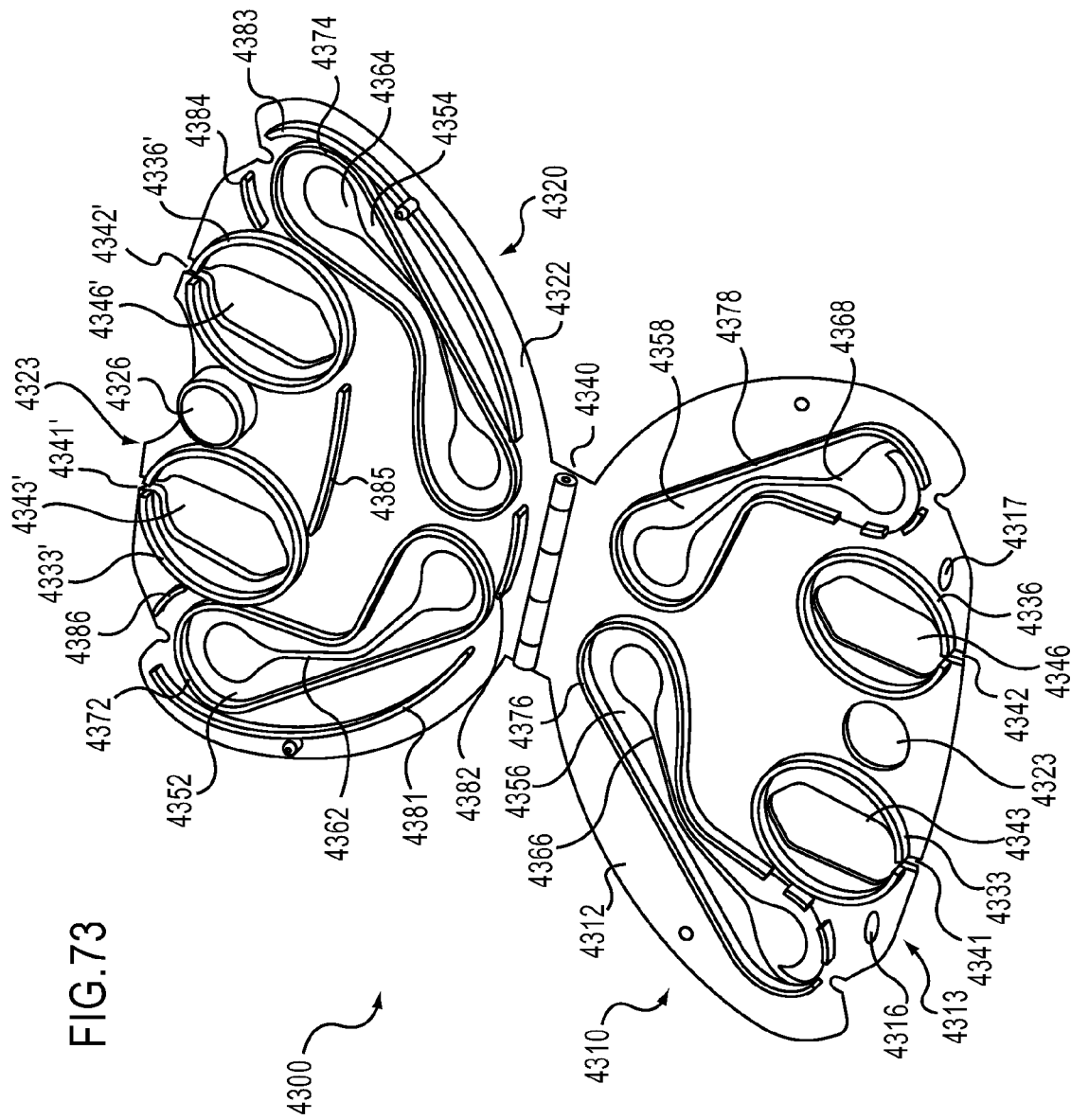
FIGS. 73-76 are perspective views of the implant dispenser of FIG. 72 and the implant of FIG. 71.
Figure 74:
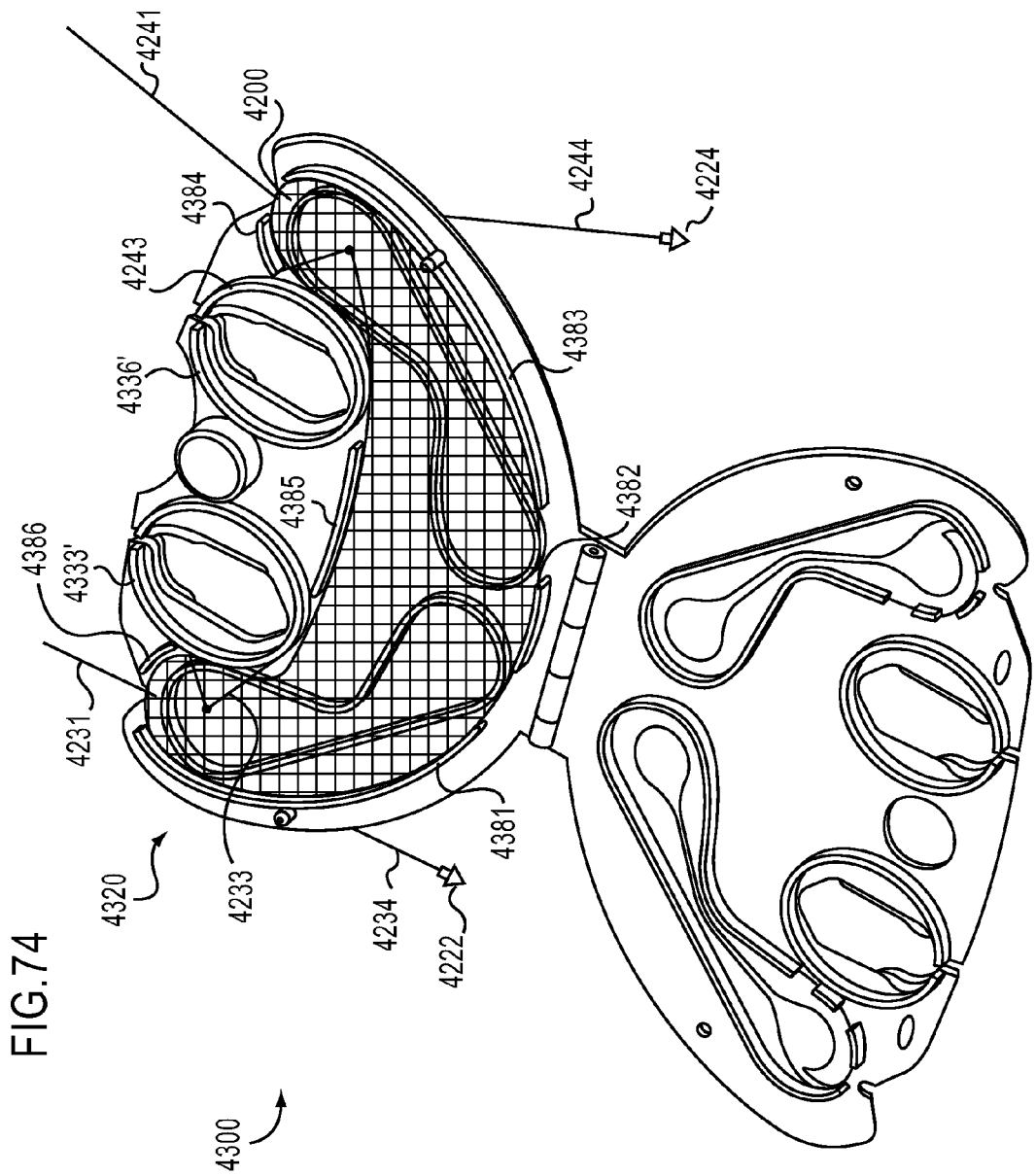
Figure 75:
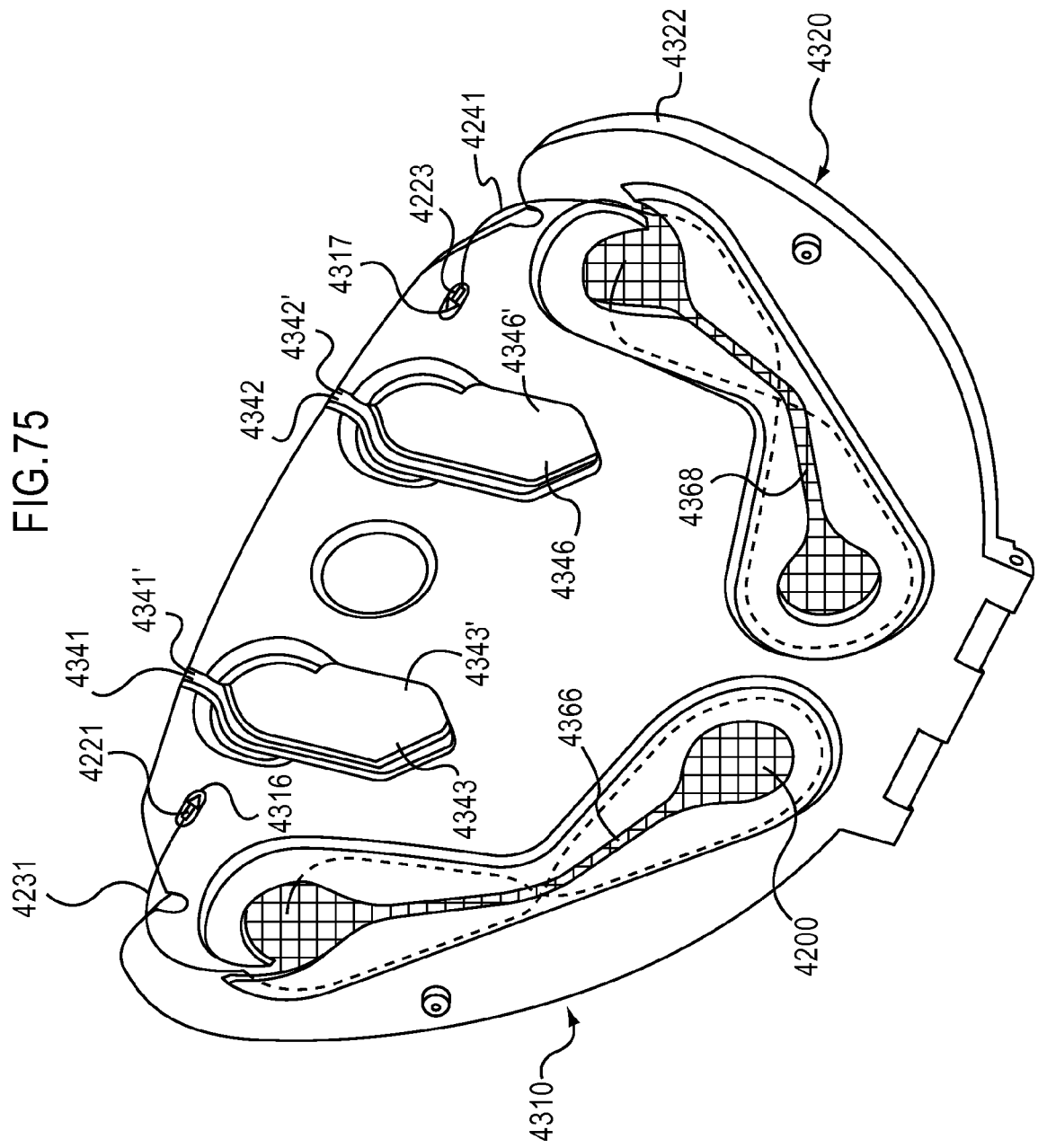

FIGS. 72-76 are perspective views of a implant dispenser, according to another embodiment. FIG. 72 shows implant dispenser 4300 and implant 4390. Implant dispenser 4300 has first body portion 4310 and second body portion 4320. First body portion 4310 is movably coupled to second body portion 4320 by hinge 4340. First body portion 4310 has exterior surface 4311 and an interior surface (not shown in FIG. 72) opposite exterior surface 4311. Second body portion 4320 has interior surface 4322 and an exterior surface (not shown in FIG. 72) opposite interior surface 4322. Implant dispenser 4300 as shown in FIG. 72 is in a partially closed configuration. FIG. 73, discussed in more detail below, shows implant dispenser 4300 in an open configuration for placing an implant into implant dispenser 4300 and/or for removing the implant from implant dispenser 4300. FIG. 75, discussed in more detail below, shows implant dispenser 4300 in a closed configuration such that the interior surface of first body portion 4310 and interior surface 4322 of second body portion 4320 are substantially adjacent or flush one to another. In other words, second body portion 4320 can be moved between an open configuration and a closed configuration relative to first body portion 4310. Alternatively, it can also be said that first body portion 4310 can be moved between an open configuration and a closed configuration relative to second body portion 4320.

An implant dispenser can be formed from a variety of materials. For example, in some embodiments, an implant dispenser can be rigid. In other embodiments, an implant dispenser can be semi-rigid or flexible. In some embodiments, an implant dispenser can be translucent or clear such that a person using the implant dispenser can see or partially see through the first body portion and/or the second body portion.

In some embodiments, the first body portion and/or the second body portion are formed using an injection-molding procedure. In other embodiments, the first body portion and/or the second body portion are milled or cut from a piece of material.

The first body portion and/or the second body portion can include markers including words and/or symbols to help a person properly use the implant dispenser. For example, the first body portion and/or the second body portion can include orientation markers to help a person properly orient the implant dispenser with respect to the body of a patient. Other examples of markers include labeling of various components of the implant dispenser and/or providing directions for use printed on the implant dispenser. For example, the implant dispenser can include markers indicating through which apertures a portion of a suturing device may be passed. In one embodiment, the first body portion and/or the second body portion approximate a shape and/or dimensions of an implant.

FIG. 73 is a perspective view of implant dispenser 4300 in an open configuration illustrating interior surface 4312 of first body portion 4310 and interior surface 4322 of second body portion 4320. First body portion 4310 is movably coupled to second body portion 4320 by hinge 4340. First body portion 4310 includes aperture 4343 and 4346 and second body portion 4320 includes apertures 4343' and 4346'. As illustrated in FIG. 75, apertures 4343 and 4343' are configured to align such that a portion of a suturing device can be passed through implant dispenser 4300 via both apertures 4343 and 4343' when implant dispenser 4300 is in a closed configuration. Apertures 4346 and 4346' are similarly configured to align such that a portion of a suturing device can be passed through implant dispenser 4300 via both apertures 4346 and 4346' when implant dispenser 4300 is in a closed configuration.

A suturing device can be any device configured to aid in attaching a suture to a tissue within the body of a patient. In some embodiments, a suturing device can capture a portion of a suture after the suture is attached to a tissue within the body of a patient. For example, a Capio™ device manufactured by Boston Scientific Corporation can be used with the implant dispenser.

The apertures can have a variety of shapes and sizes. The size and shape of the apertures can vary, for example, to accommodate different instruments or implants. For example, in some embodiments, the apertures are substantially circular or oval. In other embodiments, the apertures are square, rectangular, hexagonal, or some other shape allowing a suturing device to be passed through the apertures.

In some embodiments, the apertures can be configured to be coupled to a portion of a suturing instrument. In some embodiments, the apertures can be configured to be coupled to a portion of a suturing instrument based on, for example, a compression or friction fit, or can be configured to be lockably coupled to a suturing instrument based on, for example, ridges, protrusion, tabs and/or snaps on the implant dispenser configured to engage a portion of the suturing instrument.

Figure 77:
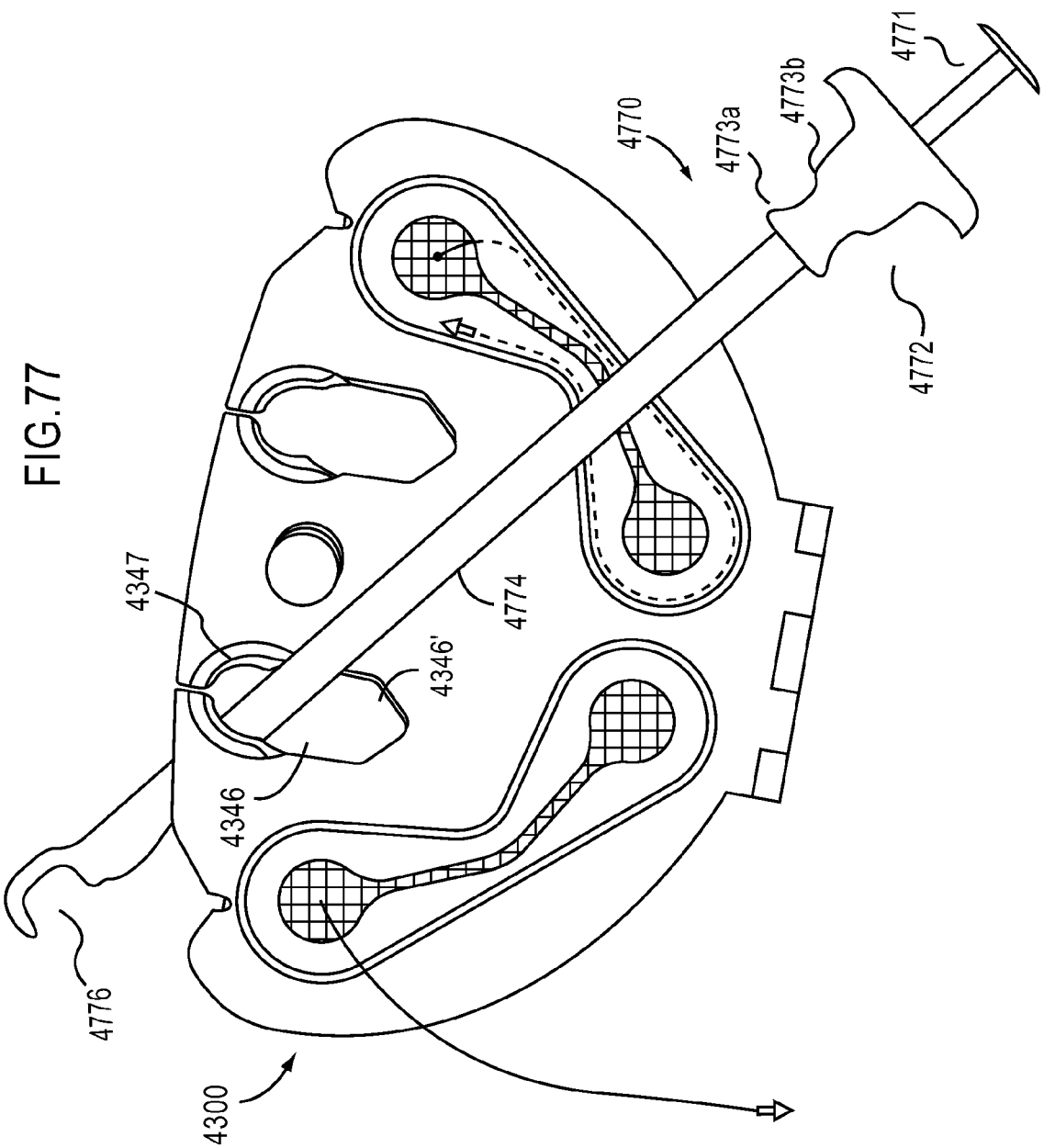
FIG. 77 is a perspective view of the implant dispenser of FIG. 72, the implant of FIG. 71 and a suturing device.

FIG. 77 is a perspective view of the implant dispenser of FIG. 72, the implant of FIG. 71 and a suturing device. As illustrated in FIG. 77, suturing device 4770 has been passed through the aperture created by apertures 4346 and 4346' of implant dispenser 4300. Suturing device 4770 includes handle portion 4772, elongated portion 4774, and suturing portion 4776. Suturing device 4770 also includes actuator 4771 for actuating a needle or suture dart coupled to suturing portion 4776 to deploy a suture in a tissue of a patient. Implant dispenser 4300 includes ridge 4347 configured to engage suturing device 4770 between ridge 4773a and ridge 4773b such that suturing device 4770 can be removably coupled to implant dispenser 4300.

Referring to FIG. 73, aperture 4343 is in communication with outside edge 4313 of first body portion 4310 via opening 4341. Opening 4341 is configured to allow a suture to be removed from implant dispenser 300 by being passed from aperture 4343 to outside edge 4313 through opening 4341. Aperture 4346 and opening 4342 are similarly configured to allow a suture to be removed from implant dispenser 4300 by being passed from aperture 4346 through opening 4342. Aperture 4343' and opening 4341', and aperture 4346' and opening 4342' are also similarly configured to allow a suture to be removed from implant dispenser 4300 by being passed from aperture 4343' through opening 4341', and to allow a suture to be removed from implant dispenser 4300 by being passed from aperture 4346' to outside edge 4323 through opening 4342'.

As illustrated in FIG. 75, opening 4341 and opening 4341', and opening 4342 and opening 4342' are configured to substantially align when implant dispenser 4300 is in the closed configuration. Thus, when implant dispenser 4300 is in the closed configuration, the aperture through implant dispenser 4300 formed by aperture 4343 and aperture 4343' is in communication with the outside edge defined by outside edge 313 of first body portion 4310 and outside edge 4323 of second body portion 4320 via the opening formed by opening 4341 and opening 4341'. Opening 4342 and opening 4342' are similarly configured such that when implant dispenser 4300 is in the closed configuration, the aperture through implant dispenser 4300 formed by aperture 4346 and aperture 4346' is in communication with the outside edge defined by outside edge 4313 of first body portion 4310 and outside edge 4323 of second body portion 4320 via the opening formed by opening 4342 and opening 4342'.

The openings can vary in size and shape according to different embodiments. In some embodiments, the openings are narrow, such as openings to allow passage of sutures. In other embodiments, the openings are sufficiently wide to allow passage of larger devices and/or instruments. For example, in one embodiment a suturing device can be passed through the openings.

Referring to FIG. 73, implant dispenser 4300 includes retention structure 4333' disposed around aperture 4343' and retention structure 4336' disposed around aperture 4346'. Retention structure 4333' is configured to maintain a loop in a suture in an open configuration around aperture 4343'. Retention structure 4336' is similarly configured with respect to aperture 4346'. The retention structures can maintain a loop in a suture entirely open about the apertures or partially open about the apertures.

In some embodiments, additional retention structures can help prevent a loop in a suture from becoming disengaged from other retention structures. For example, as illustrated in FIG. 73, retention structure 4333 is configured to align substantially with retention structure 4333' to help prevent the loop in the suture disposed around retention structure 4333' from slipping off retention structure 4333'. Retention structure 4336 is similarly configured with respect to retention structure 4336' to help prevent the loop in the suture disposed around retention structure 4336' from slipping off retention structure 4336'.

In some embodiments, retention structures include tabs, clips, ridges, and/or adhesive to help secure loops in sutures to the retention structures. In the illustrated embodiment, the retention structures are a continuous rib or protrusion on an interior surface. In other embodiments, the retention structures are multiple ribs or protrusions around the apertures.

Rib 4376 and rib 4378 are disposed on interior surface 4312 of first body portion 4310 around slot 4366 and slot 4368, respectively. Rib 4376 and internal surface 4312 form cavity 4356, which is a retention structure configured to hold or manage a portion of a suture. For example, a suture can be looped or coiled within cavity 4356 to prevent tangling of the suture. Rib 4378 similarly forms cavity 4358. Slot 4366 is configured to allow a portion of a suture to be inserted into and/or removed from cavity 4356 when implant dispenser 4300 is in a closed configuration. Slot 4368 is similarly configured with respect to cavity 4358 (to allow a portion of a suture to be inserted into and/or removed from cavity 4358 when implant dispenser 4300 is in a closed configuration).

Rib 4372, slot 4362 and cavity 4352, and rib 4374, slot 4364, and cavity 4354 are also similarly configured with respect to interior surface 4322 of second body portion 4320. Rib 4372 and interior surface 4322 form cavity 4352 that is a retention structure configured to hold or manage a portion of a suture. Rib 4374 similarly forms cavity 4354. Slot 4362 is configured to allow a portion of a suture to be inserted into and/or removed from cavity 4352 when implant dispenser 4300 is in a closed configuration. Slot 4364 is similarly configured with respect to cavity 4354 to allow a portion of a suture to be inserted into and/or removed from cavity 4354 when implant dispenser 4300 is in a closed configuration.

The slots can be dumbbell-shaped as illustrated in implant dispenser 4300. In other embodiments, the slots can be of other shapes such as, for example, an oval or a channel having a substantially constant width, that are configured to allow a portion of a suture to be inserted into and/or removed from a cavity in an implant dispenser when the implant dispenser is in a closed configuration.

In some embodiments, the ribs are each a single rib or protrusion. In other embodiments, the ribs are each multiple ribs or protrusions configured to be a retention structure for a portion of suture.

Second body portion 4320 includes protrusions 4381, 4382, 4383, 4384, 4385, and 4386 configured to approximate the shape of an implant for use with implant dispenser 4300 and reduce movement of the implant in implant dispenser 4300. Protrusions 4381, 4382, 4383, 4384, 4385, and 4386 are configured to retain an implant in a substantially single position within the implant dispenser.

In other embodiments, an implant dispenser can include a single protrusion approximating the shape of an implant to reduce movement of the implant in the implant dispenser. In yet other embodiments, more or fewer protrusions than illustrated in FIG. 73 can be included on an implant dispenser for helping to hold or reduce movement of the implant in the implant dispenser.

Implant dispenser 4300 can includes a structure for resisting separation of first body portion 4310 from second body portion 4320. In the illustrated embodiment, first body portion 4310 includes lock hole 4323, and second body portion 4320 includes lock button 4326. When first body portion 4310 is closed onto second body portion 4320, lock button 4326 engages lock hole 4323, retaining implant dispenser 4300 in its closed configuration.

In other embodiments, different locking mechanisms can be employed to couple and/or retain an implant dispenser in a closed configuration. For example, one or more tabs coupled to a first body portion and/or a second body portion can engage an edge of the second body portion and/or the first body portion, respectively. A hook portion on the first body portion can engage a loop portion on the second body portion to lockably couple the first body portion and the second body portion. The locking device can have a first configuration in which it is separate from the first body portion and the second body portion, and a second configuration in which it is coupled to the first body portion and the second body portion to hold the first body portion and the second body portion in a closed configuration.

Implant dispenser 4300 includes dart retention structures 4316 and 4317. Dart retention structures 4316 and 4317 are configured to secure, for example, a suture dart to implant dispenser 4300. Dart retention structures can be, for example, slots in an implant dispenser for frictionally coupling with a suture dart. In other embodiments, dart retention structures can be clips, tabs, and/or adhesives for securing a suture dart to a implant dispenser.

Implant dispenser 4300 as illustrated in FIG. 73 is in an open configuration and can be assembled with, in one embodiment, implant 4200 as illustrated in FIG. 74. When implant dispenser 4300 is in an open or semi-open configuration, end portion 4234 of suture 4230 including suture dart 4222 can be threaded or directed through slot 4362 in a direction from internal surface 4322 to the external surface of second body portion 4320 as illustrated in FIG. 74. Similarly, end portion 4244 of suture 4240 including suture dart 4224 can be threaded or directed through slot 4364. Implant 4200 is then placed on second body portion 4320 such that ribs 4381, 4382, 4383, 4384, 4385, and 4386 help prevent implant 4200 from shifting or moving during shipment, sterilization and/or implantation.

After implant 4200 has been placed on second body portion 4320 as illustrated in FIG. 74, loops 4233 and 4243 of sutures 4230 and 4240, respectively, can be placed around retention structures 4333' and 4336', respectively. End portions 4231 and 4241 are positioned to extend off implant 4200 and from second body portion 4320 between interior surface 4312 and implant 4200 in a direction opposite hinge 4340 such that end portions 4231 and 4241 extend outside of implant dispenser 4300 when implant dispenser 4300 is in the closed configuration. With the implant disposed on second body portion 4320, implant dispenser 4300 is converted or moved to the closed configuration as illustrated in FIG. 75, by pivoting first body portion 4310 about hinge 4340 onto second body portion 4320.

When implant dispenser 4300 is in the closed configuration, portions of sutures can be threaded through slots 4362, 4364, 4366 and 4368 into cavities 4352, 4354, 4356 and 4358 to hold, manage and/or secure portions of the sutures.

Figure 76:
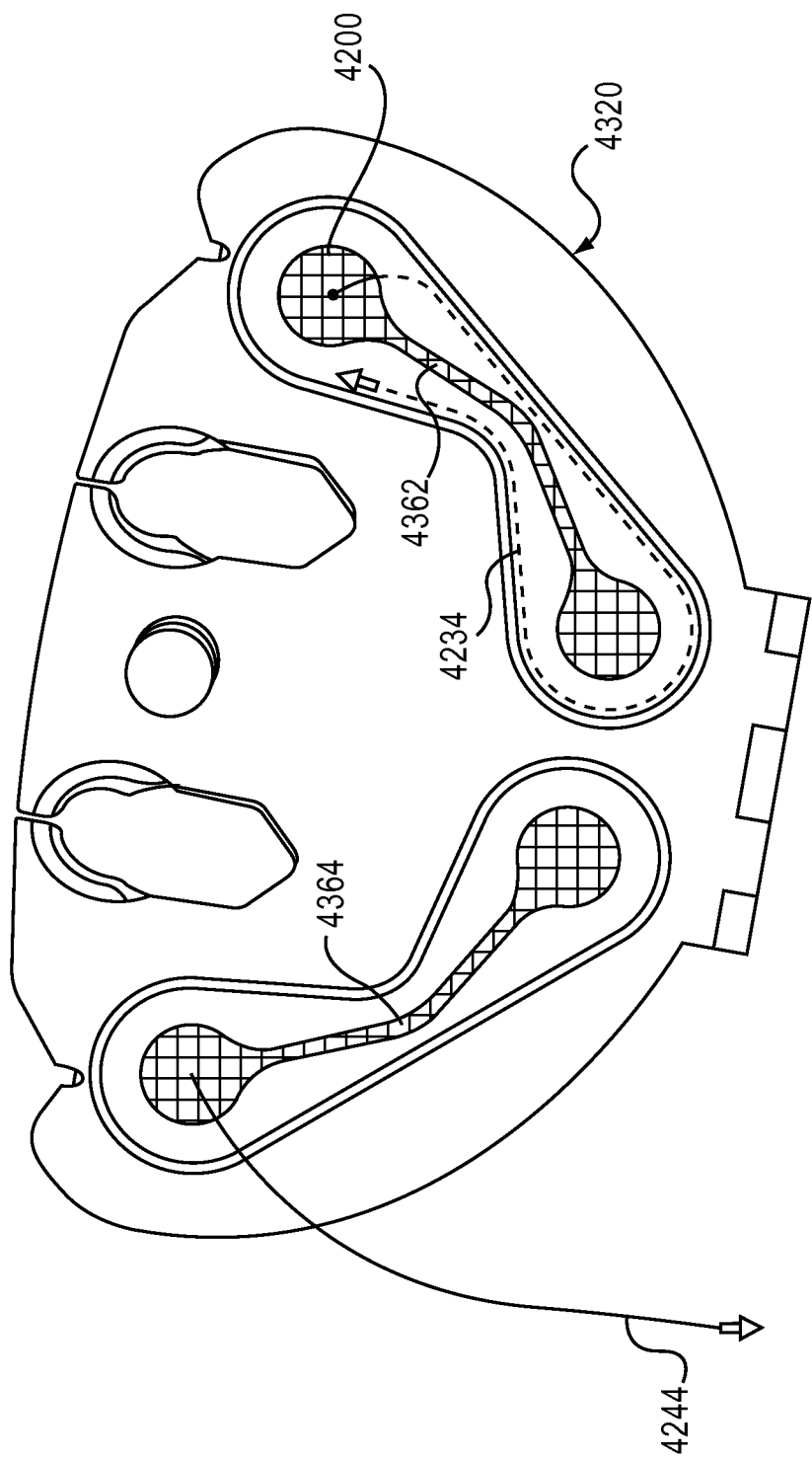

As illustrated in FIG. 76, suture end portions 4234 and 4244 can be threaded or inserted into the area between second body portion 4320 and implant 4200 via slots 4362 and 4364, respectively. In some embodiments, for example, suture end portions 4234 and 4244 can be disposed within the area between second body portion 4320 and implant 4200 in a figure-8 pattern. In other embodiments, suture end portions 4234 and 4244 can be disposed within the area between second body portion 4320 and implant 4200 in a coiled manner or in any other arrangement to help prevent suture ends 4234 and 4244 from becoming tangled.

As illustrated in FIG. 75, a portion of each of suture ends 4231 and 4241 can be inserted into the area between first body portion 4310 and implant 4200 via slots 4366 and 4368, respectively, when implant dispenser 4300 is in the closed configuration. For example, each of suture ends 4231 and 4241 can be disposed between first body portion 4310 and implant 4200 in a figure-8 pattern. In other embodiments, suture ends 4231 and 4241 can be disposed between first body portion 4310 and implant 4200 in a coiled manner or in any other arrangement to help prevent suture ends 4231 and 4241 from becoming tangled. In some embodiments, a portion of each of suture ends 4231 and 4241 can extend out of slots 4366 and 4368, such that suture darts 4221 and 4223 can be removably coupled to dart retention structures 4316 and 4317, respectively.

Figure 78:
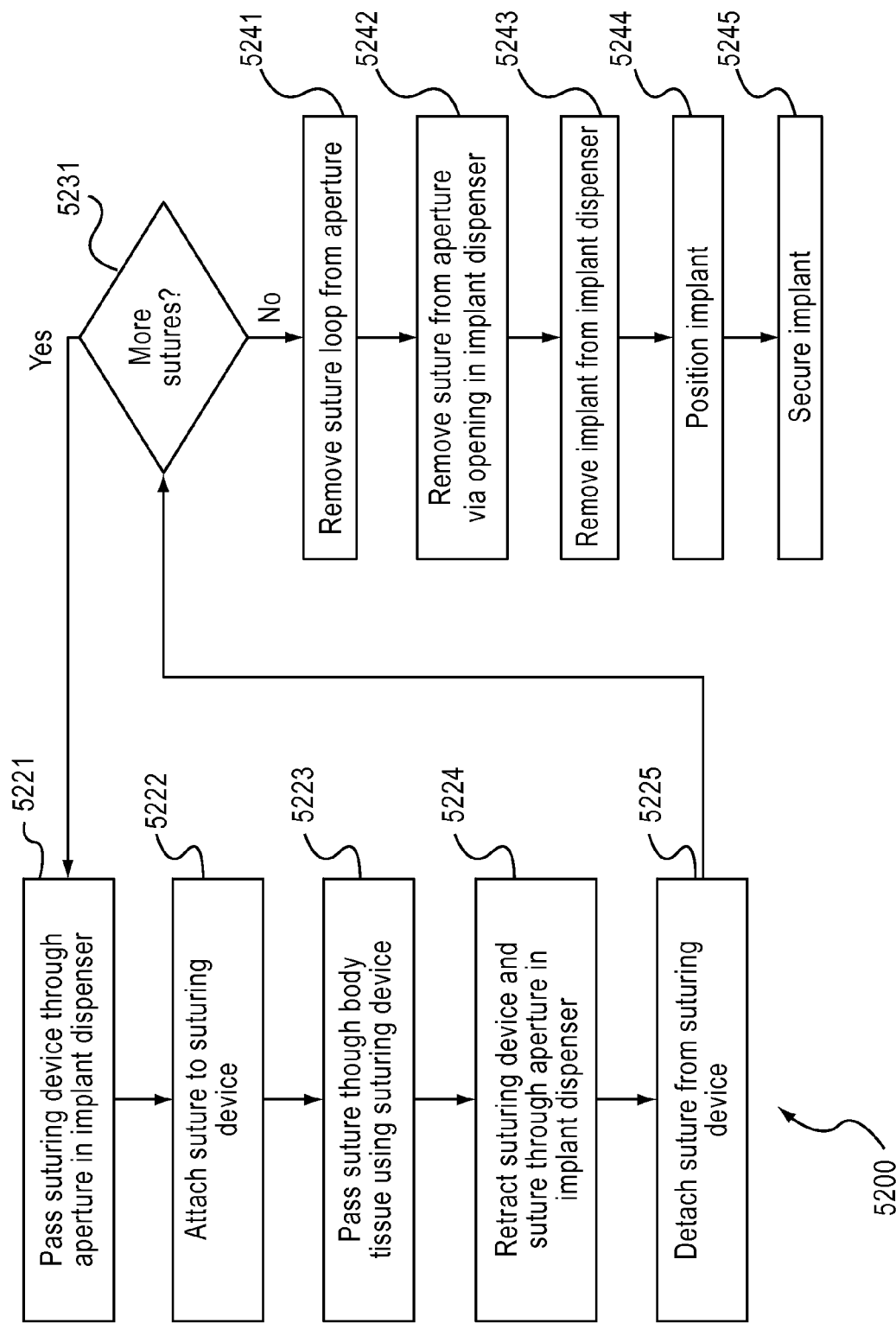
FIG. 78 is a flow chart of a process for implanting a medical implant using an implant dispenser.

In one example of a pelvic floor reconstruction, vaginal vault support, or uterine support procedure, implant dispenser 4300 is used in implantation of implant 4200 into the body of a patient as illustrated in FIG. 78. FIG. 78 is a flow chart of a process for implanting a medical implant using an implant dispenser. Implant 4200 is placed in implant dispenser 4300 as described above, and implant dispenser 4300 is disposed in the closed configuration. The doctor prepares the patient for implantation of the implant, and makes a vaginal anterior incision to effect access to the pelvic bowl of the patient. At step 5221, the doctor places a suturing device through the aperture formed by aperture 4343 and aperture 4343' and removes suture dart 4221 from dart retention structure 4316. The doctor then attaches suture dart 4221 to the suturing device at step 5222, and removes suture end portion 4231 from cavity 4356 via slot 4366. Optionally, in some embodiments, the doctor couples implant dispenser 4300 to the suturing device.

The doctor inserts the suturing device into the pelvic bowl of the patient and at step 5223 deploys suture dart 4221 and suture end portion 4231 through an anchoring tissue such as, for example, the sacrospinous ligament such that suture dart 4221 is captured by the suturing device. The doctor then detaches the suturing device from implant dispenser 4300, if the suturing device is coupled to implant dispenser 4300, and at step 5224 retracts the suturing device and suture end portion 4231 from the pelvic bowl of the patient and through the aperture formed by aperture 4343 and aperture 4343'. Suture end portion 4231 passes through suture loop 4233 secured about aperture 4343' and a knot is formed in suture 4230.

At step 5225, the doctor removes suture dart 4221 and suture end portion 4231 from the suturing device. At step 5231, if there are more sutures to be deployed using implant dispenser 4300, the doctor repeats steps 5221, 5222, 5223, 5224 and 5225. The doctor places the suturing device through the aperture formed by aperture 4346 and aperture 4346', attaches implant dispenser 4300 to the suturing device, and removes suture dart 4223 from dart retention structure 4317.

The doctor then attaches suture dart 4223 to the suturing device and removes suture end portion 4241 from cavity 4358 via slot 4368.

The doctor inserts the suturing device into the pelvic bowl of the patient and deploys suture dart 4223 and suture end portion 4241 through an anchoring tissue such as, for example, the sacrospinous ligament such that suture dart 4223 is captured by the suturing device. The doctor then detaches the suturing device from implant dispenser 4300, if the suturing device is coupled to implant dispenser 4300, and retracts the suturing device and suture end portion 4241 from the pelvic bowl of the patient and through the aperture formed by aperture 4346 and aperture 4346'. Suture end portion 4241 passes through suture loop 4243 secured about aperture 4346' and a knot is formed in suture 4240. The doctor then remove suture dart 4223 from the suturing device.

Again at step 5231, if there are no more sutures to be deployed while the implant device is in the closed configuration, the doctor moves implant dispenser 4300 into the open configuration. Suture end portion 4231 passes outside implant dispenser 4300 from aperture 4343 through opening 4341, and suture end portion 4241 passes outside implant dispenser 3400 through opening 4342 from aperture 4346 as implant 4300 is moved to the open configuration. At step 5241, the doctor removes suture loop 233 from retention structure 4333', and at step 5242 removes suture end portion 4231 from aperture 4343' via opening 4341'. Similarly, the doctor removes suture loop 4243 from retention structure 4336', and removes suture end portion 4241 from aperture 4346' via opening 4342'. At step 5243, the doctor then removes implant body 4210 from second body portion 4320 of implant dispenser 4300 and discards implant dispenser 4300. Removing implant body 4210 from second body portion 4320 of implant dispenser 4300 also removes suture end portion 4234 from cavity 4352, and suture end portion 244 from cavity 4354.

The doctor then attaches suture dart 4222 to the suturing device, inserts the suturing device and suture end portion 4234 into the pelvic bowl of the patient, and deploys suture dart 4222 and suture end portion 4234 through another anchoring tissue such as, for example, the vaginal formix of the patient such that suture dart 4222 and suture end portion 4234 are captured by the suturing device. The doctor retracts the suturing device and suture end portion 4234 from the pelvic bowl of the patient, and removes suture dart 4222 and suture end portion 4234 from the suturing device.

The doctor then attaches suture dart 4224 to the suturing device, inserts the suturing device and suture end portion 4244 into the pelvic bowl of the patient, and deploys suture dart 4224 and suture end portion 244 through another anchoring tissue such as, for example, the vaginal formix of the patient such that suture dart 4224 and suture end portion 4244 are captured by the suturing device. The doctor retracts the suturing device and suture end portion 4244 from the pelvic bowl of the patient, and removes suture dart 4224 and suture end portion 4244 from the suturing device.

At step 5244, the doctor pulls suture end portions 4231 and 4241 together and suture end portions 4234 and 4244 together to position implant 4200 to pull the apex of the vagina toward the sacrospinous ligament such that the apex of the vagina is supported to in a therapeutic position. At step 5245, suture end portions 4231 and 4241 can be tied together using multiple knots, secured to implant 4300, and/or secured to a tissue within the body of the patient to secure the implant and hold the apex of the vagina in the therapeutic position. Similarly, in other embodiments, suture end portions 4234 and 4244 can be tied together using multiple knots, secured to implant 4300, secured to a tissue within the body of the patient, and/or otherwise secured to hold the apex of the vagina in the therapeutic position.

In other embodiments, the steps described above can be rearranged into different orders. In other embodiments, additional steps can be used to further secure the implant to the body of the patient.

In some embodiments, the implant is used to support a body tissue other than a vagina. In other embodiments, more or fewer sutures are used to support a tissue within the body of the patient. In yet other embodiments, sutures or portions of sutures are deployed in or attached to body tissues other than or in addition to the sacrospinous ligament and/or the vaginal formix.

Figure 79:
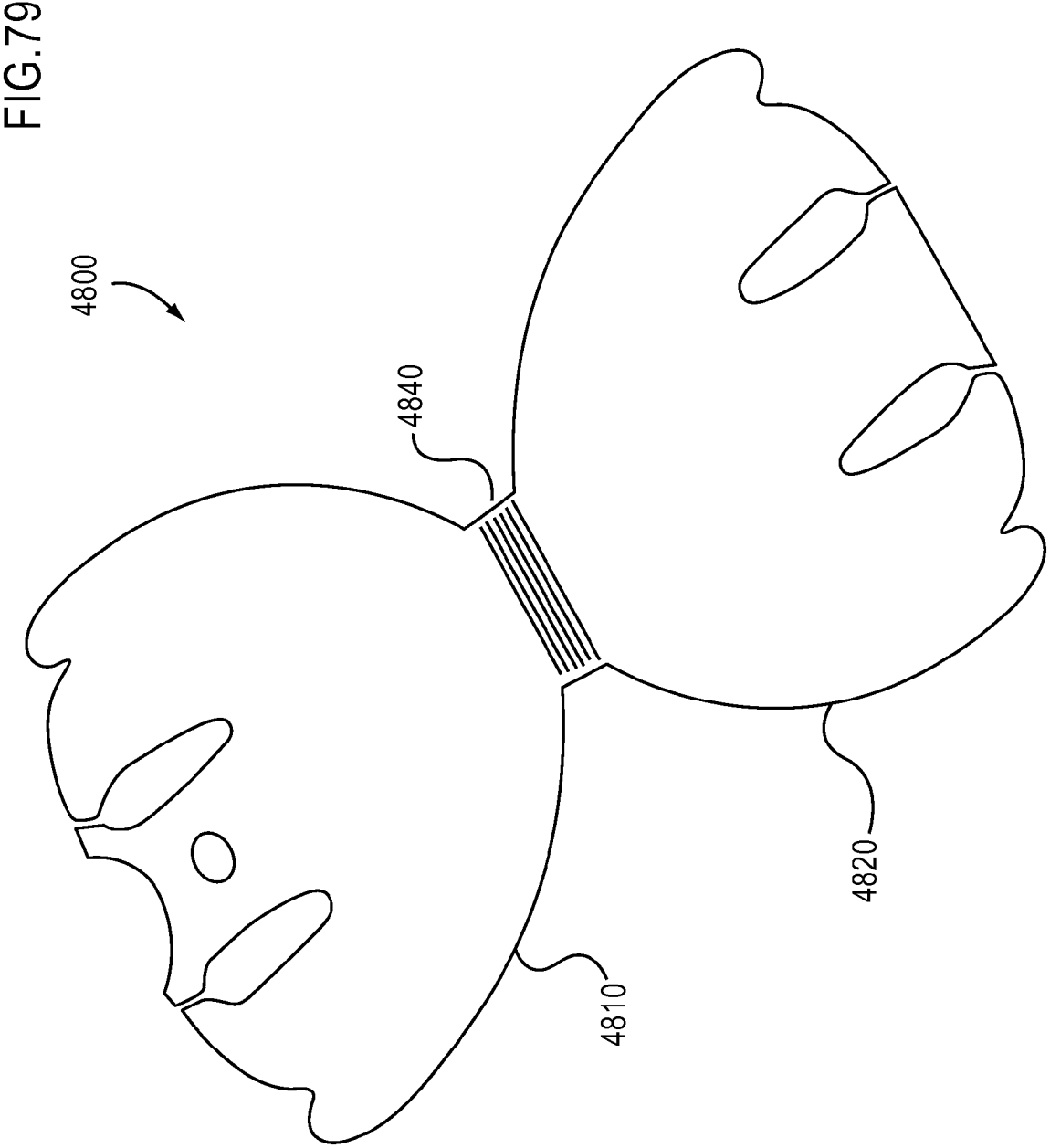
FIGS. 79-84 are each a perspective view of other embodiments of implant dispensers.

FIG. 79 is a perspective view of an implant dispenser 4800. Implant dispenser 4800 includes first body portion 4810 and second body portion 4820 movably coupled by living hinge 4840. In other words, first body portion 4810 and second body portion 4820 are movably coupled by a single piece of material configured to bend or flex without breaking, such as by having one or more portions of substantially reduced thickness. In one such embodiment, the implant dispenser is constructed from a single piece of material. In other embodiments, a first portion and a second portion of an implant dispenser can be coupled using, for example, a flexible material coupled to the first portion and the second portion of the implant dispenser.

Figure 80:
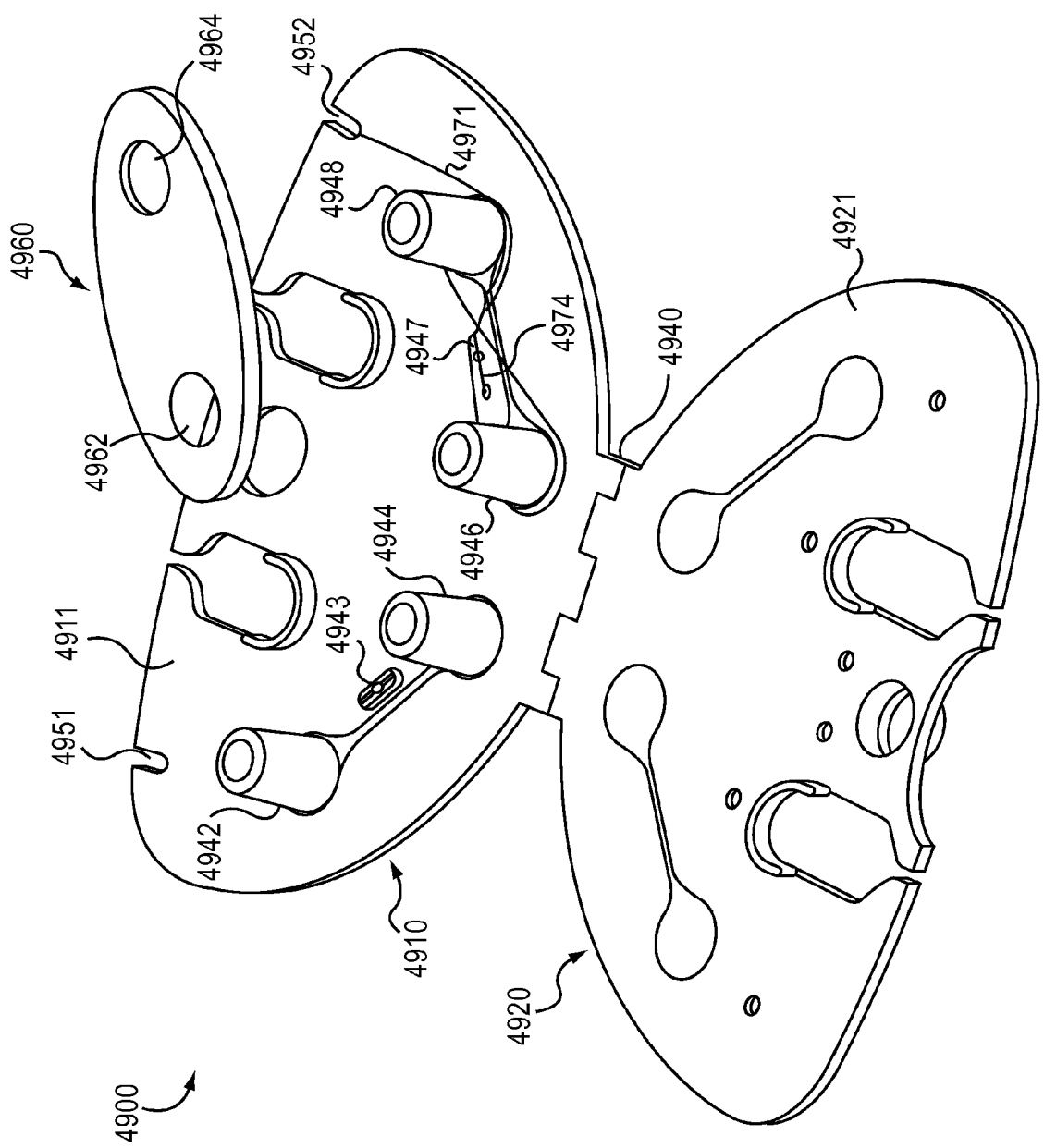

FIG. 80 is a perspective view of an implant dispenser 4900. Implant dispenser 4900 includes first portion 4910 and second portion 4920. First portion 4910 and second portion 4920 are coupled by hinge 4940. First portion 4910 has external surface 4911 and an internal surface (not shown in FIG. 80) opposite external surface 4911. First portion 4910 includes post 4942, post 4944, post 4946, post 4948, dart retention structure 4943, dart retention structure 4947, notch 4951, notch 4952. Second portion 4920 has external surface 4921 and an internal surface (not shown in FIG. 80) opposite external surface 4921.

Implant dispenser 4900 is illustrated in an open configuration. Implant dispenser 4900 can also be configured in a closed configuration. In the closed configuration, external surfaces 4911 and 4921 are exposed, and internal surface of first body portion 4910 and internal surface of second body portion 4920 face toward one another.

Posts 4942, 4944, 4946, and 4948 are retention structures for holding and/or managing sutures, for example, sutures 4230 and 4240 of implant 4200, used for implantation of implant 4200. For example, implant 4200 can be disposed within implant dispenser 4900 when implant dispenser is in a closed configuration, and portions of sutures 4230 and 4240 can be routed from implant 4200 positioned between internal surfaces of first portion 4910 and second portion 4920 to posts 4942, 4944, 4946 and 4948 on external surface 4911 via notch 4951 and notch 4952.

Referring to FIG. 80, portions of suture 4971 are disposed or wound around posts 4946 and 4948. Suture dart 4974 is removably coupled to dart retention structure 4947 to, for example, help prevent suture 4971 from becoming unwound from posts 4946 and 4948. Similarly, a suture can be disposed or wound around posts 4942 and 4944 and a suture dart can be removably coupled to dart retention structure 4943 to prevent the suture from becoming unwound from posts 4942 and 4944.

Dart retention structures can include any structure for holding suture darts. For example, tabs, clips, and/or a space between two protrusions for frictionally securing a suture dart. In some embodiments, adhesives can be used with or in place of dart retention structures to secure a dart to the implant dispenser.

Cover 4960 can be disposed on posts 4946 and 4948 to cover a portion of a suture to protect the portion of the suture and/or to help prevent the portion of the suture from unwinding from posts 4946 and 4948. Openings 4962 and 4964 in cover 4960 are configured to engage posts 4946 and 4948, respectively, when pressed onto posts 4946 and 4948 to create a friction or compression fit.

A second cover, similar to cover 4960, can be coupled to posts 4942 and/or 4944. In some embodiments, posts 4942, 4944, 4946 and/or 4948 are break-away posts configured to be removed from implant dispenser 4900. As such, a person using the implant dispenser can remove sutures from the posts without unwinding the sutures from the posts. Rather, the posts can be removed from the implant dispenser and the sutures can be removed from the posts by sliding the posts from the sutures without unwinding the sutures.

In some embodiments, a tab, snap or other locking and/or coupling device can be added to one or more posts and/or a cover to provide for lockable coupling of the cover to the implant dispenser. In yet other embodiments, adhesive, epoxy and/or glue can be used to secure the cover to one or more of the posts.

Figure 81:
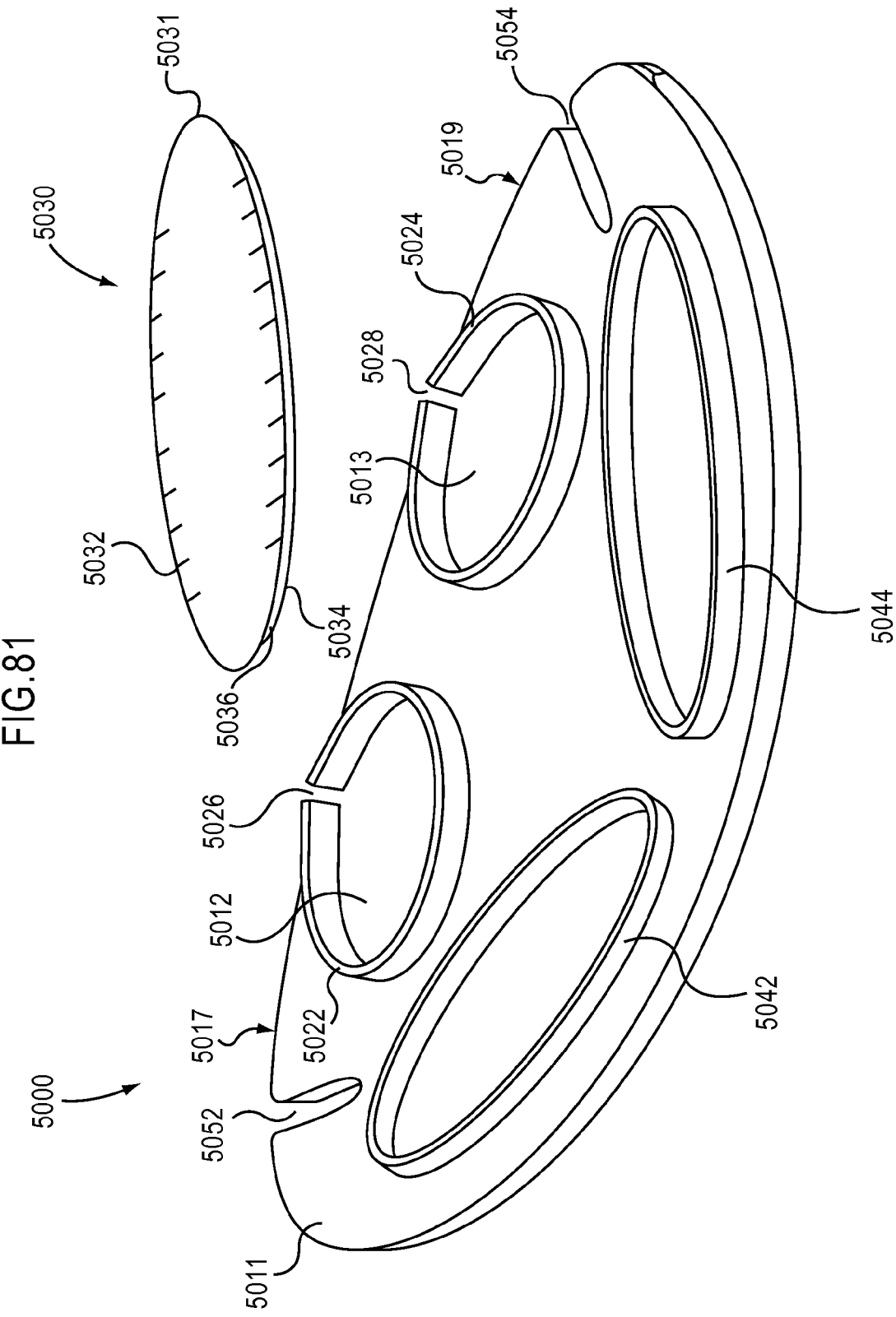
Figure 82:
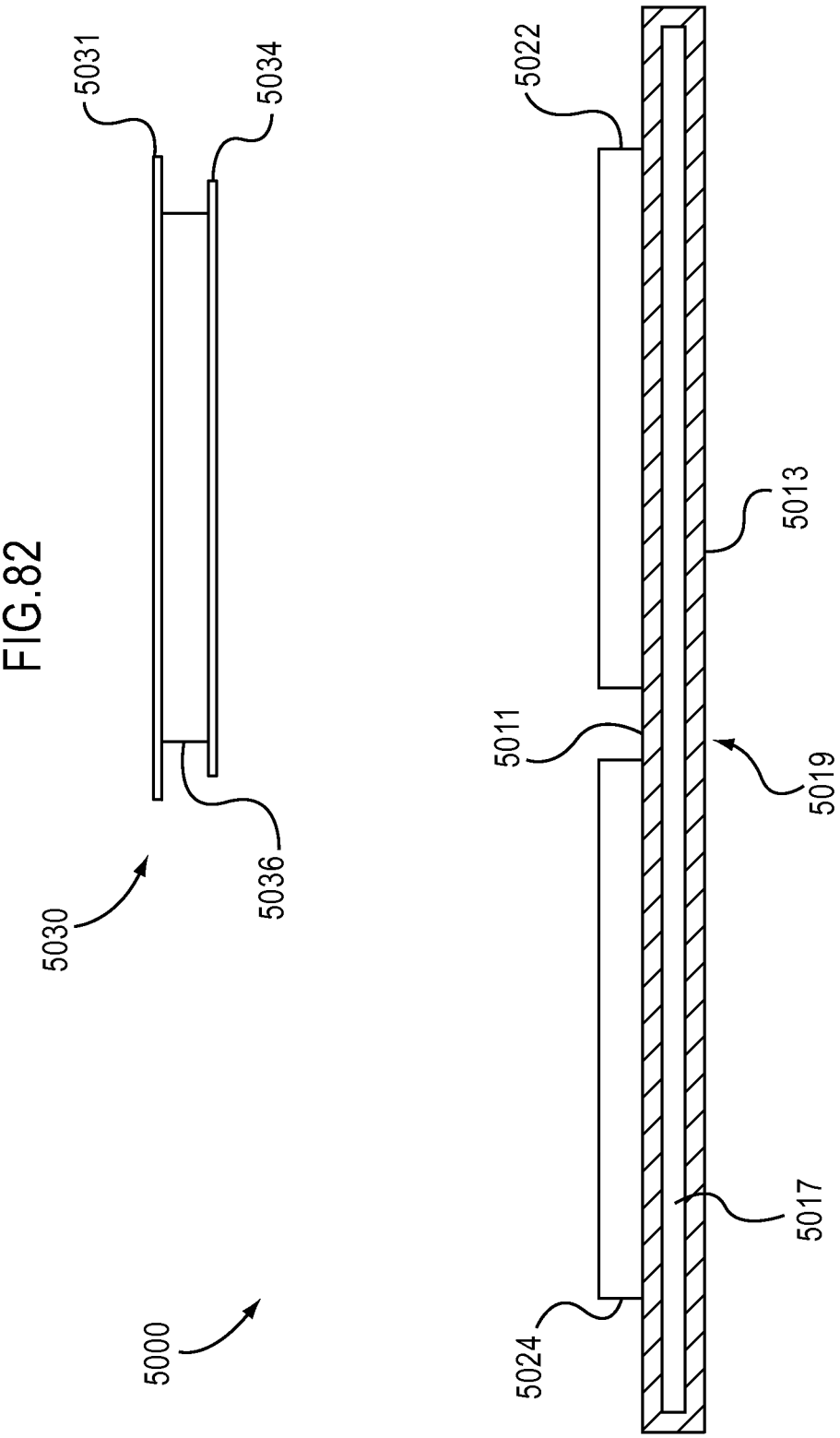

FIG. 81 illustrates a top perspective view of another embodiment of an implant dispenser and FIG. 82 illustrates a side perspective view of the implant dispenser. Implant dispenser 5000 includes first body portion 5011, a second body portion 5013 opposite first body portion 5011, and a cavity 5017 defined between first body portion 5011 and the second body portion 5013. Cavity 5017 is configured to house an implant during shipment, sterilization and/or implantation. Apertures 5012 and 5015 are in communication with an outside edge 5019 via opening 5026 and opening 5028, respectively. Retention structures 5022 and 5024 are configured to maintain loops in sutures in an open configuration about apertures 5012 and 5015.

A cover 5030 is configured to manage sutures used during implantation of an implant. Suture end portions can be routed from an implant in cavity 5017 through notch 5052 and/or 5054 and wound or wrapped around a rib 5036 on cover 5030 between a top portion 5031 and a lip 5034. A portion of a suture and/or a suture dart attached to a suture can be coupled or affixed to cover 5030 by, for example, a compression fit in slits 5032 to prevent the suture from unwinding from rib 5036. Cover 5030 can be pressed to fit around or couple to rib 5044 (or rib 5042). Cover 5030 and rib 5044 can be sized such that a friction fit helps prevent cover 5030 from decoupling from rib 5044. Although not shown in FIGS. 81 and 82, in some embodiments, an implant dispenser can include a second cover that can be coupled to another rib (e.g., rib 5042) for managing additional suture end portions.

Ribs 5044 and 5042 are contiguous protrusions from first body portion 5011. In other embodiments, ribs can be multiple protrusions from a body portion of the implant dispenser.

In one embodiment, a cover includes more than one lip and slit for managing multiple sutures. For example, a cover can include two lips on a rib such that a first suture can be wound onto the rib between a top portion of the cover and a first lip, and a second suture can be would onto the rib between the first lip and a second lip such that the first lip separates the first suture and the second suture. The first suture can be secured to a first slit in the cover and the second suture can be secured to a second slit in the cover.

In some embodiments, a cover and/or implant dispenser includes a locking mechanism such as a tab and/or adhesive for lockably coupling the cover to the implant dispenser. In some embodiments, the cover is removably coupled to the implant dispenser.

In one embodiment, an implant having two sutures is disposed in cavity 5017. A loop in a first suture is disposed about retention structure 5022, and a loop in a second suture is disposed about retention structure 5024. An end portion of the first suture is routed from cavity 5017 toward an external portion of first body portion 5011 via notch 5054 and wrapped around rib 5036 of cover 5030 between top portion 5031 and lip 5034 of cover 5030. A portion of the first suture is pressed to frictionally engage slit 5032 of cover 5030. Cover 5030 is then pressed onto rib 5044 of the implant dispenser. Similarly, an end portion of the second suture is routed from cavity 5017 toward an external portion of first body portion 5011 via notch 5052 and wrapped around a rib of a second cover (not shown in FIGS. 81 and 82) between a top portion and a lip of the second cover. A portion of the second suture is pressed to frictionally engage a slit of the second cover. The second cover is then pressed onto rib 5042 of the implant dispenser.

In one embodiment, implant dispenser 5000 is used in a pelvic floor reconstruction, vaginal vault support, or uterine support procedure. Implant dispenser 5000 can be used in a pelvic floor reconstruction, vaginal vault support, or uterine support procedure with implant 4200 similar to implant dispenser 4300 as described above. However, implant dispenser 5000 does not have an open configuration and a closed configuration. Thus, suture end portions 4231, 4234, 4241 and 4244 are removed from ribs on covers of implant dispenser 5000, for example, rib 5036 on cover 5030. Also, after deploying suture darts 4221 and 4223, and first end portions 4231 and 4241 through the sacrospinous ligament, implant body 4210 is removed from cavity 5017 rather than by moving the implant dispenser into an open configuration.

Figure 83:
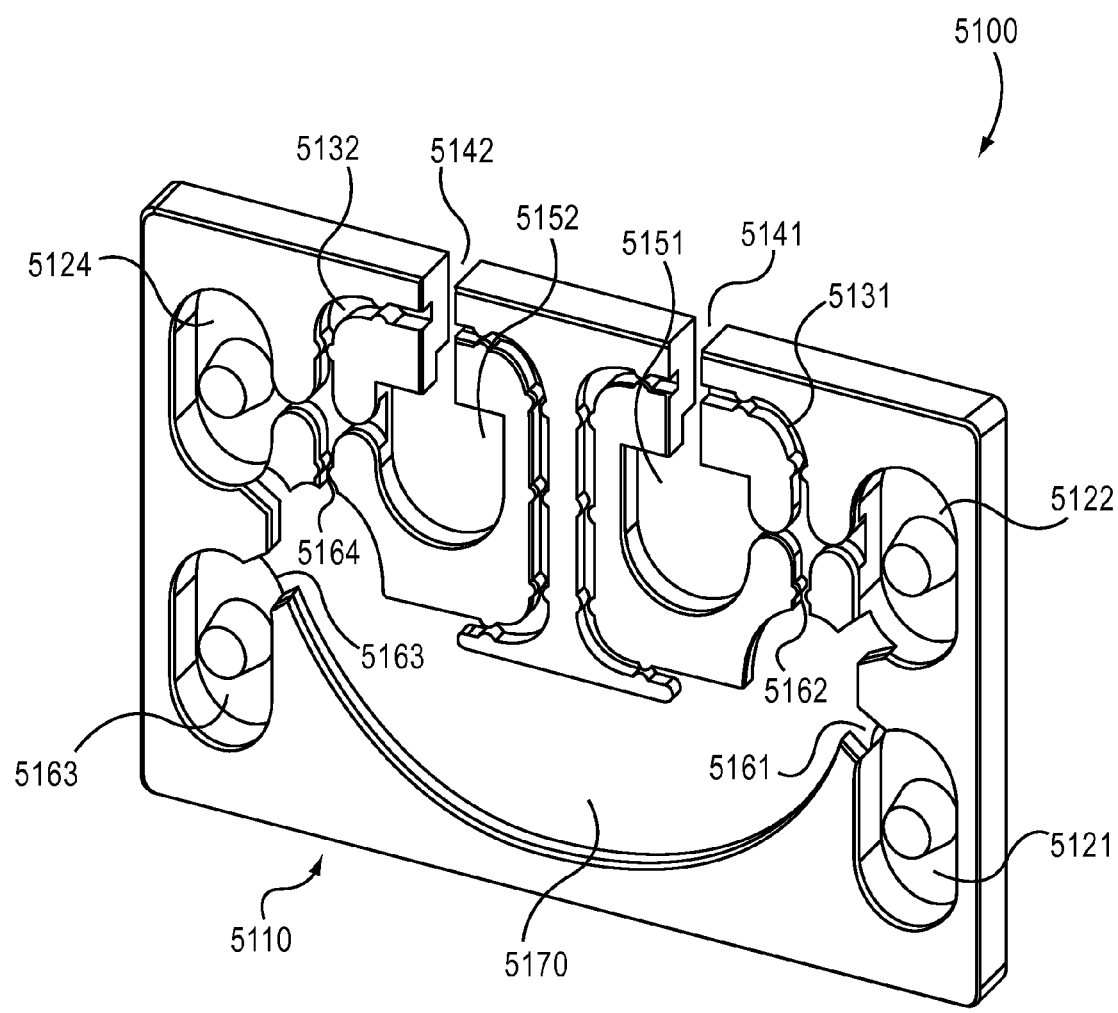

FIG. 83 is a perspective view of implant dispenser 5100 configured to secure an implant, according to another embodiment. Retention cavities 5121, 5122, 5123, and 5124 are each configured to receive and/or house a portion of a suture within each of retention cavities 5121, 5122, 5123, and 5124. Specifically, a portion of a suture can be coiled or looped within each of retention cavities 5121, 5122, 5123, and 5124.

Implant cavity 5170 is configured to allow an implant to be disposed within implant cavity 5170. In some embodiments, implant cavity 5170 can be shaped to approximate the shape of an implant disposed within implant cavity 5170.

Apertures 5151 and 5152 are configured to allow a suturing device to be passed through body 5110 via apertures 5151 and 5152. Apertures 5151 and 5152 are in communication with an outside edge of body 5110 via openings 5141 and 5142, respectively.

Retention cavities 5131 and 5132 are each configured to maintain a suture in an open configuration about apertures 5151 and 5152, respectively. In some embodiments, retention cavities 5131 and 5132 can include retention structures such as tabs or narrow portions configured to form a compression fit with a suture pressed into the narrow portions.

Openings 5141 and 5142 extend from an outside edge of body 5110 to apertures 5151 and 5152 and are configured such that a suture passed through body 1110 via aperture 5151 or aperture 5152 can be removed from body 5110 via opening 5141 or opening 5142, respectively.

In some embodiments, a body of an implant dispenser can be configured using channels and/or routes between various cavities in the body to allow a protective film or cover to be applied or disposed on the body, without the protective film or cover coming into contact with sutures extending from one cavity to another in the body. A protective film can, for example, help prevent an implant from becoming displaced from an implant cavity in the body or help prevent portions of sutures from becoming displaced from retention cavities in the body.

In the illustrated embodiment, implant dispenser 5100 includes channel 5161 and channel 5163 that allow sutures attached to an implant to extend from implant cavity 5170 into retention cavity 5121 and retention cavity 5123, respectively. For example, implant 4200 can be disposed in implant cavity 5170. Second end portion 4244 of suture 4240 can extend from implant cavity 5170 where second end portion 4244 is attached to implant 4200, through channel 5161, and be coiled in retention cavity 5121. Channel 5163 is similarly configured with respect to cavity 5170 and cavity 5123.

Body 5110 also includes channels 5162 and 5164. Channel 5162 is configured to allow a portion of a suture attached to an implant disposed within implant cavity 5170 to pass through channel 5162 and into retention cavity 5131 such that the portion of the suture can be held in an open configuration about aperture 5151. Channel 5164 is configured to allow a portion of a suture attached to an implant disposed within implant cavity 5170 to pass through channel 5164 and into retention cavity 5132 such that the portion of the suture can be held in an open configuration about aperture 5152.

In other embodiments, a body of an implant dispenser can include additional or fewer channels. For example, channels in addition to those shown in FIG. 83 can exist between an implant cavity and retention cavities to provide routes for suture between various cavities in the body of the implant dispenser.

Implant dispenser 5100 can be used similarly to implant dispenser 4300 and implant dispenser 5000. An implant such as implant 4200 can be disposed on implant dispenser 5100. Implant body 4210 can be placed in implant cavity 5170. Suture end portions 4231, 4234, 4241 and 4244 can be disposed in retention cavities 5121, 5122, 5123 and 5124 for securing and managing suture end portions 4231, 4234, 4241 and 4244 via, for example, cavities 5161, 5162, 5163 and 5164. Suture loops 4233 and 4234 can be secured about apertures 5151 and 5152 within retention cavities 5131 and 5132.

Implant dispenser 5100 can be used in implantation of an implant similarly to implantation of implant 4200 using implant dispenser 4300 and implant dispenser 5000 described above. However, rather than removing implant body 4210 from a cavity or by moving an implant dispenser to an open configuration, implant body 4210 can be removed from implant cavity 5170.

In some embodiments, an implant cavity includes tabs, clips and/or other structures for securing an implant. In some embodiments, an implant cavity includes adhesive for securing an implant to the implant cavity. In yet other embodiments, an implant dispenser is covered with a protective film or material to secure an implant to the implant dispenser.

Figure 84:
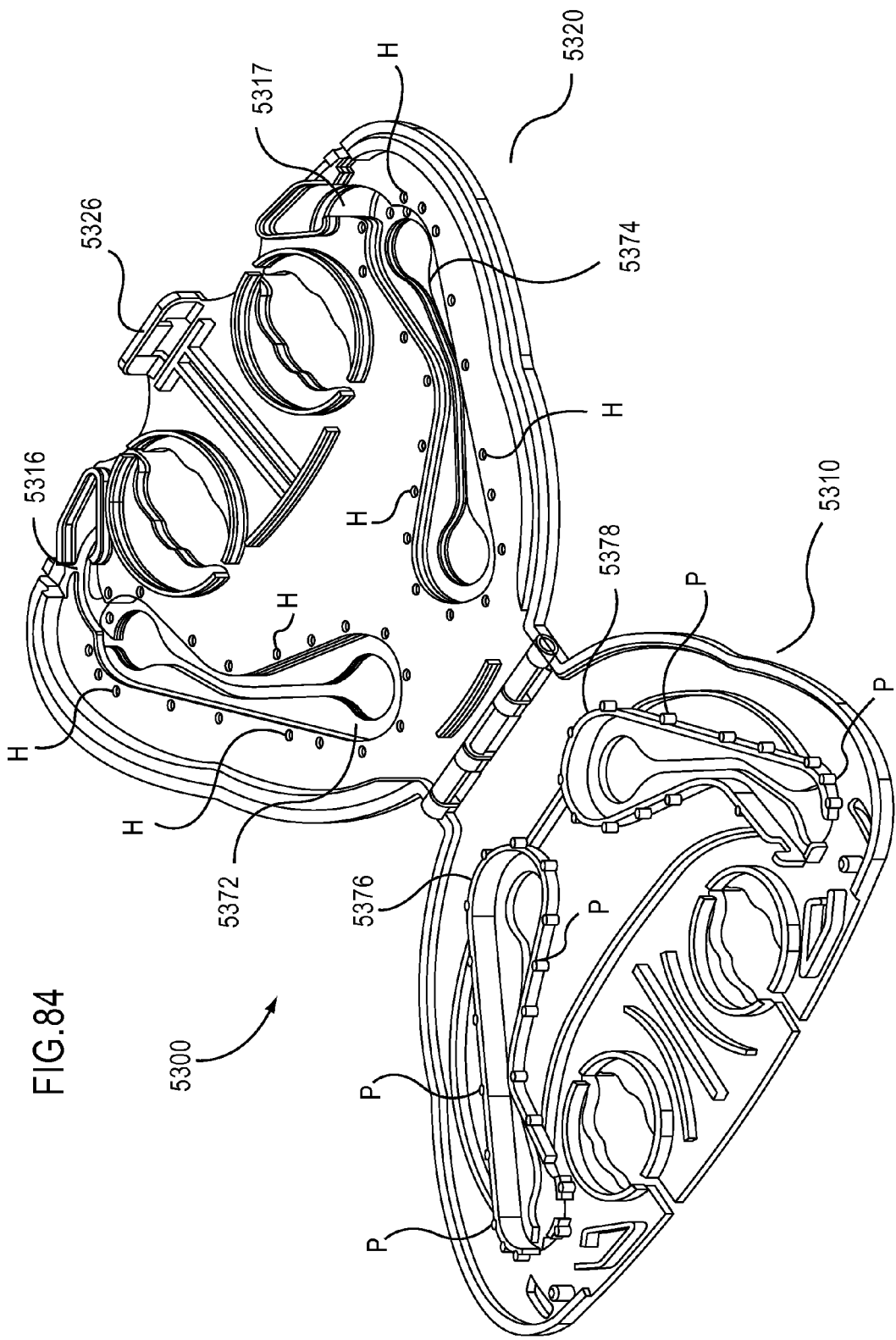

FIG. 84 illustrates an implant dispenser according to another embodiment. An implant dispenser 5300 includes a first body portion 5310 and a second body portion 5320. Implant dispenser 5300 includes additional protrusions, holes, and tabs configured to aid in securing an implant to implant dispenser 5300.

More specifically, rib 5376 and rib 5378 include protrusions P configured the fit within the holes disposed around the periphery of cutout portion 5372 and cutout portion 1374 in second body portion 5320. In some embodiments, holes H are disposed within cutout portion 5372 and within cutout portion 5374 in second body portion 5320 and are configured to engage the protrusion on rib 5376 and rib 1378, respectively, within the cutout portions. In some embodiments, the holes and protrusions are configured to frictionally couple first body portion 5310 to second body portion 5320 in a closed position. In some embodiments, the protrusions and/or ribs can be configured to secure an implant and/or prevent migration of one or more sutures into the cavities defined by the ribs.

Second body portion 5320 includes dart retention structures 5316 and 5317. Dart retention structures 5316 and 5317 are configured to receive and engage curved darts or needles such that the curved darts or needles are secured to second body portion 5320. Additionally, second body portion includes tab 5326 configured to engage first body portion 5310 such that first body portion 5310 is lockably coupled to second body portion 5320.

Other configurations for an implant dispenser can alternatively be used, such as, for example, the procedure assistant device described with reference to FIGS. 44-46. In another example, a device to aid in the delivery of an implant can include a ring with a groove to maintain a loop in a suture in an open position. In some embodiments, the ring (or loop retaining structure) can be separate from a retention structure configured to secure a free end portion of the suture.

In some embodiments, an implant dispenser is used to protect and house an implant during sterilization, shipment and implantation. Alternatively, an implant is attached to an implant dispenser just prior to implantation, after shipment and/or sterilization to aid in the implantation of the implant.

In some embodiments, an implant dispenser can include additional structures and/or devices for securing an implant to the implant dispenser. For example, an adhesive can be disposed on a portion of the implant dispenser to secure a portion of an implant to the implant dispenser. One or more tabs can be coupled to the implant dispenser to hold an implant to the implant dispenser. The implant dispenser can include a cavity that receives a portion of an implant.

In some embodiments, the implant dispenser includes additional apertures, openings and/or retention structures to accommodate additional parts of an implant, including additional sutures and/or additional loops in sutures. In such embodiments, attaching an implant to the implant dispenser can include disposing additional loops in sutures about additional retention structures, securing additional free end portions of sutures to retention structures and/or securing additional sutures or portions of sutures to retention structures.

Figure 85:
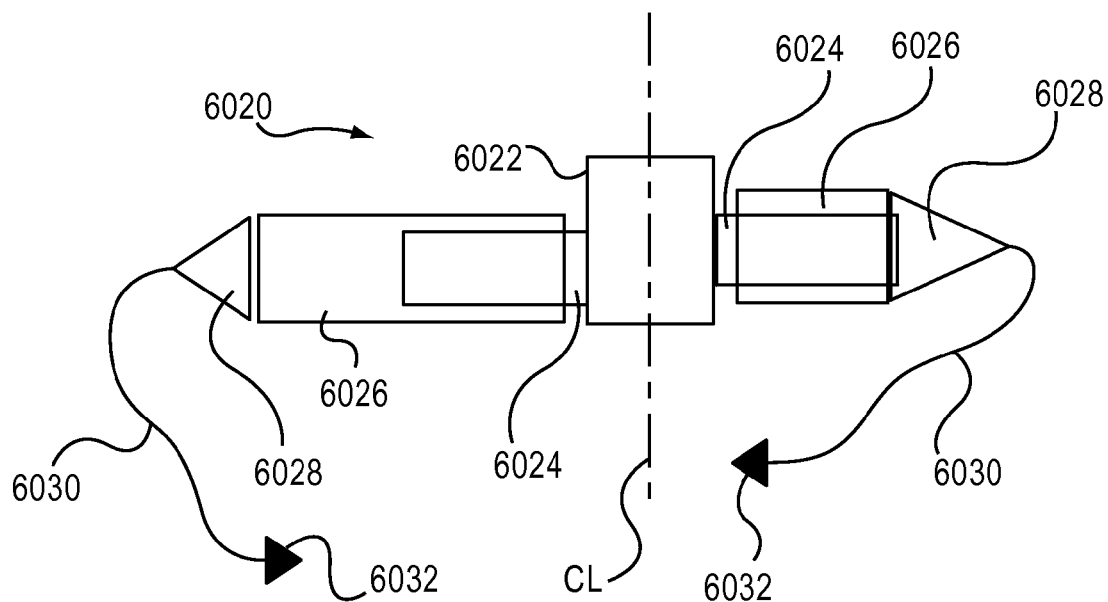
FIG. 85 is a schematic illustration of an implant according to an embodiment.

FIG. 85 is a schematic illustration of an implant 6020 according to another embodiment. The implant 6020 can be used, for example, to treat various conditions, including, but not limited to a hysterocele. The implant 6020 includes a support portion 6022, and one or more straps 6024. The support portion 6022 can be a variety of different shapes, sizes and configurations depending on the intended use for the particular implant. For example, in some embodiments, the support portion 6022 can be substantially rectangular, square, oval, or elliptical. The support portion 6022 can be shaped and sized to support a bladder (e.g., to treat a cystocele) and/or a bladder neck and/or support a uterus (e.g., to treat a hysterocele) and/or to support a rectum (e.g. to treat a rectocele).

The support portion 6022 and/or the straps 6024 can each be formed with a mesh material to allow tissue in-growth to the implant 6020 after implantation. For example, some or all of the implant 6020 can be formed with a mesh material as described in U.S. Patent Pub. 2005/0038452 A1 to Chu, the disclosure of which is hereby incorporated by reference in its entirety. In some embodiments, some or all of an implant 6020 can be formed with the Advantage® Mesh or the Polyform™ Synthetic Mesh material each provided by Boston Scientific Corporation ("BSC"). The implant 6020 can be monolithically formed or alternatively, the implant 6020 can be formed with multiple different materials and/or can include multiple different components or portions coupled together. In some embodiments, an implant 6020 can be formed with a combination of materials including synthetic and biological materials. For example, the support portion 6022 can be formed with a first biocompatible material and the straps 6024 can be formed with a second biocompatible material different than the first biocompatible material. In another example, the support portion 6022 can be formed with a biological material, and the straps can be formed with a synthetic material. The straps 6024 and support portion 6022 can also have a different weave, pitch, texture, color, and pattern from each other.

The straps 6024 can be formed monolithically with the support portion 6022 or can each be a separate component coupled to the support portion 6022. A strap 6024 and support portion 6022 can be coupled in an abutting relationship, an overlapping relationship, or can be bridged. The straps 6024 can be coupled to the support portion 6022 by, for example, heat bonding, gluing, using fasteners, and/or sewing. In some embodiments, a strap 6024 can include a heat seal along its length or a portion of its length to help prevent or reduce stretching of the strap 6024.

In some embodiments the support portion 6022 and/or straps 6024 include one or more tanged portions (as described above). The tangs allow the implant 6020 to be anchored within pelvic tissue without the use of additional anchoring mechanisms or sutures. In some embodiments, an implant 6020 includes tangs on an edge along an entire length of the implant 6020. In other embodiments, the implant 6020 includes tangs covering substantially all of an exterior surface of the implant. In some embodiments, tangs are only on the straps 6024 of the implant 6020. For example, in some embodiments the straps 6024 include a tanged portion to engage and help secure the implant to pelvic tissue. Pelvic tissue can include, for example, ligaments (such as a sacrospinous ligament), muscle (such as an obturator internus muscle or an obturator externus muscle), fascia, or any other structure or tissue within a pelvic region of a patient.

As with the support portion 6022, the straps 6024 can have a variety of different configurations and/or different sizes (e.g. lengths, widths), depending on the intended use for the particular implant and the intended implantation site for the straps within the pelvic region. For example, straps 6024 can have a length to accommodate securing the strap 6024 to a specific anatomical location within the pelvic region, such as a sacrospinous ligament, an arcus tendineus, a levator muscle, etc. In some embodiments, an implant for use in supporting a bladder neck includes straps that are secured to the arcus tendineus. Such straps are typically relatively short in length, as the distance from the placement of the support portion of the implant to the arcus tendineus does not require a long strap.

The length of a particular strap 6024 can depend on the particular tissue (e.g., ligament, muscle) that the strap 6024 is intended to be secured to, such that trimming of the strap 6024 during or after placement can be reduced or eliminated. For example, a posterior strap 6024 can have a length such that the strap 6024 can be placed through, or secured to, tissue, such as a sacrospinous ligament, but is not long enough to return back through a vaginal insertion point. In some embodiments, a strap 6024 has a length such that it extends from a pelvic region through an exterior incision of the patient.

The implant 6020 also includes sleeve members 6026 (also referred to as a "sleeves") each coupled to one of the straps 6024. For example, a sleeve member 6026 can be coupled to the strap 6024 via a suture (not shown in FIG. 85), with a heat seal (not shown in FIG. 85), or other attachment methods, such as with fasteners or adhesive. The sleeve member 6026 can be used during the insertion of the implant into a pelvic region to prevent the straps 6024 from prematurely engaging tissue during the delivery procedure. For example, if a strap 6024 includes a tanged portion, a sleeve member 6026 can prevent the tangs from engaging tissue as the implant is being delivered into the pelvic region. Conversely, when no sleeve 6026 is disposed on a strap 6024 having tanged edges, the tangs can engage the surrounding tissue making it difficult to smoothly slide the strap 6024 for adjustment. A sleeve 6026 can also help in a process to adjust the tension of a strap 6024, for example, to relieve strap tension.

The sleeves 6026 can also protect the straps 6024 from damage during delivery. A sleeve 6026 can have a reduced profile at a distal end portion, enabling it to more easily travel through the tissue during delivery. For example, a sleeve 6026 can be tapered. The same type or configuration of sleeve 6026 can be disposed over each strap 6024 of an implant 6020, or a different type of sleeve 6026 can be disposed over each strap 6024 of an implant 6020. In some embodiments, there is no sleeve 6026, or a sleeve 6026 is disposed over only one or some of the straps 6024. The sleeve 6026 can be transparent, semi-transparent, colored, non-colored, or a combination thereof. The sleeve 6026 can be, for example, tapered, flat, and/or tubular. A sleeve 6020 can be formed for example, with a clear, thin, flexible biocompatible polymer, and be configured to allow the user to examine or view the implant 6020 (e.g., straps) disposed within the sleeve 6026. After the straps 6024 are positioned at a desired location within the pelvic region, the sleeves 6026 can be removed from the implant 6020, as described in more detail below. Although the sleeves 6026 are described herein as being part of a sleeve assembly or dilator assembly, it should be understood that a sleeve 6026 can alternatively be individually coupled to a strap.

As stated previously, an implant 6020 can have any number of straps 6024 depending on the particular intended use for the implant 6020. For example, an implant 6020 can have between one and twenty straps 6024. In some embodiments, one or more straps 6024 can extend from the support portion 6022 at an angle. Such an angle of a strap 6024 can vary in different embodiments, for example between 6020 and 160 degrees from a centerline CL of the support portion 6022.

In some embodiments, the straps 6024 are configured to be secured to tissue by an interference fit or frictional fit with the surrounding tissue. For example, the strap 6024 can be pulled through a pelvic tissue using, for example, a sleeve or dilator (as described herein) that is configured to dilate or expand the tissue and provide a lead-in (e.g., passageway) for the strap to be pulled through the tissue. The pelvic tissue is dilated such that the strap 6024 can be pulled through the tissue, but then prolapses or retracts to a smaller size to provide a frictional interaction between the tissue and the strap 6024. The strap 6024 can also be flexible such that even if a width of the strap 6024 is greater than a width of a corresponding passage in the tissue formed by the lead-in device (e.g., dilator or sleeve), the strap 6024 can flex to be pulled through the tissue, and the tissue can dilate or expand to receive the strap 6024. In some embodiments, one or more straps 6024 are tapered toward their distal end, and are larger in width near the support portion 6022, which further provides a lead-in through the tissue.

In some embodiments, one or more of the straps 6024 are substantially the same length as their corresponding sleeves 6026. In other embodiments, one or more straps are shorter than their corresponding sleeves. In such an embodiment, the sleeve can be used to provide an extension to the strap to help in the insertion process. By forming the strap 6024 with a length just sufficient to be secured to a target tissue site, the implant 6020 can be formed with less material. For example, in many cases, as mentioned above, a strap 6024 may need to be trimmed after placement in a pelvic region, and the trimmed material is then discarded. The use of a strap 6024 having a length configured for the particular use can thus eliminate the need for trimming and also reduce the costs to manufacture the implant 6020. Such embodiments of a strap 6024 can also help prevent strap stretch that can occur during insertion of the implant due to pulling on a longer length strap. A strap having a length shorter than a corresponding sleeve can also help maintain the cleanliness of a strap during insertion as a substantial portion of the strap that will be secured within the pelvic region will be protected within the sleeve. A strap having a shorter length than its corresponding sleeve can also reduce friction between the strap and an interior surface of the sleeve (due to reduced surface area contact) allowing easier, removal of the sleeve.

As stated above, in some embodiments, the support portion 6022 and the straps 6024 are separate components. In some embodiments, a sleeve and strap assembly is provided that is configured to be coupled to a support portion 6022 of an implant 6020. For example, a support portion 6022 and one or more sleeve and strap assembly can be provided to a user (e.g., a physician) unassembled. The user can then secure one or more of the sleeve and strap assemblies to the support portion to form the implant 6020.

In some embodiments, the centerline CL of the support portion 6022 is marked using a marking (such as an ink marking) or a colored thread woven into the support portion 6022. The marked centerline may aid in the placement of the implant 6020 within the body of the patient. Specifically, a user may use the marked centerline to appropriately place and/or adjust the implant within the body of the patient (for example, the marked centerline may be lined up with the mid-line of the patient). In some embodiments, the centerline CL of the support portion 6022 is marked with blue ink or a blue thread.

As shown in FIG. 85, a dilator 6028 is coupled to each of the sleeves 6026 and used to assist in the delivery of the implant 6020 to the pelvic region. A proximal end portion (or trailing end) of a dilator 6028 is coupled to the sleeve 6026 by, for example, crimping, knotting, heat bonding, heat sealing, stitching, stretching, or tipping or a combination thereof. In some embodiments, the sleeve 6026 is formed monolithically with the dilator 6028. The dilator 6028 is configured to produce a passage through tissue to facilitate strap placement. Using a dilator 6028 to introduce a strap 6024 into a pelvic region can help reduce handling or pulling of the implant 6020 itself, thereby reducing or eliminating potential damage to the implant 6020.

The dilator 6028 can have a variety of different configurations. For example, the dilator 6028 can be a variety of different lengths, shapes, diameters, etc. The dilator 6028 can expand a passage formed by a needle 6032 (as described below) during insertion through a tissue, to ease the transition of the opening of the tissue to a cross-section of the sleeve 6026. The dilator 6028 can be flexible, semi rigid, or rigid. The dilator 6028 can be curved or substantially linear. In some embodiments, the dilator 6028 is tubular shaped. For example, the dilator device 6028 can define a lumen therethrough. The dilator 6028 can also be tapered from a larger diameter at a proximal or trailing end to a smaller diameter at a distal or leading end of the dilator 6028. The dilator 6028 can also be color-coded. For example, when an implant 6020 having multiple straps 6024 is to be delivered to a pelvic region, dilators 28 each having a unique color to indicate where that strap 6024 is to be placed within a pelvic region can be coupled to each strap. Such color-coding can help with the organization of the delivery process. In some embodiments, the sleeves 6026 associated with the straps 6024 can be color-coded in a similar manner as described for the dilators 6028. In some embodiments, both the sleeves 6026 and the dilators 6028 are color-coded.

As shown in FIG. 85, a leader 6030 is coupled to a distal end of the dilator 6028 and a needle 6032 is coupled to a distal end of the leader 6030. The leader 6030 can be a suture, formed, for example, with a polymer. In other embodiments, the leader can be made from metal or other fiber and can be attached at one or more locations of a sleeve and/or dilator. For example, the leader 6030 can be coupled to the dilator 6030 and/or sleeve 6026 by, for example, gluing, thermobonding, knotting or other methods of attachment. In some embodiments, the leader 6030 can be a portion of (or formed monolithically with) a suture used to couple the sleeve 6026 to a strap 6024.

The needle 6032 can be formed with various biocompatible materials, such as, for example, stainless steel, or other surgical steel. In some embodiments, the needle 6032 is used to associate the strap 6024 of the implant 6020 to a delivery device, such as those described in further detail herein.

A length of the leader 6030 (measured from a distal end of the dilator 6028) can vary. For example, in some embodiments, a length of a leader 6030 is sufficiently long to be placed through a selected tissue anchoring site (after entering the pelvic region via a vaginal incision), and passed out through the vaginal incision, without requiring the dilator 6028 to enter the vagina (e.g., after passing through a tissue within the pelvic region). In some embodiments, a length of the leader 6030 can allow the physician to remove the needle 6032 from a delivery device external to the body before an attached dilator 6028 is pulled into the tissue or ligament. The insertion and delivery of an implant using a delivery device is described in further detail herein.

In other embodiments, rather than a leader and a needle, the dilator or sleeve can include a connector portion that can be used to associate the straps to a delivery device. For example, the dilator or sleeve can include a connector portion (not shown). In some embodiments, a loop connector is coupled to the sleeve or dilator. Such a connector or connector portion can be used to associate the dilator or sleeve to a delivery device, as described herein.

Delivery devices can be used to deliver selected straps of the implant 6020 to or through a pelvic tissue, such as, for example, a levator muscle (e.g., levator ani muscle), a sacrospinous ligament, a tendineus arch of levator muscle (also referred to herein as "arcus tendineus" or "white line"), obturator muscles, or to an iliococcygeus muscle, or to other anatomical securement sites within the pelvic region of a patient. The delivery device can also be used to pass a suture end through a wall of a vagina or to pass a suture through the epithelium of a vaginal wall without passing the suture through the vaginal wall. For example, straps 6024 of the implant 6020 can be deposited at selected tissue sites within the pelvic region and a portion of an implant 6020 can also be coupled to a vagina of the patient, to a wall of the vagina, secured inside the vagina (e.g., within a vaginal lumen) or within the pelvic region.

In one example, an implant 6020 can be delivered using a transvaginal approach using for example, a Capio® Suture Capture Device manufactured by BSC. An example of such a suturing device is described in U.S. Pat. No. 5,741,277 incorporated by reference above. Other types of delivery devices can alternatively be used, such as, for example, the suturing device described in U.S. Patent Pub. 2004/0181243 A1 to Chu et al., entitled Re-shapeable Medical Device, the disclosure of which is hereby incorporated by reference in its entirety. A similar delivery device is also described below with reference to FIG. 88. In such a procedure, the implant 6020 is inserted through, for example, a single vaginal incision. The incision can be, for example, through the anterior vaginal mucosa.

The straps 6024 of implant 6020 can alternatively be implanted using, for example, a delivery needle, such as an Obtryx® Halo, Curve, Advantage® or Lynx® device each manufactured by BSC. An example of such devices is described in U.S. Patent Pub. No. 2005/0075660 and U.S. Patent Pub. No. 2005/0177022, incorporated by reference above.

The implant 6020 can also be configured to be associated to other delivery devices not specifically described herein. In some embodiments, a strap 6024 of the implant 6020 itself is configured to be associated to a delivery device. For example, a connector can be coupled directly to a strap 6024 for association to a delivery device, or the strap 6024 can include, for example, an opening or hole configured to associate the strap 6024 to a delivery device. In some embodiments, the leader 6030 and needle 6032 can be coupled directly to a strap 6024.

Although the above-described embodiments describe securing a strap 6024 to tissue without the use of a separate anchoring device (for example, securing with tangs of a strap), it should be understood that the implants described herein can also include anchors or other mechanical fasteners to secure one or more straps 6024 to the pelvic tissue. For example, a suture can be used to secure a strap or other portion of an implant 6020 to pelvic tissue.

In other embodiments, the straps of the implant are delivered to or through a pelvic tissue without the use of a delivery device. In such an embodiment, the needles and the straps are inserted into the sacrospinous ligament by hand. In this manner, the straps are secured to the sacrospinous ligament.

In some embodiments, a portion of the support portion 6022 is separately attached to a tissue within the pelvic region. Said another way, a portion of the support portion 6022 can be secured by means additional to the straps. For example, a suture can be threaded through the mesh support portion 6022 and attached to adjacent pelvic tissue. This can provide additional support for the support portion 6022.

Figure 86:
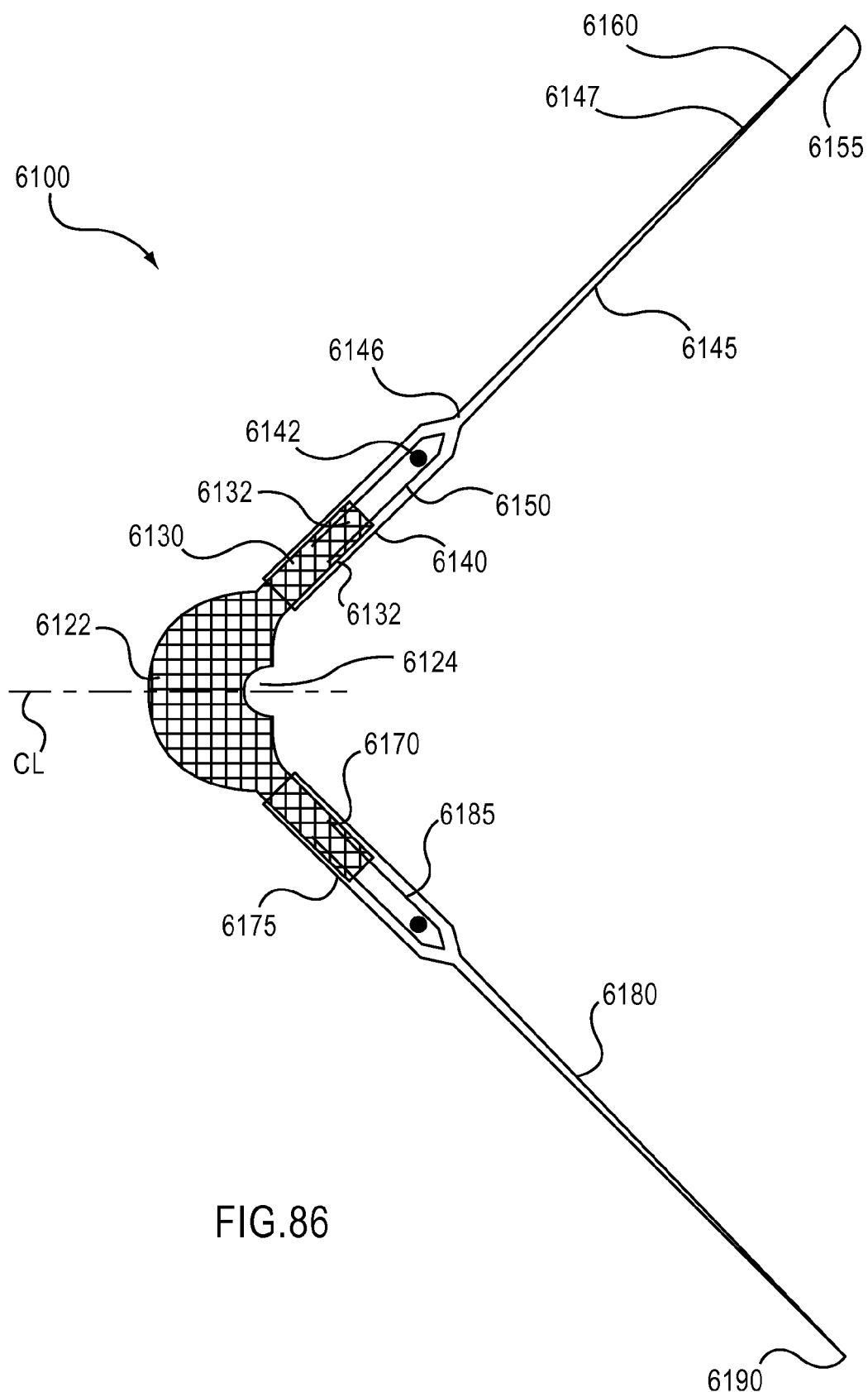
FIG. 86 is a top view of an implant according to an embodiment.
Figure 87:
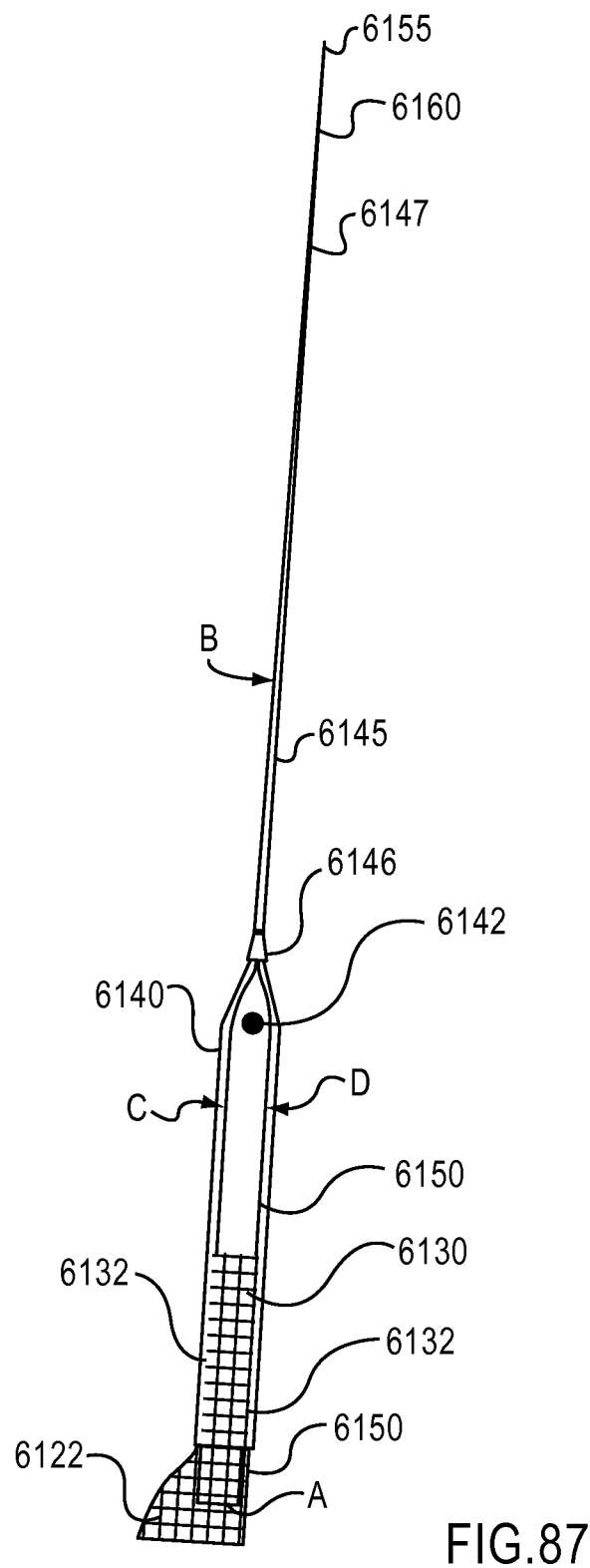
FIG. 87 is a top view of a portion of the implant shown in FIG. 86.

FIGS. 86-87 illustrate an example of an embodiment of an implant 6100. Implant 6100 includes a first strap 6130 and a second strap 6170. The implant 6100 also includes a support portion 6122. The support portion 6122 defines a notch 6124. In some embodiments the notch 6124 is configured to receive a portion of a body of a patient. For example, in some embodiments the notch 6124 is configured to receive a portion of a uterus of a patient. The support portion can be any suitable shape or size. For example, the support portion can be substantially rectangular, square, oval, or elliptical. In some embodiments, the straps 6130, 6170 extend from the support portion 6122 at an angle. Such an angle of a strap 6130, 6170 can vary in different embodiments, for example between 20 and 160 degrees from a centerline CL of the support portion 6122.

The support portion 6122 and/or the straps 6130, 6170 can each be formed with a mesh material to allow tissue in-growth to the implant 6100 after implantation. For example, some or all of the implant 6100 can be formed with a mesh material as described in U.S. Patent Pub. 2005/0038452 A1 to Chu, incorporated by reference above. In some embodiments, some or all of an implant 6100 can be formed with the Advantage® Mesh or the Polyform™ Synthetic Mesh material each provided by BSC. The implant 6100 can be monolithically formed or alternatively, the implant 6100 can be formed with multiple different materials and/or can include multiple different components or portions coupled together. In some embodiments, the implant can be formed with a combination of materials including synthetic and biological materials. For example, the support portion can be formed with a first biocompatible material and the straps can be formed with a second biocompatible material different than the first material. In other embodiments, the support portion is formed with a biological material, and the straps are formed with a synthetic material. In some embodiments, the straps and support portion have a different weave, pitch, texture, color, and pattern from each other.

The straps 6130, 6170 are formed monolithically with the support portion 6122. In other embodiments, the straps are formed separate from the support portion and can be coupled to the support portion. In such an embodiment, the straps and the support portion can be coupled in an abutting relationship, an overlapping relationship, or can be bridged. The straps can be coupled to the support portion by, for example, heat bonding, gluing, using fasteners, and/or sewing. In some embodiments, a strap can include a heat seal along its length or a portion of its length to help prevent or reduce stretching of the strap.

As with the support portion 6122, the straps 6130, 6170 can have a variety of different configurations and/or different sizes (e.g. lengths, widths), depending on the intended use for the particular implant and the intended implantation site for the straps within the pelvic region. For example, straps 6130, 6170 can have a length to accommodate securing the straps 6130, 6170 to specific anatomical locations within the pelvic region, such as a sacrospinous ligament SSL, an arcus tendineus, a levator muscle, etc. In this embodiment, a length of each of the straps 6130, 6170 is sufficient to secure the strap to a sacrospinous ligament SSL.

As best shown in FIG. 87, the first strap 6130 includes tangs 6132. As described above, the tangs allow the implant 6100 to be anchored within pelvic tissue without the use of additional anchoring mechanisms or sutures. The tangs 6132 are configured to help retain the implant 6100 within a body of a patient. In other embodiments, the first strap can include barbs, dimples and/or other protrusions configured to engage tissue to help retain the implant within the tissue.

A first sleeve 6140 is disposed over the first strap 6130. A first dilator 6145 defining a lumen is coupled to the first sleeve 6140 by, for example, crimping, heat sealing, stitching, stretching, tip tipping, etc. Alternatively, the first sleeve can be formed to include a portion that forms a tapered dilator. The first dilator 6145 can be used to expand or enlarge a passage during insertion through a tissue, to ease the transition to a cross-section or size of the first sleeve 6140. In some embodiments, the first sleeve 6140 is also tapered, which also helps provide a lead-in through the tissue.

The first sleeve 6140 is secured to the first strap 6130 with a first suture 6150. The first suture 6150 is looped through the first strap 6130. In this embodiment, the first suture 6150 is weaved or threaded through the first strap 6130. For example, as shown in FIG. 87, the first suture 6150 is weaved through the first strap 6130 at location A, as well as other locations along the first strap 6130. The threading of the first suture 6150 through the first strap 6130 can also help prevent strap stretch during implantation. The strands of the first suture 6150 forming the loop through the first sleeve 6140 extend through an interior lumen (not shown) of the first dilator 6145 and are crimped closed and heat bonded to an interior wall of the first dilator 6145 at, for example, a location B shown in FIG. 87, to maintain the first strap 6130 within the first sleeve 6140 and the first dilator 6145.

The first suture can alternatively be coupled to the first strap by, for example, crimping, heat sealing, stitching, stretching, tip tipping, etc. In some embodiments, a suture can be threaded to or secured to a strap, for example by knotting.

The first suture 6150 includes a leader portion 6160 that extends distally from the leading end 6147 of the first dilator 6145. Alternatively, a separate suture can be coupled to and extend distally from the first dilator. A first needle 6155 is coupled to a distal end of the leader portion 6160 of the first suture 6150. The first needle 6155 can be used to associate the implant 6100 to a delivery device, as described in further detail herein.

The first sleeve 6140 includes a separator 6142 disposed between two strands of the first suture 6150 and near a distal end of the first sleeve 6140, as best viewed in FIG. 87. The separator 6142 maintains separation of the strands of the first suture 6150 within the first sleeve 6140. The separation of the strands of the first suture 6150 enables or helps facilitate a cut to be made through only a single strand of the first suture 6150 at, for example, location C or D, during removal of the first sleeve 140, as described in more detail below. In this embodiment, the separator 6142 is a seal, which can be formed, for example, by heat stamping two sides of the first sleeve 6140 together. Other types of separators can alternatively be used, such as for example, a separate component coupled within the first sleeve, or an adhesive can be used to couple the two sides of the first sleeve together at a location between the strands.

The first dilator 6145 tapers from a first diameter at a trailing end 6146 to a second, smaller diameter at a leading end 6147 (see FIG. 87). The first diameter can be, for example, between about 0.2 and 0.5 cm (0.08 to 0.2 inches) and the second diameter can be, for example, between about 0.03 to 0.2 cm (0.01 to 0.08 inches). For example, in some embodiments, the first diameter can be about 0.37 cm (0.15 inches) and the corresponding second diameter can be, 0.03 cm (0.01 inches). The first dilator 6145 can be formed, for example, by molding, extruding, casting, sintering, forging, machining, or other known methods of manufacturing such medical devices.

As shown in FIG. 86, the second strap 6170, a second sleeve 6175, a second dilator 6180, a second suture 6185, and a second needle 6190 are structurally and functionally similar to the first strap 6130, the first sleeve 6140, the first dilator 6145, the first suture 6150, and the first needle 6155. As such, they are not described in detail herein.

The implant 6100 can be inserted into a body of a patient. More specifically, the implant 6100 can be inserted into a pelvic region of a patient. Once inserted into the pelvic region, the straps 6130, 6170 are attached to surrounding tissue. In this manner, the support member 6122 can help support a portion of a uterus.

Figure 89:
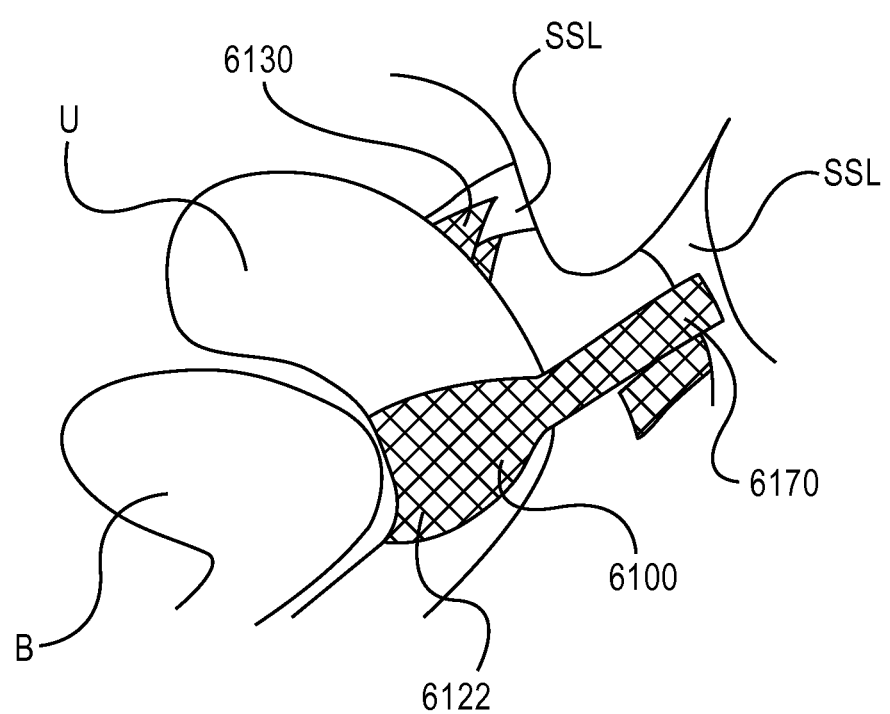
FIG. 89 is an illustration of the implant shown in FIG. 86 disposed within a body of a patient.

FIG. 89 shows the implant 6100 positioned within the pelvic region of a patient. The first strap 6130 is attached to a first portion of the sacrospinous ligament SSL and the second strap 6170 is attached to a second portion of the sacrospinous ligament SSL. The support portion 6122 helps prevent the uterus U of the patient from descending into the vagina of the patient. Additionally, the support portion 6122 helps prevent the uterus U from constricting the bladder B of the patient.

In some embodiments, the implant 6100 can be delivered into a pelvic region through a vaginal incision (e.g., a transvaginal approach). An incision can be made, for example, along an anterior vaginal mucosa. The incision can be, for example, 4 cm to 6 cm (1.57 to 2.36 inches) in length and can extend approximately 2 cm to 3 cm (0.79 inches to 1.18 inches) to the meatus. The vaginal epithelium is dissected from the underlying periurethral fascia toward the sacrospinous ligament SSL. Specifically, the anterior vaginal wall is opened and the endopelvic connective tissue is separated from the pubic ramus at the level of the bladder neck to the ischial spine, exposing the paravesical and pararectal space. The sacrospinous ligament SSL is identified and isolated through this defect. The anterior incision to place the implant 6100 is about 4 cm long extending about 1 cm from the cervix to the level of the proximal urethra. The incision is also known to be an anterior corporaphy incision. Variations in the incision can depend, for example, on the size of the implant 6100, the needed repair or disease state to be treated, and/or the location of the intended placement of the implant 6100.

Figure 88:
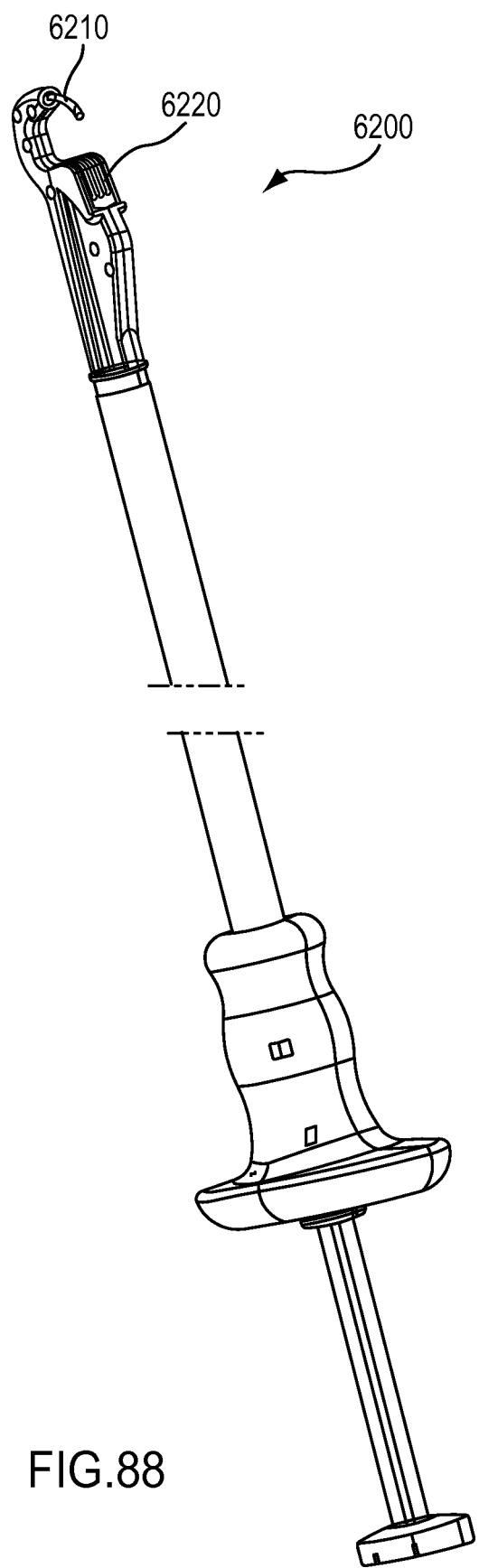
FIG. 88 is a perspective view of a tool configured to deliver the implant shown in FIG. 86 to a body of a patient.

The straps 6130, 6170 of the implant 6100 can each be delivered through the sacrospinous ligament SSL using, for example, the suturing delivery device 6200, as shown in FIG. 88. For example, the needle 6155 on the first strap 6130 is loaded into the carrier 6210 (shown partially extended in FIG. 88) of the delivery device 6200. The delivery device 6200 can then be used to pass the needle 6155 and the first strap 6130 (with the first sleeve 6140 and the first dilator 6145 attached thereto) through the sacrospinous ligament SSL. Specifically, the carrier 6210 of the delivery device 6200 is inserted into a body of a patient through the vagina and positioned adjacent the sacrospinous ligament SSL. The carrier 6210 is then actuated such that the needle 6155 pierces through the sacrospinous ligament SSL. The needle 6155 and a distal end of the leader portion 6160 of the first suture 6150 are caught or retrieved by a catch 6220 of the delivery device 6200 after passing through the sacrospinous ligament SSL. The delivery device 6200 is then removed through the vagina, and the needle 6155 is removed from the catch 6220. The first sleeve 6140 and the first dilator 6145 are pulled through the sacrospinous ligament SSL. For example, the user can pull the leader portion 6160 of the first suture 6150 or the first dilator 6145 through the sacrospinous ligament SSL such that the first strap 6130 is disposed within the sacrospinous ligament SSL. This procedure is then repeated to deliver the second strap 6170 into the sacrospinous ligament SSL. After the straps 6130, 6170 are disposed within the sacrospinous ligament SSL the straps 6130, 6170 can be adjusted to position and tension the support portion 6122. Each strap 6130, 6170 can be delivered sequentially using the same delivery device, or separate delivery devices can be used for some or all of the straps 6130, 6170. The straps 6130, 6170 (with sleeves 6140, 6175 still attached) can be tensioned using visual guidance as the user observes the positioning of the support portion 6122 for the correct tension through the vaginal incision.

After the straps 6130, 6170 (with sleeves 6140, 6175 and dilators 6145, 6180 attached thereto) have been placed through the sacrospinous ligament SSL and adjusted as described above, the first sleeve 6140 and the first dilator 6145 can be removed from the first strap 6130. For example, as shown in FIG. 87, to remove the first sleeve 6140 and the first dilator 6145 from the first strap 6130, a portion of the first sleeve 6140 and one strand of the loop of the first suture 6150 can be cut, for example, at location C or D. Since the first strap 6130 is coupled to the first sleeve 6140 via the first suture 6150, cutting through a portion of the first sleeve 6140, and one strand of the loop of the first suture

6150, the first sleeve 6140 will be freely movable relative to the first strap 6130. The first sleeve 6140 (and first dilator 6145 coupled to the first sleeve 6140) can then be pulled off of the first strap 6130 by pulling on the first sleeve 6140 and the uncut strand of the first suture 6150. The cut first suture 6150 will also be free to pull through the first strap 6130. Thus, the first suture 6150 remains secured to the first sleeve 6140 and will simply unravel or unthread itself from the first strap 6130. With the first sleeve 6140 removed from the first strap 6130, the tangs 6132 on the first strap 6130 can engage the surrounding tissue into which the first strap 6130 has been placed. The second sleeve 6175 and the second dilator 6180 are then removed from the second strap 6170 in a manner similar to removing the first sleeve 6140 and the first dilator 6145, described above.

After the straps 6130, 6170 are secured within the sacrospinous ligament SSL, excess portions of the straps 6130, 6170 can be trimmed as needed. For example, if a portion of the first strap 6130 and/or the second strap 6170 extends through the sacrospinous ligament SSL after the straps are placed within the sacrospinous ligament SSL, the portion of the first strap 6130 and/or the second strap 6170 extending through the sacrospinous ligament SSL can be removed.

As stated above, the straps 6130, 6170 can be secured within a pelvic region at various different tissue sites. For example, the straps 6130, 6170 of the implant 6100 can be placed, for example, in a sacrospinous ligament SSL or coccygeus muscle. In other embodiments, the straps are placed through, endopelvic fascia, or through tissue or ligaments near or in the pubococcygeus muscle, puborectalis muscle, distal tendineus arch of levator ani muscle or obturator internus or externus muscle, or obturator membrane or other tissue locations within a pelvic region. In still other embodiments, the straps are placed, for example, within a ischio-coccygeus muscle, an arcus tendineus or obturator muscle or membrane.

In some embodiments, a portion of the support portion 6122 is separately attached to a tissue within the pelvic region. Said another way, a portion of the support portion 6122 can be secured by means additional to the straps. For example, a suture can be threaded through the mesh support portion 6122 and attached to adjacent pelvic tissue. This can provide additional support for the support portion 6122.

Figure 90:
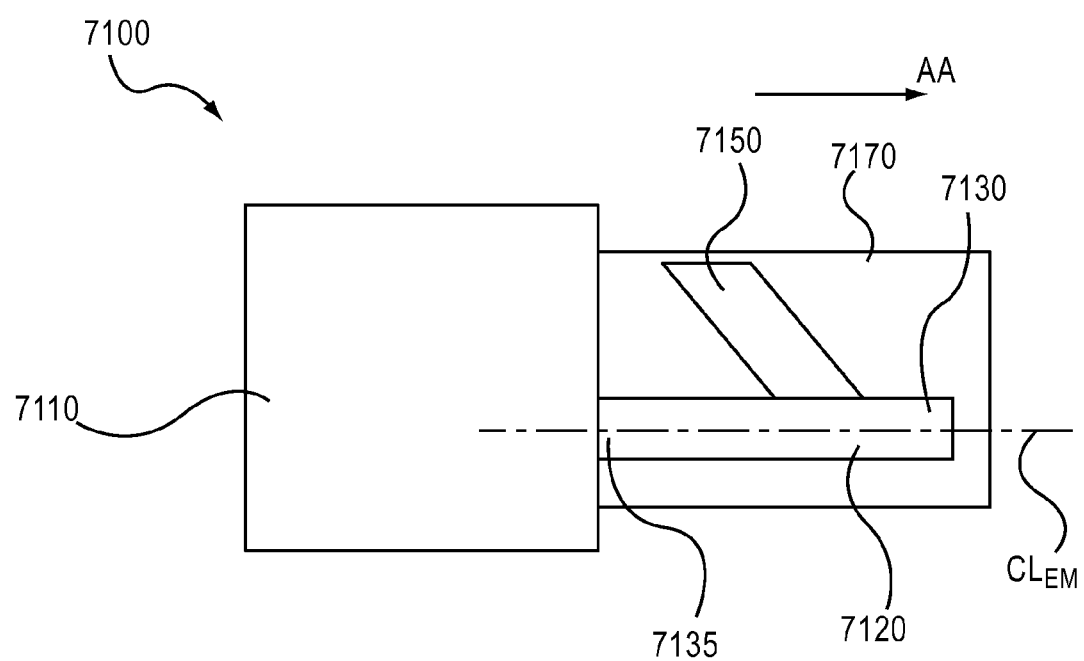
FIG. 90 is a schematic illustration of an implant according to an embodiment.

FIG. 90 is a schematic illustration of an implant 7100 according to an embodiment. Implant 7100 includes a support member 7110, a suture 7120 and a sleeve 7170. The support member 7110 can be a graft as described above. For example, the support member 7110 can be made of any material suitable to support a portion of the body of the patient. In some embodiments, the support member 7110 is made of a synthetic mesh such as macroporous polypropylene, polyester, nylon and/or a bioresorbable or a permanent matrix. In other embodiments, the support member is made of biologic graft material such as human, porcine, or bovine derived tissue. The support member 7110 is configured to support a portion of a body of a patient. In some embodiments, the support member 7110 supports a portion of a body of a patient located at or near the pelvic floor of the patient. The support member 7110 can, for example, provide support where natural tissue is weak.

The suture 7120 includes an elongate member 7130 and a barb 7150. The suture 120 is configured to be inserted into a tissue, as described in further detail herein. The elongate member 7130 of the suture 7120 includes an end portion 7135 coupled to the support member 7110. Further, the elongate member 7130 of the suture 7120 defines a center line $CL_{EM}$.

In some embodiments, the elongate member 7130 of the suture 7120 is made from a permanent material such as, for example, polypropylene and/or nylon. In other embodiments, the elongate member of the suture is made from a bioresorbable material such as, for example, polydioxanone and/or a polyglycolic acid/trimethylene carbonate.

The barb 7150 of the suture 7120 is coupled to the elongate member 7130 of the suture 7120. In other embodiments, the barb is integrally formed with the elongate member. The barb 7150 extends from the elongate member 7130 of the suture such that the barb 7150 forms an acute angle with the center line $CL_{EM}$ of the elongate member 7130. In this manner, the barb 7150 allows the suture to move with respect to a tissue in the direction shown by the arrow AA in FIG. 90 when the suture is disposed within the tissue. Further, the barb 7150 is sufficiently rigid such that movement of the suture 7120 with respect to a tissue in a direction different than the direction shown by the arrow AA in FIG. 90 is substantially prevented, when the suture 7120 is disposed within the tissue. In this manner, the suture 7120 helps retain the implant 7100 within a body of a patient.

The barb 7150 can be any length sufficient to help retain the implant 7100 within a body of a patient. For example, in one embodiment the barb 7150 is long enough that when the suture 7120 is moved in a direction different than the direction shown by the arrow AA in FIG. 90, the barb 7150 engages the surrounding tissue and helps prevent such movement.

The sleeve 7170 defines a lumen configured to receive the suture 7120. In this manner, the sleeve 7170 is disposed about the barb 7150 of the suture 7120. The sleeve 7170 prevents the barb 7150 from engaging the tissue adjacent the sleeve 7170. This allows the suture 7120 to be adjusted and/or removed prior to final placement. In other embodiments, the implant does not include a sleeve.

In use, the implant 7100 may be inserted into a body of a patient using a delivery device. In some embodiments, the implant 7100 is inserted into the pelvic region of a patient. For example, the support member 7110 can be positioned such that it supports a portion of a body of a patient located at or near the pelvic floor of the patient. For example, in some embodiments, the implant 7100 supports the uterus of the patient.

The implant 7100 is secured to the adjacent tissue by the suture 7120. The elongate member 7130 of the suture 7120 is inserted into the tissue of the patient adjacent to the implant 7100 in the direction shown by the arrow AA in FIG. 90. In some embodiments, the suture has a second end portion coupled to a needle or a dart. The needle or dart is configured to penetrate tissue when the suture is inserted into the tissue of a patient. As stated above, the barb allows the elongate member 7130 to move with respect to the tissue in the direction shown by the arrow AA in FIG. 90. Once the suture 7120 is in place, the sleeve 7170 is removed from the suture 7120 allowing the barb 7150 to engage the tissue.

The implant 7100 can be coupled to various different tissues within the pelvic region, such as, for example, a sacrospinous ligament, a tendineus arch of levator muscle (also referred to herein as "arcus tendineus" and/or "white line"), or to an iliococcygeus muscle, or to other anatomical and/or tissue securement sites within the pelvic region of a patient. The implant 7100 can also be coupled to a vagina of the patient, such as to the vaginal apex, to a wall of the vagina, secured inside the vagina (e.g., within a vaginal lumen) or within the pelvic region. In some embodiments only one implant is implanted on one side of the pelvic region. In other embodiments, more than one implant is implanted. In yet other embodiments, a single implant assembly is implanted that spans both sides of the pelvic region.

In some embodiments, the second end portion of the elongate member 7130 of the suture 7120 can be disposed outside the tissue after the suture 7120 is placed within the tissue of the patient. This enables future tension adjustment if needed. For example, if the suture 7120 over time begins to slip and not retain the support member 7110 as needed, the second end portion of the elongate member 7130 can be pulled in the direction shown by the arrow AA in FIG. 90. In this manner the implant 7100 can be readjusted such that the suture 7120 is taut and provides adequate support to the support member 7110.

In some embodiments, the suture is provided to a practitioner separate from the support member. This allows the practitioner to attach the suture to the support member in an optimal location for the particular procedure and/or patient. In other embodiments, the suture is provided to the practitioner already attached to the support member. In still other embodiments, the suture is detachably coupled to the support member. Said another way, the suture can be detached from the support member and reattached to the support member at the same position on the support member or at a different position on the support member. This allows a practitioner to determine the optimal position for the sutures and to readjust the position of the sutures with respect to the support member if necessary.

Various delivery devices can be used to insert or deliver the implant 7100 into a pelvic region. For example, a delivery device can be used to pass an end of the suture 7120 of the implant 7100 through a pelvic tissue. The delivery device can be, for example, the Capio® Suture Capture Device manufactured by Boston Scientific Corporation. An example of such a suturing delivery device is also described in U.S. Pat. No. 5,741,277 to Gordon et al., and U.S. Pat. No. 7,122,039 to Chu, both of which were incorporated by reference above.

Depending on the configuration of the implant 7100 and/or the targeted location for securing the implant 7100 within a patient, other types of delivery devices may be used to deliver the implant 7100 into the pelvic region. For example, a delivery device can be inserted through an incision of a vagina, or through an exterior entry site (e.g., exterior incision through skin) on the patient. The delivery device can be, for example, an Obtryx® Curve device, an Obtryx® Halo device, or a Lynx device all manufactured by Boston Scientific Corporation. An example of such a device is also described in U.S. Patent Pub. No. 2005/0075660 and U.S. Patent Pub. No. 2005/0177022, incorporated by reference above. Such a delivery device creates a path or passageway through, for example, an obturator muscle or through, for example, an arcus tendineus. For example, the delivery device can be passed through the exterior incision and into the vagina where it can be coupled to an end of an implant. Such a delivery device can be used to draw the implant assembly through a passageway formed by the delivery device and through the exterior entry site.

In some embodiments, a hollow needle, a needle with a partial side wall, and/or a needle with an open slit is used to deliver the suture 7120 into a body of a patient. The partial side wall and the open slit can be configured to allow the needle to be removed from an insertion port. In other embodiments, the delivery device includes a solid member configured to hold the suture in place during delivery. In still other embodiments, the delivery device uses the barb to secure the suture to the delivery device.

Once the suture 7120 is positioned such that it sufficiently supports the support member 7110, the delivery device can be removed from the body of the patient. As stated above, the barb 7150 helps prevent movement of the suture 7120 in a direction different than the direction shown by the arrow AA in FIG. 90. In this manner the barb 7150 helps retain the support member 7110 within the body of the patient.

Figure 91:
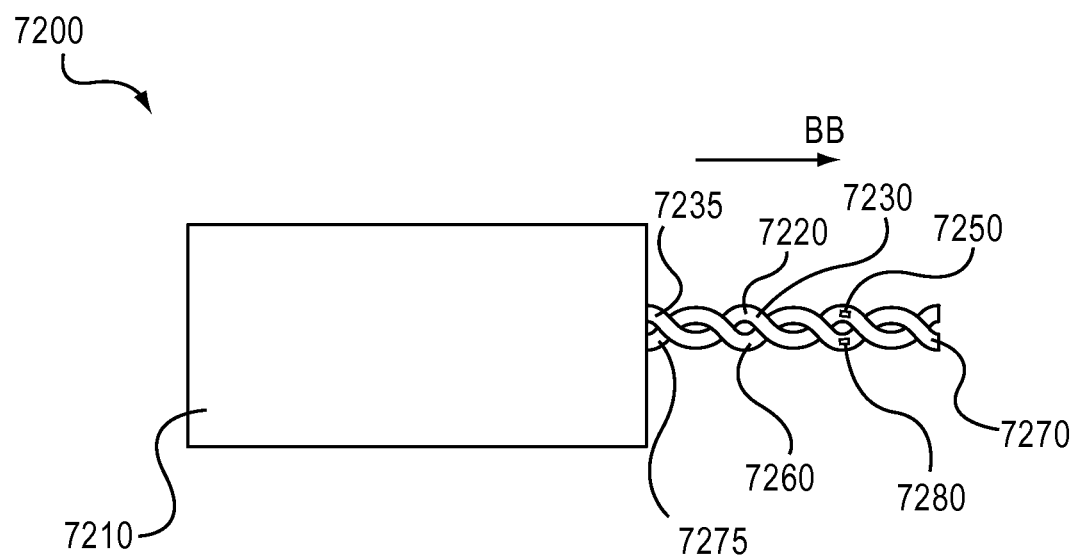
FIG. 91 is a schematic illustration of an implant according to an embodiment.

While FIG. 90 shows a single suture 7120 having a single barb 7150, in other embodiments, the implant can have any number of sutures having any number of barbs. For example, FIG. 91 is a schematic illustration of an implant 7200 having a first suture 7220 and a second suture 7260, according to an embodiment. Implant 7200 also includes a support member 7210. Support member 7210 is similar to support member 7110 and is configured to support a portion of a body of a patient when disposed within a body of a patient. In some embodiments, the support member 7210 supports a portion of a body of a patient located at or near the pelvic floor of the patient. In other embodiments, the support member is a urinary incontinence sling configured to support the urethra and/or bladder of a patient.

The first suture 7220 includes an elongate member 7230 and a retention member 7250. The first suture 7220 is configured to be inserted into a tissue, as described in further detail herein. The elongate member 7230 of the first suture 7220 includes an end portion 7235 coupled to the support member 7210.

The retention member 7250 of the first suture 7220 is coupled to the elongate member 7230 of the first suture 7220. In other embodiments, the retention member is integrally formed with the elongate member. The retention member 7250 allows the first suture 7220 to move with respect to a tissue in the direction shown by the arrow BB in FIG. 91 when the first suture 7220 is disposed within a tissue. Further, the retention member 7250 is configured such that movement of the first suture 7220 with respect to a tissue in a direction different than the direction shown by the arrow BB in FIG. 91 is substantially prevented, when the first suture 7220 is disposed within the tissue. Said another way, the retention member 7250 of the first suture 7220 provides resistance to movement of the first suture 7220 with respect to a tissue in a direction different than the direction shown by the arrow BB in FIG. 91. Specifically, as the first suture 7220 is moved in a direction different than the direction shown by the arrow BB in FIG. 91, the retention member 7250 of the first suture 7220 engages the tissue surrounding the elongate member 7230 of the first suture 7220 and helps prevent such motion. In this manner, the first suture 7220 helps retain the implant 7200 within a body of a patient.

The second suture 7260 includes an elongate member 7270 and a retention member 7280. The second suture 7260 is configured to be inserted into a tissue, as described in further detail herein. The elongate member 7270 of the second suture 7260 includes an end portion 7275 coupled to the support member 7210.

The retention member 7280 of the second suture 7260 is coupled to the elongate member 7270 of the second suture 7260. In other embodiments, the retention member is integrally formed with the elongate member. The retention member 7280 allows the second suture 7260 to move with respect to a tissue in the direction shown by the arrow BB in FIG. 91 when the second suture 7260 is disposed within a tissue. Further, the retention member 7280 is configured such that movement of the second suture 7260 with respect to a tissue in a direction different than the direction shown by the arrow BB in FIG. 91 is substantially prevented, when the second suture 7260 is disposed within the tissue. Said another way, the retention member 7280 of the second suture 7260 provides resistance to movement of the second suture 7260 with respect to the tissue in a direction different than the direction shown by the arrow BB in FIG. 91. Specifically, as the second suture 7260 is moved in a direction different than the direction shown by the arrow BB in FIG. 91, the retention member 7280 of the second suture 7260 engages the tissue surrounding the elongate member 7270 of the second suture 7260 and helps prevent such motion. In this manner, the second suture 7260 helps retain the implant 7200 within a body of a patient.

The first suture 7220 and the second suture 7260 are intertwined. In other embodiments, the first suture and the second suture are interlaced, woven and/or braided together. In still other embodiments, three or more sutures can be intertwined, interlaced, woven and/or braided together. Having multiple sutures woven together may increase the strength and holding force of the sutures. This allows the support member 7210 to support more weight and/or better secures the support member within the body of the patient. Additionally, the first suture 7220 and the second suture 7260 can be placed within the tissue with a single insertion. This maximizes the holding strength of the implant 7200 while minimizing the number of suture insertions.

The elongate member 7230 of the first suture 7220 and the elongate member 7270 of the second suture 7260 are inserted into the adjacent tissue of the patient in the direction shown by the arrow BB in FIG. 91. In some embodiments, the first suture and/or the second suture has a second end portion coupled to a needle or a dart. The needle or dart is configured to penetrate tissue when the first suture and/or the second suture is inserted into the tissue of a patient.

As stated above, the retention member 7250 of the first suture 7220 and the retention member 7280 of the second suture 7260 allow the elongate member 230 of the first suture 7220 and the elongate member 7270 of the second suture 7260, respectively, to move with respect to the tissue in the direction shown by the arrow BB in FIG. 91. In some embodiments, the first suture 7220 and the second suture 7260 can be coupled to various different tissues within the pelvic region, such as those discussed in relation to suture 7120.

In use, the implant 7200 is inserted into a body of a patient using a delivery device, such as those described above in relation to implant 7100. In some embodiments, the implant 7200 is inserted into the pelvic region of a patient. For example, the support member 7210 can be positioned such that it supports a portion of a body of a patient located at or near the pelvic floor of the patient. In some embodiments, the support member can be positioned to support a urethra and/or a bladder.

Once the first suture 7220 and the second suture 7260 are positioned such that they sufficiently support the support member 7210, the delivery device can be removed from the body of the patient. As stated above, the retention member 7250 of the first suture 7220 and the retention member 7280 of the second suture 7260 help prevent movement of the first suture 7220 and the second suture 7260, respectively, in a direction different than the direction shown by the arrow BB in FIG. 91. In this manner the retention member 7250 of the first suture 7220 and the retention member 7280 of the second suture 7260 help retain the support member 7210 within the body of the patient.

Figure 92:
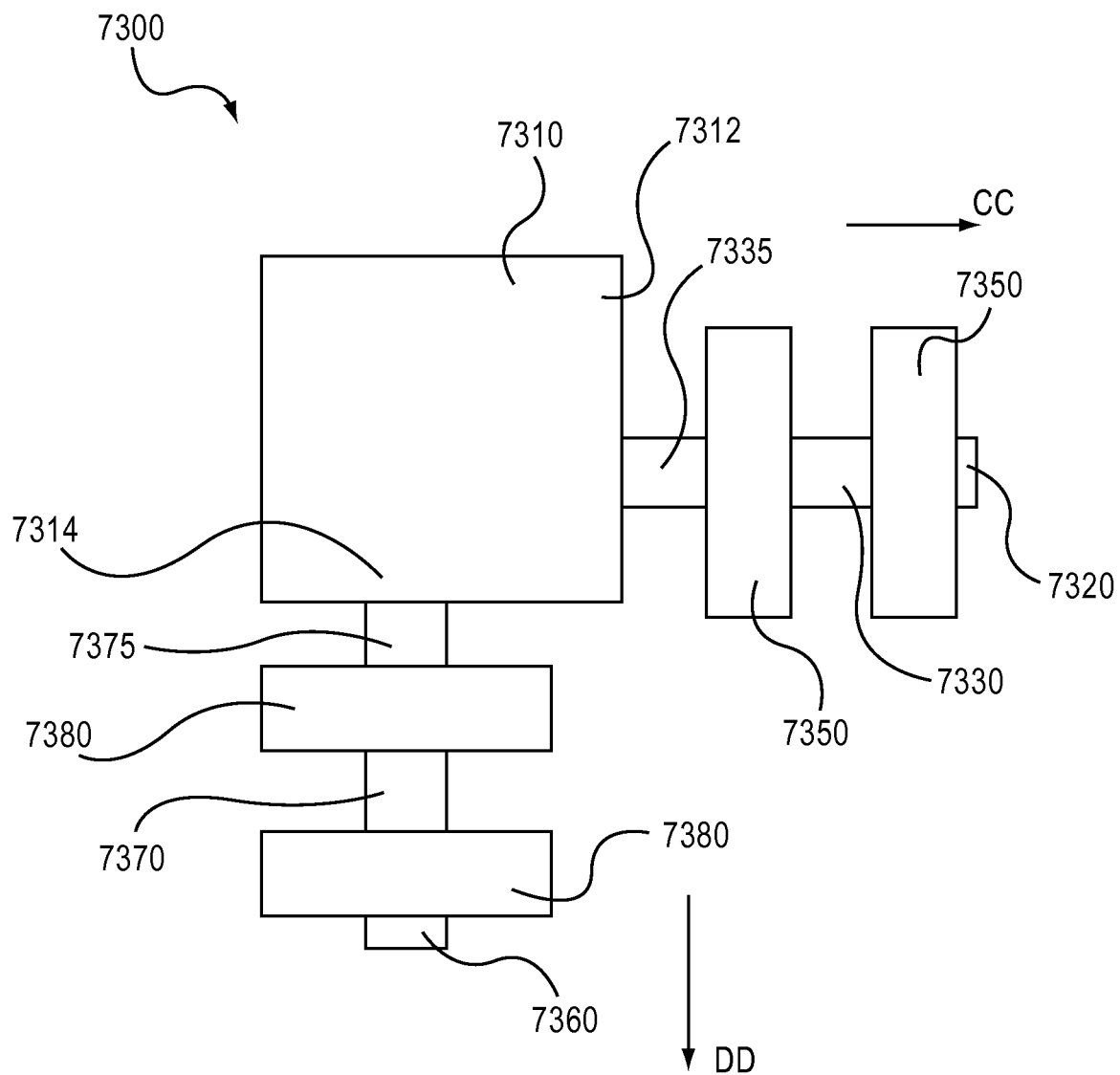
FIG. 92 is a schematic illustration of an implant according to an embodiment.

FIG. 92 is a schematic illustration of an implant 7300 according to an embodiment. The implant 7300 includes a support member 7310, a first suture 7320 and a second suture 7360. The support member 7310 includes a first side portion 3712 and a second side portion 7314. Support member 7310 is similar to support member 7110 and is configured to support a portion of a body of a patient when disposed within a body of a patient. For example, in some embodiments, the support member 7310 supports a portion of a body of a patient located at or near the pelvic floor of the patient. In other embodiments, the support member is a urinary incontinence sling configured to support a urethra and/or bladder of a patient.

The first suture 7320 includes an elongate member 7330 and a plurality of retention members 7350. The first suture 7320 is configured to be inserted into a tissue, as described in further detail herein. The elongate member 7330 of the first suture 7320 includes an end portion 7335 coupled to the first side portion 7312 of the support member 7310.

The plurality of retention members 7350 of the first suture 7320 are coupled to the elongate member 7330 of the first suture 7320. In other embodiments, the plurality of retention members are integrally formed with the elongate member. The plurality of retention members 7350 allow the first suture 7320 to move with respect to a tissue in the direction shown by the arrow CC in FIG. 92 when the first suture 7320 is disposed within a tissue. Further, the plurality of retention members 7350 are configured such that movement of the first suture 7320 with respect to a tissue in a direction different than the direction shown by the arrow CC in FIG. 92 is substantially prevented, when the first suture 7320 is disposed within the tissue. Said another way, the plurality of retention members 7350 of the first suture 7320 provide resistance to movement of the first suture 7320 with respect to the tissue in a direction different than the direction shown by the arrow CC in FIG. 92. Specifically, if the first suture 7320 is moved in a direction different than the direction shown by the arrow CC in FIG. 92, the plurality of retention members 7350 of the first suture 7320 engage the tissue surrounding the elongate member 7330 of the first suture 7320 and help prevent such motion. In this manner, the first suture 7320 helps retain the implant 7300 within a body of a patient.

The second suture 7360 includes an elongate member 7370 and a plurality of retention members 7380. The second suture 7360 is configured to be inserted into a tissue, as described in further detail herein. The elongate member 7370 of the second suture 7360 includes an end portion 7375 coupled to the second side portion 7314 of the support member 7310.

The plurality of retention members 7380 of the second suture 7360 are coupled to the elongate member 7370 of the second suture 7360. In other embodiments, the plurality of retention members are integrally formed with the elongate member. The plurality of retention members 7380 allow the second suture 7360 to move with respect to a tissue in the direction shown by the arrow DD in FIG. 92 when the second suture 7360 is disposed within a tissue. Further, the plurality of retention members 7380 are configured such that movement of the second suture 7360 with respect to a tissue in a direction different than the direction shown by the arrow DD in FIG. 92 is substantially prevented, when the second suture 7360 is disposed within the tissue. Said another way, the plurality of retention members 7380 of the second suture 7360 provide resistance to movement of the second suture 7360 with respect to the tissue in a direction different than the direction shown by the arrow DD in FIG. 92. Specifically, if the second suture 7360 is moved in a direction different than the direction shown by the arrow DD in FIG. 92, the plurality of retention members 7380 of the second suture 7360 engage the tissue surrounding the elongate member 7370 of the second suture 7360 and help prevent such motion. In this manner, the second suture 7360 helps retain the implant 7300 within a body of a patient.

The elongate member 7330 of the first suture 7320 is inserted into the tissue of the patient in the direction shown by the arrow CC in FIG. 92. The elongate member 7370 of the second suture 7360 is inserted into the tissue of the patient in the direction shown by the arrow DD in FIG. 92. In some embodiments, the first suture and/or the second suture has a second end portion coupled to a needle or a dart. The needle or dart is configured to penetrate tissue when the first suture and/or the second suture is inserted into the tissue of a patient. In some embodiments, the first suture 7320 and the second suture 7360 are coupled to various different tissues within the pelvic region, such as those discussed in relation to suture 7120.

In use, the implant 7300 is inserted into a body of a patient using a delivery device such as those described above in relation to implant 7100. In some embodiments, the implant 7300 is inserted into the pelvic region of a patient. For example, the support member 7310 can be positioned such that it supports a portion of a body of a patient located at or near the pelvic floor of the patient. For example, in some embodiments, the support member can be positioned to support the urethra and/or bladder.

Once the first suture 7320 and the second suture 7360 are positioned such that they sufficiently support the support member 7310, the delivery device can be removed from the body of the patient. The plurality of retention members 7350 of the first suture 7320 help prevent movement of the first suture 7320 in a direction different than the direction shown by the arrow CC in FIG. 92. The plurality of retention members 7380 of the second suture 7360 help prevent movement of the second suture 7360 in a direction different than the direction shown by the arrow DD in FIG. 92. In this manner the plurality of retention members 7350 of the first suture 7320 and the plurality of retention members 7380 of the second suture 7360 help retain the support member 7310 within the body of the patient.

Figure 93:
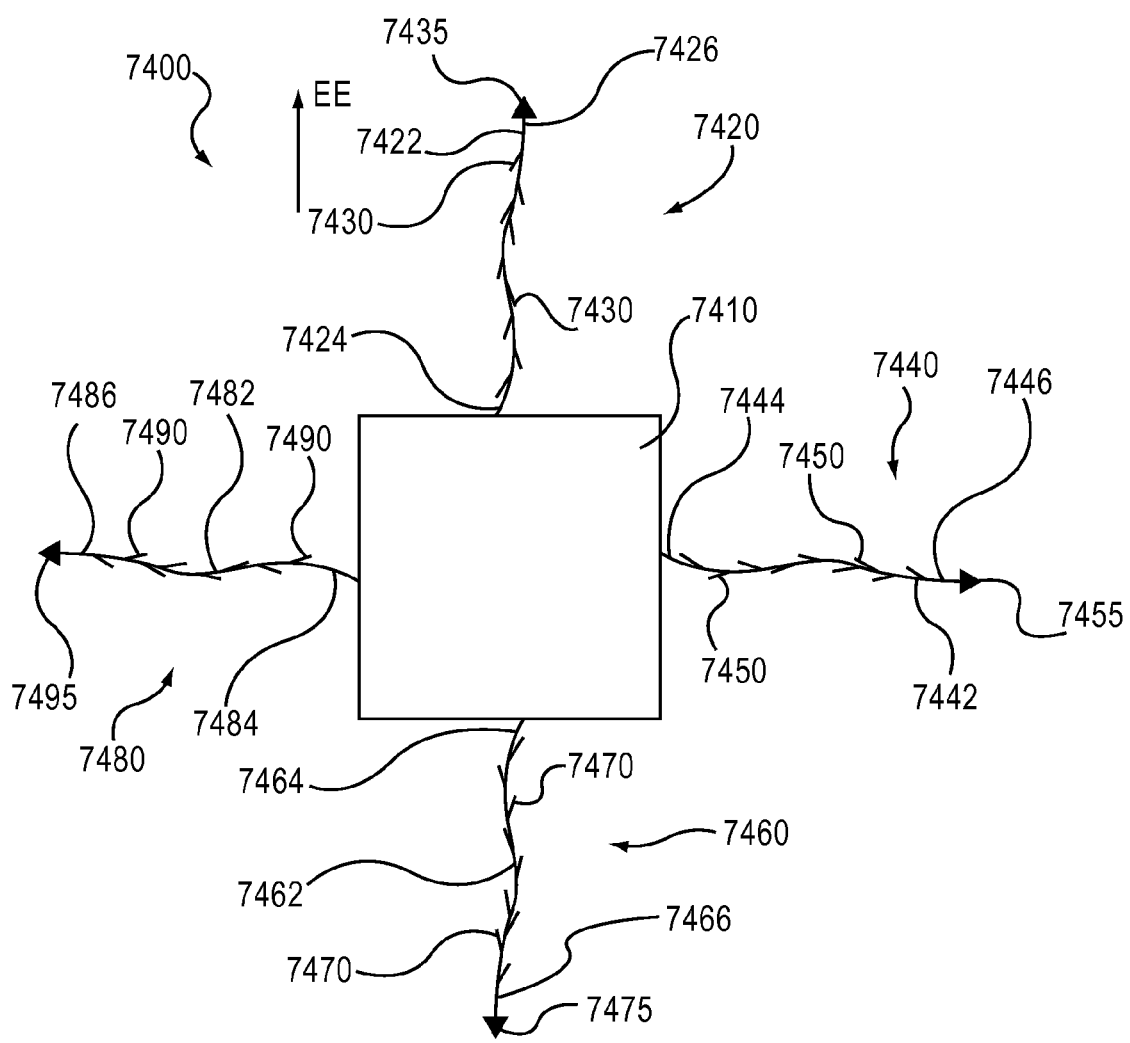
FIG. 93 is a top view of an implant according to an embodiment.

While FIG. 92 shows an implant having a first suture 7320 and a second suture 7360 coupled to a first side portion 7312 and a second side portion 7314 of a support member 7310, other embodiments can have three or more sutures coupled to three or more side portions of a support member. For example, FIG. 93 shows an implant having a first suture 7420, a second suture 7440, a third suture, 7460 and a fourth suture 7480. Implant 7400 also includes a support member 7410. Support member 7410 is configured to support a portion of a body of a patient when disposed within a body of a patient. In some embodiments, the support member 7410 supports a portion of a body of a patient located at or near the pelvic floor of the patient. For example, the support member can be a urinary incontinence sling configured to support a urethra and/or bladder of a patient.

The first suture 7420 includes an elongate member 7422, a needle 7435 and a plurality of retention members 7430. The first suture 7420 is configured to be inserted into a tissue. The elongate member 7422 of the first suture 7420 includes a first end portion 7424 and a second end portion 7426. The first end portion 7424 of the elongate member 7422 is coupled to the support member 7410. The second end portion 7426 of the elongate member 7422 is coupled to the needle 7435. The needle 7435 of the first suture 7420 is configured to penetrate tissue to facilitate insertion of the first suture 7420 into the tissue of a patient. In other embodiments, the needle is separately and distinctly formed from the first suture and is coupled to the first suture by a knot, a heat weld and/or an adhesive.

The plurality of retention members 7430 of the first suture 7420 are integrally formed with the elongate member 7422 of the first suture 7420. The plurality of retention members 430 allow the first suture 7420 to move with respect to a tissue in the direction shown by the arrow EE in FIG. 93 when the first suture 7420 is disposed within a tissue. Further, the plurality of retention members 7430 are configured such that movement of the first suture 7420 with respect to a tissue in a direction different than the direction shown by the arrow EE in FIG. 93 is substantially prevented, when the first suture 7420 is disposed within the tissue. Said another way, the plurality of retention members 7430 of the first suture 7420 provide resistance to movement of the first suture 7420 with respect to the tissue in a direction different than the direction shown by the arrow EE in FIG. 93. Specifically, if the first suture 7420 is moved in a direction different than the direction shown by the arrow EE in FIG. 93, the plurality of retention members 7430 of the first suture 7420 engage the tissue surrounding the elongate member 7422 of the first suture 7420 and help prevent such motion. In this manner, the first suture 7420 helps retain the implant 7400 within a body of a patient.

The second suture 7440, the third suture 7460 and the fourth suture 7480 are functionally and structurally similar to the first suture 7420 and all include an elongate member 7442, 7462, 7482, a needle 7455, 7475, 7495, and a plurality of retention members 7450, 7470, 7490. In other embodiments, the sutures include a single retention member. The elongate members 7442, 7462, 7482 include first end portions 7444, 7464, 7484 coupled to the support member 7410 and second end portions 7446, 7466, 7486 coupled to needles 7455, 7475, 7495, respectively. When the sutures 7420, 7440, 7460, 7480 are disposed within a tissue of a patient, the support member 7410 is configured to support a portion of a body of a patient.

In use, the implant 7400 is inserted into a body of a patient using a delivery device, such as those described above in relation to implant 7100. In some embodiments, the implant 7400 is inserted into the pelvic region of a patient. For example, the support member 410 can be positioned such that it supports a portion of a body of a patient located at or near the pelvic floor of the patient, such as the urethra and/or bladder. The sutures 7430, 7450, 7470, 7490 are inserted into the body of the patient similar to the methods described above with respect to other embodiments.

Figure 94:
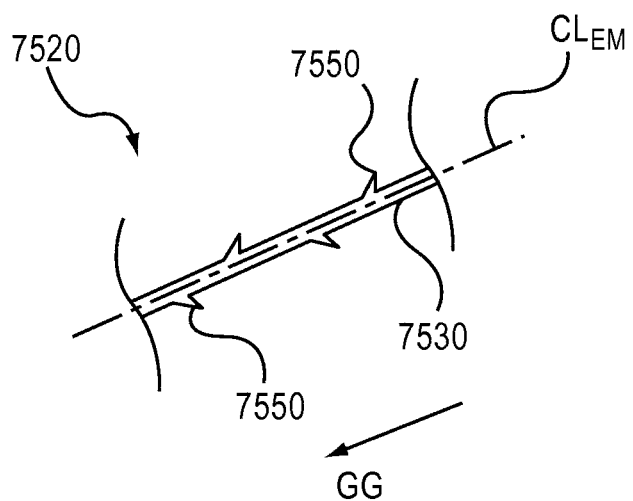
FIG. 94 is a side view of a portion of a suture of an implant according to an embodiment.

FIG. 94 is a side view of a portion of a suture 7520 of an implant according to an embodiment. Suture 7520 includes an elongate member 7530 and a plurality of barbs 7550. The plurality of barbs 7550 are integrally formed with the elongate member 7530. Each barb of the plurality of barbs 7550 extends from the elongate member 7530 such that each barb forms an acute angle with respect to a center line $CL_{EM}$ defined by the elongate member 7530. This configuration allows the suture 7520 to move within a tissue of a patient in the direction shown by the arrow GG in FIG. 94. Similarly, the configuration of the barbs 7550 helps prevent the suture 7520 from moving with respect to the tissue in the direction different than the direction shown by the arrow GG in FIG. 94, when disposed within the tissue. Said another way, the configuration of the barbs 7550 provides resistance to movement of the suture 7520 with respect to the tissue in a direction different than the direction shown by the arrow GG in FIG. 94. Specifically, as the suture 7520 is moved in a direction different than the direction shown by the arrow GG in FIG. 94, the barbs 7550 engage the tissue surrounding the elongate member 7530 and help prevent such motion.

The plurality of barbs 7550 are randomly spaced along the elongate member 7530. In other embodiments, the plurality of barbs can be uniformly spaced along the elongate member. For example, in some embodiments, the plurality of barbs can be spaced 90 degrees from each other, can be lined up with each other and/or can be distally offset from each other. In other embodiments, the suture includes a single barb.

Figure 95:
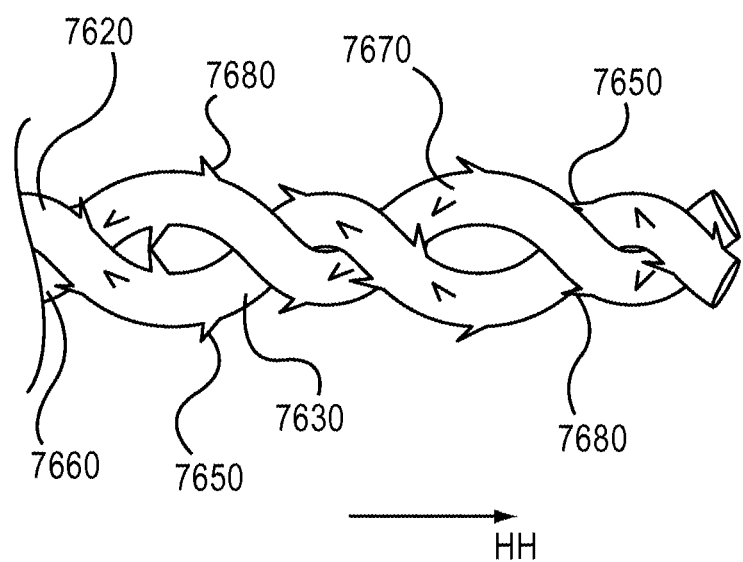
FIG. 95 is a side view of a portion of a first suture and a second suture of an implant according to an embodiment.

FIG. 95 is a side view of a portion of a first suture 7620 intertwined with a portion of a second suture 7660. The first suture 7620 and the second suture 7660 are functionally and structurally similar to the suture 7520 described above. As such, the first suture 7620 and the second suture 7660 each include an elongate member 7630, 7670 and a plurality of barbs 7650, 7680. The plurality of barbs 7650 of the first suture 7620 and the plurality of barbs 7680 of the second suture 7660 allow the first suture 7620 and the second suture 7660, respectively, to move within a tissue in the direction shown by the arrow HH in FIG. 95. Further, the plurality of barbs 7650 and the plurality of barbs 7680 help prevent the first suture 7620 and the second suture 7660, respectively, from moving within the tissue in the direction different than the direction shown by the arrow HH in FIG. 95. Said another way, the plurality of barbs 7650 of the first suture 7620 and the plurality of barbs 7680 of the second suture 7660 provide resistance to movement of the first suture 7620 and the second suture 7660, respectively, with respect to the tissue in a direction different than the direction shown by the arrow HH in FIG. 95. Specifically, as the first suture 7620 and/or the second suture 7660 is moved in a direction different than the direction shown by the arrow HH in FIG. 95, the plurality of barbs 7650 of the first suture 7620 and/or the plurality of barbs 7680 of the second suture 7660 engage the tissue surrounding the elongate member 7630 of the first suture 7620 and/or the tissue surrounding the elongate member 7670 of the second suture 7660, and help prevent such motion.

The first suture 7620 and the second suture 7660 are intertwined. In other embodiments, the first suture and the second suture are interlaced, woven and/or braided together. In still other embodiments, three or more sutures can be intertwined, interlaced, woven and/or braided together. As stated above, having multiple sutures woven together may increase the strength and holding force of the sutures. This allows a support member to support more weight and/or better secures the support member within the body of the patient. Additionally, the first suture 7620 and the second suture 7660 can be placed within the tissue with a single insertion. This maximizes the holding strength of an implant while minimizing the number of suture insertions needed to retain the implant.

Figure 96:
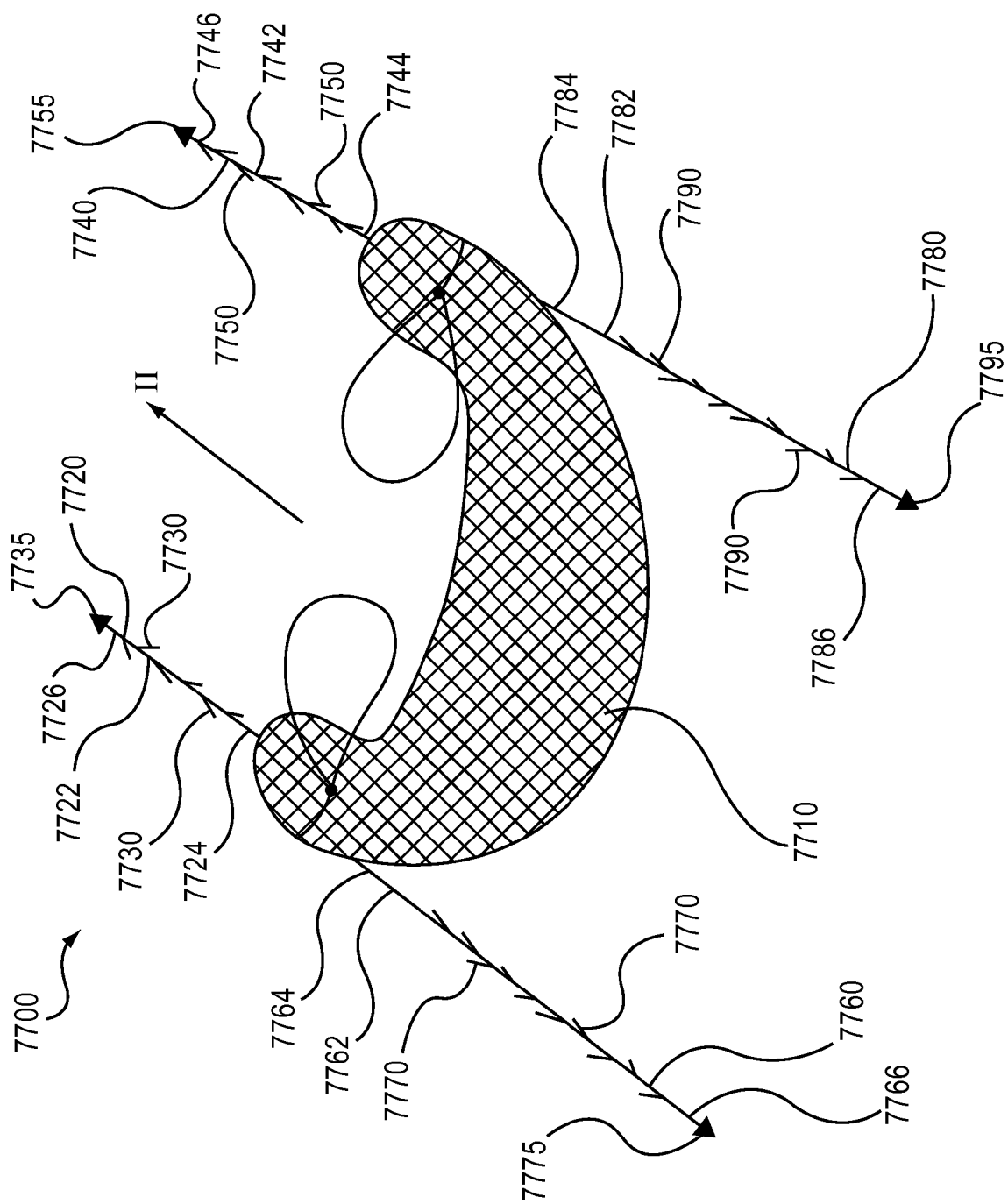
FIG. 96 is a top view of an implant according to an embodiment.

FIG. 96 is a top view of an implant 7700 according to an embodiment. Implant 7700 includes a support member 7710, a first suture 7720, a second suture 7740, a third suture 7760 and a fourth suture 7780. The support member 7710 is a pelvic floor repair graft configured to support areas in a body of a patient where the natural tissue is weak. The support member 7710 can be, for example, a synthetic mesh such as macroporous polypropylene, polyester, nylon and/or a bioresorbable or a permanent matrix. In other embodiments, the support member is made of biologic graft material such as human, porcine, or bovine derived tissue.

The first suture 7720 includes an elongate member 7722, a needle 7735 and a plurality of retention members 7730. The first suture 7720 is configured to be inserted into a tissue. The elongate member 7722 of the first suture 7720 includes a first end portion 7724 and a second end portion 7726. The first end portion 7724 of the elongate member 7722 is coupled to the support member 7710. The second end portion 7726 of the elongate member 7722 is coupled to the needle 7735. The needle 7735 of the first suture 7720 is configured to penetrate tissue to facilitate insertion of the first suture 7720 into the tissue of a patient. In other embodiments, the needle is separately and distinctly formed from the first suture and is coupled to the first suture by a knot, a heat weld and/or an adhesive.

The plurality of retention members 7730 of the first suture 7720 are barbs that are integrally formed with the elongate member 7722 of the first suture 7720. The plurality of retention members 7730 allow the first suture 7720 to move with respect to a tissue in the direction shown by the arrow II in FIG. 96, when the first suture 7720 is disposed within a tissue. Further, the plurality of retention members 7730 are configured such that movement of the first suture 7720 with respect to a tissue in a direction different than the direction shown by the arrow II in FIG. 96 is substantially prevented, when the first suture 7720 is disposed within the tissue. Said another way, the plurality of retention members 7730 of the first suture 7720 provide resistance to movement of the first suture 7720 with respect to the tissue in a direction different than the direction shown by the arrow II in FIG. 96. Specifically, as the first suture 7720 is moved in the direction different than the direction shown by the arrow II in FIG. 96, the plurality of retention members 7730 of the first suture 7720 engage the tissue surrounding the elongate member 7722 of the first suture and help prevent such motion. In this manner, the first suture 7720 helps retain the implant 7700 within a body of a patient.

The second suture 7740, the third suture 7760 and the fourth suture 7780 are functionally and structurally similar to the first suture 7720 and all include an elongate member 7742, 7762, 7782, a needle 7755, 7775, 7795, and a plurality of retention members 7750, 7770, 7790. The elongate members 7742, 7762, 7782 include first end portions 7744, 7764, 7784 coupled to the support member 710 and second end portions 7746, 7766, 7786 coupled to needles 7755, 7775, 7795, respectively. When the sutures 7720, 7740, 7760, 7780 are disposed within a tissue of a patient, the support member 7710 is configured to support a portion of a body of a patient.

While shown in FIG. 96 as having four sutures 7720, 7740, 7760, 7780, in other embodiments, the implant can have any number of sutures. For example, in some embodiments, the implant has a first suture and a second suture.

In use, the implant 7700 is inserted into a body of a patient using a delivery device, such as those described above in relation to implant 7100. In some embodiments, the implant 7700 is inserted into the pelvic region of a patient. For example, the support member 7710 can be positioned such that it supports a portion of a body of a patient located at or near the pelvic floor of the patient. The sutures 7720, 7740, 7760, 7780 are inserted into the body of the patient similar to the methods described above with respect to other embodiments.

Figure 97:
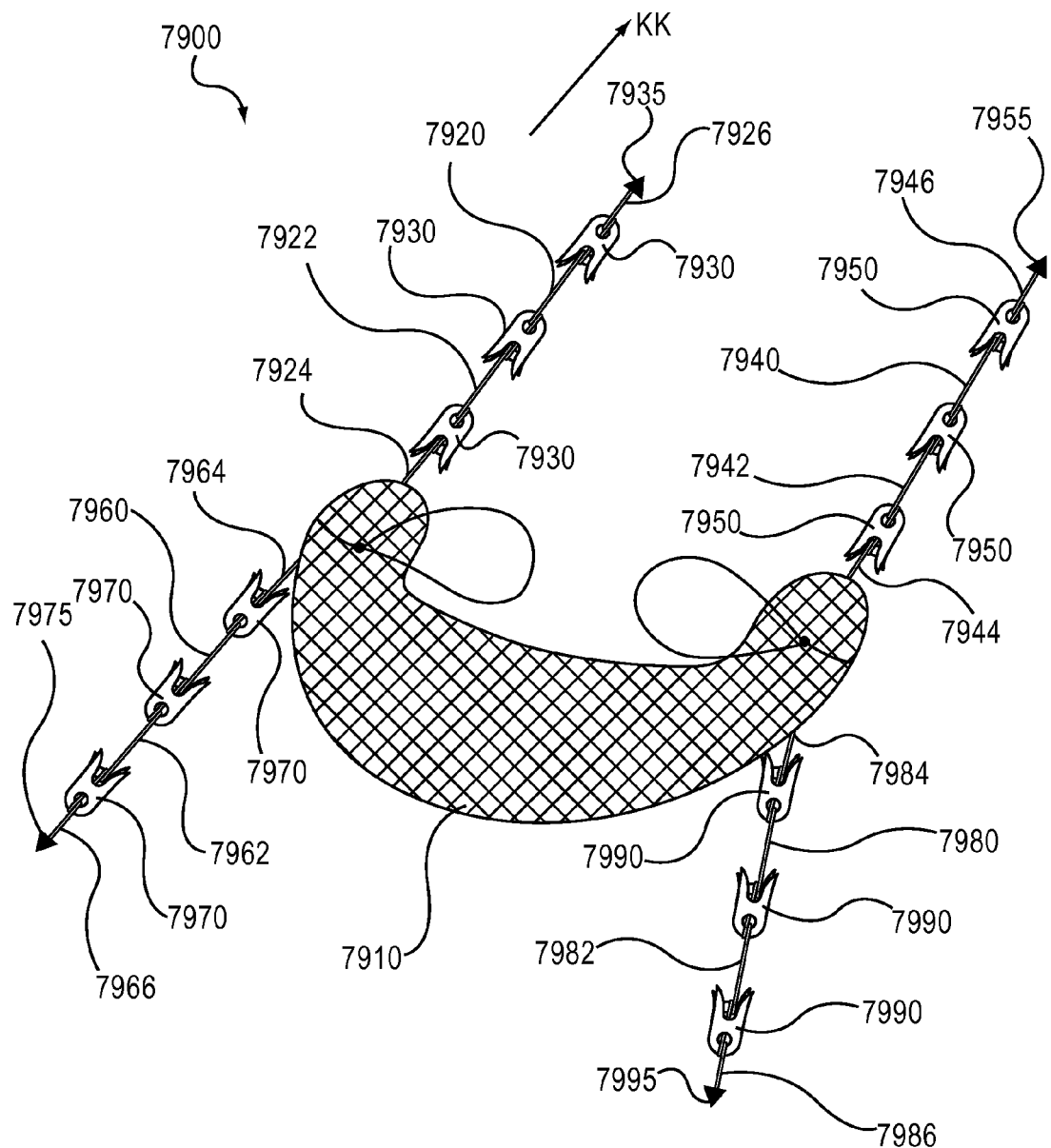
FIG. 97 is a top view of an implant according to an embodiment.

While FIG. 96 shows sutures including retention members that are integrally formed with the elongate member, in other embodiments the retention members are separately formed and attached to the elongate member. For example, FIG. 97 shows a top view of an implant 7900 according to an embodiment. Implant 7900 is similar to implant 7700 and includes a support member 7910, a first suture 7920, a second suture 7940, a third suture 7960 and a fourth suture 7980. While shown in FIG. 97 as having four sutures 7920, 7940, 7960, 7980, the implant can have any number of sutures. The support member 7910 is a pelvic floor repair graft configured to support areas in a body of a patient where the natural tissue is weak. The support member 7910 can be, for example, a synthetic mesh such as macroporous polypropylene, polyester, nylon and/or a bioresorbable or a permanent matrix. In other embodiments, the support member is made of biologic graft material such as human, porcine, or bovine derived tissue.

The first suture 7920 includes an elongate member 7922, a needle 7935 and a plurality of retention members 7930. The first suture 7920 is configured to be inserted into a tissue. The elongate member 7922 of the first suture 7920 includes a first end portion 7924 and a second end portion 7926. The first end portion 7924 of the elongate member 7922 is coupled to the support member 7910. The second end portion 7926 of the elongate member 7922 is coupled to the needle 7935. The needle 7935 of the first suture 7920 is configured to penetrate tissue to facilitate insertion of the first suture 7920 into the tissue of a patient.

The plurality of retention members 7930 of the first suture 7920 are similar to the tissue anchors described in U.S. Patent Application No. 61/071,726 entitled "Surgical composite barbed suture," filed May 14, 2008, which is hereby incorporated by reference in its entirety. In other embodiments, the first suture is similar to the other sutures found in U.S. Patent Application No. 61/071,726.

The plurality of retention members 7930 allow the first suture 7920 to move with respect to a tissue in the direction shown by the arrow KK in FIG. 97, when the first suture 7920 is disposed within a tissue. Further, the plurality of retention members 7930 are configured such that movement of the first suture 7920 with respect to a tissue in a direction different than the direction shown by the arrow KK in FIG. 97 is substantially prevented, when the first suture 7920 is disposed within the tissue. Said another way, the plurality of retention members 7930 of the first suture 7920 provide resistance to movement of the first suture 7920 with respect to the tissue in a direction different than the direction shown by the arrow KK in FIG. 97. Specifically, as the first suture 7920 is moved in the direction different than the direction shown by the arrow KK in FIG. 97, the plurality of retention members 7930 of the first suture 7920 engage the tissue surrounding the elongate member 7922 of the first suture 7920 and help prevent such motion. In this manner, the first suture 7920 helps retain the implant 7900 within a body of a patient.

The second suture 7940, the third suture 7960 and the fourth suture 7980 are functionally and structurally similar to the first suture 920 and all include an elongate member 7942, 7962, 7982 a needle 7955, 7975, 7995 and a plurality of retention members 7950, 7970, 7990. The elongate members 942, 962, 982 include first end portions 7944, 7964, 7984 coupled to the support member 7910 and second end portions 7946, 7966, 7986 coupled to needles 7955, 7975, 7995, respectively. When the sutures 7920, 7940, 7960, 7980 are disposed within a tissue of a patient, the support member 7910 is configured to support a portion of a body of a patient.

In use, the implant 7900 is inserted into a body of a patient using a delivery device, such as those described above in relation to implant 7100. In some embodiments, the implant 7900 is inserted into the pelvic region of a patient. For example, the support member 7910 can be positioned such that it supports a portion of a body of a patient located at or near the pelvic floor of the patient. The sutures 7930, 7950, 7970, 7990 are inserted into the body of the patient similar to the methods described above with respect to other embodiments.

Figure 98:
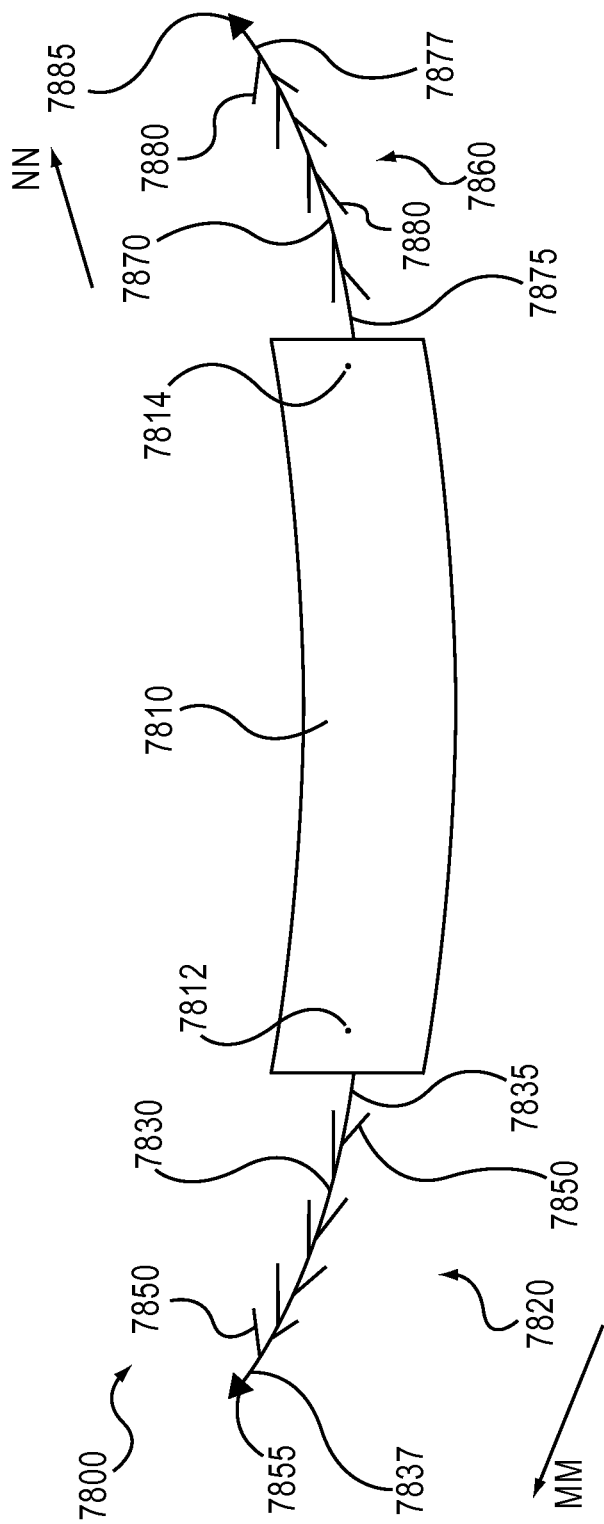
FIG. 98 is a top view of an implant according to an embodiment.

While FIG. 96 and FIG. 97 show implants 7700, 7900 as pelvic floor repair grafts, in other embodiments, the implant is a urinary incontinence sling. For example, FIG. 98 shows an implant 7800 according to an embodiment. The implant 7800 includes a support member 7810, a first suture 7820, and a second suture 7860.

The support member 7810 is configured to reconstitute the support for the urethra and/or the bladder. The support member 7810 includes a first end portion 7812 configured to be coupled to a first end portion 7835 of the first suture 7820, and a second end portion 7814 configured to be coupled to a first end portion 7875 of the second suture 7860. The support member 7810 can be made of synthetic and/or biologic material. For example, the support member 7810 can be constructed similar to the support member 7100, described above.

The first suture 7820 includes an elongate member 7830, a needle 7855 and a plurality of retention members 7850. The first suture 7820 is configured to be inserted into a tissue. The elongate member 7830 of the first suture 7820 includes a first end portion 7835 and a second end portion 7837. The first end portion 7835 of the elongate member 7830 is coupled to the first end portion 7812 of the support member 7810. The second end portion 7837 of the elongate member 7830 is coupled to the needle 7855. The needle 7855 of the first suture 7820 is configured to penetrate tissue to facilitate insertion of the first suture 7820 into the tissue of a patient.

The plurality of retention members 7850 of the first suture 7820 are barbs that are integrally formed with the elongate member 7830 of the first suture 7820. The plurality of retention members 7850 allow the first suture 7820 to move with respect to a tissue in the direction shown by the arrow MM in FIG. 98 when the first suture 7820 is disposed within a tissue. Further, the plurality of retention members 7850 are configured such that movement of the first suture 7820 with respect to a tissue in a direction different than the direction shown by the arrow MM in FIG. 98 is substantially prevented, when the first suture 7820 is disposed within the tissue. Specifically, the plurality of retention members 7850 of the first suture 7820 provide resistance to movement of the first suture 7820 with respect to the tissue in a direction different than the direction shown by the arrow MM in FIG. 98. Said yet another way, as the first suture 7820 is moved in a direction different than the direction shown by the arrow MM in FIG. 98, the plurality of retention members 7850 of the first suture 7820 engage the tissue surrounding the elongate member 7830 of the first suture 7820 and help prevent such motion. In this manner, the first suture 7820 helps retain the implant 7800 within a body of a patient.

The second suture 7860 is functionally and structurally similar to the first suture 7820 and includes an elongate member 7870 a needle 7885 and a plurality of retention members 7880. The elongate member 7870 includes a first end portion 7875 coupled to the second end portion 7814 of the support member 7810 and a second end portion 7877 coupled to the needle 7885. The plurality of retention members 7880 of the second suture 7860 allow the second suture 7860 to move with respect to a tissue in the direction shown by the arrow NN in FIG. 98 and limit movement of the second suture 7860 with respect to the tissue in a direction different than the direction shown by the arrow NN in FIG. 98, when the second suture 7860 is disposed within the tissue. Said another way, the plurality of retention members 7880 of the second suture 7860 provide resistance to movement of the second suture 7860 with respect to the tissue in a direction different than the direction shown by the arrow NN in FIG. 98. Specifically, as the second suture 7860 is moved in a direction different than the direction shown by the arrow NN in FIG. 98, the plurality of retention members 7880 of the second suture 7860 engage the tissue surrounding the elongate member 7870 of the second suture 7860 and help prevent such motion. In this manner, the second suture 7860 helps retain the implant 7800 within a body of a patient.

In use, the implant 7800 is inserted into a body of a patient using a delivery device such as those described above in relation to implant 7100. The first suture 7820 and the second suture 7860 are inserted into the body of the patient similar to the methods described above with respect to other embodiments. For example, the sutures can be inserted through muscle and fascia around the area of the urethra. This can include, for example, the obturator internus and externus muscles, the rectus fascia, and the abdominal muscles. When the first suture 7820 and the second suture 7860 are disposed within a tissue of a patient, the support member 7810 is configured to support a portion of a body of a patient, such as the urethra.

A suture assembly according to embodiments of the invention can be used in conjunction with a variety of different types of implant assemblies as described herein. For example, an anterior, posterior or total pelvic floor repair implant can be used. In addition, devices other than a suturing delivery device, such as delivery device 7144, can be used to deploy and secure a suture assembly. For example, a free needle can be used to pass a suture through a vaginal wall.

The implant member (or implant) and suture for any of the embodiments can be assembled by a user or provided preassembled. The sutures can be absorbable or non-absorbable and the implant member can be a variety of different materials including various grades of implantable material. The implant member can also be any suitable shape or size, such as circular, oval, rectangular, square, elliptical, etc. In some embodiments, the implant member is formed with a mesh material to promote tissue in-growth.

In one embodiment, a method includes securing an implant the implant having a suture including a pre-formed loop coupled thereto, to a vagina apex. The suture is secured to a selected portion of a pelvic tissue such that at least a portion of the implant is disposed within a pelvic region of the patient. A portion of the suture is drawn through the loop while simultaneously advancing a uterus to approximate the vaginal apex to the selected portion of pelvic tissue. In some embodiments, a retainer member is releasably coupled to the loop of the suture to assist in maintaining a loop configuration of the suture. In some embodiments, the method includes securing the implant to the vaginal apex prior to inserting the end of the suture through the selected portion of pelvic tissue. In some embodiments, the method includes securing the implant to the vaginal apex after inserting the suture through the selected portion of pelvic tissue. In some embodiments, the method includes securing the implant to the vaginal apex by securing the implant to an interior wall of the vagina. In some embodiments, the selected portion of pelvic tissue is a sacrospinous ligament. In some embodiments, the method includes advancing a medical device that is coupled to the inverted vagina in a direction toward the selected portion of the pelvic tissue to advance the uterus such that at least a portion of the uterus is moved upward.

In another embodiment, a method includes inserting at least a portion of an implant through an incision in a vagina. The implant has a first substantially planar surface and a second substantially planar surface. The implant is secured to a selected portion of a pelvic tissue such that the first substantially planar surface of the implant contacts the pelvic tissue. The implant is also secured to the vagina such that the second substantially planar surface of the implant contacts the vaginal apex. In some embodiments, the method includes securing the implant to the vaginal apex prior to securing the implant to the pelvic tissue. In some embodiments, the method includes securing the implant to the vaginal apex after securing the implant to the pelvic tissue. In some embodiments, the implant is secured to the vaginal apex such that the implant is secured to an interior wall of the vagina. In some embodiments, the method also includes repositioning a uterus of the patient into a normal anatomic position by advancing the inverted vagina in a direction toward the selected portion of the pelvic tissue such that at least a portion of the uterus is moved upward. In some embodiments, the selected portion of pelvic tissue is a sacrospinous ligament.

In another embodiment, an apparatus includes a pelvic implant and a suture coupled to the pelvic implant. The suture has a pre-formed loop. The apparatus also includes a needle coupled to an end of the suture that is configured to be releasably coupled to a delivery device. The needle is further configured to be inserted through a pelvic tissue and drawn through the loop to secure the implant to the pelvic tissue. In some embodiments, the end of the suture is a first end and the suture has a second end, the needle is a first needle and the apparatus further includes a second needle coupled to the second end of the suture. The second needle is configured to draw the second end of the suture through a portion of the vagina. In some embodiments, the implant is formed with a mesh material and in some embodiments the implant is disc shaped. In some embodiments, the implant has a first substantially planar surface configured to be placed in contact with the pelvic tissue and a second substantially planar surface configured to be placed in contact with a portion of the vagina. In some embodiments, the apparatus includes a removable sleeve coupled to and at least partially covering the implant. In some embodiments, the suture includes at least one barbed portion configured to engage pelvic tissue to help secure the implant to the pelvic tissue.

In another embodiment, an apparatus includes a procedure assistance member having an open configuration and a closed configuration. An implant assembly that includes a suture is coupled to the procedure assistance member. The suture is at least partially covered by a portion of the procedure assistance member when the procedure assistance member is in the closed configuration. The procedure assistance member is configured to assist in the delivery of the implant assembly to a pelvic region of a patient. In some embodiments, the implant assembly also includes an implant and the suture is coupled to the implant. In some embodiments, the suture defines a loop and the suture is coupled to the procedure assistance member such that the loop is configured to receive a portion of an implant delivery device therethrough. In some embodiments, the implant assembly also includes an implant and the procedure assistance member includes a flap configured to at least partially cover the implant.

In another embodiment, an apparatus includes an implant member configured to be coupled to a vaginal apex of a patient and a suture coupled to the implant member. A portion of the suture extends from an end of the implant member. A sleeve is releasably coupled to the implant member and at least partially covering the implant member. A coupling member is coupled to at least one of the sleeve or the suture. The coupling member is configured to be releasably coupled to an implant delivery device. In some embodiments, the coupling member includes a loop. In some embodiments, the implant member is formed with a mesh material. In some embodiments, the sleeve includes a window portion and a portion the implant member is accessible through the window portion. In some embodiments, a needle is removably coupled to an end of the suture. In some embodiments, the implant member is a mesh and the suture is weaved intermittently through the implant member. In some embodiments, the suture is tied to the implant member at least one location. In some embodiments, the apparatus further includes a dilator coupled to the connector.

In another embodiment, a method includes securing a first portion of an implant assembly to a vaginal apex of the patient. A delivery device is maneuvered through an exterior incision in the patient and to a location within the vagina. A second portion of the implant assembly is releasably coupled to the delivery device. The second portion of the implant assembly is drawn through a passageway formed by the delivery device and through the exterior incision using the delivery device. In some embodiments, the implant assembly includes an implant, a sleeve covering at least a portion of the implant, and a suture coupled to the implant, and the method further includes cutting a portion of the sleeve and the suture of the implant assembly after drawing the second portion of the implant assembly through the passageway and the sleeve is then removed from the implant. In some embodiments, the second portion of the implant assembly is drawn through an arcus tendineus muscle. In some embodiments, the second portion of the implant assembly is drawn through an obturator muscle. In some embodiments, a uterus is moved to a correct anatomical position simultaneously with drawing the second portion of the implant through the passageway. In some embodiments, the implant member is formed with mesh having an edge configured to engage surrounding tissue to secure the implant member to the surrounding tissue. In some embodiments, the implant assembly is a first implant assembly, and the method further includes securing a portion of a second implant assembly to the vaginal apex of the patient and securing another portion of the second implant assembly to a portion of pelvic tissue.

In another embodiment, an apparatus includes an implant member and a suture coupled to the implant member. The suture is configured to secure a first portion of the implant member to a vaginal apex of a patient. The apparatus also includes a coupling member coupled to a second portion of the implant member and configured to associate the implant member to an implant delivery device. The second portion of the implant member is configured to engage a portion of pelvic tissue to secure the implant member within a pelvic region of the patient. In some embodiments, the apparatus also includes a sleeve at least partially covering the implant member and the coupling member is attached to at least one of the implant member or the sleeve. In some embodiments, the apparatus also includes a strengthening member coupled to the implant member that is configured to reduce stretching of the implant member. In some embodiments, the apparatus also includes a sleeve at least partially covering the implant member. The sleeve defines a window portion that exposes at least a portion of the implant member. In some embodiments, the coupling member of the apparatus is a loop formed by a portion of the suture. In some embodiments, the coupling member includes a loop or includes a low-profile connector. In some embodiments, the coupling member is an attachment hole defined by the implant member. In some embodiments, the portion of pelvic tissue is a first sacrospinous ligament and the implant member is configured to be coupled to a second sacrospinous ligament on an opposite side of a uterus.

In another embodiment, an apparatus includes an implant having a first end portion, a second end portion and a middle portion. A first sleeve is releasably coupled to the first end portion of the implant and at least partially covering the first end portion of the implant. A second sleeve is releasably coupled to the second end portion of the implant and at least partially covering the second end portion of the implant. The apparatus also includes a suture coupled to the middle portion of the implant and configured to secure the implant to a vaginal apex of a patient. In some embodiments, the apparatus also includes a first coupling member coupled to at least one of an end of the first end portion of the implant or an end of the first sleeve, and a second coupling member coupled to at least one of an end of the second end portion of the implant or an end of the second sleeve. The first coupling member is configured to be coupled to a first delivery device and the second coupling member is configured to be coupled to a second delivery device. In some embodiments, the suture of the apparatus is a first suture and the apparatus further includes a second suture coupled to the implant member that is configured to secure the implant member to the vaginal apex. In some embodiments, the first portion of the implant is configured to be secured to an iliococcygeus muscle, and the second portion of the implant configured to be secured to an iliococcygeus muscle on an opposite side of a pelvic region of the patient. In some embodiments, the implant includes a third end portion configured to be secured to a sacrospinous ligament on a first side of a pelvic region and a fourth end portion configured to be secured to a sacrospinous ligament on an opposite side of the pelvic region. In some embodiments, the middle portion of the implant includes a flap portion configured to support a uterus.

In another embodiment, an apparatus includes an implant member having a first end portion and a second end portion. A first suture is coupled to the implant member to secure the implant to a first portion of a sacrospinous ligament, and a second suture is coupled to the implant to secure the implant to a second portion of a sacrospinous ligament on a contra lateral side of a pelvic region. At least one of the first suture or the second suture are configured to secure the implant to a vaginal apex. In some embodiments, the implant includes a first strap configured to be secured to an obturator muscle, and a second strap configured to be secured to an obturator muscle on the contra lateral side of the pelvic region. In some embodiments, at least one of the first end portion or the second end portion of the implant is configured to fold when the associated suture is secured to the associated sacrospinous ligament. In some embodiments, at least one of the first suture or the second suture is configured to be tied within the pelvic region. In some embodiments, the implant includes a first strap configured to be secured to an arcus tendineus and a second strap configured to be secured to an arcus tendineus on the contra lateral side of the pelvic region. In some embodiments, the implant includes a first strap configured to be secured to an arcus tendineus, a second strap configured to be secured to an arcus tendineus on a contra lateral side of the pelvic region, a third strap configured to be secured to an obturator muscle, and a fourth strap configured to be secured to an obturator muscle on the contra lateral side of the pelvic region. In some embodiments, the first end portion is configured to be secured to an arcus tendineus and the second end portion is configured to be secured to an arcus tendineus on the contra lateral side of the pelvic region.

In another embodiment, an apparatus includes an implant having a first strap configured to be inserted into and engage a pelvic tissue, and a second strap configured to be inserted into and engage a pelvic tissue on a contra lateral side of a pelvic region. A suture is coupled to the implant that is configured to secure the implant to a vaginal apex. In some embodiments, the suture is secured to at least one of the first strap or the second strap at multiple locations along the length of the strap. In some embodiments, the suture has a first end coupled to the vaginal apex and a second end coupled to at least one of the first strap or the second strap, and the second end is configured to be drawn through a pelvic tissue. In some embodiments, the implant includes a third strap configured to be inserted into and engage a pelvic tissue different than the pelvic tissue engaged by the first strap and the second strap, and a fourth strap configured to be inserted into and engage pelvic tissue different than the pelvic tissue engaged by the first strap, the second strap, and the third strap. In some embodiments, the implant is configured to support a uterus of a patient in a correct anatomical position.

In another embodiment, a method includes securing a first portion of an implant assembly to a sacrospinous ligament of a patient using a first delivery device and drawing a second portion of the implant assembly through one of an arcus tendineus or an obturator muscle using a second delivery device inserted through an exterior incision. The second delivery device is different than the first delivery device. The method also includes securing a third portion of the implant assembly to a vaginal apex. In some embodiments, the method also includes drawing a fourth portion of the implant assembly through the other of the arcus tendineus or the obturator muscle. In some embodiments, the method also includes drawing a fourth portion of the implant assembly through the other of the arcus tendineus or the obturator muscle using a third delivery device that is different than the first delivery device and the second delivery device. In some embodiments, the second portion of the implant assembly includes a coupling member coupled to an implant member and the coupling member is configured to be coupled to an end of the second delivery device. In some embodiments, the securing the first portion of the implant assembling includes suturing the first portion of the implant assembly to the sacrospinous ligament. In some embodiments, the method also includes coupling a third portion of the implant assembly to a vaginal apex and tensioning the implant assembly such that the vaginal apex is approximated to a uterus.

In another embodiment, a method includes securing a first suture to a first sacrospinous ligament on a first side of a pelvic region and securing a second suture to a second sacrospinous ligament on a second side of a pelvic region, opposite the first side of the pelvic region. The method also includes securing the first suture to a vaginal apex at a first location and securing the second suture to the vaginal apex at a second location. The first and second suture are tensioned such that the vaginal apex is approximated to the first sacrospinous ligament and the second sacrospinous ligament. In some embodiments, at least one of the first suture or the second suture defines a loop configured to receive a portion of a delivery device therethrough. In some embodiments, the method also includes associating a trocar needle coupled to the first suture to a delivery device prior to securing the first suture to a sacrospinous ligament. In some embodiments, the method also includes associating a trocar needle coupled to the first suture to a delivery device after securing the first suture to a sacrospinous ligament and prior to securing the first suture to the vaginal apex. In some embodiments, securing the first suture to the sacrospinous ligament includes pulling the first suture through a loop defined by the first suture. In some embodiments, securing the first suture to the vaginal apex includes forming a knot in a pelvic space between the vaginal apex and the sacrospinous ligament.

In another embodiment, a method includes securing an implant assembly to a selected portion of tissue within a pelvic region, and securing the implant assembly to a vaginal apex. The method also includes securing a suture assembly to a sacrospinous ligament, and securing the suture assembly to the vaginal apex. In some embodiments, the suture assembly is a first suture assembly and the method further includes securing a second suture assembly to a sacrospinous ligament on a contra lateral side of the pelvic region. In some embodiments, the implant assembly is secured to the selected portion of pelvic tissue with a suture. In some embodiments, the implant assembly is secured within a pelvic region that does not include a uterus. In some embodiments, the method further includes moving the vagina apex in a direction toward the sacrospinous ligament. simultaneously with securing the implant assembly. In some embodiments, the method further includes tensioning the suture assembly while simultaneously moving the vaginal apex in a direction toward the sacrospinous ligament. In some embodiments, the suture assembly is coupled to the implant assembly.

In another embodiment, an apparatus includes an anchor member configured to be passed through and anchored to a sacrospinous ligament. A suture is coupled to the anchor member and a needle is coupled to an end of the suture. The needle is configured to pass the end of the suture through a portion of a vaginal apex. In some embodiments, the needle is a first needle, the end of the suture is a first end, and the apparatus includes a second needle coupled to a second end of the suture that is configured to pass the second end of the suture through the vaginal apex. In some embodiments, the needle is configured to be releasably coupled to a first delivery device and the anchor member is configured to be releasably coupled to a second delivery device different than the first delivery device to pass the anchor member through the sacrospinous ligament. In some embodiments, the anchor member has a substantially planar configuration. In some embodiments, the anchor member is configured to be inserted through the sacrospinous ligament in a first orientation and subsequently be moved to a second orientation that is substantially transverse to the first orientation.

In some embodiments, an apparatus includes a first body having a first retention structure, a second retention structure, a first opening, and a first aperture. The first retention structure is configured to hold or maintain a loop in a suture formed or defined by a sliding knot in a suture in an open position about the first aperture. The second retention structure is configured to secure a free end portion of the suture. The first aperture is configured to permit passage of a suturing device and the free end portion of the suture through the first body. The first opening is configured to permit the free end portion of the suture to exit the first body through the first opening when the free end portion of the suture is passed through the first body.

In some embodiments, the first retention structure is recessed in the first body. In some embodiments, the first body further includes a clip, a tab, or an adhesive attached to the first body to secure an implant to the first body. In some embodiments, the aperture is configured to engage and be removably coupled to a suturing device.

In some embodiments, the apparatus further includes a third retention structure, a fourth retention structure, a second aperture, and a second opening. The third retention structure is configured to hold or maintain a loop in a suture formed or defined by a sliding knot in a suture in an open position about the third aperture. The fourth retention structure is configured to secure a free end portion of the suture. The second aperture is configured to permit passage of a suturing device and the free end portion of the suture through the first body. The second opening is configured to permit the free end portion of the suture to exit the first body through the second opening when the free end portion of the suture is passed through the first body.

In some embodiments, the apparatus further includes a second body movably coupled to the first body. The second body includes a first aperture and a first opening. The second body can be in an open configuration or a closed configuration relative to the first body. The second body is movably coupled to the first body such that the first aperture of the second body is at least partially open to the first aperture of the first body, and the first opening of the second body is at least partially aligned with the first opening of the first body in the closed configuration.

In some embodiments, the first body is configured to be fixedly coupled to the second body when the second body is in the closed configuration. In some embodiments, the first body is translucent. In some embodiments, the first body includes a cavity configured to house or receive at least a portion of the implant. In some embodiments, the first body includes a suture retainer. In some embodiments, the second retention structure is recessed in the first body.

In some embodiments, a method includes attaching an implant to an implant dispenser. The implant includes a body portion and a first suture. The first suture has a loop and a free end portion. The implant dispenser has a first aperture, a first retention structure and a second retention structure. The method includes placing the loop of the first suture about or around the first retention structure such that a portion of the loop of the first suture is open to a portion of the first aperture, securing the free end portion of the first suture to the second retention structure, and disposing the body portion of the implant on the implant dispenser.

In some embodiments, an implant includes a second suture and an implant dispenser includes a second aperture, a third retention structure and a fourth retention structure. The second suture includes a free end portion and a loop. A method of attaching the implant to the implant dispenser includes placing the loop of the second suture about or around the third retention structure such that a portion of the loop of the second suture is open to a portion of the second aperture, and securing the free end portion of the second suture to the fourth retention structure.

In some embodiments, the method includes moving the implant dispenser to a closed configuration. In some embodiments, the method includes disposing a protective material on the implant dispenser. The protective material is configured to prevent the implant from detaching from the implant dispenser.

In some embodiments, a method of forming a knot includes passing a suturing device through a loop in a first suture and passing a first portion of the first suture through a tissue in the body of a patient with the suturing device. The loop is secured to an implant dispenser about an aperture in the implant dispenser. The first suture is attached to the suturing device. The method further includes retracting the suturing device through the loop such that the first portion of the first suture passes through the loop, removing the loop from the implant dispenser, and pulling the first portion of the first suture to tighten the knot.

In some embodiments, the method further includes passing a second portion of the suture through a tissue in the body of the patient, and tying the first portion of the suture to the second portion of the suture.

In some embodiments, a method of implanting an implant in a body of a patient includes passing a suturing device through a first aperture in an implant dispenser and attaching the first end portion of the first suture to the suturing device. The implant is attached to or housed by the implant dispenser. The implant includes a first suture that has a first end portion, a second end portion, and a loop open about the first aperture. The method further includes passing the first end portion of the first suture through a tissue within the body of the patient, retracting the first end portion of the first suture and the suturing device through the first aperture, and removing the implant from the implant dispenser. The method also includes passing the second end portion of the first suture through a tissue within the body of the patient, positioning the implant within the body of the patient to support a tissue within the body of the patient, and securing the first end portion and the second end portion of the first suture to maintain the positioning of the implant.

In some embodiments, the method further includes passing the suturing device through a second aperture in the implant dispenser, attaching a first end portion of a second suture to the suturing device, the second suture having the first end portion, a second end portion and a loop open about the second aperture, and passing the first end portion of the first suture through a tissue within the body of the patient. The method further includes retracting the first end portion of the second suture and the suturing device through the second aperture, passing the second end portion of the second suture through a tissue within the body of the patient, and securing the first end portion and the second end portion of the second suture to maintain the positioning of the implant.

In one embodiment, an apparatus comprises a support member configured to support a uterus of a patient, a first strap extending from the support member and configured to be secured to a first portion of a sacrospinous ligament, and a second strap extending from the support member configured to be secured to a second portion of the sacrospinous ligament. The first strap and the second strap are configured to help retain the support member at least partially adjacent the uterus when the first strap is secured to the first portion of the sacrospinous ligament and the second strap is secured to the second portion of the sacrospinous ligament.

In some embodiments, the apparatus of includes a first sleeve releasably disposed over at least a portion of the first strap. The first sleeve is configured to be removed from the first strap when the first strap is secured to the first sacrospinous ligament. The apparatus may also include a second sleeve releasably disposed over at least a portion of the second strap. The second sleeve is configured to be removed from the second strap when the second strap is secured to the second sacrospinous ligament. In some embodiments, the first sleeve has a length greater than the length of the first strap. In some embodiments, the support member is mesh.

In some embodiments, the apparatus includes a dilator having a first end portion and a second end portion. The first end portion of the dilator is coupled to the first sleeve. The first end portion of the dilator has a diameter larger than a diameter of the second end portion of the dilator. The apparatus also includes a needle coupled to the second end portion of the dilator. The needle is configured to attach to a delivery device.

In some embodiments, the needle is configured to penetrate the sacrospinous ligament. In some embodiments, the first strap is secured to the first sleeve with a suture. In some embodiments, the first strap has a plurality of tangs. The plurality of tangs are configured to help secure the first strap to the first portion of the sacrospinous ligament.

In some embodiments, the support member has a first side portion and a second side portion different than the first side portion. The first strap extends from the first side portion of the support member and the second strap extends from the second side portion of the support member. In some embodiments, the support member defines a notch configured to receive at least a portion of a uterus. In some embodiments, the support member is substantially rectangular in shape. In other embodiments, the support member is substantially oval in shape. In further embodiments, the support member is substantially elliptical in shape.

In one embodiment, a method includes inserting a pelvic implant through an incision in the anterior vaginal mucosa. The pelvic implant includes a support portion, a first strap extending from the support portion, and a second strap extending from the support portion. The method also includes pulling the first strap at least partially through a first portion of a sacrospinous ligament such that the first strap is disposed at least partially within the first portion of the sacrospinous ligament but does not extend through the incision and pulling the second strap at least partially through a second portion of the sacrospinous ligament such that the second strap is disposed at least partially within the second portion of the sacrospinous ligament but does not extend through the incision.

In some embodiments, the inserting includes positioning the support portion adjacent a uterus of a patient. The support portion is configured to support the uterus of the patient. In some embodiments, the pulling includes pulling a first sleeve disposed over the first strap at least partially through the first portion of the sacrospinous ligament such that a first portion of the first sleeve is disposed within the first sacrospinous ligament and a second portion of the first sleeve extends through the incision.

In some embodiments, the method includes removing a first sleeve from the first strap and leaving the first strap at least partially disposed within the first sacrospinous ligament. In some embodiments, the removing the first sleeve includes cutting a suture. The suture is attached to the first sleeve to the first strap.

In some embodiments, an implant includes a graft and a suture. The graft is configured to support a portion of a body of a patient. The suture includes an elongate member and a barb coupled to the elongate member. The elongate member has an end portion coupled to the graft. The elongate member defines a center line. The barb extends from the elongate member at an angle acute to the center line of the elongate member when the elongate member is in a linear configuration. The suture is configured to be inserted into a tissue. The barb is configured to allow movement of the suture with respect to the tissue in a first direction and to help prevent movement of the suture with respect to the tissue in a second direction when the elongate member is disposed within the tissue of the patient. The second direction is different from the first direction. In some embodiments, the elongate member of the suture is flexible.

In some embodiments, the barb of the suture is a first barb and the suture has a second barb configured to allow movement of the suture with respect to the tissue in the first direction and to help prevent movement of the suture with respect to the tissue in the second direction. In some embodiments, the suture is a first suture and the implant includes a second suture. In some embodiments, the second suture is intertwined with the first suture.

In some embodiments, the graft includes a knitted mesh. In some embodiments, the graft includes polyester. In some embodiments, the graft includes nylon. In some embodiments, the graft includes polypropylene. In some embodiments, the graft includes a biological material.

In some embodiments, the end portion of the elongate member of the suture is a first end portion and the elongate member has a second end portion. The implant includes a needle coupled to the second end portion of the elongate member. The needle is configured to penetrate tissue when the suture is inserted into the tissue.

In some embodiments, the end portion of the elongate member of the suture is a first end portion and the elongate member has a second end portion. The second end portion of the elongate member is coupled to a needle configured to penetrate tissue when the suture is inserted into the tissue.

In some embodiments, the barb of the suture is a first barb and the suture has a plurality of barbs. In some embodiments, the suture is made of bioresorbable material. In some embodiments, the portion of the body of the patient is a pelvic floor of the patient.

In some embodiments, an implant includes a support member, a first suture and a second suture. The first suture includes an elongate member and a retention member. The elongate member has an end portion coupled to the support member. The retention member is coupled to the elongate member. The retention member of the first suture is configured to help retain the support member within a body of a patient. The second suture includes an elongate member and a retention member. The elongate member has an end portion coupled to the support member. The retention member of the second suture is coupled to the elongate member and is configured to help retain the support member within the body of the patient. The second suture is intertwined with the first suture. In some embodiments, the retention member of the first suture is a first retention member and the first suture includes a second retention member. In some embodiments, the elongate member of the first suture is flexible.

In some embodiments, the implant includes a third suture and a fourth suture. The third suture includes an elongate member and a retention member. The elongate member of the third suture has an end portion coupled to the support member. The retention member of the third suture is coupled to the elongate member of the third suture and is configured to help retain the support member within the body of the patient. The fourth suture includes an elongate member and a retention member. The elongate member of the fourth suture has an end portion coupled to the support member. The retention member of the fourth suture is coupled to the elongate member of the fourth suture and is configured to help retain the support member within the body of the patient. The fourth suture is intertwined with the third suture.

In some embodiments, the graft includes a knitted mesh. In some embodiments, the graft includes polyester. In some embodiments, the graft includes nylon. In some embodiments, the graft includes polypropylene. In some embodiments, the graft includes a biological material.

In some embodiments, the end portion of the elongate member of the first suture is a first end portion and the elongate member of the first suture has a second end portion. The implant includes a needle coupled to the second end portion of the elongate member of the first suture. The needle is configured to penetrate tissue when the implant is inserted into the body of the patient.

In some embodiments, the end portion of the elongate member of the first suture is a first end portion and the elongate member of the first suture has a second end portion. The second end portion of the elongate member is coupled to a needle configured to penetrate tissue when the implant is inserted into the body of the patient. In some embodiments, the support member is a urinary incontinence sling. In some embodiments the support member is a pelvic floor repair graft.

In some embodiments the first suture is removably coupled to the support member such that the end portion of the first suture can be detached from the support member, moved with respect to the support member from a first position to a second position, and reattached to the support member at the second position. In some embodiments, the retention member of the first suture is a barb. In some embodiments, the first suture is made of bioresorbable material.

In some embodiments, an implant includes a support member having a first side portion and a second side portion, a first suture, and a second suture. The first suture includes an elongate member and a plurality of retention members coupled to the elongate member. The elongate member has an end portion coupled to the first side portion of the support member. The first suture is configured to be inserted into a tissue. The plurality of retention members being configured to allow movement of the first suture with respect to the tissue in a first direction and to help prevent movement of the first suture with respect to the tissue in a second direction when the elongate member is disposed within the tissue. The second direction is different than the first direction. The second suture includes an elongate member and a plurality of retention members coupled to the elongate member. The elongate member has an end portion coupled to the second side portion of the support member. The second suture is configured to be inserted into a tissue. The plurality of retention members are configured to allow movement of the second suture with respect to the tissue in a third direction and configured to help prevent movement of the second suture with respect to the tissue in a fourth direction when the elongate member is disposed within the tissue. The fourth direction is different than the third direction.

In some embodiments, the elongate member of the first suture is flexible. In some embodiments, the plurality of retention members are a plurality of barbs nonuniformly spaced along the elongate member. In some embodiments, the plurality of retention members are a plurality of barbs uniformly spaced along the elongate member.

In some embodiments, the implant includes a third suture intertwined with the first suture and a fourth suture intertwined with the second suture. In some embodiments, the graft includes a knitted mesh. In some embodiments, the graft includes polyester. In some embodiments, the graft includes nylon. In some embodiments, the graft includes polypropylene. In some embodiments, the graft includes a biological material.

In some embodiments, the support member is a urinary incontinence sling. In some embodiments the support member is a pelvic floor repair graft. In some embodiments, the end portion of the elongate member of the first suture is a first end portion and the elongate member of the first suture has a second end portion. The implant includes a needle coupled to the second end portion of the elongate member of the first suture. The needle is configured to penetrate tissue when the first suture is inserted into the tissue.

In some embodiments, the end portion of the elongate member of the first suture is a first end portion and the elongate member of the first suture has a second end portion. The second end portion of the elongate member is coupled to a needle configured to penetrate tissue when the first suture is inserted into the tissue. In some embodiments, the first suture is made of bioresorbable material.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the various embodiments of an implant assembly is provided to enable any person skilled in the art to make or use the invention. While the invention has been particularly shown and described with reference to embodiments thereof, it will be understood by those skilled in art that various changes in form and details may be made therein. Thus, it should be understood that the devices and methods described herein can include various combinations and/or sub-combinations of the components and/or features of the different embodiments described.

Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above.

For example, a variety of different implant assemblies (e.g., 120, 220, 320, etc.) can be used in any of the medical procedures described herein. An implant assembly can be a variety of different configurations, shapes and/or sizes and be formed with various different materials not specifically described. An implant assembly can include various combinations and sub-combinations of the implant assemblies, and their components, described herein. For example, an implant assembly can include one or more straps, one or more tabs, no straps or tabs, sutures for delivery, sutures for implantation, and/or sutures that are permanent or sutures that are absorbable, and/or various needles that can be removed after insertion of the implant assembly into a pelvic region. The implant assemblies can have sleeves, dilators, connectors or any combination of the various embodiments described herein.

In addition, the delivery devices and needles can also include any combination or sub-combination of the various features and components described herein. Further, other configurations for a delivery device can be used to perform the medical procedures described herein, while still remaining within the scope of the invention.

For any of the embodiments of an implant assembly, a single implant assembly can be delivered and secured on one side of the pelvic region, or an implant assembly can be implanted on both sides. In some embodiments, a single implant assembly spans across the pelvic region to support the uterus and is secured to a tissue site on each side of the uterus. In some embodiments, the implant assembly includes only sutures (e.g., a suture assembly) or only an implant member. In addition, some components of an implant assembly are used only for delivering and securing the implant assembly and are subsequently removed from the assembly, leaving only the implant member and/or sutures within the patient's body. For example, a trocar needle, curved needle, straight needle, etc. can be cut off from a suture. In another example, in some embodiments, a sleeve and/or dilator are removed from the implant assembly after delivery of the implant assembly. In another example, in some embodiments the implant may be altered or cut to a custom size by the physician before delivery of the implant assembly.

Although embodiments of an implant, an implant assembly, or a suture assembly have been described as being coupled within a pelvic region at specific locations, it should be understood that such embodiments can be coupled to different locations within a pelvic region than shown for a particular embodiment. For example, various embodiments of an implant, an implant assembly and/or a suture assembly can be coupled within a pelvic region at locations such as, an arcus tendineus (i.e., white line), a sacrospinous ligament, a uterosacral ligament, a cardinal ligament, an iliococcygeus muscle, a levator ani muscle or other levator muscles. In some embodiments, the devices can be coupled to an obturator muscle or other anatomical structures.

In addition, features of an implant dispenser described in relation to one embodiment of an implant dispenser can be applicable to other embodiments of an implant dispenser.

Similarly, methods of using an implant dispenser discussed in relation to one embodiment of an implant dispenser can be used with other embodiments of implant dispensers. Furthermore, implant dispensers can vary in size and shape with implants used therewith. In some embodiments, an implant can be folded or compressed to reduce the size of an implant dispenser housing the implant.

In another example, similar to implant 900, implant 800 can have sutures having retention members such as those described in U.S. Patent Application No. 61/071,726. Additionally, any of the embodiments described herein can be constructed with retention members integrally formed with an elongate member or retention members separately formed from an elongate member.

What is claimed is:

1. A method, comprising: securing an implant to a vaginal apex, the implant having a suture including a loop coupled thereto, the loop being disposed about a portion of a shaft of a delivery device; securing, using the delivery device, the suture to a selected portion of a pelvic tissue such that at least a portion of the implant is disposed within a pelvic region; and drawing a portion of the suture and a portion of the delivery device through the loop while simultaneously advancing a uterus to approximate the vaginal apex to the selected portion of pelvic tissue.

2. The method of claim 1, wherein the securing the implant to the vaginal apex is prior to the securing, using the delivery device, the suture to the selected portion of pelvic tissue.

3. The method of claim 1, wherein the securing the implant to the vaginal apex is after the securing, using the delivery device, the suture to the selected portion of pelvic tissue.

4. The method of claim 1, wherein the advancing the uterus includes advancing a medical device coupled to an inverted vagina in a direction toward the selected portion of the pelvic tissue such that at least a portion of the uterus is moved upward.

5. A method, comprising:
inserting at least a portion of an implant through an incision in a vagina, the implant having a first substantially planar surface and a second substantially planar surface, the implant being coupled to a suture, the suture including a first portion woven to and extending along a portion of the implant and a second portion extending from the implant, the second portion including a loop, the loop being disposed about a portion of a shaft of a delivery device;
securing, using the delivery device, the implant to a selected portion of a pelvic tissue such that the first substantially planar surface of the implant contacts the pelvic tissue;
securing, using the suture, the implant to a vaginal apex, such that the second substantially planar surface of the implant contacts the vaginal apex; and
drawing a portion of the suture and a portion of the delivery device through the loop while simultaneously approximating the vaginal apex to the selected portion of the pelvic tissue.

6. The method of claim 5, further comprising: repositioning a uterus into a normal anatomic position by advancing the vaginal apex in a direction toward the selected portion of the pelvic tissue such that at least a portion of the uterus is moved upward.

7. The method of claim 5, wherein the selected portion of pelvic tissue is a sacrospinous ligament.

8. An apparatus, comprising:
a pelvic implant having a first end and a second end;
a suture coupled to at least a portion of the pelvic implant, the suture having a first end and a second end;
a first needle coupled to the first end of the suture;
a second needle coupled to the second end of the suture, the suture having a first portion extending from the pelvic implant to the first needle, a second portion extending from a first portion of the pelvic implant to a second portion of the pelvic implant, and a third portion extending from the pelvic implant to the second needle, the second portion of the suture being a loop,
the second needle configured to be inserted through a pelvic tissue and drawn through the loop to secure the implant to the pelvic tissue, wherein the implant is disc shaped defining a plurality of through-holes within an outer perimeter of the implant, the suture extending through the through-holes in a manner that forms the loop; and
a delivery device having a shaft, the loop being disposed about a portion of the shaft of the delivery device.

9. The apparatus of claim 8, wherein the implant is formed with a mesh material.

10. The apparatus of claim 8, wherein the implant has a first substantially planar surface and a second substantially planar surface, the first substantially planar surface configured to be placed in contact with the pelvic tissue, the second substantially planar surface configured to be placed in contact with a portion of a vagina.

11. The apparatus of claim 8, further comprising:
a removable sleeve coupled to the implant and at least partially covering the implant.

12. The apparatus of claim 8, wherein the suture includes at least one barbed portion, the barbed portion configured to engage pelvic tissue to help secure the implant to the pelvic tissue.

13. An apparatus, comprising: an implant member configured to be coupled to a vaginal apex of a patient; a first suture coupled to the implant member, a portion of the first suture extending from an end of the implant member; a first needle coupled to an end portion of the first suture; a second suture coupled to the implant member and extending from a midportion of the implant member, the second suture forming a loop; a second needle coupled to an end portion of the second suture; a sleeve releasably coupled to the implant member and at least partially covering the implant member; a coupling member coupled to the first suture, the coupling member including a suture loop; an implant delivery device releasably coupled to the coupling member, the implant delivery device having a shaft, the shaft of the implant delivery device being disposed through the suture loop of the second suture.

* * * * *